United States Patent
Sepp-Lorenzino et al.

(10) Patent No.: US 11,324,820 B2
(45) Date of Patent: May 10, 2022

(54) METHODS FOR THE TREATMENT OF SUBJECTS HAVING A HEPATITIS B VIRUS (HBV) INFECTION

(71) Applicants: Alnylam Pharmaceuticals, Inc., Cambridge, MA (US); Technische Universität München, Munich (DE)

(72) Inventors: Laura Sepp-Lorenzino, Cambridge, MA (US); Ulrike Protzer, Munich (DE); Thomas Michler, Munich (DE)

(73) Assignees: ALNYLAM PHARMACEUTICALS, INC., Cambridge, MA (US); TECHNISCHE UNIVERSITÄT MÜNCHEN, Munich (DE)

( * ) Notice: Subject to any disclaimer, the term of this patent is extended or adjusted under 35 U.S.C. 154(b) by 0 days.

(21) Appl. No.: 16/606,069

(22) PCT Filed: Apr. 18, 2018

(86) PCT No.: PCT/US2018/028116
§ 371 (c)(1),
(2) Date: Oct. 17, 2019

(87) PCT Pub. No.: WO2018/195165
PCT Pub. Date: Oct. 25, 2018

(65) Prior Publication Data
US 2020/0038506 A1 Feb. 6, 2020

Related U.S. Application Data

(60) Provisional application No. 62/485,618, filed on Apr. 18, 2017, provisional application No. 62/553,358, filed on Sep. 1, 2017, provisional application No. 62/646,978, filed on Mar. 23, 2018, provisional application No. 62/655,862, filed on Apr. 11, 2018.

(51) Int. Cl.
| | |
|---|---|
| *A61K 31/713* | (2006.01) |
| *A61K 31/7088* | (2006.01) |
| *A61K 39/12* | (2006.01) |
| *A61K 39/29* | (2006.01) |
| *A61K 47/54* | (2017.01) |
| *A61P 31/20* | (2006.01) |
| *A61K 39/00* | (2006.01) |

(52) U.S. Cl.
CPC .......... *A61K 39/292* (2013.01); *A61K 31/713* (2013.01); *A61K 47/549* (2017.08); *A61P 31/20* (2018.01); *A61K 2039/545* (2013.01); *A61K 2039/55555* (2013.01); *A61K 2039/55561* (2013.01)

(58) Field of Classification Search
None
See application file for complete search history.

(56) References Cited

U.S. PATENT DOCUMENTS

| | | |
|---|---|---|
| 5,571,026 A | 11/1996 | Kahre |
| 5,604,118 A | 2/1997 | Giri et al. |
| 5,610,050 A | 3/1997 | Blum et al. |
| 5,629,153 A | 5/1997 | Urdea |
| 5,843,770 A | 12/1998 | Ill et al. |
| 5,981,274 A | 11/1999 | Tyrrell et al. |
| 5,994,517 A | 11/1999 | Ts'o et al. |
| 5,998,203 A | 12/1999 | Matulic-Adamic et al. |
| 6,001,990 A | 12/1999 | Wands et al. |
| 6,057,153 A | 5/2000 | George et al. |
| 6,287,770 B1 | 9/2001 | Weston et al. |
| 6,503,533 B1 | 1/2003 | Korba et al. |
| 6,518,417 B1 | 2/2003 | Sczakiel et al. |
| 6,558,954 B1 | 5/2003 | Takle et al. |
| 6,573,048 B1 | 6/2003 | VanAtta et al. |

(Continued)

FOREIGN PATENT DOCUMENTS

| | | |
|---|---|---|
| CN | 1566131 A | 1/2005 |
| CN | 1793359 A | 6/2006 |

(Continued)

OTHER PUBLICATIONS

Ren et al. Changes in Innate and Permissive Immune Responses after HBV Transgenic Mouse Vaccination and ILong-Term-siRNA Treatment. PLoS ONE, 2013, 8(3): e57525.*

(Continued)

*Primary Examiner* — Nianxiang Zou
(74) *Attorney, Agent, or Firm* — Seed Intellectual Property Law Group LLP

(57) ABSTRACT

The present invention provides methods for the treatment of a subject having a Hepatitis B virus (HBV) infection, e.g., a chronic HBV infection, using a combination of an RNAi agent that targets HBV and an HBV vaccine. It is disclosed a RNAi agent and an HBV vaccine for use in treatment of HBV infection, comprising sequentially administering to the subject having an HBV infection: a) an RNAi agent that inhibits expression of at least three HBV transcripts, wherein the RNAi agent forms a double stranded region; b) a protein-based vaccine comprising a first HBV core antigen (HBcAg) polypeptide, and a first HBV surface antigen (HBsAg) polypeptide; and c) a nucleic acid-based vaccine comprising an expression vector construct encoding a second HBcAg polypeptide, and/or a second HBsAg polypeptide, wherein the second HBcAg polypeptide, and/or the second HBsAg polypeptide, shares at least one epitope with at least one of the first HBcAg polypeptide, and/or the first HBsAg polypeptide.

34 Claims, 18 Drawing Sheets

Specification includes a Sequence Listing.

(56) References Cited

U.S. PATENT DOCUMENTS

| | | |
|---|---|---|
| 6,906,182 B2 | 6/2005 | Ts'o et al. |
| 7,109,165 B2 | 9/2006 | Matulic-Adamic et al. |
| 7,491,805 B2 | 2/2009 | Vargeese et al. |
| 7,829,691 B2 | 11/2010 | Anthony et al. |
| 7,985,581 B2 | 7/2011 | Pachuk et al. |
| 7,989,612 B2 | 8/2011 | McSwiggen et al. |
| 8,350,021 B2 | 1/2013 | Pachuk et al. |
| 8,450,467 B2 | 5/2013 | Manoharan et al. |
| 8,575,327 B2 | 11/2013 | Pachuk et al. |
| 8,598,334 B2 | 12/2013 | Hamatake |
| 8,618,277 B2 | 12/2013 | Beigelman et al. |
| 8,648,185 B2 | 2/2014 | McSwigen et al. |
| 8,809,293 B2 | 8/2014 | Chin et al. |
| 9,029,341 B2 | 5/2015 | Bartz et al. |
| 9,034,841 B2 | 5/2015 | Swayze et al. |
| 9,200,281 B2 | 12/2015 | Pachuk et al. |
| 9,352,048 B2 | 5/2016 | Manoharan et al. |
| 9,464,290 B2 | 10/2016 | Bartz et al. |
| 9,879,262 B2 | 1/2018 | Bartz et al. |
| 9,982,263 B2 | 5/2018 | Pachuk et al. |
| 10,407,682 B2 | 9/2019 | Bartz et al. |
| 10,513,703 B2 | 12/2019 | Hinkle et al. |
| 10,662,428 B2 | 5/2020 | Beigelman et al. |
| 10,793,860 B2 | 10/2020 | Bartz et al. |
| 10,982,212 B2 | 4/2021 | Pachuk et al. |
| 2002/0086356 A1 | 7/2002 | Tuschl et al. |
| 2002/0155124 A1 | 10/2002 | Sallberg et al. |
| 2003/0083294 A1 | 5/2003 | Sullenger et al. |
| 2003/0087855 A1 | 5/2003 | Ward et al. |
| 2003/0143732 A1 | 7/2003 | Fosnaugh et al. |
| 2003/0148928 A1 | 8/2003 | Beigelman et al. |
| 2003/0190659 A1 | 10/2003 | LaCasse et al. |
| 2003/0206887 A1 | 11/2003 | Morrissey et al. |
| 2004/0091457 A1 | 5/2004 | John et al. |
| 2004/0110296 A1 | 6/2004 | Vargeese et al. |
| 2004/0180351 A1 | 9/2004 | Giese et al. |
| 2004/0235775 A1 | 11/2004 | Kung et al. |
| 2004/0259247 A1 | 12/2004 | Tuschl et al. |
| 2005/0020521 A1 | 1/2005 | Rana |
| 2005/0080246 A1 | 4/2005 | Allerson et al. |
| 2006/0148740 A1 | 7/2006 | Platenburg |
| 2006/0275762 A1 | 12/2006 | Saigo et al. |
| 2007/0027099 A1 | 2/2007 | Lin et al. |
| 2007/0031844 A1 | 2/2007 | Khvorova et al. |
| 2009/0325297 A1 | 12/2009 | Tian et al. |
| 2010/0145038 A1 | 6/2010 | McSwiggen et al. |
| 2013/0005793 A1 | 1/2013 | Chin et al. |
| 2013/0150433 A1 | 6/2013 | Bartz et al. |
| 2015/0374844 A1 | 12/2015 | Degrado et al. |
| 2016/0076034 A1 | 3/2016 | Bartz et al. |
| 2017/0349900 A1 | 12/2017 | Hinkle et al. |
| 2018/0008724 A1 | 1/2018 | Rajeev et al. |
| 2018/0037886 A1 | 2/2018 | Bettencourt et al. |
| 2018/0195071 A1 | 7/2018 | Bartz et al. |
| 2019/0100757 A1 | 4/2019 | Pachuk et al. |
| 2019/0233821 A1 | 8/2019 | Beigelman et al. |
| 2020/0140864 A1 | 5/2020 | Hinkle et al. |

FOREIGN PATENT DOCUMENTS

| | | |
|---|---|---|
| CN | 101314047 A | 12/2008 |
| CN | 101322847 A | 12/2008 |
| CN | 101603042 A | 12/2009 |
| CN | 101948827 A | 1/2011 |
| CN | 102559657 A | 7/2012 |
| CN | 102762215 A | 10/2012 |
| CN | 103014045 A | 4/2013 |
| CN | 103275971 A | 9/2013 |
| CN | 103333890 A | 10/2013 |
| CN | 103582648 A | 2/2014 |
| DE | 197 25 803 C1 | 2/1999 |
| EP | 0 957 107 A1 | 11/1999 |
| EP | 1 591 524 A1 | 11/2005 |
| EP | 2 071 030 A2 | 6/2009 |
| JP | 5-507203 A | 10/1993 |
| JP | 7-303485 A | 11/1995 |
| JP | 2002-335968 A | 11/2002 |
| JP | 2003-515327 A | 5/2003 |
| JP | 2007-503474 A | 2/2007 |
| JP | 2008-510489 A | 4/2008 |
| JP | 2010-519203 A | 6/2010 |
| JP | 2011-224013 A | 11/2011 |
| WO | 90/12096 A1 | 10/1990 |
| WO | 95/27788 A1 | 10/1995 |
| WO | 96/03152 A1 | 2/1996 |
| WO | 97/33991 A1 | 9/1997 |
| WO | 98/28004 A1 | 7/1998 |
| WO | 98/58055 A2 | 12/1998 |
| WO | 99/13886 A1 | 3/1999 |
| WO | 99/52932 A1 | 10/1999 |
| WO | 99/65925 A1 | 12/1999 |
| WO | 00/44914 A1 | 8/2000 |
| WO | 01/38498 A2 | 5/2001 |
| WO | 01/40279 A2 | 6/2001 |
| WO | 01/75164 A2 | 10/2001 |
| WO | 02/072763 A2 | 9/2002 |
| WO | 02/085908 A1 | 10/2002 |
| WO | 02/094185 A2 | 11/2002 |
| WO | 03/006477 A1 | 1/2003 |
| WO | 03/033700 A1 | 4/2003 |
| WO | 03/050308 A1 | 6/2003 |
| WO | 03/070918 A2 | 8/2003 |
| WO | 03/074654 A2 | 9/2003 |
| WO | 2004/011624 A2 | 2/2004 |
| WO | 2004/024757 A2 | 3/2004 |
| WO | 2004/045543 A2 | 6/2004 |
| WO | 2004/048566 A1 | 6/2004 |
| WO | 2004/063375 A1 | 7/2004 |
| WO | 2004/078181 A1 | 9/2004 |
| WO | 2004/078974 A1 | 9/2004 |
| WO | 2004/080406 A2 | 9/2004 |
| WO | 2004/090108 A2 | 10/2004 |
| WO | 2004/094595 A2 | 11/2004 |
| WO | 2005/014806 A2 | 2/2005 |
| WO | 2006/020768 A2 | 2/2006 |
| WO | 2006/033756 A2 | 3/2006 |
| WO | 2006/069064 A2 | 6/2006 |
| WO | 2006/078278 A2 | 7/2006 |
| WO | 2007/022369 A2 | 2/2007 |
| WO | 2007/032794 A2 | 3/2007 |
| WO | 2007/054279 A2 | 5/2007 |
| WO | 2008/103276 A2 | 8/2008 |
| WO | 2010/080724 A1 | 7/2010 |
| WO | 2011/047312 A1 | 4/2011 |
| WO | 2012/024170 A2 | 2/2012 |
| WO | 2012/145697 A1 | 10/2012 |
| WO | 2013/003520 A1 | 1/2013 |
| WO | 2013/074974 A2 | 5/2013 |
| WO | 2013/075035 A1 | 5/2013 |
| WO | 2013/155204 A2 | 10/2013 |
| WO | 2016/077321 A1 | 5/2016 |
| WO | 2017/027350 A2 | 2/2017 |
| WO | 2017/121791 A1 | 7/2017 |
| WO | 2018/027106 A2 | 2/2018 |

OTHER PUBLICATIONS

Chen et al. RNAi for Treating Hepatitis B Viral Infection. Pharmaceutical Research, 2008, 25(1): 72-86.*

Al-Mahtab et al. Therapeutic potential of a combined hepatitis B virus surface and core antigen vaccine in patients with chronic hepatitis B. Hepatology International, 2013, 7: 981-989.*

Chen et al. Optimisation of Prime-Boost Immunization in Mice Using Novel Protein-Based and Recombinant Vaccinia (Tiantan)-Based HBV Vaccine. PLoS ONE 2012, 7(9): e43730.*

GenBank: AFY08738.1, large S protein, partial [Hepatitis B virus]. dated Jan. 31, 2013.*

Nair et al. Multivalent N-acetylgalactosamine-conjugated siRNA localizes in hepatocytes and elicits robust RNAi-mediated gene silencing. J Am Chem Soc. Dec. 10, 2014;136(49):16958-61.*

GenBank: AJR19223.1. core protein [Hepatitis B virus]. Dated Mar. 8, 2015.*

(56) References Cited

OTHER PUBLICATIONS

"AASLD Abstracts, Poster Session 4: Hepatitis B Therapy, *Hepatology* 60: 1088A-1128A, 2014,".
Amarzguioui et al., "Tolerance for mutations and chemical modifications in a siRNA" *Nucl. Acids. Res.* 31(2):589-595, 2003.
Andino, "RNAi puts a lid on virus replication," *Nature Biotechnology* 21(6):629-630, 2003.
Australian Search Report, dated Oct. 12, 2006, for Singaporean Application No. 200507781-3, 7 pages.
Australian Written Opinion, dated Oct. 12, 2006, for Singaporean Application No. 200507781-3, 6 pages.
Backes et al., "Protein-prime/modified vaccinia virus Ankara vector-boost vaccination overcomes tolerance in high-antigenemic HBV-transgenic mice," *Vaccine* 34(7):923-932, 2016.
Bertoletti et al., "Adaptive immunity in HBV infection," *Journal of Hepatology* 64(1):S71-S83, 2016.
Bertrand et al., "Comparison of antisense oligonucleotides and siRNAs in cell culture and in vivo," *BBRC* 296:1000-1004, 2002.
Biessen et al., "Synthesis of Cluster Galactosides with High Affinity for the Hepatic Asialoglycoprotein Receptor," *J. Med. Chem.* 38(9):1538-1546, 1995.
Biessen et al., "The Cholesterol Derivative of a Triantennary Galactoside with High Affinity for the Hepatic Asialoglycoprotein Receptor: a Potent Cholesterol Lowering Agent," *J. Med. Chem.* 38(11):1846-1852, 1995.
Braasch et al., "Novel antisense and peptide Nucleic Acid Strategies for Controlling Gene Expression," *Biochem.* 41(14):4503-4510, 2002.
Caplen et al., "Specific inhibition of gene expression by small double-stranded RNAs in invertebrate and vertebrate systems," *Proc. Natl. Acad. Sci.* 98(17):9742-9747, 2001.
Chen et al., "RNAI for treating Hepatitis B Viral Infection," *Pharmaceutical Research* 25(1):72-86, 2008.
Chiu et al., "RNAi in Human Cells: Basic Structural and Functional Features of Small Interfering RNA," *Mol. Cell* 10:549-561, 2002.
Choi et al., "Targeting Cancer Cells with DNA-Assembled Dendrimers," *Cell Cycle* 4(5):669-671, 2005.
Chouteau et al., "A short N-proximal region in the large envelope protein harbors a Determinant That Contributes to the Species Specificity of Human Hepatitis B Virus," *Journal of Virology* 75(23):11565-11572, 2001.
Connolly et al., "Binding and Endocytosis of Cluster Glycosides by Rabbit Hepatocytes," *J. Biol. Chem.* 257(2):939-945, 1982.
Couzin, "Mini RNA Molecules Shield Mouse Liver From Hepatitis," *Science* 299:995, 2003. (2 pages).
Crossman Jr. et al., "Synthesis of some second-generation substrate analogues of early intermediates in the biosynthetic pathway of glycosylphosphatidylinositol membrane anchors," *Carbohydrate Research* 321(1-2):42-51, 1999.
Di Bisceglie, "Hepatitis B and Hepatocellular Carcinoma," *Hepatology* 49(5 Suppl):S56-S60, 2009 (NIH Public Access Author Manuscript, available in PMC Mar. 2, 2011)(10 pages).
Dubber et al., "Solid-Phase Synthesis of Multivalent Glycoconjugates on a DNA Synthesizer," *Bioconjugate Chem.* 14(1):239-246, 2003.
Elbashir et al., "Duplexes of 21-nucleotide RNAs mediate RNA interference in cultured mammalian cells," *Nature* 411:494-498, 2001.
Elbashir et al., "Functional anatomy of siRNA for mediating efficient RNAi in *Drosophila melanogaster* embryo lysate," *EMBO J.* 20(23):6877-6888, 2001.
European Association for the Study of the Liver, "EASL 2017 Clinical Practice Guidelines on the management of hepatitis B virus infection," *Journal of Hepatology* 67:370-398, 2017.
European Search Report, dated Jan. 14, 2008, for European Application No. 04776661.3-1212, 2 pages.
Feitelson et al., "New Animal Models of Hepatitis B and C," *ILAR Journal* 42(2):127-138, 2001.
Freier et al., "The ups and downs of nucleic acid duplex stability: structure-stability studies on chemically-modified DNA:RNA duplexes," *Nucl. Acids Res.* 25(22):4429-4443, 1997.

Galibert et al., "Nucleotide sequence of the hepatitis B virus genome (subtype ayw) cloned in *E. coli*," *Nature* 281:646-650, 1979.
Giladi et al., "Small Interfering RNA Inhibits Hepatitis B Virus Replication in Mice," *Mol. Ther.* 8(5):769-776, 2003.
Guo et al., "Construction of Folate-Conjugated pRNA of bacteriophage phi29 DNA packaging motor for delivery of chimeric siRNA to nasopharyngeal carcinoma cells," *Gene Ther.* 13(10):814-820, 2006 (NIH Public Access Author Manuscript, available in PMC Mar. 17, 2010)(14 pages).
Hamasaki et al., "Short interfering RNA-directed inhibition of hepatitis B virus replication," *FEBS Letters* 543(1-3):51-54, 2003.
Hamzavi et al., "Modulation of the Pharmacokinetic Properties of PNA: Preparation of Galactosyl, Mannosyl, Fucosyl, N-Acetylgalactosaminyl, and N-Acetylglucosaminyl Derivatives of Aminoethylglycine Peptide Nucleic Acid Monomers and Their Incorporation into PNA Oligomers," *Bioconjugate Chem.* 14:941-954, 2003.
Holen et al., "Positional effects of short interfering RNAs targeting the human coagulation trigger Tissue Factor," *Nucleic Acids Research* 30(8):1757-1766, 2002.
Holen T. et al., "Similar behavior of single-strand and double-strand siRNSs suggests they act through a common RNAi pathway," *Nucleic Acids Research* 31(9):2401-2407, 2003.
Hung et al., "Specific inhibition of gene expression and transactivation functions of hepatitis B virus X protein and c-myc by small interfering RNAs," *FEBS Letters* 560(1-3):210-214, 2004.
Ikeda et al., "Ligand-Targeted Delivery of Therapeutic siRNA," *Pharm. Res.* 23(8):1631-1640, 2006.
International Preliminary Report on Patentability, dated Jan. 7, 2007, for International Application No. PCT/US2004/019229, 6 pages.
International Search Report, dated Sep. 16, 2005, for International Application No. PCT/US2004/019229, 8 pages.
Kapadia et al., "Interference of hepatitis C virus RNA replication by short interfering RNAs," *Proceedings of the National Academy of Sciences of the USA* 100(4):2014-2018, 2003.
Karskela et al., "Synthesis and Cellular Uptake of Fluorescently Labeled Multivalent Hyaluronan Disaccharide Conjugates of Oligonucleotide Phosphorothioates," *Bioconjugate Chem.* 19(12):2549-2558, 2008.
Katajisto et al., "An Aminooxy-Functionalized Non-Nucleosidic Phosphoramidite for the Construction of Multiantennary Oligonucleotide Glycoconjugates on a Solid Support," *Current Protocols in Nucleic Acid Chemistry* 21(1):4.26.1-4.26.16, 2005.
Katajisto et al., "Solid-Phase Synthesis of Multiantennary Oligonucleotide Glycoconjugates Utilizing On-Support Oximation," *Bioconjugate Chem.* 15(4):890-896, 2004.
Katajisto et al., "Solid-Phase Synthesis of Oligonucleotide Glycoconjugates Bearing Three Different Glycosyl Groups: Orthogonally Protected Bis(hydroxymethyl)-N, N'-bis(3-hydroxypropyl)malondiamide Phosphoramidite as Key Building Block," *J. Org. Chem.* 69(22):7609-7615, 2004.
Kim et al., "Increased in vivo immunological potency of HB-110, a novel therapeutic HBV DNA vaccine, by electroporation," *Experimental and Molecular Medicine* 40(6):669-676, 2008.
Krapcho et al., "Mono-Protected Diamines. N-tert-BUTOXYCARBONYL-α,ω-ALKANEDIAMINES FROM α, ω-ALKANEDIAMINES," *Synthetic Communications* 20(16):2559-2564, 1990.
Li et al., "Folate-Mediated Targeting of Antisense Oligodeoxynucleotides to Ovarian Cancer Cells," *Pharm. Res.* 15(10):1540-1545, 1998.
Li et al., "siRNA Combinations Mediate Greater Suppression of Hepatitis B vims Replication in Mice," *Cell Biochemistry and Biophysics* 69(3):641-647, 2014.
Liang, "Hepatitis B: The Virus and Disease," *Hepatology* 49(Suppl 5): S13-S21, 2009 (NIH Public Access Author Manuscript, available in PMC Jan. 20, 2010)(17 pages).
Liu et al., "Targeted Drug Delivery to Chemoresistant Cells: Folic Acid Derivatization of FdUMP[10] Enhances Cytotoxicity toward 5-FU-Resistant Human Colorectal Tumor Cells," *J. Org. Chem.* 66(17):5655-5663, 2001.

(56) References Cited

OTHER PUBLICATIONS

Mahato et al., "Modulation of gene expression by antisense and antigene oligodeoxynucleotides and small interfering RNA," *Expert Opin. Drug Deliv.* 2(1):3-28, 2005.

Mahato et al., "Physicochemical and Disposition Characteristics of Antisense Oligonucleotides Complexed with Glycosylated Poly(L-lysine)," *Biochem. Pharmacol.* 53:887-895, 1997.

Maier et al., "Synthesis of Antisense Oligonucleotides Conjugated to a Multivalent Carbohydrate Cluster for Cellular Targeting," *Bioconjugate Chem.* 14:18-29, 2003.

Manoharan, "GalNAc-siRNA with Enhanced Stabilization Chemistry: ESC-GalNAc-siRNA," TIDES: Oligonucleotide and Peptide Research, Technology and Product Development, May 14, 2014, URL=http://www.alnylam.com/web/assets/ALNY-ESC-GalNAc-siRNA-TIDES-May2014-Capella.pdf, download date Feb. 2, 2016, 28 pages.

McCaffrey et al., "Inhibition of hepatitis B virus in mice by RNA interference," *Nature Biotechnology* 21(6):639-644, 2003 (Supplemental Online Data (1)), XP055535056, retrieved from the Internet: https://media.nature.com/original/nature-assets/nbt/journal/v21/n6/extref/nbt824-S1.pdf (1 page).

McCaffrey et al., "Inhibition of hepatitis B virus in mice by RNA interference," *Nature Biotechnology* 21(6):639-644, 2003 (Supplemental Online Data (2)), XP055535057, retrieved from the Internet: https://media.nature.com/original/nature-assets/nbt/journal/v21/n6/extref/nbt824-S2.pdf (2 pages).

McCaffrey et al., "Inhibition of hepatitis B virus in mice by RNA interference," *Nature Biotechnology* 21(6):639-644, 2003.

McCaffrey et al., "RNA interference in adult mice," *Nature* 418(6893):38-39, 2002.

Meyers, "RNAi Roundtable: Advances in Delivery of RNAi Therapeutics with Enhanced Stabilization Chemistry (ESC)-GalNAc-siRNA Conjugates," Jul. 22, 2014, URL=http://www.alnylam.com/web/assets/Roundtable_ESC-GalNAc-Conjugates_072214.pdf, download date Feb. 2, 2016, 40 pages.

Michler et al., "Combinatorial RNAi/vaccination therapy for chronic hepatitis B achieves long-term functional cure in preclinical mouse model," *Journal of Hepatology* 68(Supp 1):S16, 2018.

Michler et al., "Preclinical study of a combinatorial RNAi/vaccination therapy as a potential cure for chronic hepatitis B," *Journal of Hepatology* 66(1):S112, 2017.

Murata et al., "Design of quaternary chitosan conjugate having antennary galactose residues as a gene delivery tool," *Carbohydrate Polymers* 32(2):105-109, 1997.

Okamoto et al., "Full-Length Sequence of a Hepatitis C Virus Genome Having Poor Homology to Reported Isolates: Comparative Study of Four Distinct Genotypes," *Virology* 188(1):331-341, 1992.

Olie et al., "Analysis of ribosyl-modified, mixed backbone analogs of a bcl-2/bcl-xL antisense oligonucleotide," *Biochim. Biophys. Acta* 1576(1-2):101-109, 2002.

Parrish et al., "Functional Anatomy of a dsRNA Trigger: Differential Requirement for the Two Trigger Strands in RNA interference," *Mol. Cell* 6:1077-1087, 2000.

Putlitz et al., "Antisense RNA Complementary to Hepatitis B Virus Specifically Inhibits Viral Replication," *Gastroenterology* 115:102-713, 1998.

Radhakrishnan et al., "RNA interference as a new strategy against viral hepatitis," *Virology* 323(2):173-181, 2004.

Randall et al., "Clearance of replicating hepatitis C virus replicon RNAs in cell culture by small interfering RNAs," *PNAS* 100(1):235-240, 2003.

Reid et al., "RNAi Roundtable: ALN-HBV in Development for the Treatment of Hepatitis B Virus (HBV) Infection," Jul. 29, 2014, URL=http://www.alnylam.com/web/assets/Roundtable_ALN-HBV_072914.pdf, download date Feb. 2, 2016, 56 pages.

Rensen et al., "Design and Synthesis of Novel N-Acetylgalactosamine-Terminated Glycolipids for Targeting of Lipoproteins to the Hepatic Asialoglycoprotein Receptor," *J. Med. Chem.* 47(23):5798-5808, 2004.

Seo et al., "Small Interfering RNA-Mediated Inhibition of Hepatitis C Virus Replication in the Human Hepatoma Cell Line Huh-7," *J Virol.* 77(1):810-812, 2003.

Shlomai et al., "Inhibition of Hepatitis B Virus Expression and Replication by RNA Interference," *Hepatology* 37(4):764-770, 2003.

Sioud, "On the delivery of small interfering RNAs into mammalian cells," *Expert Opin. Drug Deliv.* 2(4):639-651, 2005.

Six et al., "An Efficient and Stereoselective Synthesis of 1,2-0-DIALKYL-3-0-β-D-GLYCOSYL-sn-GLYCEROLS," *Tetrahedron Lett.* 24(12):1229-1232, 1983.

Six et al., "Influence of Carbohydrate Moities on Monolayer Properties of Dialkylglycerylether glycosides, Simple Model Compounds of the Glycolipids of Halophilic Bacteria," *J. Colloid Interface Sci.* 93(1):109-114, 1983.

Sliedregt et al., "Design and Synthesis of Novel Amphiphilic Dendritic Galactosides for Selective Targeting of Liposomes to the Hepatic Asialoglycoprotein Receptor," *J. Med. Chem.* 42(4):609-618, 1999.

Sui et al., "A DNA vector-based RNAi technology to suppress gene expression in mammalian cells," *PNAS* 99(8):5515-5520, 2002.

Tuschl et al., "The siRNA user guide," Revised Aug. 26, 2001, URL=http://www.mpibpc.gwdg.de/abteilungen/100/105/sirna_u.html, download date Nov. 14, 2001, 5 pages.

Tuschl et al., "The siRNA user guide," Revised May 6, 2004, URL=http://diyhpl.us/~bryan/irc/protocol-online/protocol-cache/sirna.html, download date Oct. 10, 2018, 7 pages.

Vaino et al., "Synthesis of a $_D$-lactosyl cluster-nucleoside conjugate," *Chem. Commun.* 19:1871-1872, 1997.

Vital et al., "The use of non-human primates as animal models for the study of hepatitis viruses," *Brazilian Journal of Medical and Biological Research* 31(8):1035-1048, 1998.

Wang et al., "Immunotherapeutic interventions in chronic hepatitis B virus infection: A review," *Journal of Immunological Methods* 407:1-8, 2014.

Wilson et al., "RNA interference blocks gene expression and RNA synthesis from hepatitis C replicons propagated in human liver cells," *Proceedings of the National Academy of Sciences of the USA* 100(5):2783-2788, 2003.

Wolfrum et al., "Mechanisms and optimization of in vivo delivery of lipophilic siRNAs," *Nature Biotechnology* 25(10):1149-1157, 2007.

Wong et al., "Lipid, Sugar and Liposaccharide Based Delivery Systems," *Curr. Med. Chem.* 8(9):1123-1136, 2001.

Yu et al., "The Role of Antiviral Therapy for HBV-Related Hepatocellular Carcinoma," *International Journal of Hepatology* 2011:416459, 2011. (9 pages).

Zatsepin et al., "Synthesis and Applications of Oligonucleotide-Carbohydrate Conjugates," *Chem. Biodivers.* 1(10):1401-1417, 2004.

Zheng et al., "Distribution and anti-HBV effects of antisense oligodeoxynu-cleotides conjugated to galactosylated poly-L-lysine," *World J. Gastroenterol.* 9(6):1251-1255, 2003.

Zimmermann et al., "RNAi-mediated gene silencing in non-human primates," *Nature* 441(7089):111-114, 2006.

Chi et al., "Comparison between Coexistence of HBV and HDV Infection and Simple HBV Infection," *Chinese Journal of Public Health* 13(4):254, 1997 (with English machine translation).

"EASL 2017 Clinical Practice Guidelines on the management of hepatitis B virus infection," *Journal of Hepatology* 67:370-398, 2017.

Fu et al., "Optimal design and validation of antiviral siRNA for targeting hepatitis B virus," *Acta Pharmacol Sin* 29(12):1522-1528, 2008.

Lv et al., "RNA Interference Inhibitis Hepatitis B Virus Gene," *Progress in Modern Biomedicine* 11(23):4569-4572, 2011 (with English abstract).

Nassal, "HBV cccDNA: viral persistence reservoir and key obstacle for a cure of chronic hepatitis B," *Gut* 64:1972-1984, 2015.

Okamoto et al., "Hepatitus B virus, complete genome," NCBI GenBank NC_003977.1, URL=https://www.ncbi.nlm.nih.gov/nuccore/21326584, accessed Mar. 1, 2021 (3 pages).

Pavot et al., "Generation and Production of Modified Vaccinia Virus Ankara (MVA) as a Vaccine Vector," *Methods in Molecular Biology* 1581:97-119, 2017.

(56) References Cited

OTHER PUBLICATIONS

Zhang et al., "Effects of Long-Term siRNA Treatment on the Immune System of HBV Transgene Mice," *Letters in Biotechnology* 2:217-220, 2014 (with English abstract).
Zhang et al., "RNA Interference inhibits Hepatitis B Virus of different genotypes in Vitro and in Vivo," *BMC Microbiology* 10:214, 2010 (10 pages).
Martin et al., "TG1050, an immunotherapeutic to treat chronic hepatitis B, induces robust T cells and exerts an antiviral effect in HBV-persistent mice," *Gut 64*: 1961-1971, 2015.

\* cited by examiner

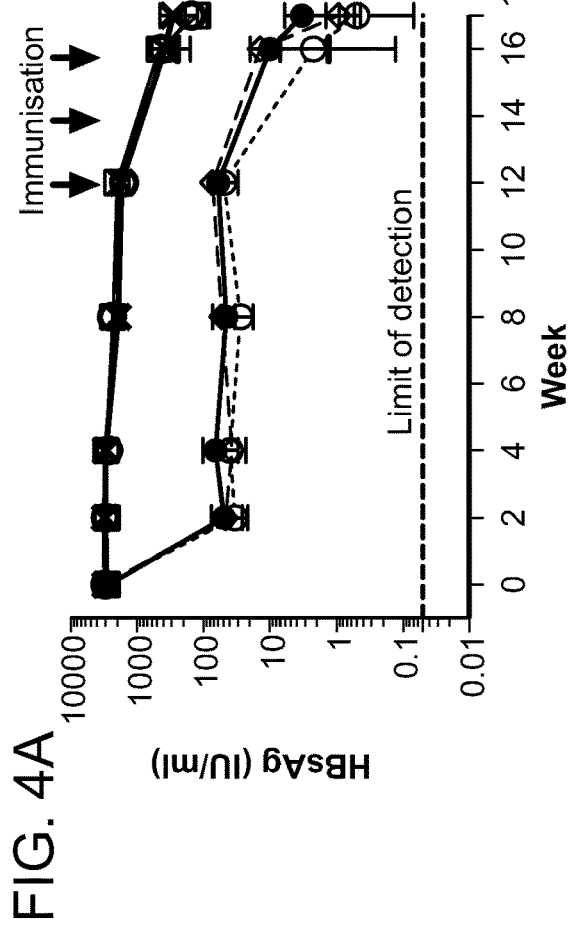
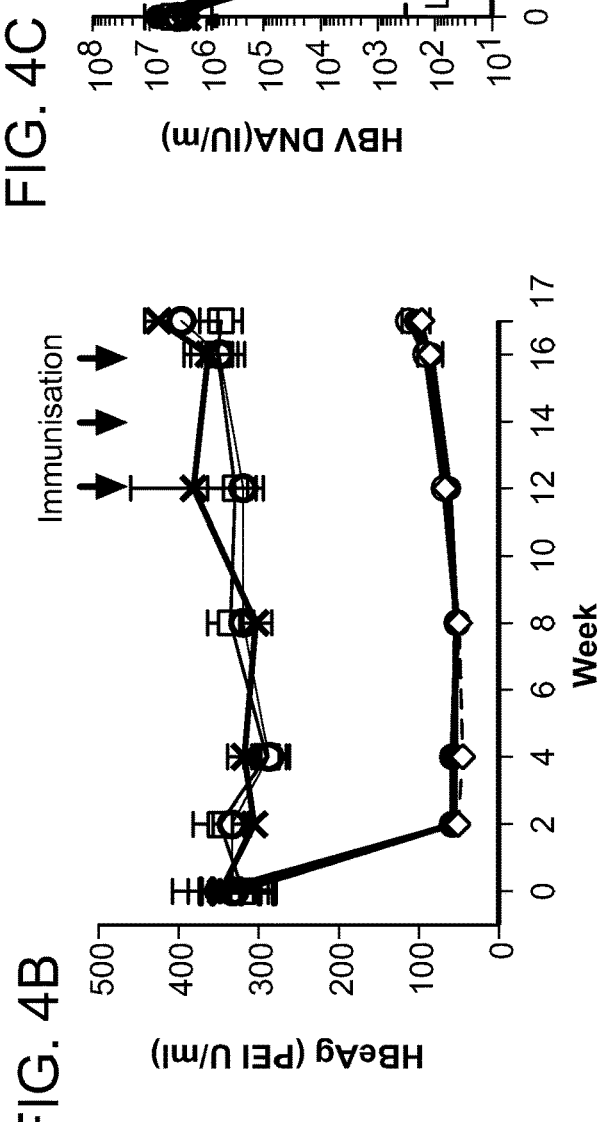
FIG. 4A
FIG. 4B
FIG. 4C

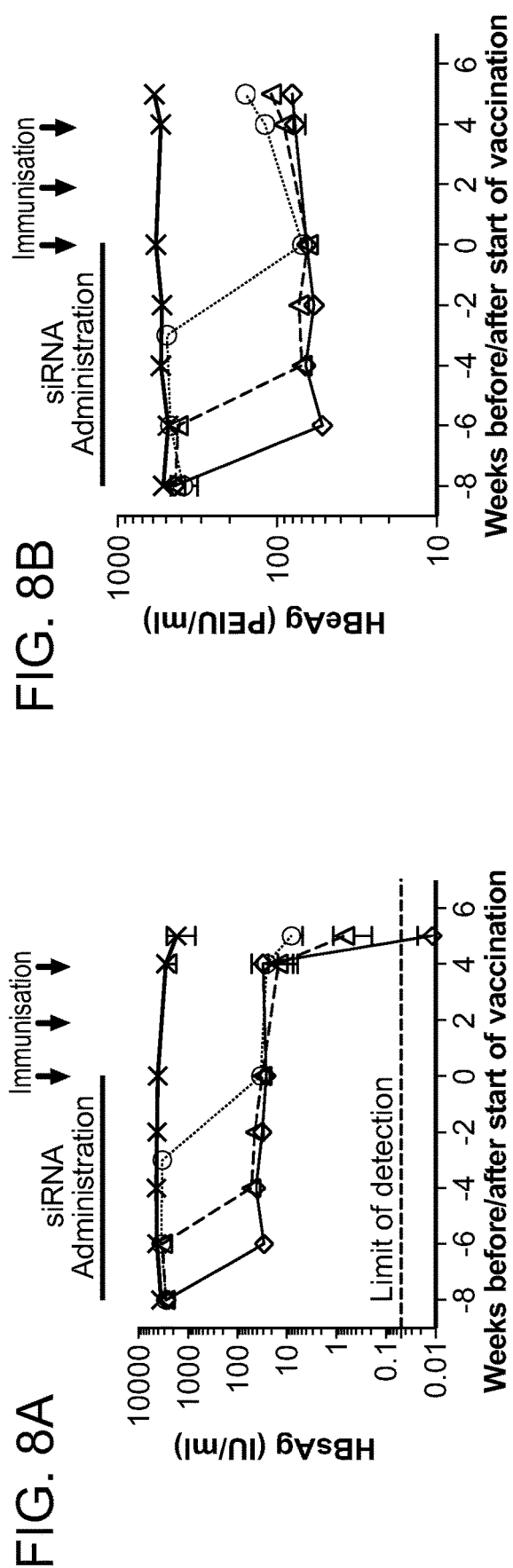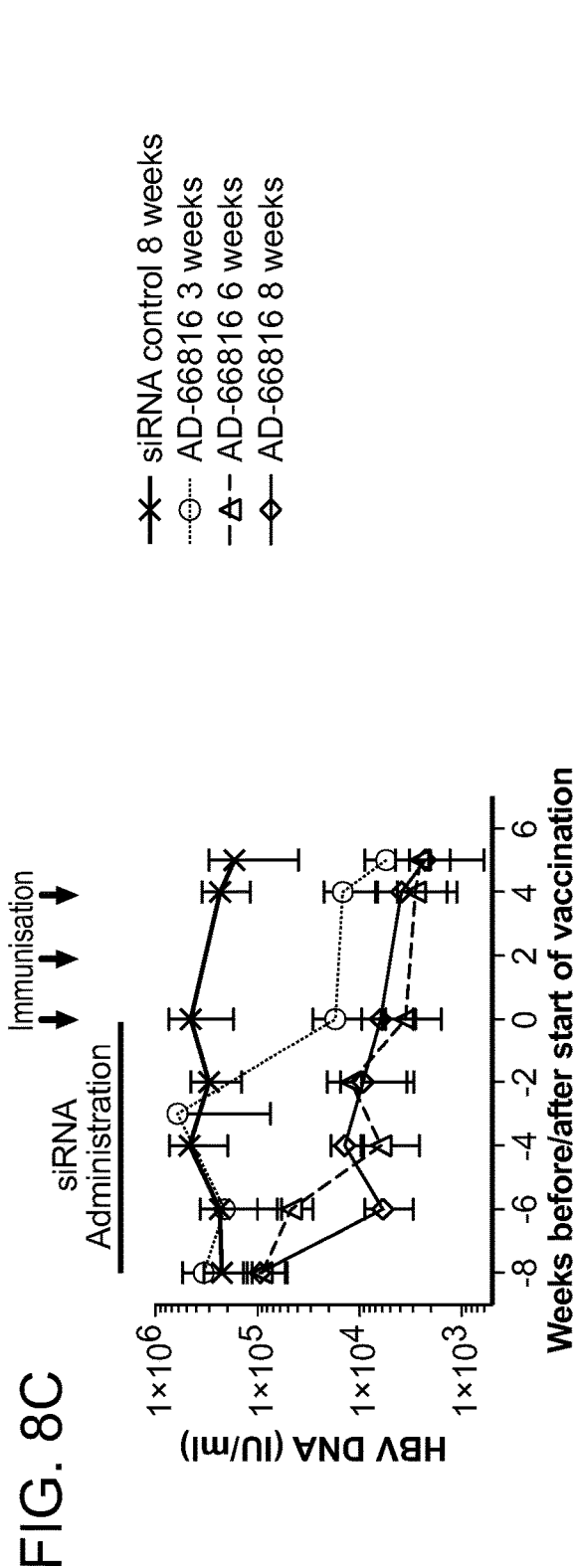
FIG. 8A
FIG. 8B
FIG. 8C

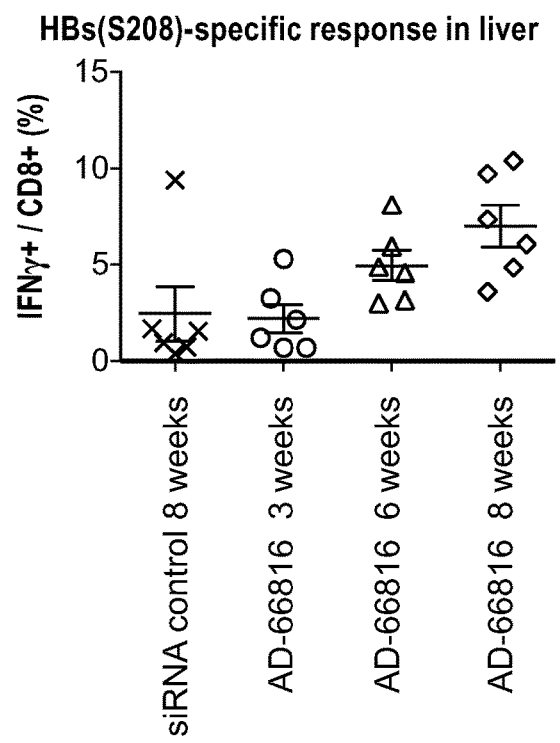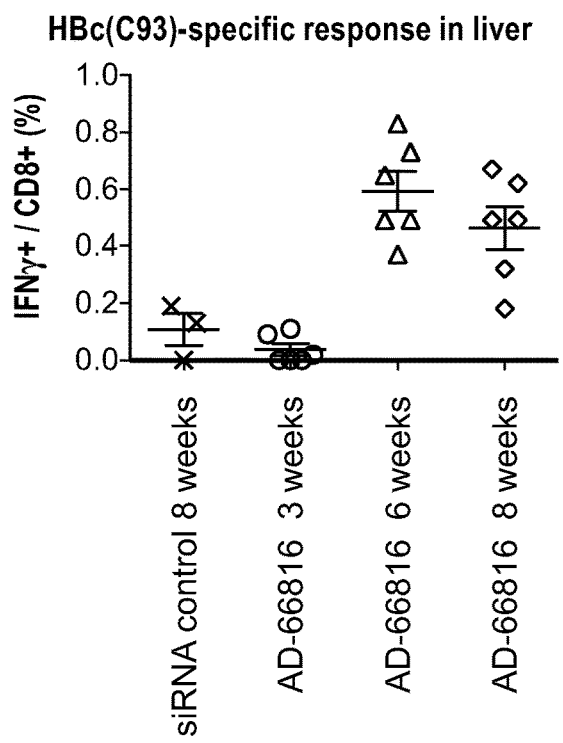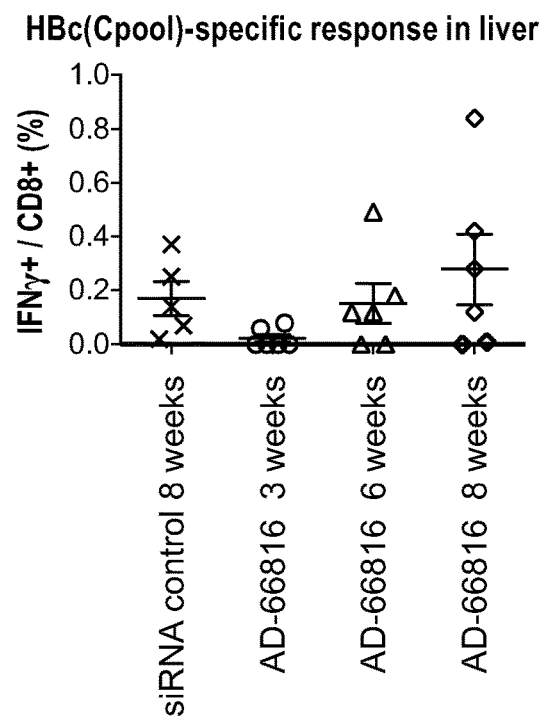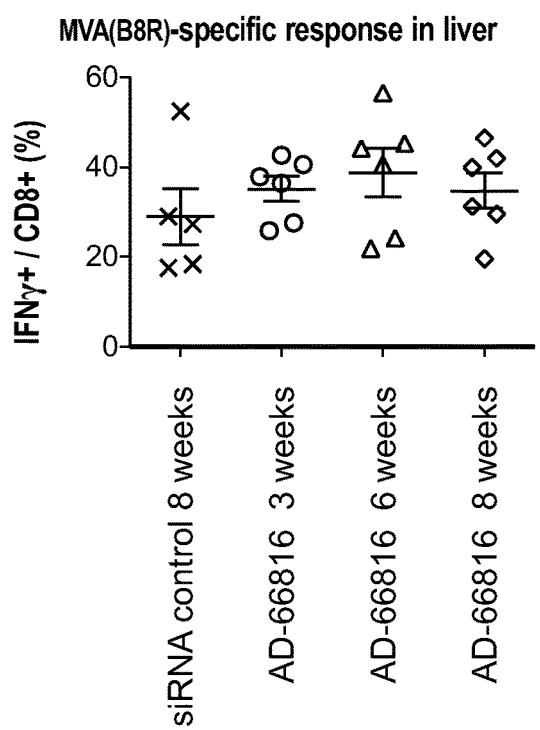

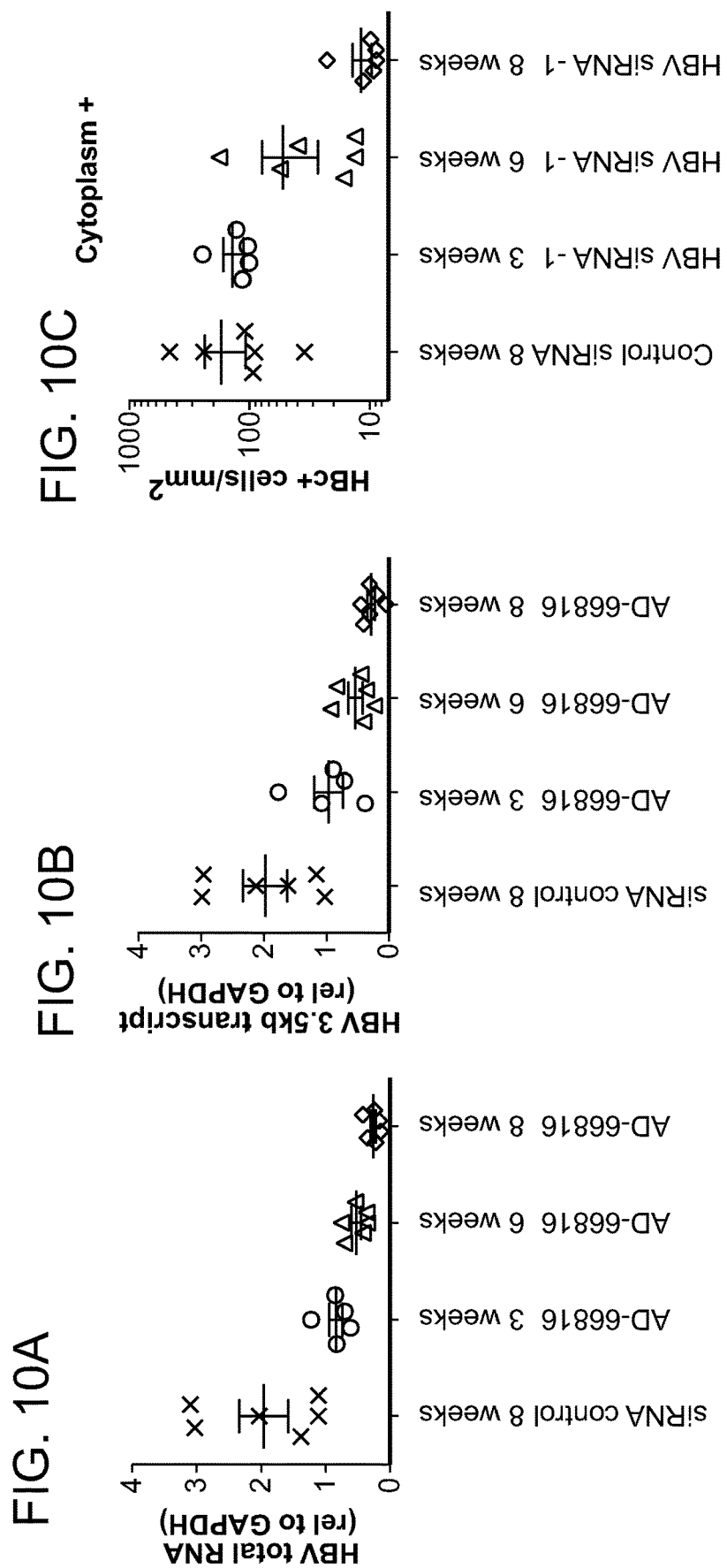

- ◇ - Control siRNA
- ◆ - Control siRNA + vaccine
- ◇ --- AD-66816
- ◇ — AD-66816 + vaccine
- ◇ - - AD-66810
- ◆ — AD-66810 + vaccine

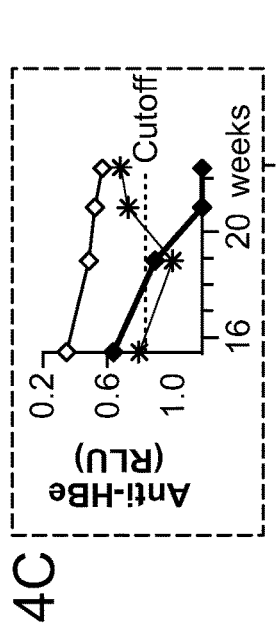
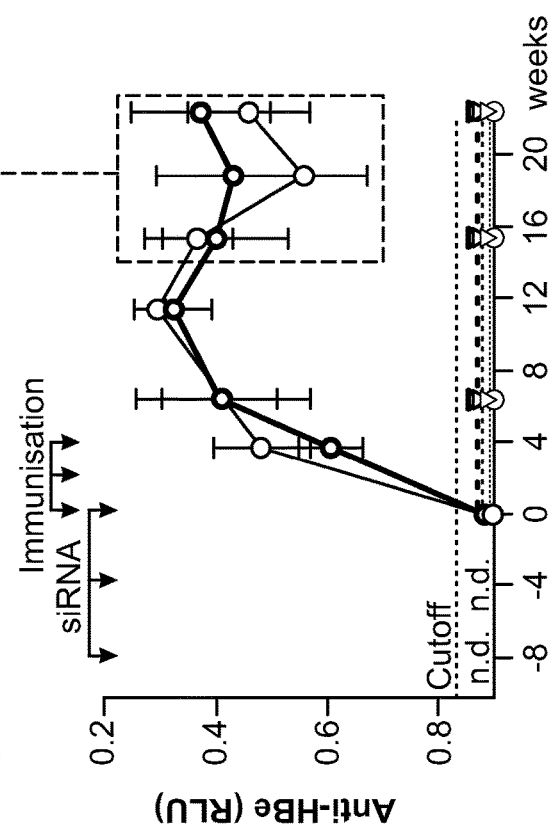
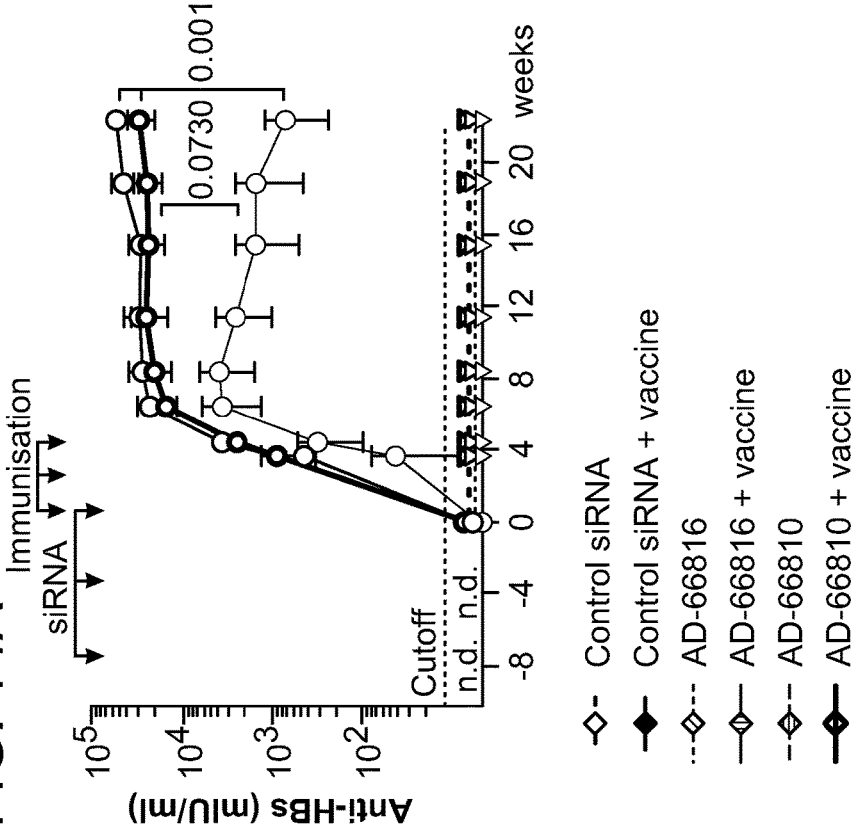

METHODS FOR THE TREATMENT OF SUBJECTS HAVING A HEPATITIS B VIRUS (HBV) INFECTION

RELATED APPLICATIONS

This application is a 35 U.S.C. § 371 application entitled to the right of priority of International Application No. PCT/US2018/028116, filed Apr. 18, 2018, which claims the benefit of priority to U.S. Provisional Patent Application No. 62/486,618, filed on Apr. 18, 2017, U.S. Provisional Patent Application No. 62/553,358, filed on Sep. 1, 2017, U.S. Provisional Patent Application No. 62/646,978, filed on Mar. 23, 2018, and U.S. Provisional Patent Application No. 62/655,862, filed on Apr. 11, 2018. The entire contents of each of the foregoing patent applications are incorporated herein by reference.

SEQUENCE LISTING

The instant application contains a Sequence Listing which has been submitted electronically in ASCII format and is hereby incorporated by reference in its entirety. Said ASCII copy, created on Oct. 17, 2019, is named SequenceListing_930385_409USPC.txt, and is 429,978 bytes in size.

BACKGROUND OF THE INVENTION

Hepatitis B virus (HBV) is an enveloped DNA virus that infects the liver that causes hepatocellular necrosis, inflammation, and is a major risk factor for development of cirrhosis and hepatocellular carcinoma (HCC). The World Health Organization (WHO) estimates that there are 240 million chronically HBV infected individuals worldwide largely in low to middle income countries and that about 650,000 people will die annually of complications from HBV infection. Although an effective HBV vaccine is available and efforts to vaccinate infants at birth have been effective in reducing incidence and prevalence of HBV infection, such programs do not have a demonstrable effect on death rates for years (WHO Guidelines for prevention, care and treatment of persons with chronic Hepatitis B Infection, 2015 at apps.who.int/iris/bitstream/10665/154590/1/9789241549059_eng.pdf?ua=1&ua=1).

A number of therapeutic agents have been developed for the treatment of HBV that effectively reduce the disease burden of HBV infection, but they are not typically curative as they do not fully eliminate all replicative forms of the virus including the covalently closed circular DNA (cccDNA) that resides in the hepatocyte nucleus and becomes a template for viral replication and transcription of viral RNAs. Nucleotide and nucleoside analogs, typically considered to be the gold standard for treatment of chronic HBV infection due to their safety and efficacy, are effective in suppressing HBV replication, but they do not eliminate cccDNA, do not prevent expression of viral proteins, must be dosed chronically, and can result in the development of resistance. Further, treatment with nucleot(s)ide inhibitors does not fully mitigate the risk of the development of hepatocellular carcinoma (HCC) which remains significant (about 7% in 5-7 years despite treatment). Interferon-based therapies can result in sero-conversion and cure of about 10-15% of patients allowing discontinuation of treatment, but the agents have severe side effects and must be refrigerated for long term storage making them less desirable for use in countries where HBV infection is most prevalent.

Treatment of chronic HBV is further complicated by the ability of HBV to evade or suppress the immune response resulting in persistence of the infection. The HBV proteins have immune-inhibitory properties, with hepatitis B s antigen (HBsAg) comprising the overwhelming majority of HBV protein in the circulation of HBV infected subjects. Additionally, while the removal (via seroconversion) of hepatitis B e antigen (HBeAg) or reductions in serum viremia are not correlated with the development of sustained control of HBV infection off treatment, the removal of serum HBsAg from the blood (and seroconversion) in HBV infection is a well-recognized prognostic indicator of antiviral response to treatment which will lead to control of HBV infection off treatment. However, this only occurs in a small fraction of patients receiving immunotherapy. Therefore, it is possible, although rare, for patients to mount a sufficiently robust immune response to suppress or clear an HBV infection resulting in at least a functional cure of the disease.

SUMMARY OF THE INVENTION

The invention provides RNAi agents and HBV vaccines for use in treatment of hepatitis B virus (HBV) infection and methods for the treatment of a subject having a hepatitis B virus (HBV) infection, e.g., a chronic HBV infection, which includes a combination therapy or treatment regimen including an RNAi agent targeting at least one HBV transcript and a therapeutic vaccination.

Accordingly, in one aspect, the present invention provides RNAi agents and HBV vaccines for use in treatment of hepatitis B virus (HBV) infection and methods for treating a subject having a hepatitis B virus (HBV) infection, e.g., a chronic HBV infection. The methods include a regimen which includes administering, e.g., sequentially administering, to the subject having the HBV infection, an RNAi agent that targets at least three HBV transcripts, wherein the RNAi agent comprises a sense strand and an antisense strand; a protein-based vaccine comprising an HBV core antigen (HBcAg) and an HBV surface antigen (HBsAg); and a nucleic acid-based vaccine comprising an expression construct encoding an HBcAg or an HBsAg, wherein the construct encodes a protein that shares an epitope with the protein-based vaccine, thereby treating the subject.

In another aspect, the present invention provides a regimen for treating a subject having a hepatitis B virus (HBV) infection, e.g., a chronic HBV infection. The regimen includes the use of an RNAi agent that targets at least three HBV transcripts, wherein the RNAi agent comprises a sense strand and an antisense strand; a protein-based vaccine comprising an HBV core antigen (HBcAg) and an HBV surface antigen (HBsAg); and a nucleic acid-based vaccine comprising an expression construct encoding an HBcAg or an HBsAg, wherein the construct encodes a protein that shares an epitope with the protein-based vaccine.

In one embodiment, the HBcAg protein, or immunogenic fragment thereof, shares an epitope with the HBV core antigen (HBcAg) polypeptide, or immunogenic fragment thereof, present in the protein-based vaccine and/or the HBsAg protein, or immunogenic fragment thereof, shares an epitope with the HBV surface antigen (HBsAg) polypeptide, or immunogenic fragment thereof, present in the protein-based vaccine.

In certain embodiments, the RNAi agent comprises at least one modified nucleotide.

In certain embodiments, the nucleic acid-based vaccine comprises an expression construct encoding an HBcAg and an HBsAg.

In certain embodiments, the RNAi agent targeting HBV is administered to the subject at least two times.

In certain embodiments, the RNAi agent targeting HBV administered to the subject decreases HBsAg in the serum of the subject by at least 0.5 log 10 IU/ml. In certain embodiments, the subject has at least a 0.5 log 10 IU/ml decrease in HBsAg in serum prior to administration of the first dose of the protein based vaccine. In certain embodiments, the subject has at least a 1 log 10 IU/ml decrease in HBsAg in serum prior to administration of the first dose of the protein based vaccine. In certain embodiments, the subject has an HBsAg of 2 log 10 IU/ml or less in serum prior to administration of the vaccine.

In certain embodiments, the RNAi agent is administered to the subject no more than once per week. In certain embodiments, the RNAi agent is administered to the subject no more than once every four weeks.

In certain embodiments, the RNAi agent is administered to the subject at a dose of 0.01 mg/kg to 10 mg/kg; or 0.5 mg/kg to 50 mg/kg; or 10 mg/kg to 30 mg/kg. In certain embodiments, the RNAi agent is administered to the subject at a dose selected from 0.5 mg/kg, 1 mg/kg, 1.5 mg/kg, 3 mg/kg, 5 mg/kg, 10 mg/kg, and 30 mg/kg. In some embodiments, a dose of the RNAi agent is administered to the subject about once per week; about one every two weeks; about once every three weeks; about once every four weeks; or a dose of the RNAi agent is administered to the subject not more than once per week; or a dose of the RNAi agent is administered to the subject no more than once every four weeks.

In certain embodiments, the protein-based vaccine comprises an amino acid sequence of at least one determinant of HBsAg and at least one determinant of HBcAg.

In certain embodiments, the nucleic acid-based vaccine comprising an expression vector construct encoding an HBcAg or an HBsAg encodes an amino acid sequence comprising at least one determinant of HBsAg or at least one determinant of HBcAg In certain embodiments, the determinant of HBsAg comprises a sequence at least 90% identical to amino acids 124 to 147 of SEQ ID NO: 22. In certain embodiments, the determinant of HBsAg comprises a sequence at least 90% identical to amino acids 99 to 168 of SEQ ID NO: 23.

In certain embodiments, the determinant of HBcAg comprises a sequence comprising amino acid 80 of SEQ ID NO: 24. In certain embodiments, the sequence comprising amino acid 80 of SEQ ID NO: 24 comprises an amino acid sequence at least 90% identical to at least amino acids 70 to 90 of SEQ ID NO: 24. In certain embodiments, the determinant of HBcAg comprises a sequence comprising amino acid 138 of SEQ ID NO: 24. In certain embodiments, the sequence comprising amino acid 80 of SEQ ID NO: 14 comprises an amino acid sequence at least 90% identical to at least amino acids 128 to 143 of SEQ ID NO: 24. In certain embodiments, the determinant of HBcAg comprises an amino acid sequence at least 90% identical to at least 40, 50, 60, 70, 80, 90, or 100 contiguous amino acids of SEQ ID NO: 24. In certain embodiments, the determinant of HBcAg comprises a sequence at least 90% identical to amino acids 18 to 143 of SEQ ID NO: 24.

In certain embodiments, the protein-based vaccine administered to the subject comprises a dose of 0.1 μg to 1.0 mg of the HBcAg and a dose of 0.1 μg to 1.0 mg of HBsAg. In some embodiments, a dose of the protein-based vaccine is administered to the subject about once per week; about one every two weeks; about once every three weeks; about once every four weeks; or a dose of the protein-based vaccine is administered to the subject no more than once per week; or a dose of the protein-based vaccine is administered to the subject no more than once every four weeks.

In certain embodiments, the HBcAg protein and the HBsAg protein are present in a single formulation. In certain embodiments, the HBcAg protein and the HBsAg protein are not present in a single formulation. In certain embodiments, the protein-based vaccine comprises an adjuvant. In some embodiments, the adjuvant stimulates a balanced Th1/Th2 response. In certain embodiments, the adjuvant is selected from monophosphoryl lipid A (MPL), poly(I:C), polyICLC adjuvant, CpG DNA, polyICLC adjuvant, a STING agonist, c-di-AMP, c-di-GMP, c-di-CMP; short, blunt-ended 5'-triphosphate dsRNA (3pRNA) Rig-I ligand, poly[di(sodiumcarboxylatoethylphenoxy)phosphazene] (PCEP)), alum, virosomes, cytokines, IL-12, AS02, AS03, AS04, MF59, ISCOMATRIX®, IC31®, or Rig-I ligand. In certain embodiments, the adjuvant is selected from polyI:C adjuvant, a CpG adjuvant, a STING agonist, or a PCEP adjuvant.

In certain embodiments, the protein based vaccine is administered to the subject at least two times. In certain embodiments, the protein-based vaccine is administered to the subject no more than once every two weeks. In certain embodiments, the protein-based vaccine is administered to the subject no sooner than the day on which the final dose of the RNAi agent has been administered to the subject. In certain embodiments, the protein-based vaccine is administered to the subject on the same day on which the final dose of the RNAi agent has been administered to the subject. In certain embodiments, the protein based vaccine is administered to the subject no later than one month after the final dose of the RNAi agent has been administered to the subject. In certain embodiments, the protein based vaccine is administered to the subject no later than two months after the final dose of the RNAi agent has been administered to the subject. In certain embodiments, the protein based vaccine is administered to the subject no later than three months after the final dose of the RNAi agent has been administered to the subject.

In certain embodiments the methods of the invention further comprise determining the serum HBsAg level after administration of at least one dose of the RNAi agent and prior to administration of the protein based vaccine. That is, the serum HBsAg level is determined in the subject after administration of at least one dose of the RNAi agent and prior to administration of the protein based vaccine.

In certain embodiments the methods of the invention further comprise determining the serum HBeAg level after administration of at least one dose of the RNAi agent and prior to administration of the protein based vaccine. That is, the serum HBeAg level is determined in the subject after administration of at least one dose of the RNAi agent and prior to administration of the protein based vaccine.

In certain embodiments the methods of the invention further comprise determining the serum HBsAg level and the HBeAg level after administration of at least one dose of the RNAi agent and prior to administration of the protein based vaccine. That is, the serum HBsAg level and the serum HBeAg level are determined in the subject after administration of at least one dose of the RNAi agent and prior to administration of the protein based vaccine.

In certain embodiments, the nucleic acid-based vaccine comprises at least one expression vector construct encoding both an HBcAg and an HBsAg. In certain embodiments, the expression construct promotes expression of HBcAg and HBsAg from a single promoter. In other embodiments, the expression construct promotes expression of HBcAg and HBsAg from separate promoters.

In certain embodiments, at least one promoter is selected from a respiratory syncytial virus (RSV) promoter, a cytomegalovirus (CMV) promoter, a PH5 promoter, and an H1 promoter. In certain embodiments, the expression construct comprises a viral vector. In certain embodiments, the viral vector is selected from adenovirus vector; retrovirus vector, lentiviral vector, moloney murine leukemia virus vector, adeno-associated virus vector; herpes simplex virus vector; SV 40 vector; polyoma virus vector; papilloma virus vector; picornavirus vector; pox virus vector, orthopox virus vector, vaccinia virus vector, modified vaccinia virus Ankara (MVA) vector, avipox vector, canary pox vector, fowl pox vector, adenovirus vector, and Epstein Barr virus vector. In certain embodiments, the viral vector is an MVA vector.

In certain embodiments, the nucleic acid-based vaccine administered to the subject comprises a tissue-culture infectious dose (TCID$_{50}$) of $10^6$ to $10^{10}$ TCID$_{50}$; or $10^6$ to $10^9$ TCID$_{50}$; or $10^6$ to $10^8$ TCID$_{50}$ In certain embodiments, the nucleic acid-based vector is administered to the subject no sooner than two weeks after administration of the final dose of the protein-based vaccine is administered to the subject.

In certain embodiments, the methods further comprise determining the serum HBsAg level after administration of at least one dose of the RNAi agent and prior to administration of the nucleic acid-based vaccine. That is, the serum HBsAg level is determined in the subject after administration of at least one dose of the RNAi agent and prior to administration of the nucleic acid-based vaccine. In certain embodiments, the nucleic acid-based vaccine is administered to the subject after a further decrease of at least 0.5 log 10 of serum HBsAg after at least one dose of the protein-based vaccine is administered to the subject. In certain embodiments of the regimen, a single dose of the nucleic-acid based vaccine is administered to the subject.

In certain embodiments, the methods further comprise determining the serum HBeAg level after administration of at least one dose of the RNAi agent and prior to administration of the nucleic acid-based vaccine. That is, the serum HBeAg level is determined in the subject after administration of at least one dose of the RNAi agent and prior to administration of the nucleic acid-based vaccine. In certain embodiments, the nucleic acid-based vaccine is administered to the subject after a further decrease of at least 0.5 log 10 of serum HBeAg after at least one dose of the protein-based vaccine is administered to the subject. In certain embodiments of the regimen, a single dose of the nucleic-acid based vaccine is administered to the subject.

In certain embodiments, the methods further comprise determining the serum HBsAg level and the HBeAg level after administration of at least one dose of the RNAi agent and prior to administration of the nucleic acid-based vaccine. That is, the serum HBsAg level and the serum HBeAg level are determined in the subject after administration of at least one dose of the RNAi agent and prior to administration of the nucleic acid-based vaccine. In certain embodiments, the nucleic acid-based vaccine is administered to the subject after a further decrease of at least 0.5 log 10 of serum HBsAg and serum HBeAg after at least one dose of the protein-based vaccine is administered to the subject. In certain embodiments of the regimen, a single dose of the nucleic-acid based vaccine is administered to the subject.

In certain embodiments, the methods further comprise administering a nucleot(s)ide analog to the subject at least prior to administration of the iRNA targeted to HBV. In certain embodiments, the nucleot(s)ide analog is administered throughout the entire regimen. In certain embodiments, the nucleot(s)ide analog is selected from Tenofovir disoproxil fumarate (TDF), Tenofovir alafenamide (TAF), Lamivudine, Adefovir dipivoxil, Entecavir (ETV), Telbivudine, AGX-1009, emtricitabine, clevudine, ritonavir, dipivoxil, lobucavir, famvir, FTC, N-Acetyl-Cysteine (NAC), PC1323, theradigm-HBV, thymosin-alpha, and ganciclovir, besifovir (ANA-380/LB-80380), and tenofovir-exaliades (TLX/CMX157).

In certain embodiments, the subject has serum HBsAg below 3000 IU/ml prior to administration of the RNAi agent. In certain embodiments, the subject has serum HBsAg below 4000 IU/ml prior to administration of the RNAi agent. In certain embodiments, subject has serum HBsAg below 5000 IU/ml prior to administration of the RNAi agent.

In certain embodiments, the subject has a reduction of HBsAg level of at least 2 $\log_{10}$ scales after administration of the RNAi agent and prior to administration of the first dose of a protein-based vaccine. In certain embodiments, the subject has a reduction of HBeAg level of at least 1 $\log_{10}$ scale after administration of the RNAi agent and prior to administration of the first dose of a protein-based vaccine. In certain embodiments, the subject has a reduction of HBsAg level of at least 2 $\log_{10}$ scales and a reduction of HBeAg level of at least 1 $\log_{10}$ scale after administration of the RNAi agent and prior to administration of the first dose of a protein-based vaccine.

In certain embodiments, the subject has a reduction of HBsAg level to 500 IU/ml or less after administration of the RNAi agent and prior to administration of a first dose of the protein based vaccine. In certain embodiments, the subject has a reduction of HBsAg level to 200 IU/ml or less after administration of the RNAi agent and prior to administration of a first dose of the protein based vaccine. In certain embodiments, the subject has a reduction of HBsAg level to 100 IU/ml or less after administration of the RNAi agent and prior to administration of a first dose of the protein based vaccine.

In certain embodiments, the subject has a reduction of HBeAg level to 500 IU/ml or less after administration of the RNAi agent and prior to administration of a first dose of the protein based vaccine. In certain embodiments, the subject has a reduction of HBeAg level to 200 IU/ml or less after administration of the RNAi agent and prior to administration of a first dose of the protein based vaccine. In certain embodiments, the subject has a reduction of HBeAg level to 100 IU/ml or less after administration of the RNAi agent and prior to administration of a first dose of the protein based vaccine.

In certain embodiments, the subject has a reduction of HBsAg level and HBeAg level to 500 IU/ml or less after administration of the RNAi agent and prior to administration of a first dose of the protein based vaccine. In certain embodiments, the subject has a reduction of HBsAg level and HBeAg level to 200 IU/ml or less after administration of the RNAi agent and prior to administration of a first dose of the protein based vaccine. In certain embodiments, the subject has a reduction of HBsAg level and HBeAg level to 100 IU/ml or less after administration of the RNAi agent and prior to administration of a first dose of the protein based vaccine.

In certain embodiments, the level of serum HBsAg and HBeAg in the subject are decreased to below the level of detection using a clinical assay for at least three months after the end of the dose of the nucleic acid-based vaccine. In certain embodiments, the level of serum HBsAg and HBeAg in the subject are decreased to below the level of detection using a clinical assay for at least six months after the end of the dose of the nucleic acid-based vaccine.

In certain embodiments, serum HBsAg in the subject is decreased to below the level of detection using a clinical assay for at least six months after the end of the dose of the nucleic acid-based vaccine.

In certain embodiments, the methods further comprise administration of an immune stimulator to the subject. In certain embodiments, the immune stimulator is selected from the group pegylated interferon alfa 2a (PEG-IFN-alpha-2a), Interferon alfa-2b, PEG-IFN-alpha-2b, Interferon lambda a recombinant human interleukin-7, and a Toll-like receptor 3, 7, 8 or 9 (TLR3, TLR7, TLR8, TLR9) agonist, a viral entry inhibitor, Myrcludex, an oligonucleotide that inhibits the secretion or release of HBsAg, REP 9AC, a capsid inhibitor, Bay41-4109, NVR-1221, a cccDNA inhibitor, IHVR-25) a viral capsid, an MVA capsid, an immune checkpoint regulator, an CTLA-4 inhibitor, ipilimumab, a PD-1 inhibitor, Nivolumab, Pembrolizumab, BGB-A317 antibody, a PD-L1 inhibitor, atezolizumab, avelumab, durvalumab, and an affimer biotherapeutic.

In certain embodiments of the regimen, the subject is human.

In certain embodiments of the regimen, the RNAi agent targets four transcripts of HBV. In certain embodiments, the RNAi agent is selected from an iRNA in Appendix A. In certain embodiments, the RNAi agent is selected from any of the agents in any one of Tables 2-11 in Appendix A. In certain embodiments, the RNAi agent targets at least 15 contiguous nucleotides of nucleotides 206-228, 207-229, 210-232, 212-234, 214-236, 215-237, 216-238, 226-248, 245-267, 250-272, 252-274, 253-275, 254-276, 256-278, 258-280, 263-285, 370-392, 373-395, 375-397, 401-423, 405-427, 410-432, 411-433, 422-444, 424-446, 425-447, 426-448, 731-753, 734-756, 1174-1196, 1250-1272, 1255-1277, 1256-1278, 1545-1567, 1547-1569, 1551-1571, 1577-1597, 1579-1597, 1580-1598, 1806-1825, 1812-1831, 1814-1836, 1829-1851, 1831-1853, 1857-1879, 1864-1886, 2259-2281, 2298-2320, or 2828-2850 of SEQ ID NO: 1 (NC_003977.1). In certain embodiments, the RNAi agent targets at least 15 contiguous nucleotides of nucleotides 1579-1597 or 1812-1831 of SEQ ID NO: 1 (NC_003977.1). In certain embodiments, the RNAi agent targets nucleotides 1579-1597 or 1812-1831 of SEQ ID NO: 1 (NC_003977.1).

In certain embodiments, the antisense strand of the RNAi agent comprises a nucleotide sequence of at least 15 contiguous nucleotides of UGUGAAGCGAAGUGCACACUU (SEQ ID NO: 25) or AGGUGAAAAAGUUGCAUGGUGUU (SEQ ID NO: 26). In certain embodiments, the antisense strand of the RNAi agent comprises a nucleotide sequence of at least 19 contiguous nucleotides of UGUGAAGCGAAGUGCACACUU (SEQ ID NO: 25) or AGGUGAAAAAGUUGCAUGGUGUU (SEQ ID NO: 26). In certain embodiments, the antisense strand of the RNAi agent comprises a nucleotide sequence of UGUGAAGCGAAGUGCACACUU (SEQ ID NO: 25) or AGGUGAAAAAGUUGCAUGGUGUU (SEQ ID NO: 26).

In certain embodiments, the sense strand of the RNAi agent comprises a nucleotide sequence of at least 15 contiguous nucleotides of GUGUGCACUUCGCUUCACA (SEQ ID NO: 27) or CACCAUGCAACUUUUUCACCU (SEQ ID NO: 28). In certain embodiments, the sense strand of the RNAi agent comprises a nucleotide sequence of at least 19 contiguous nucleotides of GUGUGCACUUCGCUUCACA (SEQ ID NO: 27) or CACCAUGCAACUUUUUCACCU (SEQ ID NO: 28). In certain embodiments, the sense strand of the RNAi agent comprises a nucleotide sequence of GUGUGCACUUCGCUUCACA (SEQ ID NO: 27) or CACCAUGCAACUUUUUCACCU (SEQ ID NO: 28).

In certain embodiments, the antisense strand of the RNAi agent comprises a nucleotide sequence of at least 15 contiguous nucleotides of UGUGAAGCGAAGUGCACACUU (SEQ ID NO: 25) and the sense strand comprises a nucleotide sequence of at least 15 contiguous nucleotides of GUGUGCACUUCGCUUCACA (SEQ ID NO: 27). In certain embodiments, the antisense strand of the RNAi agent comprises a nucleotide sequence of at least 19 contiguous nucleotides of UGUGAAGCGAAGUGCACACUU (SEQ ID NO: 25) and the sense strand comprises a nucleotide sequence of at least 19 contiguous nucleotides of GUGUGCACUUCGCUUCACA (SEQ ID NO: 27). In certain embodiments, the antisense strand of the RNAi agent comprises a nucleotide sequence of UGUGAAGCGAAGUGCACACUU (SEQ ID NO: 25) and the sense strand comprises a nucleotide sequence of GUGUGCACUUCGCUUCACA (SEQ ID NO: 27).

In certain embodiments, the antisense strand of the RNAi agent comprises a nucleotide sequence of at least 15 contiguous nucleotides of AGGUGAAAAAGUUGCAUGGUGUU (SEQ ID NO: 26) and the sense strand of the RNAi agent comprises a nucleotide sequence of at least 15 contiguous nucleotides of CACCAUGCAACUUUUUCACCU (SEQ ID NO: 28). In certain embodiments, the antisense strand of the RNAi agent comprises a nucleotide sequence of at least 19 contiguous nucleotides of AGGUGAAAAAGUUGCAUGGUGUU (SEQ ID NO: 26) and the sense strand of the RNAi agent comprises a nucleotide sequence of at least 19 contiguous nucleotides of CACCAUGCAACUUUUUCACCU (SEQ ID NO: 28). In certain embodiments, the antisense strand of the RNAi agent comprises a nucleotide sequence of AGGUGAAAAAGUUGCAUGGUGUU (SEQ ID NO: 26) and the sense strand of the RNAi agent comprises a nucleotide sequence of CACCAUGCAACUUUUUCACCU (SEQ ID NO: 28).

In certain embodiments of the regimen, substantially all of the nucleotides of said sense strand and substantially all of the nucleotides of said antisense strand are modified nucleotides, wherein said sense strand is conjugated to a ligand attached at the 3'-terminus. In certain embodiments, the ligand is one or more GalNAc derivatives attached through a monovalent linker, bivalent branched linker, or trivalent branched linker. In certain embodiments, the at least one of said modified nucleotides is selected from the group consisting of a deoxy-nucleotide, a 3'-terminal deoxythymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, and a nucleotide comprising a 5'-phosphate mimic.

In certain embodiments, at least one strand of the RNAi agent comprises a 3' overhang of at least 1 nucleotide. In certain embodiments, at least one strand if the RNAi agent comprises a 3' overhang of at least 2 nucleotides. In certain embodiments, the double-stranded region of the RNAi agent is 15-30 nucleotide pairs in length; 17-23 nucleotide pairs in length; 17-25 nucleotide pairs in length; 23-27 nucleotide pairs in length; 19-21 nucleotide pairs in length; 21-23 nucleotide pairs in length.

In certain embodiments, each strand of the RNAi agent has 15-30 nucleotides.

In certain embodiments, each strand of the RNAi agent has 19-30 nucleotides.

In certain embodiments, the ligand is

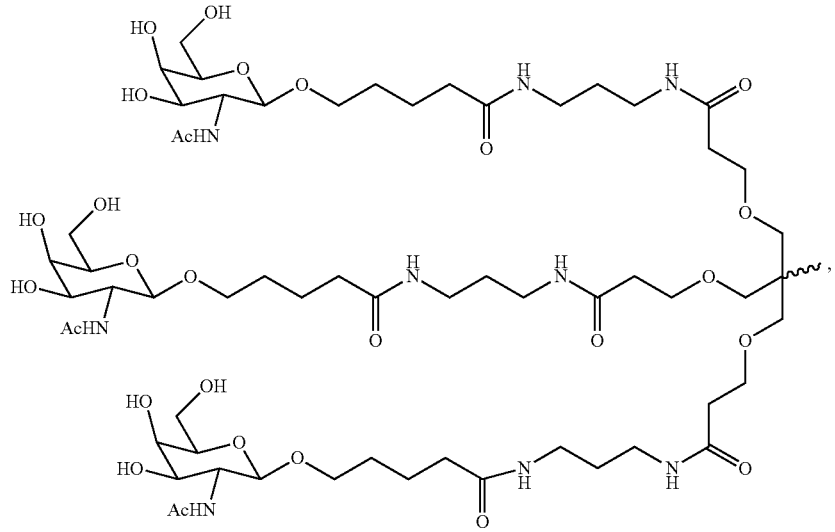 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

and the RNAi agent is optionally conjugated to the ligand as shown in the following schematic

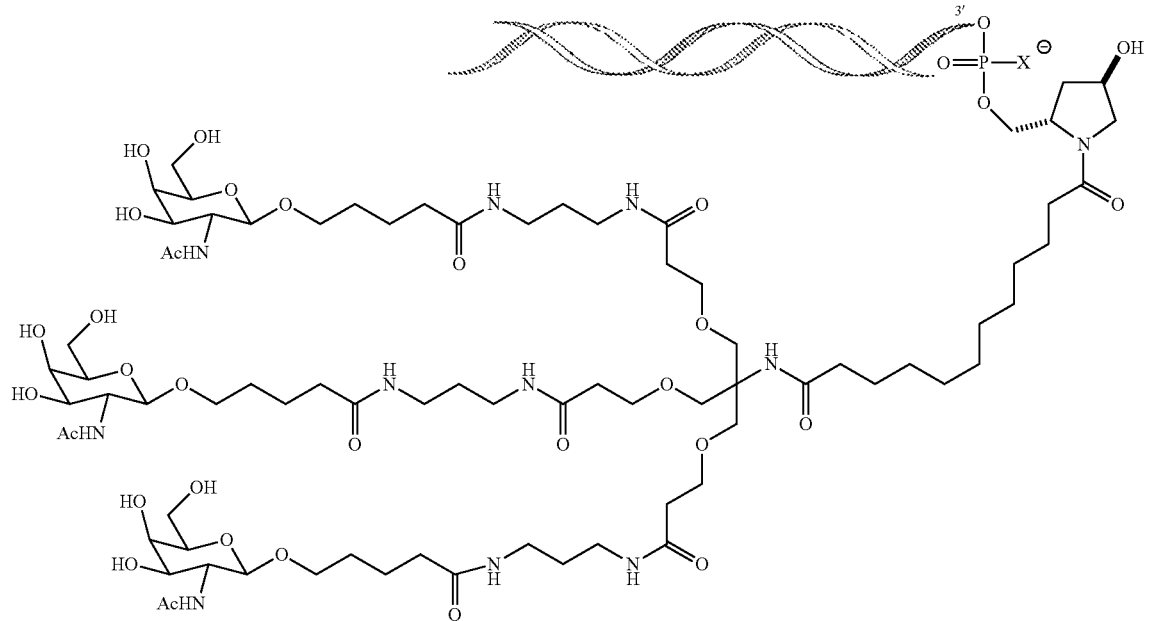

wherein X is O or S.

In certain embodiments, the sense strand comprises the nucleotide sequence 5'-gsusguGfcAfCfUfucgcuucaca-3' (SEQ ID NO: 29) and the antisense strand comprises the nucleotide sequence 5'-usGfsugaAfgCfGfaaguGfcAfcacsusu-3' (SEQ ID NO: 30); or the sense strand comprises the nucleotide sequence 5'-csasccauGfcAfAfCfuuuuucaccu-3' (SEQ ID NO: 31) and the antisense strand comprises the nucleotide sequence 5'-asGfsgugAfaAfAfaguuGfcAfuggugsusu-3' (SEQ ID NO: 32), wherein a, c, and u are 2'-O-methyladenosine-3'-phosphate, 2'-O-methylcytidine-3'-phosphate, and 2'-O-methyluridine-3'-phosphate, respectively; as, cs, gs, and us are 2'-O-methyladenosine-3'-phosphorothioate, 2'-O-methylcytidine-3'-phosphorothioate, 2'-O-methylguanosine-3'-phosphorothioate, and 2'-O-methyluridine-3'-phosphorothioate, respectively; Af, Cf, Gf, and Uf are 2'-fluoroadenosine-3'-phosphate, 2'-fluorocytidine-3'-phosphate, 2'-fluoroguanosine-3'-phosphate, and 2'-fluorouridine-3'-phosphate, respectively; and Gfs is 2'-fluoroguanosine-3'-phosphorothioate. In certain embodiments, the RNAi agent is AD-66810 or AD-66816.

In certain embodiments, the protein-based vaccine comprises epitopes present in at least 4, 5, 6, 7, 8, 9, or 10 genotypes of HBV.

In certain embodiments, the nucleic acid-based vaccine comprises epitopes present in at least 4, 5, 6, 7, 8, 9, or 10 genotypes of HBV.

The present invention further provides uses of the RNAi agents and vaccines provided herein for treatment of subjects having a hepatitis B virus infection based on the methods provided herein. In certain embodiment, the RNAi agents and the HBV vaccines are used in the manufacture of medicaments for treatment of a subject with an HBV infection.

The present invention further provides kits comprising RNAi agents and vaccines provided herein and instructions providing treatment regimens for their use for treatment of subjects having a hepatitis B virus infection.

The present invention is further illustrated by the following detailed description and drawings.

BRIEF DESCRIPTION OF THE DRAWINGS

FIGS. 4A-4C are graphs showing the level of (4A) HBsAg, (4B) HBeAg, and (4C) HBV-DNA in serum of HBV1.3-xfs mice after treatment based on the dosing regimen provided in FIG. 3.

FIGS. 5D-5F show a reanalysis of the same data in FIGS. 5A-5C performed to accommodate for an insufficient exclusion of dead immune cells and shows T cell immune response in the liver against peptides (5D) HBs(S208), (5E) HBc(C93), and (5F) MVA(B8R).

FIG. 6A shows total HBV RNA. FIG. 6B shows HBV 3.5 kb transcript relative to GAPDH as determined by RT-qPCR. FIG. 6C shows the number of HBcAg positive cells per $mm^2$ of liver section detected by immunohistochemical staining.

FIGS. 8A-8C are graphs showing the level of (8A) HBsAg, (8B) HBeAg, and (8C) HBV-DNA in serum of HBV1.3-xfs mice after treatment based on the dosing regimen provided in FIG. 7.

FIGS. 9A-9D are graphs showing T cell immune response in the liver against peptides (9A) HBs(S208), (9B) HBc (C93), (9C) HBc(Cpool) and (9D) MVA(B8R) in HBV1.3-xfs mice after treatment based on the dosing regimen provided in FIG. 7.

FIGS. 10A-10C show the level of HBV RNA and protein levels in liver cells of HBV1.3-xfs mice after treatment based on the dosing regimen provided in FIG. 7. FIG. 10A shows total HBV RNA. FIG. 10B shows HBV 3.5 kb transcript relative to GAPDH as determined by RT-qPCR. FIG. 10C shows the number of HBcAg positive cells per $mm^2$ of liver section detected by immunohistochemical staining.

FIGS. 13A and 13B are graphs showing the level of (13A) HBsAg and (13B) HBeAg in serum of HBV-AAV mice (inset 13C is an exploded portion of the later time points in graph 13B). FIG. 13D shows the serum HBV DNA level at week 22. FIGS. 13D and 13E show the number of copies per liver cell of (13D) total HBV DNA and (13E) AAV-DNA at week 22. FIGS. 13F and 13G show the relative expression in liver of (13F) HBV 3.5 RNA relative to GAPDH RNA and (13G) total HBV RNA relative to GAPDH RNA.

FIGS. 14A-14C are graphs showing (14A) anti-HBs antibody response throughout the course of the experiment and (14B) anti-HBe antibody response at day 116 of the experiment based on the dosing regimen provided in FIG. 12. FIG. 14C is an exploded portion of the later time points in graph 14B.

Figure 1:
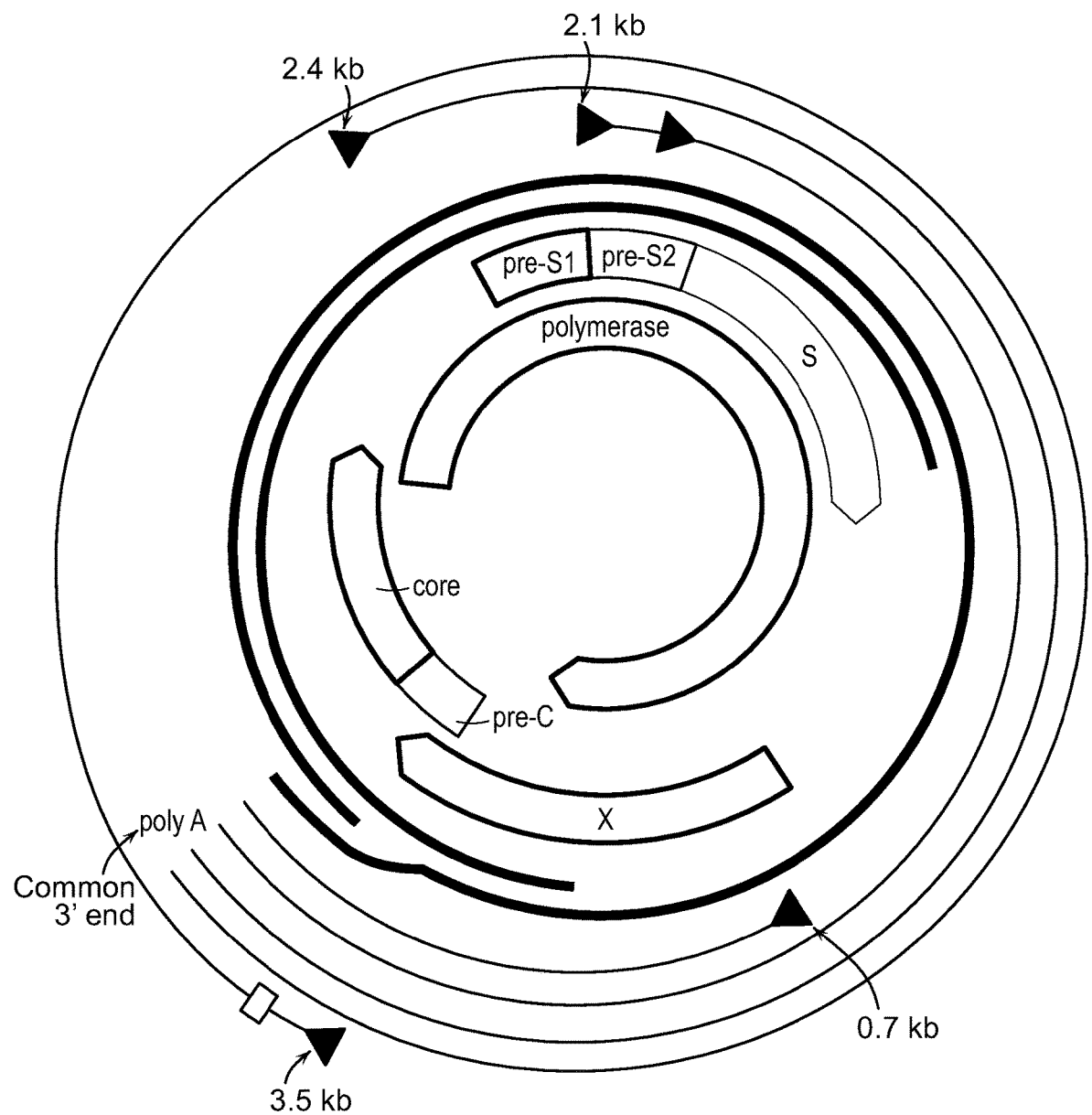
FIG. 1 schematically depicts the structure of the approximately 3.2 kb double-stranded HBV genome. Replication of the HBV genome occurs through an RNA intermediate and produces 4 overlapping viral transcripts of about 3.5 kb, 2.4 kb, 2.1 kb, and 0.7 kb (termination sites indicated by arrows), and the common 3' end encoding seven viral proteins (pre-S1, pre-S2, S, P, X, pre-C, and C) that are translated across three reading frames.

A formal sequence listing is provided herewith that forms part of the specification.

An Appendix A providing exemplary target sequences for siRNA targeting and iRNA agents is provided herewith and forms part of the specification.

DETAILED DESCRIPTION OF THE INVENTION

The present invention provides treatment regimens and methods of use of iRNA agents which effect the RNA-induced silencing complex (RISC)-mediated cleavage of RNA transcripts of one or more HBV genes (open reading frames/transcripts) and hepatitis B vaccines to stimulate an immune response against one or more HBV proteins in the treatment of HBV infection. The treatment regimens and methods preferably provide a functional cure within a defined period of time.

The following detailed description discloses how to make and use compositions containing iRNAs to inhibit the expression of an HBV gene as well as compositions, uses, and methods for treating subjects having diseases and disorders that would benefit from inhibition or reduction of the expression of an HBV gene.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

The term "about" is used herein to mean within the typical ranges of tolerances in the art. For example, "about" can be understood as within 2 standard deviations from the mean. In certain embodiments, "about" means +/−10%. In certain embodiments, "about" means +/−5%. When about is present before a series of numbers or a range, it is understood that "about" can modify each of the numbers in the series or range.

The term "at least" prior to a number or series of numbers is understood to include the number adjacent to the term "at least", and all subsequent numbers or integers that could logically be included, as clear from context. For example, the number of nucleotides in a nucleic acid molecule must be an integer. For example, "at least 18 nucleotides of a 21 nucleotide nucleic acid molecule" means that 18, 19, 20, or 21 nucleotides have the indicated property. When at least is present before a series of numbers or a range, it is understood that "at least" can modify each of the numbers in the series or range.

As used herein, "no more than" or "less than" is understood as the value adjacent to the phrase and logical lower values or integers, as logical from context, to zero. For example, a duplex with an overhang of "no more than 2 nucleotides" has a 2, 1, or 0 nucleotide overhang. When "no more than" is present before a series of numbers or a range, it is understood that "no more than" can modify each of the numbers in the series or range. As used herein, ranges include both the upper and lower limit.

In the event of a conflict between a sequence and its indicated site on a transcript or other sequence, the nucleotide sequence recited in the specification takes precedence.

Various embodiments of the invention can be combined as determined appropriate by one of skill in the art.

As used herein, "Hepatitis B virus," used interchangeably with the term "HBV" refers to the well-known non-cytopathic, liver-tropic DNA virus belonging to the Hepadnaviridae family.

The HBV genome is partially double-stranded, circular DNA with overlapping reading frames (see, e.g., FIG. 1).

There are four transcripts (that may be referred to herein as "genes" or "open reading frames") based on size, encoded by the HBV genome. These contain open reading frames called C, X, P, and S. The core protein is coded for by gene C (HBcAg). Hepatitis B e antigen (HBeAg) is produced by proteolytic processing of the pre-core (pre-C) protein. The DNA polymerase is encoded by gene P. Gene S is the gene that codes for the surface antigens (HBsAg). The HBsAg gene is one long open reading frame which contains three in frame "start" (ATG) codons resulting in polypeptides of three different sizes called large, middle, and small S antigens, pre-S1+pre-S2+S, pre-S2+S, or S. Surface antigens in addition to decorating the envelope of HBV, are also part of subviral particles, which are produced at large excess as compared to virion particles, and play a role in immune tolerance and in sequestering anti-HBsAg antibodies, thereby allowing for infectious particles to escape immune detection. The function of the non-structural protein coded for by gene X is not fully understood, but it plays a role in transcriptional transactivation and replication and is associated with the development of liver cancer. Exemplary protein sequences are provided in the attached sequence listing (see, e.g., SEQ ID NOs:1, 3, 16, and 20).

HBV is one of the few DNA viruses that utilize reverse transcriptase in the replication process which involves multiple stages including entry, uncoating, and transport of the virus genome to the nucleus. Initially, replication of the HBV genome involves the generation of an RNA intermediate that is then reverse transcribed to produce the DNA viral genome.

Upon infection of a cell with HBV, the viral genomic relaxed circular DNA (rcDNA) is transported into the cell nucleus and converted into episomal covalently closed circular DNA (cccDNA), which serves as the transcription template for the viral mRNAs. After transcription and nuclear export, cytoplasmic viral pregenomic RNA (pgRNA) is assembled with HBV polymerase and capsid proteins to form the nucleocapsid, inside which polymerase-catalyzed reverse transcription yields minus-strand DNA, which is subsequently copied into plus-strand DNA to form the progeny rcDNA genome. The mature nucleocapsids are then either packaged with viral envelope proteins to egress as virion particles or shuttled to the nucleus to amplify the cccDNA reservoir through the intracellular cccDNA amplification pathway. cccDNA is an essential component of the HBV replication cycle and is responsible for the establishment of infection and viral persistence.

HBV infection results in the production of two different particles: 1) the infectious HBV virus itself (or Dane particle) which includes a viral capsid assembled from the HBcAg and is covered by an envelope consisting of a lipid membrane with HBV surface antigens, and 2) subviral particles (or SVPs) which contain the small and medium forms of the hepatitis B surface antigen HBsAg which are non-infectious. For each viral particle produced, over 10,000 SVPs are released into the blood. As such, SVPs (and the HBsAg protein they carry) represent the overwhelming majority of viral protein in the blood. HBV infected cells also secrete a soluble proteolytic product of the pre-core protein called the HBV e-antigen (HBeAg).

Eight genotypes of HBV, designated A to H, have been determined, and two additional genotypes I and J have been proposed, each having a distinct geographical distribution. The virus is non-cytopathic, with virus-specific cellular immunity being the main determinant for the outcome of exposure to HBV-acute infection with resolution of liver diseases with 6 months, or chronic HBV infection that is frequently associated with progressive liver injury.

The term "HBV" includes any of the genotypes of HBV (A to J). The complete coding sequence of the reference sequence of the HBV genome may be found in for example, GenBank Accession Nos. GI:21326584 (SEQ ID NO:1) and GI:3582357 (SEQ ID NO:3). Antisense sequences are provided in SEQ ID NO: 2 and 4, respectively. Amino acid sequences for the C, X, P, and S proteins can be found, for example at NCBI Accession numbers YP_009173857.1 (C protein); YP_009173867.1 and BAA32912.1 (X protein); YP_009173866.1 and BAA32913.1 (P protein); and YP_009173869.1, YP_009173870.1, YP_009173871.1, and BAA32914.1 (S protein) (SEQ ID NOs: 5-13). Protein and DNA sequences from HBV genotype D, strain ayw are provided in SEQ ID NOs.: 14-17. Protein and DNA sequences from HBV genotype A, strain adw are provided in SEQ ID NOs.: 18-21.

Additional examples of HBV mRNA sequences are readily available using publicly available databases, e.g., GenBank, UniProt, and OMIM. The International Repository for Hepatitis B Virus Strain Data can be accessed at http://www.hpa-bioinformatics.org.uk/HepSEQ/main.php.

The term "HBV," as used herein, also refers to naturally occurring DNA sequence variations of the HBV genome, i.e., genotypes A-J and variants thereof.

As used herein, "epitope" also referred to as "an antigenic determinant," or "determinant," is understood as the part of a protein antigen that is recognized by the immune system, specifically by antibodies, B cells, and/or T cells. Epitopes include conformational epitopes and linear epitopes. Proteins share an epitope when they share an amino acid sequence of sufficient length or size and antigenicity to be recognized by an antibody, B cell, and/or T cell. T cell epitopes presented by MHC class I molecules are typically peptides about 8 to 11 amino acids in length, whereas MHC class II molecules present longer peptides about 13 to 17 amino acids in length. Conformational epitopes are typically discontinuous and span a longer amino acid sequence.

As used herein, the term "nucelot(s)ide analog" or "reverse transcriptase inhibitor" is an inhibitor of DNA replication that is structurally similar to a nucleotide or nucleoside and specifically inhibits replication of the HBV cccDNA and does not significantly inhibit the replication of the host (e.g., human) DNA. Such inhibitors include Tenofovir disoproxil fumarate (TDF), Tenofovir alafenamide (TAF), Lamivudine, Adefovir dipivoxil, Entecavir (ETV), Telbivudine, AGX-1009, emtricitabine, clevudine, ritonavir, dipivoxil, lobucavir, famvir, FTC, N-Acetyl-Cysteine (NAC), PC1323, theradigm-HBV, thymosin-alpha, ganciclovir, besifovir (ANA-380/LB-80380), and tenofvir-exaliades (TLX/CMX157). In certain embodiments, the nucelot(s)ide analog is Entecavir (ETV). Nucleot(s)ide analogs are commercially available from a number of sources and are used in the methods provided herein according to their label indication (e.g., typically orally administered at a specific dose) or as determined by a skilled practitioner in the treatment of HBV.

As used herein, "target sequence" refers to a contiguous portion of the nucleotide sequence of an mRNA molecule formed during the transcription of an HBV transcript, including mRNA that is a product of RNA processing of a primary transcription product. In one embodiment, the target portion of the sequence will be at least long enough to serve as a substrate for iRNA-directed cleavage at or near that portion of the nucleotide sequence of an mRNA molecule formed during the transcription of an HBV transcript. In one embodiment, the target sequence is within the protein coding region of an HBV transcript.

The target sequence may be from about 9-36 nucleotides in length, e.g., about 15-30 nucleotides in length. For example, the target sequence can be from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

As used herein, the term "strand comprising a sequence" refers to an oligonucleotide comprising a chain of nucleotides that is described by the sequence referred to using the standard nucleotide nomenclature.

"G," "C," "A," "T," and "U" each generally stand for a nucleotide that contains guanine, cytosine, adenine, thymidine, and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

As used herein, an "RNAi agent", an "iRNA agent", an "siRNA agent", and the like, is a double stranded RNA that preferably target regions in the HBV genome that are conserved across all serotypes of HBV and are preferably designed to inhibit all steps of the HBV life cycle, e.g., replication, assembly, secretion of virus, and secretion of viral antigens, by inhibiting expression of more than one HBV transcript. In particular, since transcription of the HBV genome results in polycistronic, overlapping RNAs, an RNAi agent for use in the invention targeting a single HBV transcript preferably results in significant inhibition of expression of most or all HBV transcripts. All HBV transcripts are at least partly overlapping and share the same polyadenylation signal. Therefore, all viral transcripts have an identical 3' end and, thus, an RNAi agent of the invention targeting the X gene will target all viral transcripts and should result in inhibition of not only X gene expression but also the expression of all other viral transcripts, including pregenomic RNA (pgRNA). Furthermore, the RNAi agents of the invention have been designed to inhibit HBV viral replication by targeting pgRNA, HBV structural genes, polymerase, and the HBV X gene. In addition, they have been designed to mediate the silencing of SVP and other viral proteins that play a role in immune tolerance, thereby permitting a subject's immune system to detect and respond to the presence of viral antigens such that an immune response to control and to clear an HBV infection is mounted. Without intending to be limited by theory, it is believed that a combination or sub-combination of the foregoing properties and the specific target sites and/or the specific modifications in these RNAi agents confer to the RNAi agents of the invention improved efficacy, stability, safety, potency, and durability. Such agents are provided, for example, in PCT Publication Nos. WO 2016/077321, WO 2012/024170, WO 2017/027350, and WO 2013/003520, the entire contents of each of which is incorporated herein by reference. Exemplary target sites for RNAi agents and exemplary RNAi agents are provided in Appendix A, filed herewith, which forms a part of the specification. The term RNAi agents further includes shRNAs, e.g., adeno-associated virus (AAV) 8 vectors for delivery of an shRNA in an artificial mi(cro)RNA under a liver-specific promoter; optionally co-delivered a decoy ("TuD") directed against the shRNA sense strand to curb off-target gene regulation are provided in Michler et al., 2016 (*EMBO Mol. Med.*, 8:1082-1098, incorporated herein by reference).

The majority of nucleotides of each strand of an iRNA agent may be ribonucleotides, but as described in detail herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides.

As used herein, the term "modified nucleotide" refers to a nucleotide having, independently, a modified sugar moiety, a modified internucleotide linkage, and/or modified nucleobase. Thus, the term modified nucleotide encompasses substitutions, additions or removal of, e.g., a functional group or atom, to internucleoside linkages, sugar moieties, or nucleobases. The modifications suitable for use in the agents of the invention include all types of modifications disclosed herein or known in the art. Any such modifications, as used in a siRNA type molecule, are encompassed by "RNAi agent" for the purposes of this specification and claims.

As used herein, a "therapeutic HBV vaccine," and the like, can be a peptide vaccine, a DNA vaccine including a vector-based vaccine, or a cell-based vaccine that induces an immune response, preferably an effector T cell induced response, against one or more HBV proteins. Preferably the vaccine is a multi-epitope vaccine that is cross-reactive with multiple HBV serotypes, preferably all HBV serotypes. A number of therapeutic HBV vaccines are known in the art and are at various stages of pre-clinical and clinical development. Protein based vaccines include hepatitis B surface antigen (HBsAg) and core antigen (HBcAg) vaccines (e.g., Li et al., 2015, Vaccine. 33:4247-4254, incorporated herein by reference). Exemplary DNA vaccines include HB-110 (Genexine, Kim et al., 2008. Exp Mol Med. 40: 669-676.), pDPSC18 (PowderMed), INO-1800 (Inovio Pharmaceuticals), HBO2 VAC-AND (ANRS), and CVI-HBV-002 (CHA Vaccine Institute Co., Ltd.). Exemplary protein based vaccines include Theravax/DV-601 (Dynavax Technologies Corp.), EPA-44 (Chongqing Jiachen Biotechnology Ltd.), and ABX 203 (ABIVAX S.A.). Exemplary cell based vaccines include HPDCs-T immune therapy (Sun Yat-Sen University). Combination vaccines and products are also known and include HepTcell™ (FP-02.2 vaccine (peptide)+IC31® Adjuvant (a combination peptide-oligonucleotide adjuvant), (see U.S. Patent Publication Nos. 2013/0330382, 2012/0276138, and 2015/0216967, the entire contents of each of which is incorporated herein by reference)); GS-4774 (Gilead, a fusion protein S. core X vaccine+Tarmogen T cell immune stimulator), pSG2.HBs/MVA.HBs (protein prime/viral vector boost, Oxxon Therapeutics), and a protein-prime/modified vaccinia virus Ankara vector-boost (HBsAg and HBsAg protein+HBcAg and HBsAg in MVA expression vector, Backes et al., 2016, Vaccine. 34:923-32, and WO2017121791, both of which are incorporated herein by reference).

As used herein, the term "adjuvant" is understood to be an agent that promotes (e.g., enhances, accelerates, or prolongs) an immune response to an antigen with which it is administered to elicit long-term protective immunity. No substantial immune response is directed at the adjuvant itself. Adjuvants include, but are not limited to, pathogen components, particulate adjuvants, and combination adjuvants (see, e.g., www.niaid.nih.gov/research/vaccine-adjuvants-types). Pathogen components (e.g., monophosphoryl lipid A (MPL), poly(I:C), polyICLC adjuvant, CpG DNA, c-di-AMP, c-di-GMP, c-di-CMP; short, blunt-ended 5'-triphosphate dsRNA (3pRNA) RIG-1 ligand, and emulsions such as poly[di(sodiumcarboxylatoethylphenoxy)phosphazene] (PCEP)) can help trigger early non-specific, or innate, immune responses to vaccines by targeting various receptors inside or on the surface of innate immune cells. The innate immune system influences adaptive immune responses, which provide long-lasting protection against the pathogen that the vaccine targets. Particulate adjuvants (e.g., alum, virosomes, cytokines, e.g., IL-12) form very small particles that can stimulate the immune system and also may enhance delivery of antigen to immune cells. Combination adjuvants (e.g., AS02, AS03, and AS04 (all GSK); MF59 (Novartis); ISCOMATRIX® (CSL Limited); and IC31® (Altimmune) elicit multiple protective immune responses. Adjuvants that have a modest effect when used alone may induce a more potent immune response when used together.

In preferred embodiments of the invention, adjuvants for use in the invention promote a humoral as well as a cellular immune response. For this, a balanced Th1/Th2 helper T cell response is desired to support neutralizing antibody responses as well as effector cytotoxic T cell responses. Preferably the adjuvant provides a balanced Th1/Th2 response. In certain embodiments, the adjuvant is one or more of a polyI:C adjuvant, a polyICLC adjuvant, a CpG adjuvant, a STING agonist (a c-di-AMP adjuvant, a c-di-GMP adjuvant, or a c-di-CMP adjuvant), an ISCOMATRIX® adjuvant, a PCEP adjuvant, and a Rig-I-ligand adjuvant. In certain embodiments, the adjuvant is a polyI:C adjuvant, a CpG adjuvant, a STING agonist, or a PCEP adjuvant. In certain embodiments, the adjuvant is not alum.

As used herein, an "immune stimulator" is an agent that stimulates an immune response that may or may not be administered independently of an antigen. Immune stimulators include, but are not limited to, pegylated interferon alfa 2a (PEG-IFN-alpha-2a), interferon alfa-2b, PEG-IFN-alpha-2b, interferon lambda a recombinant human interleukin-7, and a Toll-like receptor 3, 7, 8 or 9 (TLR3, TLR7, TLR8, TLR9) agonist, a viral entry inhibitor (e.g., Myrcludex), an oligonucleotide that inhibits the secretion or release of HBsAg (e.g., REP 9AC), a capsid inhibitor (e.g., Bay41-4109 and NVR-1221), a cccDNA inhibitor (e.g., IHVR-25). In certain embodiments, an immune stimulator can include a viral capsid, optionally an empty viral capsid, e.g., MVA capsid.

Immune stimulators can also include immune checkpoint regulators. Immune checkpoint regulators can be stimulatory or inhibitory. As used herein, immune checkpoint regulators potentiate an immune response. Immune checkpoint regulators include, but are not limited to, CTLA-4 inhibitors, such as ipilimumab, PD-1 inhibitors, such as Nivolumab, Pembrolizumab, and the BGB-A317 antibody. PD-L1 inhibitors include atezolizumab, avelumab, and durvalumab, in addition to an affimer biotherapeutic.

As used herein, a "subject" is an animal, such as a mammal, including a primate (such as a human, a non-human primate, e.g., a monkey, and a chimpanzee), a non-primate (e.g., a mouse model or other animal model that can be infected with HBV). In an embodiment, the subject is a human, such as a human being treated or assessed for a disease, disorder, or condition that would benefit from reduction in HBV gene expression or replication. In certain embodiments, the subject has a chronic hepatitis B virus (HBV) infection. In certain embodiments, the subject has both a chronic hepatitis B virus (HBV) infection and a hepatitis D virus (HDV) infection.

As used herein, the terms "treating" or "treatment" refer to a beneficial or desired result including, but not limited to, alleviation of one or more signs or symptoms in a subject with HBV infection including, but not limited to, the presence of serum HBV DNA or liver HBV ccc DNA, the presence of serum or liver HBV antigen, e.g., HBsAg or HBeAg. Diagnostic criteria for HBV infection are well known in the art. "Treatment" can also mean prolonging survival as compared to expected survival in the absence of treatment, or lower risk of HCC development.

In certain embodiments, an HBV-associated disease is chronic hepatitis B (CHB). In certain embodiments, subjects have been infected with HBV for at least five years. In certain embodiments, subjects have been infected with HBV for at least ten years. In certain embodiments, subjects became infected with HBV at birth. Subjects having chronic hepatitis B disease are immune tolerant, have an active chronic infection accompanied by necroinflammatory liver disease, have increased hepatocyte turn-over in the absence of detectable necroinflammation, or have an inactive chronic infection without any evidence of active disease, and they are also asymptomatic. Subjects having chronic hepatitis B disease are HBsAg positive and have either high viremia ($\geq 10^4$ HBV-DNA copies/ml blood) or low viremia ($<10^3$ HBV-DNA copies/ml blood). Patients with chronic active hepatitis, especially during the high replicative state, may have symptoms similar to those of acute hepatitis. The persistence of HBV infection in CHB subjects is the result of ccc HBV DNA persistence. In certain embodiments, a subject having CHB is HBeAg positive. In other embodiments, a subject having CHB is HBeAg negative.

In preferred embodiments, treatment of HBV infection results in a "functional cure" of hepatitis B. As used herein, the term "functional cure" is understood to be clearance of circulating HBsAg and is preferably accompanied by conversion to a status in which HBsAg antibodies become undetectable using a clinically relevant assay. For example, undetectable antibodies can include a signal lower than 10 mIU/ml as measured by Chemiluminescent Microparticle Immunoassay (CMIA) or any other immunoassay, and may be called anti-HBs seroconversion. Functional cure does not require clearance of all replicative forms of HBV (e.g., cccDNA from the liver). Anti-HBs seroconversion occurs spontaneously in about 0.2-1% of chronically infected patients per year. However, even after anti-HBs seroconversion, low level persistence of HBV is observed for decades indicating that a functional rather than a complete cure occurs. Without being bound to mechanism, it is proposed that the immune system is able to keep HBV in check. A functional cure permits discontinuation of any treatment for the HBV infection. However, it is understood that a "functional cure" for HBV infection may not be sufficient to prevent or treat diseases or conditions that result from HBV infection, e.g., liver fibrosis, HCC, cirrhosis.

The term "lower" in the context of the level of HBV gene expression or HBV replication in a subject, or a disease marker or symptom, refers to a statistically significant decrease in such level. The decrease can be, for example, at least 70%, 75%, 80%, 85%, 90%, 95%, or more. In monitoring of HBV infection, a log 10 scale is typically used to describe the level of antigenemia (e.g., HBsAg level in serum) or viremia (HBV DNA level in serum). It is understood that a 1 log 10 decrease is a 90% decrease (10% remaining), a 2 log 10 decrease is a 99% decrease (1% remaining), etc. In certain embodiments, a disease marker is lowered to below the level of detection.

In certain embodiments, the expression of a disease marker is normalized, i.e., decreased to a level accepted as within the range of normal for an individual without such disorder, e.g., the level of a disease marker, such as, ALT or AST, is decreased to a level accepted as within the range of normal for an individual without such disorder. When the disease associated level is elevated from the normal level, the change is calculated from the upper level of normal (ULN). When the disease associated level is decreased from the normal level, the change is calculated from the lower level of normal (LLN). The lowering is the percent difference in the change between the subject value and the normal value. For example, a normal AST level can be reported as 10 to 40 units per liter. If, prior to treatment, a subject has an AST level of 200 units per liter (i.e., 5 times the ULN, 160 units per liter above the upper level of normal) and, after treatment, the subject has an AST level of 120 units per liter (i.e., 3 times the ULN, 80 units per liter above the upper level of normal), the elevated AST would be lowered towards normal by 50% (80/160).

The term "inhibiting," as used herein, is used interchangeably with "reducing," "silencing," "downregulating", "suppressing", and other similar terms, and includes any level of inhibition. Preferably inhibiting includes a statistically significant or clinically significant inhibition.

The phrase "inhibiting expression of an HBV gene" is intended to refer to knockdown of any HBV transcript (e.g., 3.5 kb, 2.4 kb, 2.1 kb, or 0.7 kb transcript) encoding one or more HBV viral proteins (such as, e.g., preS1/2-S, preS, S, P, X, preC, and C), as well as variants or mutants of an HBV gene.

"Inhibiting expression of an HBV gene" includes any significant level of inhibition of an HBV gene or transcript, e.g., at least partial suppression of the expression of an HBV gene S, P, X, or C, or any combination thereof, e.g., S, P, and C. The expression of the HBV gene may be assessed based on the level, or the change in the level, of any variable associated with HBV gene expression, e.g., an HBV mRNA level, an HBV protein level, and/or an HBV cccDNA level. This level may be assessed in an individual cell or in a group of cells, including, for example, a sample derived from a subject, e.g., levels may be monitored in serum.

In some embodiments of the methods of the invention, expression of an HBV gene is inhibited by at least 70%, 75%, 80%, 85%, 90%, 95%, or to below the level of detection of the assay. In preferred embodiments, the inhibition of expression of an HBV gene results in a clinically relevant inhibition of the level of gene expression, e.g., sufficiently inhibited to permit an effective immune response to a vaccine against an HBV protein.

Inhibition of the expression of an HBV gene may be manifested by a reduction of the amount of RNA expressed by a first cell or group of cells (such cells may be present, for example, in a sample derived from a subject) in which an HBV gene is transcribed and which has or have been treated (e.g., by contacting the cell or cells with an RNAi agent of the invention, or by administering an RNAi agent of the invention to a subject in which the cells are or were present) such that the expression of an HBV gene is inhibited, as compared to a second cell or group of cells substantially identical to the first cell or group of cells but which has not or have not been so treated (control cell(s)). In preferred embodiments, the inhibition is assessed by the rtPCR method provided in Example 2 of PCT Publication No. WO 2016/077321 (the entire contents of which are incorporated herein by reference), with in vitro assays being performed in an appropriately matched cell line with the duplex at a 10 nM concentration, and expressing the level of mRNA in treated cells as a percentage of the level of mRNA in control cells, using the following formula:

$$\frac{(RNA \text{ in control cells}) - (RNA \text{ in treated cells})}{RNA \text{ in control cells}} \cdot 100\%$$

Alternatively, inhibition of the expression of an HBV gene may be assessed in terms of a reduction of a parameter that is functionally linked to HBV gene expression, e.g., as described herein. HBV gene silencing may be determined in any cell expressing an HBV gene, either constitutively or by genomic engineering, and by any assay known in the art.

Inhibition of the expression of an HBV protein may be manifested by a reduction in the level of an HBV protein that is expressed by a cell or group of cells (e.g., the level of protein expressed in a sample derived from a subject). As explained above, for the assessment of mRNA suppression, the inhibition of protein expression levels in a treated cell or group of cells may similarly be expressed as a percentage of the level of protein in a control cell or group of cells or in serum.

A control cell or group of cells that may be used to assess the inhibition of the expression of an HBV gene includes a cell or group of cells that has not yet been contacted with an RNAi agent of the invention. For example, the control cell or group of cells may be derived from an individual subject (e.g., a human or animal subject) prior to treatment of the subject with an RNAi agent. In alternative embodiments, the level may be compared to an appropriate control sample, e.g., a known population control sample.

The level of HBV RNA that is expressed by a cell or group of cells, or the level of circulating HBV RNA, may be determined using any method known in the art for assessing mRNA expression, preferably using the rtPCR method provided in Example 2 of PCT Publication No. WO 2016/077321, or Example 1 provided herein. In one embodiment, the level of expression of an HBV gene (e.g., total HBV RNA, an HBV transcript, e.g., HBV 3.5 kb transcript) in a sample is determined by detecting a transcribed polynucleotide, or portion thereof, e.g., RNA of the HBV gene. RNA may be extracted from cells using RNA extraction techniques including, for example, using acid phenol/guanidine isothiocyanate extraction (RNAzol B; Biogenesis), RNeasy RNA preparation kits (Qiagen®) or PAXgene (PreAnalytix, Switzerland). Typical assay formats utilizing ribonucleic acid hybridization include nuclear run-on assays, RT-PCR, RNase protection assays (Melton et al., *Nuc. Acids Res.* 12:7035), northern blotting, in situ hybridization, and microarray analysis. Circulating HBV mRNA may be detected using methods the described in PCT Publication No. WO 2012/177906, the entire contents of which are hereby incorporated herein by reference.

In one embodiment, the level of expression of an HBV gene is determined using a nucleic acid probe. The term "probe", as used herein, refers to any molecule that is capable of selectively binding to a specific HBV gene. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated RNA can be used in hybridization or amplification assays that include, but are not limited to, Southern or northern analyses, polymerase chain reaction (PCR) analyses, and probe arrays. One method for the determination of mRNA levels involves contacting the isolated mRNA with a nucleic acid molecule (probe) that can hybridize to an HBV mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix® gene chip array. A skilled artisan can readily adapt known mRNA detection methods for use in determining the level of an HBV mRNA.

An alternative method for determining the level of expression of an HBV gene in a sample involves the process of nucleic acid amplification or reverse transcriptase (to prepare cDNA) of, for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of an HBV gene is determined by quantitative fluorogenic RT-PCR (i.e., the TaqMan™ System), e.g., using the method provided herein.

The expression levels of an HBV RNA may be monitored using a membrane blot (such as used in hybridization analysis such as northern, Southern, dot, and the like), or microwells, sample tubes, gels, beads, or fibers (or any solid support comprising bound nucleic acids). See U.S. Pat. Nos. 5,770,722, 5,874,219, 5,744,305, 5,677,195, and 5,445,934, the entire contents of each of which are incorporated herein by reference. The determination of HBV expression level may also comprise using nucleic acid probes in solution.

In preferred embodiments, the level of RNA expression is assessed using real time PCR (qPCR). The use of these methods is described and exemplified in the Examples presented herein.

The level of HBV protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipiting reactions, absorption spectroscopy, a colorimetric assays, spectrophotometric assays, flow cytometry, immunodiffusion (single or double), immunoelectrophoresis, western blotting, radioimmunoassay (RIA), enzyme-linked immunosorbent assays (ELISAs), immunofluorescent assays, electrochemiluminescence assays, and the like.

In some embodiments, the efficacy of the methods of the invention can be monitored by detecting or monitoring a reduction in a symptom of an HBV infection. Symptoms may be assessed using any method known in the art.

As used herein, the term "Hepatitis B virus-associated disease" or "HBV-associated disease," is a disease or disorder that is caused by, or associated with HBV infection or replication. The term "HBV-associated disease" includes a disease, disorder, or condition that would benefit from reduction in HBV gene expression or replication. Non-limiting examples of HBV-associated diseases include, for example, hepatitis D virus infection; hepatitis delta; chronic hepatitis B; liver fibrosis; end-stage liver disease; cryoglobulinemia; hepatocellular carcinoma.

The term "sample," as used herein, includes a collection of similar fluids, cells, or tissues isolated from a subject or prepared therefrom, as well as fluids, cells, or tissues present within a subject. Examples of biological fluids include blood, serum, plasma, immune cells, lymph, urine, saliva, and the like. Tissue samples may include samples from tissues, organs, or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes, resident liver immune cells). In preferred embodiments, a "sample derived from a subject" refers to blood drawn from the subject or plasma, serum, or selected cell pools derived therefrom (e.g., populations of immune cells). In further embodiments, a "sample derived from a subject" refers to liver tissue (or subcomponents thereof) obtained from the subject.

As used herein, "coding sequence" is understood to refer to a DNA sequence that encodes for a specific amino acid sequence. In certain embodiments, the DNA sequence can be reverse transcribed from an RNA sequence. In certain embodiments, an iRNA, e.g., an shRNA, targets a coding sequence.

The terms, "suitable regulatory sequences," and the like, are used herein is to refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" as used herein refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. A promoter may be selected to promote expression of a coding sequence in a particular cell type or at different stages of development, or in response to different environmental conditions. In certain embodiments, the promoter is a promoter that is active in liver, e.g., a liver-specific promoter. Many promoter sequences are known in the art and selection of an appropriate promoter sequence for a specific context is within the ability of those of skill in the art.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter).

The term "expression" as used herein refers to the transcription and stable accumulation of sense (mRNA) or antisense RNA, or an RNAi agent (e.g., an shRNA) derived from the nucleic acid fragment of the subject technology. "Over-expression" refers to the production of a gene product in transgenic or recombinant organisms that exceeds levels of production in normal or non-transformed organisms.

"Expression vector" or "expression construct," as used herein, refers to a nucleic acid in which a coding sequence is operably linked to a promoter sequence to permit expression of the coding sequence under the control of the promoter. Expression vectors include, but are not limited to, viral vectors or plasmid vectors. Methods for delivery of expression vectors into cells are known in the art.

II. Treatment Methods of the Invention

The present invention provides treatment regimens and methods for the sequential use of an agent to reduce the expression of an HBV gene, e.g., iRNA agents which effect the RNA-induced silencing complex (RISC)-mediated cleavage of one or more HBV transcripts, and hepatitis B vaccines to stimulate an immune response against one or more HBV proteins in the treatment of HBV infection. The treatment regimens and methods preferably provide a functional cure of HBV within a defined period of time.

The treatment regimens and methods provided herein include the ordered administration of therapeutic agents to provide treatment, and preferably a functional cure, for HBV infection. The agents used in the methods are known in the art. However, the agents alone fail to consistently and durably decrease HBV disease burden, e.g., reducing HBsAg levels to below 2 log 10, preferably 1 log 10 IU/ml or to below the level of detection, in most subjects. Significantly reducing HBV disease burden, e.g., reducing HBsAg levels to below 2 log 10, preferably 1 log 10 IU/ml or to below the level of detection, will provide the opportunity of discontinuation of administration of therapeutic agents and provide a functional cure for HBV in a substantial number of subjects. Without being bound by mechanism, it is proposed that the treatment regimens and methods provided herein, including administration of an iRNA agent targeted to HBV, substantially reduces HBV antigens and nucleic acid for a sufficient magnitude and duration in a subject to allow an effective immune response induced by administration of multiple doses of a therapeutic vaccine. The regimens and methods, provided herein, consistently provide a substantial reduction of disease burden and a functional cure in a significant number of subjects, preferably at least 30%, 40%, 50%, 60%, or 70% of subjects.

A transgenic mouse model of HBV infection, HBV1.3 xfs was used to assess the combination therapy provided herein. Primary studies demonstrated the efficacy of two different chemically modified GalNAc-iRNA agents targeted to HBV (AD-66816 and AD-66810) to inhibit the level of HBsAg and HBeAg proteins, and HBV DNA in serum for at least 21 days with a single subcutaneous dose at 3 mg/kg or 9 mg/kg, with similar efficacy. No significant knockdown was observed with a non-HBV iRNA control (see FIG. 2). Based on this result, the lower dose of 3 mg/kg was selected for combination therapy studies.

In the first combination therapy trial (see FIG. 3), mice were pretreated with one of six treatment regimens (n=6 per group):

(1) No pretreatment;

(2) Entecavir at 1 µg/ml in water throughout the course of the study beginning on the first day of Week 0;

(3) A 3 mg/kg dose on the first day of Weeks 0, 4, 8, and 12 of the control iRNA agent.

(4) A single dose on the first day of Week 0 with an expression vector encoding an shRNA targeted to HBV (HBV-shRNA) (Michler et al., 2016); or (5-6) A 3 mg/kg dose on the first day of Weeks 0, 4, 8, and 12 of AD-66816 or AD-66810 (generically, HBV-siRNA).

On the first day of Weeks 12 and 14, a mixture of recombinantly expressed yeast HBsAg (15 µg) and E. coli expressed HBcAg (15 µg) adjuvanted with 31.9 µg synthetic phosphorothioated CpGODN 1668 (CpG) and 25 µg poly[di(sodiumcarboxylatoethyl-phenoxy)phosphazene] (PCEP) was subcutaneously administered to all mice as a protein prime vaccination (Backes, 2016).

On the first day of week 16, a mixture of modified vaccinia virus Ankara expressing HBsAg or HBcAg ($5 \times 10^7$ particles of each virus) was subcutaneously administered to all mice as a boost vaccination (Backes, 2016).

Blood samples were obtained on the first days of Week 0, 2, 4, 8, 12, 16, and 17 and were assayed for levels of HBsAg, HBeAg, and HBV DNA. Results observed for HBsAg and HBeAg levels mice in groups 1, 2, and 3 (mock, Entecavir, control iRNA agent) were similar (FIGS. 4A and 4B). The HBV-shRNA or HBV-siRNAs alone caused a significant decrease in HBsAg, HBeAg, and HBV DNA in serum. The three dose prime-boost vaccination scheme resulted in a further decrease in HBsAg in all groups, and reduced the level of HBsAg in at least some animals in the HBV-shRNA and HBV-siRNA groups to below the level of detection. However, vaccine treatment did not decrease HBeAg levels in any of the groups. HBV DNA levels were decreased to about the lower limit of quantitation with Entecavir alone so no effect of the three dose prime-boost vaccine could be detected (FIG. 4C). Mock treatment and treatment with the HBV-shRNA, the HBV-siRNAs, and control siRNA all decreased HBV DNA levels, and the level of HBV-DNA was further decreased by the prime-boost vaccine in all groups. These data demonstrate that RNAi is superior to nucleot(s)ide analog therapy in reducing viral antigens. Also, the combination of RNAi and subsequent vaccination have a greater effect on HBsAg and HBV DNA levels than either agent alone.

Figure 5C:
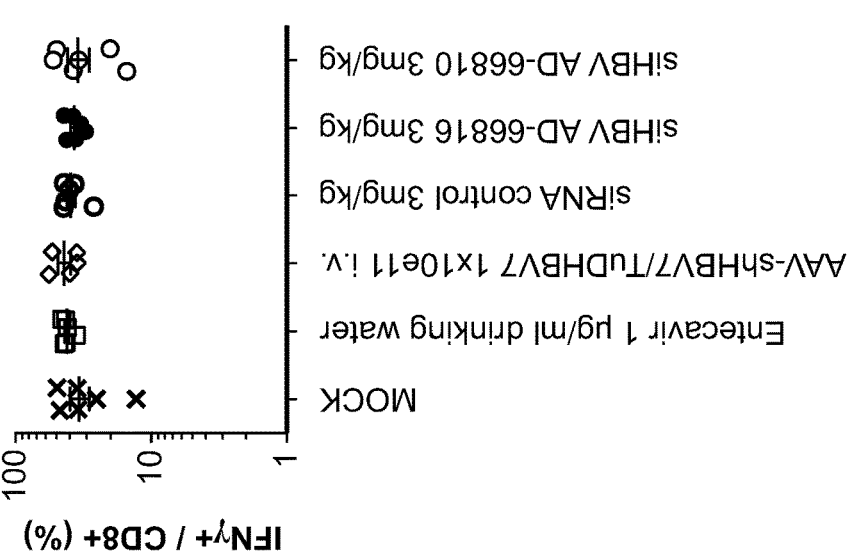
FIGS. 5A-5F are graphs showing T cell immune response in the liver against peptides (5A) HBs(S208), (5B) HBc (C93), and (5C) MVA(B8R) in HBV1.3-xfs mice after treatment based on the dosing regimen provided in FIG. 3.
Figure 5B:
Figure 5A:
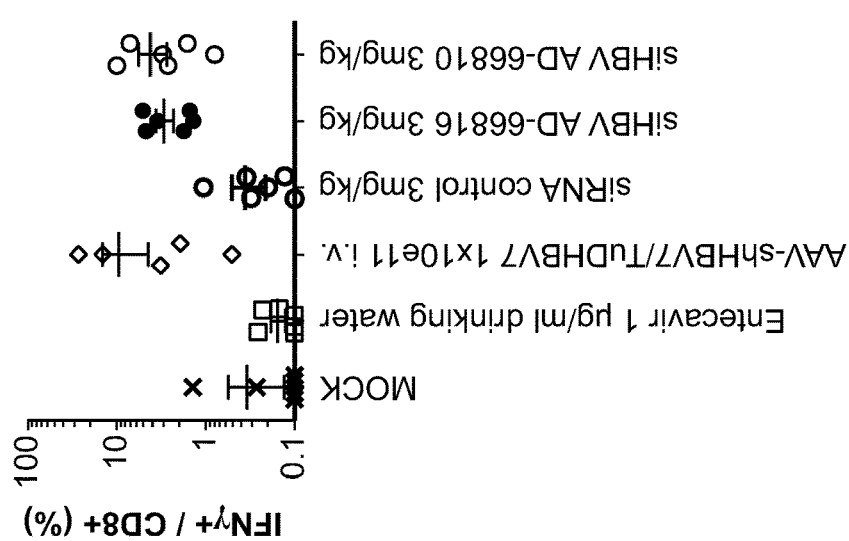

On the final day of the experiment (the first day of week 17), mice were sacrificed and their livers were harvested. Intrahepatic CD8+ T cell responses were assessed for response to HBsAg, HBcAg, and the MVA virus particle using the method provided in Backes, 2016. Mice treated with the HBV-shRNA or the HBV-siRNAs were able to generate a CD8+ immune response against the HBsAg and HBcAg (FIGS. 5A and 5B). No significant immune response against the HBV antigens was observed in the mock, Entecavir, or control siRNA groups. However, a similar immune response against the MVA virus was observed in all animals independent of pretreatment or viral antigen levels (FIG. 5C) showing that vaccination had worked equally well in all animals, demonstrating the presence of a competent immune system. The data shown in FIG. 5A-C were reanalyzed to accommodated for an insufficient exclusion of dead immune cells during the first analysis. The data obtained from the second analysis (shown in FIG. 5 D-F) again shows that only the mice pretreated with the HBV-shRNA or the HBV-siRNAs were able to generate HBV-specific CD8+ T cell responses after therapeutic vaccination, but that MVA-specific responses were not influenced by the pretreatment. The reduced variances in the second analysis are attributed to the more rigorous exclusion of dead cells. These data demonstrate that RNAi treatment, in contrast to the current standard of care treatment with a nucleoside analog, can restore HBV-specific T cell immunity and enable the induction of HBV-specific CD8 T cell responses after therapeutic vaccination.

Serum was also assessed for antibody immune response to HBV antigens. Although the vaccine was able to induce a T-cell immune response only in animals which had received HBV-siRNA or HBV-shRNA pretreatment, antibody responses against HBsAg and HBcAg were similar across all groups regardless of pretreatment at the time points evaluated until week 17. No HBeAg antibody responses could be detected. These data demonstrate that high HBV antigen loads preferentially inhibit HBV-specific T cell, not B cell responses.

Figure 6A:
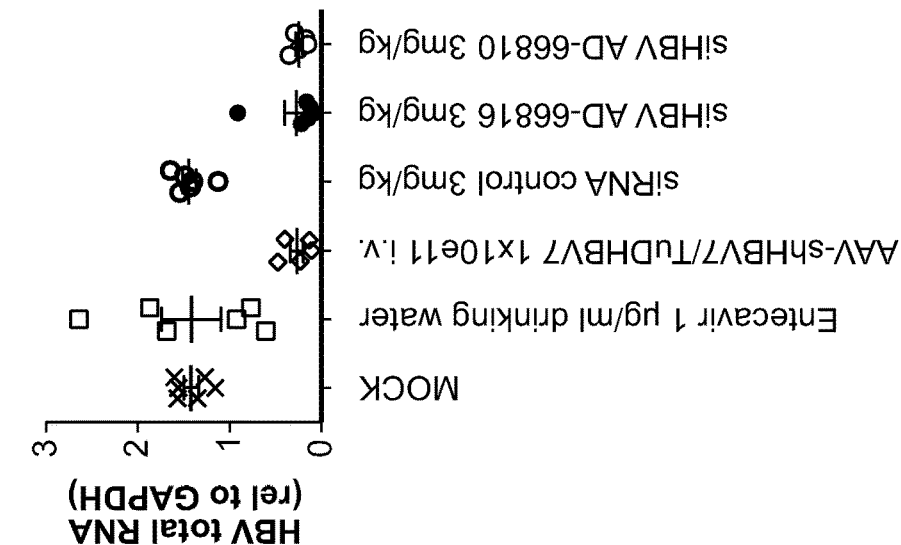
FIGS. 6A-6C show the level of HBV RNA and protein levels in liver cells in HBV1.3-xfs mice after treatment based on the dosing regimen provided in FIG. 3.
Figure 6B:
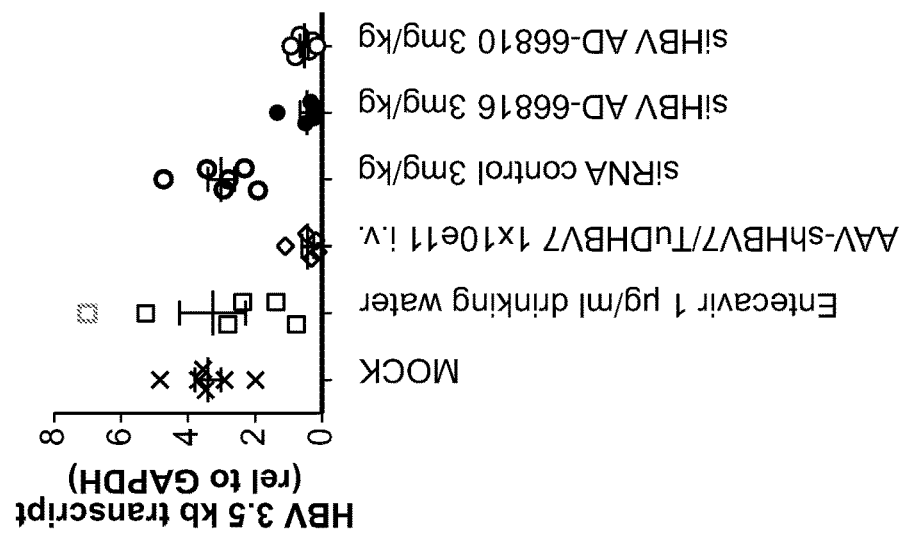
Figure 6C:
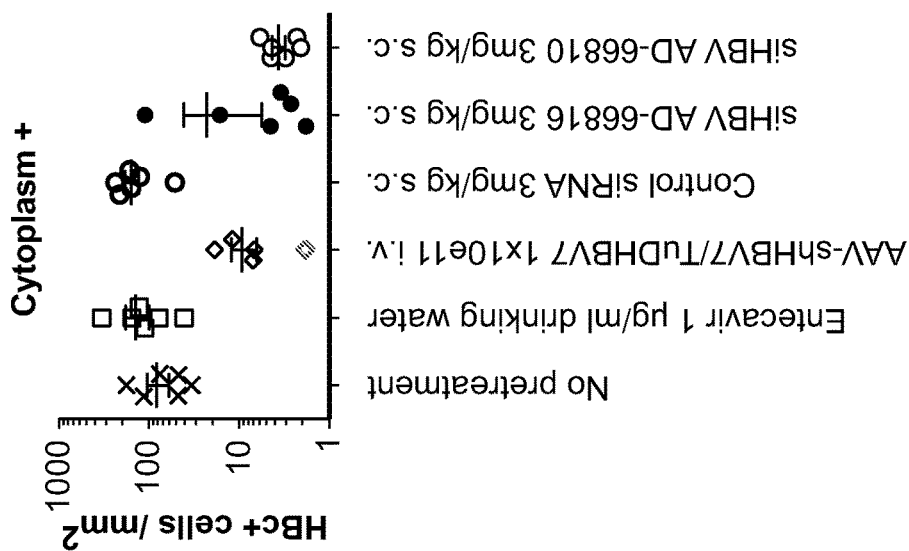

Livers were also assessed for the presence of HBV transcripts by RT-qPCR and normalized to the liver GAPDH transcript. Mice treated with the HBV-shRNA or the HBV-siRNAs demonstrated a significant decrease in HBV transcript levels (FIGS. 6A and 6B). No significant difference was observed between the mock and Entecavir or control siRNA groups. Liver sections were analysed by immunohistochemical stainings for expression of core antigen to assess the antiviral effect in the liver (FIG. 6C). In animals that were not pretreated before vaccination, there were, on average, 83 hepatocytes per $mm^2$ with cytoplasmic expression of HBc. This number was not significantly changed in animals that were pretreated with Entecavir or the control siRNA. However, the number of cytoplasmic HBcAg positive cells was significantly reduced in AAV-shRNA or HBV siRNA pretreated animals. These data demonstrate that a combinatorial RNAi/vaccination therapy suppresses not only antigens in the serum, but also viral antigen expression in the liver.

Having demonstrated that suppression of expression of HBV antigens using shRNA or siRNA is effective at potentiating an immune response to an HBV vaccine regimen, a study was designed to determine if the duration of HBV antigen suppression had an effect on the potentiation an HBV immune response. Using the HBV 1.3xfs mouse model, mice were treated for eight, six, or three weeks with HBV-siRNA AD-66816, or the control siRNA for 8 weeks, subcutaneously administered at 3 mg/kg/dose, followed by administration of the prime-boost vaccine regimen as set forth above, except 10 µg c-di-AMP was used as an adjuvant rather than PCEP+CPG (n=6 per 8 and 3 group, n=6 for 6 week group) (see FIG. 7).

A significant decrease in the levels of each of HBsAg, HBeAg, and HBV DNA was observed after the first administration of AD-66816 (FIGS. 8A-8C). A further significant decrease in HBsAg was observed after treatment with the vaccine boost with the greatest decrease observed in the 8 week pretreatment group to below the level of detection of the assay, representing a greater than 5 log 10 decrease in HBsAg level in all treated animals. Immunization caused only slight further reductions (<0.5 log 10) of HBV DNA and no further reduction in HBeAg levels. These data demonstrate that efficacy of therapeutic vaccination correlates with duration of antigen suppression before start of vaccination. Reconstitution of HBV-specific CD8 T cell responses takes several weeks, with a 6 or preferably 8 week pretreatment resulting in more HBsAg knockdown than a 3 week pretreatment.

Similarly, T-cell responses against HBsAg and HBcAg in liver corresponded with the duration of HBV antigen knockdown, with longer duration of HBV antigen suppression resulting in greater T-cell responses (FIG. 9A-9C). Similar responses to MVA virus antigens were observed across all groups independent of pretreatment (FIG. 9D). Antibody responses were similar across all groups.

Livers were also assessed for the presence of HBV transcripts by RT-qPCR and normalized to the liver GAPDH transcript. Longer pretreatment durations trended to higher levels of HBV RNA knockdown (FIGS. 10A and 10B).

Figure 11A:
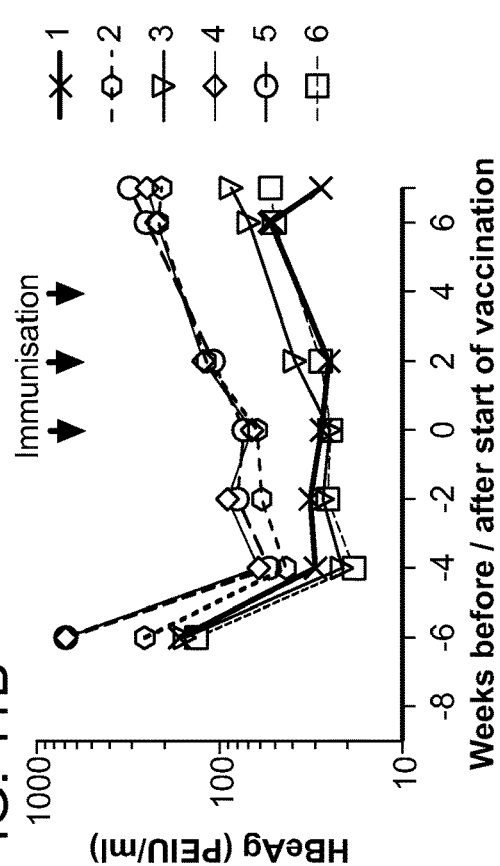
FIGS. 11A and 11B are graphs showing the level of (11A) HBsAg and (11B) HBeAg in serum of individual HBV1.3-xfs mice at week 7 after the first vaccine dose after the 6 week regimen in the dosing regimen provided in FIG. 7.
Figure 11C:
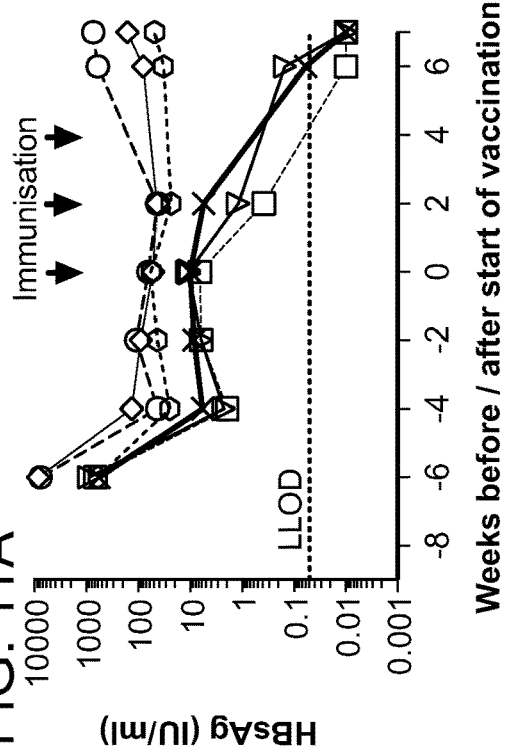
FIGS. 11C and 11D are graphs showing (11C) anti-HBs antibody response and (11D) T cell immune response in the liver against HBs(S208) of individual HBV1.3-xfs mice at week 7 after the first vaccine dose after the 6 week regimen in the dosing regimen provided in FIG. 7.
Figure 11B:
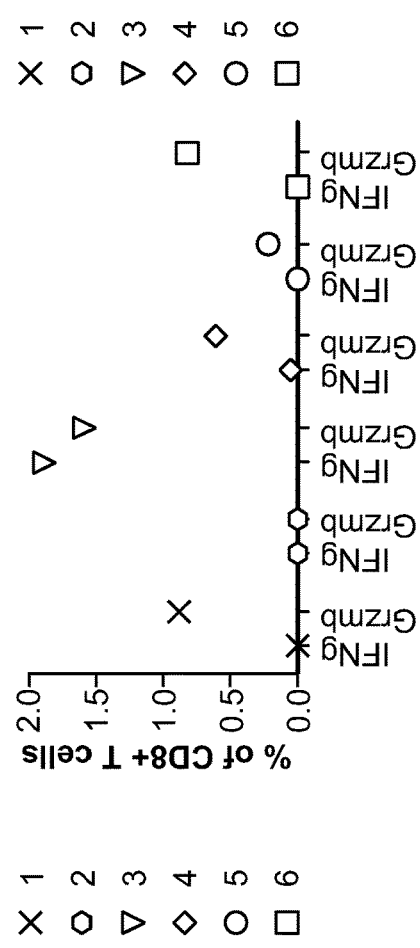
Figure 11D:
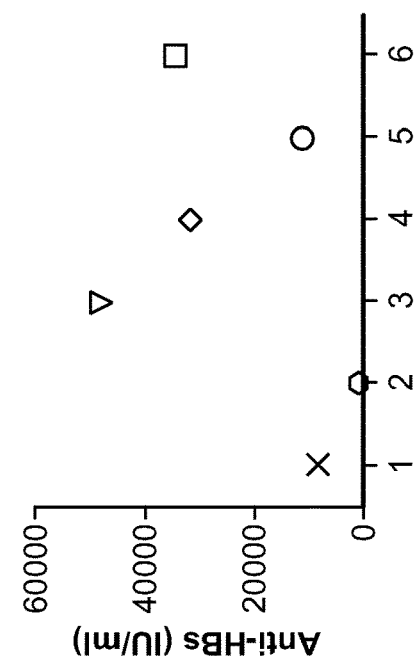

Liver sections were also analysed by immunohistochemical staining for cytoplasmic expression of HBcAg to assess the antiviral effect of the treatment in the liver (FIG. 10C). In animals pretreated with the control siRNA before vaccination, there were, on average, 172 hepatocytes per $mm^2$ which showed cytoplasmic expression of HBc. With longer duration of HBV suppression before vaccination, there was a gradual decrease of cytoplasmic HBcAg positive hepatocytes with an average of only 12 cytoplasmic HBcAg positive hepatocytes per $mm^2$ in the 8 week pretreatment group. These data demonstrate that the increasing HBV-specific CD8+ T cell response observed with longer antigen suppression before vaccination led to decreased HBV antigen expression in the liver. To assess the durability of response, blood samples were collected from mice (n=6) pretreated with the AD-66816 HBV-siRNA for six weeks at 2 and 3 weeks after administration of the boost vaccination. In three of the six mice, HBsAg levels continued to dropped to below the level of detection of the assay (FIGS. 11A and 11B). Specifically, the three animals which had the highest HBsAg and HBeAg levels at start of vaccination (2, 4, and 5) did show a decline of antigen titers after vaccination, but rebounded with antigen titers towards the end of the experiment. In contrast, the three animals with the lowest antigen titers at start of vaccination (1, 3, and 6) showed a further decline of HBsAg to below the detection limit. These data demonstrate that a functional cure is possible using the treatment regimens provided herein. These data also suggest that the antigen levels at start of vaccination can affect the response to therapeutic vaccination. Finally, without being bound by mechanism, these data suggest that the decline of antigen levels after therapeutic vaccination is mediated, at least in part, by CD8+ T cells. These data demonstrate that knockdown of circulating HBV antigens (e.g., HBsAg, HBcAg), but not inhibition of HBV DNA replication alone, potentiates immune response to HBV therapeutic vaccine, e.g., a prime boost therapeutic vaccination regimen. That is, an immune response can be potentiated by pretreatment with an siRNA, but not with nucleot(s)ide inhibitors alone as the immune response is a CD8+ T-cell based immune response.

The magnitude and duration of knockdown required depends on, for example, the level of disease burden in the subject. The higher the level of circulating antigen, the greater the magnitude and duration of HBV antigen knockdown required to potentiate an immune response. Knockdown of HBsAg in serum should be at least 0.5 log 10 (IU/ml), preferably 1 log 10 (IU/ml), 1.5 log 10 (IU/ml), 2 log 10 (IU/ml), or more from the level in the subject prior to treatment with the therapeutic vaccine. In certain embodiments, the level of serum HBsAg is no more than 2.5 log 10 (IU/ml), 2 log 10 (IU/ml), 1.5 log 10 (IU/ml) prior to vaccine administration.

Further, as demonstrated herein, a longer duration of HBV antigen knockdown trended towards a more robust immune response. Therefore, knockdown of serum HBsAg to a sufficiently low level for a duration of at least four weeks, six weeks, or eight weeks is preferred prior to administration of the vaccine.

Figure 12:
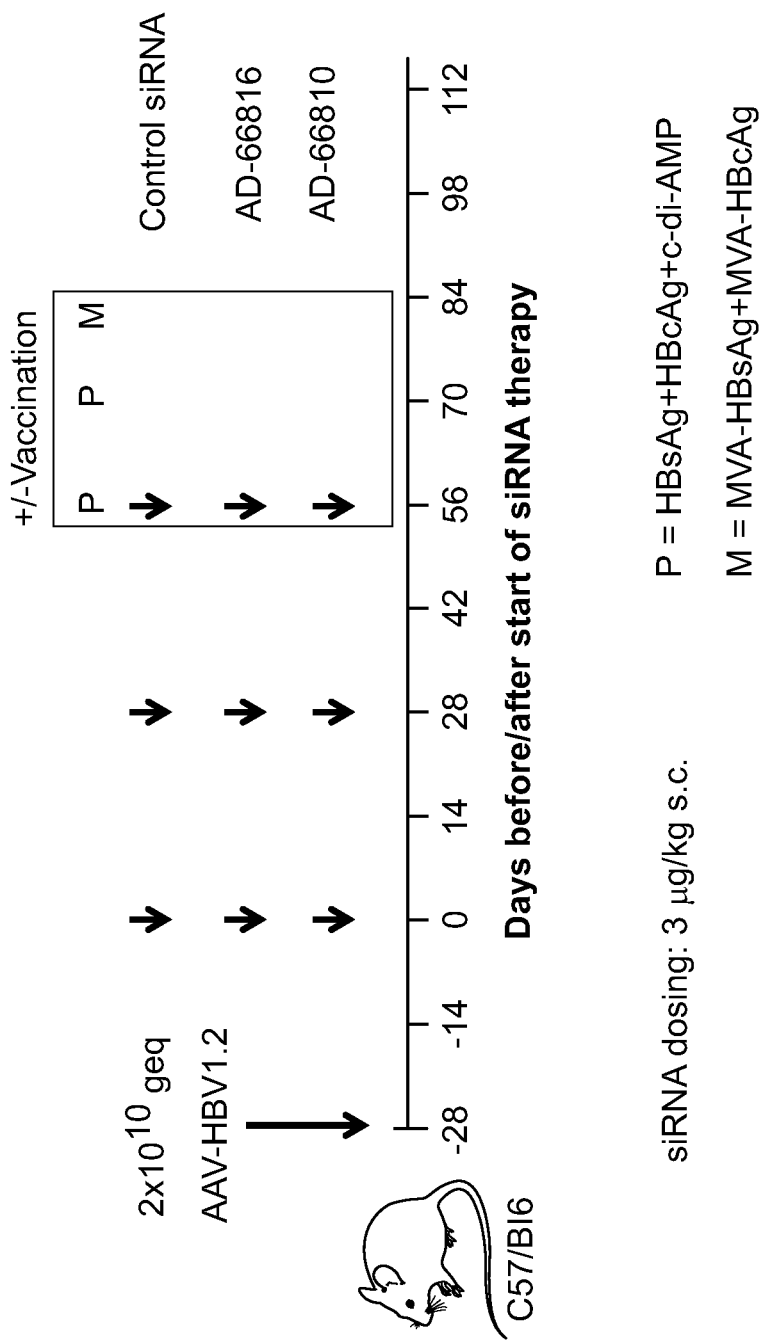
FIG. 12 is a schematic showing a dosing regimen for the experiment assaying the effect of pretreatment of mice infected with an AAV vector encoding HBV with control siRNA or AD-66816 prior to administration of a therapeutic vaccine against HBV.

A second series of experiments were designed to study the combination siRNA/vaccination treatment regimen in a mouse model of acquired HBV infection using an adeno-associated virus infection system. For these studies, wild-type C57/Bl6 mice (9 weeks of age) were injected i.v. with $2 \times 10^{10}$ genome equivalents of Adeno-Associated-Virus Serotype 8 (AAV8) carrying a 1.2-fold overlength HBV genome of genotype D (AAV-HBV1.2) (see, e.g., Yang, et al. (2014) *Cell and Mol Immunol* 11:71). Starting 4 weeks after AAV-transduction (on day −28), animals were treated with three doses of either a control siRNA, or HBV siRNA (HBV AD-66816 or AD-66810) on days 0, 29, and 57, and subsequently half of the animals in each group were treated with a vaccine regimen consisting of prime protein vaccination with HBsAg, HbcAg, and 10 µg c-di-AMP at days 57 and 70, and boosted with MVA-HBs and MVA-HBc at day 84. The treatment regimen is shown in FIG. 12.

Figure 13A:
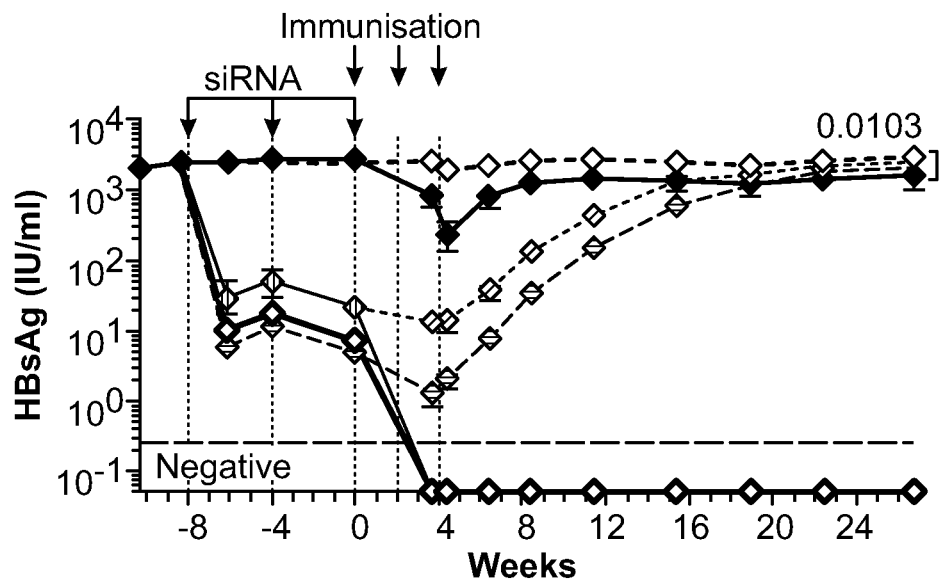
FIGS. 13A-13G are based on the dosing regimen provided in FIG. 12.
Figure 13B:
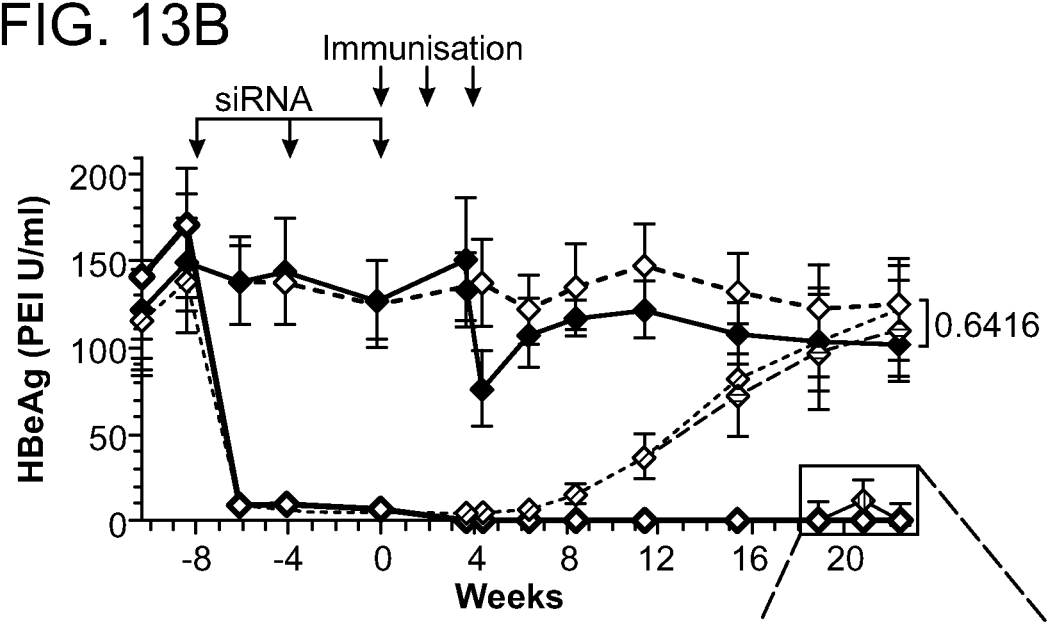

Following AAV-HBV1.2 transduction, HBsAg and HBeAg values rose to levels comparable to the levels seen in HBV transgenic mice (HBVxfs) (see, e.g., FIGS. 13A and 13B). Mice treated with the HBV siRNAs showed mean reductions of HBsAg levels of about 2 $\log_{10}$ scales and of HBeAg levels greater than 1 $\log_{10}$ scale such that HBsAg and HBeAg levels dropped to less than about 500 IU/per ml, whereas the control siRNA had no effect on antigen levels. Animals treated with one of the HBV siRNAs that did not receive the vaccine regimen showed slowly rebounding antigen levels after the last application of the siRNA. Antigenemia returned to baseline levels after 18 weeks. The combination treatment with the HBV-siRNA and vaccine regimen resulted in a durable response with a decrease in HBsAg and HBeAg to below the limit of detection through the duration of the experiment. A decrease in HBsAg and HBeAg levels was observed prior to the administration of the MVA boost, suggesting that the protein vaccination may be sufficient to affect a cure. Both serum and liver HBV DNA and RNA were significantly decreased after combination treatment with the HBV-siRNA and vaccine regimen (FIGS. 13D-13G). This demonstrates, that RNAi-mediated suppression can strongly reduce antigen expression, but that treatment with the vaccine regimen extends the durability of response.

The vaccine regimen alone in animals that received the control siRNA produced a transient decline of antigen levels which rebounded towards the end of the experiment. In contrast, all animals that received an HBV-siRNA and vaccination, HBsAg and HBeAg levels decreased to below the detection limit after start of vaccination. Antigen levels remained largely undetectable at all through the last time point measured at least 22 weeks after the last siRNA application (FIGS. 13A and 13B). The durable loss of antigenemia in HBV siRNA pretreated animals, in contrast to the antigen rebound in control siRNA pretreated animals, further demonstrates that immune control was only achieved in animals which had lowered antigen titers before vaccination.

Coinciding with the loss of antigenemia, animals treated with HBV siRNA plus the vaccine regimen developed high titers of anti-HBs antibodies and resulted in anti-HBs and anti-HBe seroconversion in all vaccinated animals (FIG. 14). siRNA-pretreated animals developed 10-fold higher and more constant anti-HBs titers and were able to completely and persistently clear serum HBsAg and HBeAg. Interestingly, 3/12 mice vaccinated after HBV siRNA treatment showed a transient drop in anti-HBe levels between week 15 and 22 resulting in a low-level relapse of HBeAg (FIG. 13C) that was again controlled. Although anti-HBs antibodies could also be measured in animals that received the control siRNA plus the vaccine regimen, the levels were lower. Further, only animals that received HBV siRNA plus the vaccine regimen developed anti-HBe antibodies. Taken together, functional cure was not achieved by the siRNA treatment regimen or the therapeutic vaccination regimen alone. However, the loss of antigenemia, as well as development of anti-HBs and anti-HBe antibodies, demonstrates that the combination HBV siRNA plus vaccine regimen can achieve a functional cure.

Figure 15A:
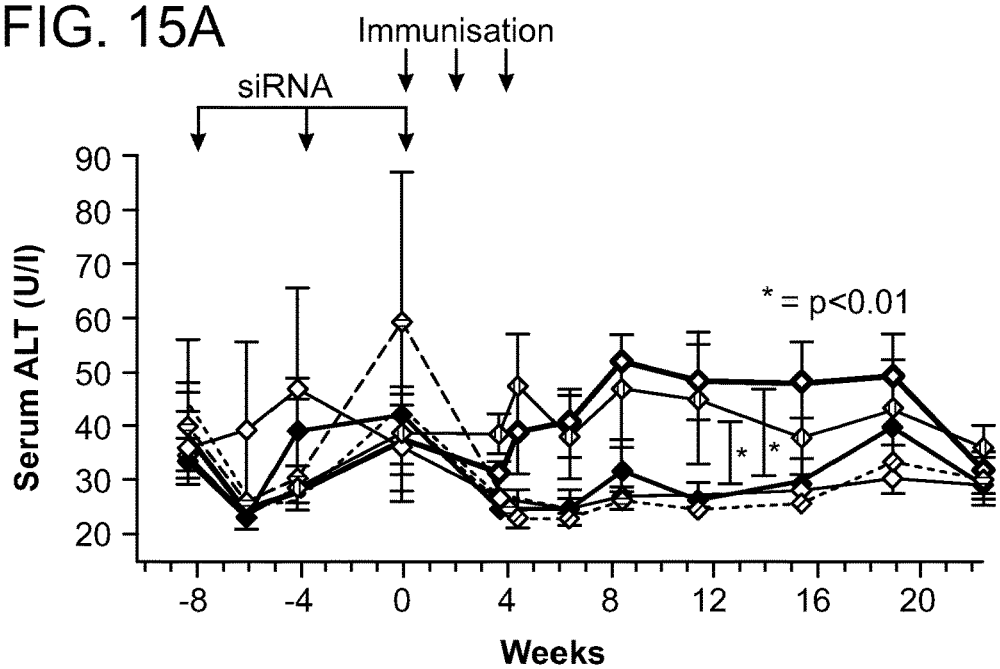
FIGS. 15A and 15B show (15A) ALT levels and (15B) body weights of the animals throughout the experiment based on the dosing regimen provided in FIG. 12.

Throughout the experiment, ALT and body weight of the animals were monitored. The loss of antigenemia coincided with slight increases of ALT activity seen in treatment groups which had received HBV siRNA in conjunction with the vaccination regimen (FIG. 15A). These groups showed significant but mild increases (both $p>0.05$ or smaller by repeated measure two-way ANOVA; only comparing time points after start of vaccination) as compared to all other treatment groups that did not receive the combination HBV-siRNA-vaccine regimen. Without being bound by mechanism, it is suggested that the CD8+ T cells induced by the combinatorial HBV siRNA-vaccine regimen killed HBV-expressing hepatocytes resulting in elevated ALT.

Figure 15B:
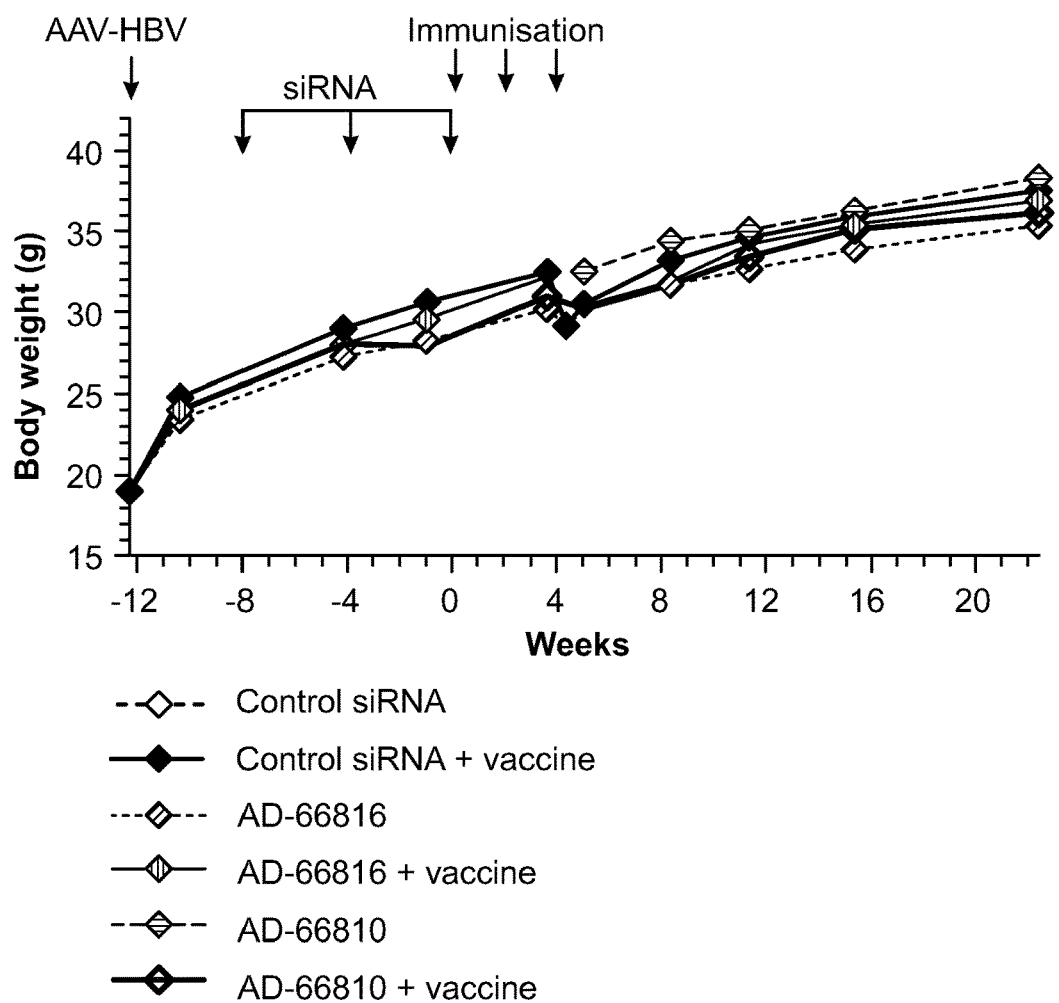

The body weight of the animals was measured throughout the experiment to assess tolerability of the treatments. There was steady increases throughout the experiment independent of siRNA treatment. Animals that were vaccinated showed a slight and transient decrease (approximately 5%) of body weight after vaccination, but rebounded to normal levels within nine days, and subsequently gained weight comparable to the control groups (FIG. 15B). Taken together, both, ALT activity and body weight data demonstrate that all examined treatments, including siRNA only, vaccine only, as well as the combinatorial siRNA/vaccine regimen are well tolerated.

The number and timing of doses of siRNA to knockdown HBsAg level in serum depends, for example, on the specific agent used. Due to the duration and potency of the exemplary GalNAc siRNAs used in the methods herein and provided, for example, in Appendix A and in PCT Publication No. WO 2016/077321 (the entire contents of which are incorporated herein by reference), a single dose of siRNA may be sufficient to provide the level and duration of knockdown required prior to administration of the therapeutic vaccine. As shown in FIG. 4, a single dose of an AAV vector encoded shRNA was sufficient to provide durable knockdown of HBV antigens and HBV DNA. Those of skill in the art are able to monitor HBV disease status, e.g., by measuring HBsAg levels in blood, to determine the timing and level of siRNA and vaccine administration appropriate for a specific subject.

A number of therapeutic HBV vaccines are known in the art and discussed herein. In preferred embodiments, a prime-boost vaccination protocol, such as the protocol that is used herein, is preferred. However, the HBV antigen knockdown method provided herein can be used in combination with other therapeutic HBV vaccines known in the art, including those found to be insufficient when administered alone. Vaccinations include at least two doses of an antigen in protein or nucleic acid form. In certain embodiments, the vaccination includes three doses of a protein-based vaccine. In preferred embodiments, the methods include heterologous vaccine administration, i.e., at least one protein-based vaccine dose and at least one nucleic-acid based vaccine dose. Exemplary embodiments of vaccines and dosing regimens are provided, for example, in PCT Publication No. WO 2017/121791, the entire contents of which are incorporated herein by reference.

The methods provided herein include the use of a nucleic acid-based vaccine comprising an expression vector construct encoding an HBcAg or an HBsAg, wherein the construct encodes a protein that shares an epitope with the protein-based vaccine. Therefore, it is clearly understood that neither the nucleic acid-based vaccine nor the protein-based vaccine are required to provide the full length protein. The nucleic acid-based vaccine and the protein-based vaccine are required to provide at least one shared epitope that is present in HBcAg or HBsAg, and does not require that the full length protein be provided. As noted above, epitopes may be relatively short, MHC class I molecules that are typically peptides about 8 to 11 amino acids in length, whereas MHC class II molecules present longer peptides about 13 to 17 amino acids in length, with conformational epitopes being longer. However, it is understood that the use of protein antigens and coding sequences for protein antigens that encode multiple epitopes is preferred. Further, it is understood that the antigens present in the protein-based vaccine and encoded by the nucleic-acid based vaccine may or may not be identical. It is also obvious that antigens should also be selected for their immunogenicity. Such antigens are well known in the art.

In certain embodiments, the order of administration of the protein-based vaccine and the nucleic acid-based vaccine are reversed as compared to the order exemplified in the methods provided herein. That is, the nucleic acid-based vaccine is administered first and the protein-based vaccine is administered second. In certain embodiments, a total of three doses of vaccine are administered, two doses of the nucleic acid-based vaccine followed by a single dose of the protein-based vaccine. In alternative embodiments, a single dose of the nucleic acid-based vaccine is followed by two doses of a protein based vaccine. In other embodiments, one dose of each vaccine is administered.

In preferred embodiments, the prime-boost vaccination method includes the use of an adjuvant with protein antigens. Appropriate adjuvants for use in the methods promote a cell-based response to the antigens. Adjuvants preferably provide a balanced Th1/Th2 response.

The siRNA+vaccine methods provided herein can be used in combination with administration of nucleot(s)ide inhibitors which are the standard of care for treatment of HBV. In certain embodiments, subjects are treated with nucleot(s)ide inhibitors prior to treatment with the siRNA+vaccine treatment regimen. In certain embodiments, subjects are treated throughout the siRNA+vaccine treatment regimen with nucleot(s)ide inhibitors. In certain embodiments, the nucleot(s)ide inhibitor is dosed to reduce pre-existing inflammation associated with HBV infection prior to administration of the nucleic acid therapeutic targeted to HBV (e.g., siRNA, shRNA, antisense oligonucleotide).

In certain embodiments, subjects may be pretreated, or concurrently treated, with other agents used for the treatment of HBV. Such agents include, but are not limited to an immune stimulator (e.g., pegylated interferon alfa 2a (PEG-IFN-α2a), Interferon alfa-2b, a recombinant human interleukin-7, and aToll-like receptor 7 (TLR7) agonist), a viral entry inhibitor (e.g., Myrcludex), an oligonucleotide that inhibits the secretion or release of HbsAg (e.g., REP 9AC), a capsid inhibitor (e.g., Bay41-4109 and NVR-1221), a cccDNA inhibitor (e.g., IHVR-25), a Rig-I ligand, or an immune checkpoint regulator. In certain embodiments, the immune stimulator is a Rig-I ligand or an immune checkpoint regulator. A functional cure includes a sustained period of at least 3 months, preferably 6 months of HBsAg below 50 IU/ml, or a detectable antibody response to HBsAg. In preferred embodiments, a functional cure includes both a sustained period of at least 3 months, preferably 6 months of HBsAg below 50 IU/ml and a detectable antibody response to HBsAg.

A. RNAi Agents for Use in the Methods of the Invention

The present invention includes the use of iRNAs, which inhibit the expression of at least one HBV transcript, and preferably three or four HBV transcripts (open reading frames, sometimes referred to herein as genes). Due to the highly condensed structure of the HBV genome, it is possible to design single iRNAs that will inhibit the expression of three or four HBV transcripts (see FIG. 1). For the sake of simplicity, the text herein refers to "an HBV transcript" or "the HBV transcript." It is understood that preferred embodiments include inhibition of more than one HBV transcript (or open reading frame), preferably at least three HBV transcripts (or open reading frames). Further, it is understood that there are eight HBV genotypes, and two proposed additional genotypes, that may further include mutations from published sequences. Therefore, certain iRNA agents may inhibit different numbers of genes based on the specific genotype and subject infected with HBV.

In some embodiments, the iRNA agent includes double stranded ribonucleic acid (dsRNA) molecules for inhibiting the expression or decreasing the level of an HBV transcript in a cell in a subject with an HBV infection. The dsRNA includes an antisense strand having a region of complementarity, which is complementary to at least a part of an mRNA formed in the expression of an HBV transcript. The region of complementarity is about 30 nucleotides or less in length (e.g., about 30, 29, 28, 27, 26, 25, 24, 23, 22, 21, 20, 19, or 18 nucleotides or less in length). Upon contact with a cell expressing the HBV gene, the iRNA selectively inhibits the expression of at least one, preferably three or four HBV genes. In preferred embodiments, inhibition of expression is determined by the qPCR method in an appropriate cell line as provided in the examples. For in vitro assessment of activity, percent inhibition is determined using the methods provided in Example 2 of PCT Publication No. WO 2016/077321 at a single dose at a 10 nM duplex final concentration. For in vivo studies, the level after treatment can be compared to, for example, an appropriate historical control or a pooled population sample control to determine the level of reduction, e.g., when a baseline value is not available for the subject. An appropriate control must be carefully selected by one of skill in the art.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of an HBV gene. As multiple HBV genotypes are known, iRNA agents are preferably designed to inhibit expression of HBV genes across as many genotypes as possible. It is understood that an siRNA that is perfectly complementary to one or more HBV genotypes will not be perfectly complementary to all genotypes. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is 15 and 30 base pairs in length, e.g., 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

Similarly, the region of complementarity to the target sequence is 15 and 30 nucleotides in length, e.g., 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

In some embodiments, the dsRNA is about 15 to 20 nucleotides in length, or about 25 to 30 nucleotides in length. In general, the dsRNA is long enough to serve as a substrate for the Dicer enzyme. For example, it is well-known in the art that dsRNAs longer than about 21-23 nucleotides in length may serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 9 to 36 base pairs, e.g., about 10-36, 11-36, 12-36, 13-36, 14-36, 15-36, 9-35, 10-35, 11-35, 12-35, 13-35, 14-35, 15-35, 9-34, 10-34, 11-34, 12-34, 13-34, 14-34, 15-34, 9-33, 10-33, 11-33, 12-33, 13-33, 14-33, 15-33, 9-32, 10-32, 11-32, 12-32, 13-32, 14-32, 15-32, 9-31, 10-31, 11-31, 12-31, 13-32, 14-31, 15-31, 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an iRNA agent useful to target HBV gene expression is not generated in the target cell by cleavage of a larger dsRNA.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 2, at least 3, at least 4, at least 5, at least 6, at least 7, at least 8, at least 9, at least 10, at least 20, at least 23 or more unpaired nucleotides.

In some embodiments, a dsRNA agent of the invention comprises a tetraloop. As used herein, "tetraloop" in the context of a dsRNA refers to a loop (a single stranded region) consisting of four nucleotides that forms a stable secondary structure that contributes to the stability of adjacent Watson-Crick hybridized nucleotides. Without being limited to theory, a tetraloop may stabilize an adjacent Watson-Crick base pair by stacking interactions. In addition, interactions among the four nucleotides in a tetraloop include, but are not limited to, non-Watson-Crick base pairing, stacking interactions, hydrogen bonding, and contact interactions (Cheong et al., Nature 1990 Aug. 16; 346(6285):680-2; Heus and Pardi, Science 1991 Jul. 12; 253(5016): 191-4). A tetraloop confers an increase in the melting temperature (Tm) of an adjacent duplex that is higher than expected from a simple model loop sequence consisting of four random bases. For example, a tetraloop can confer a melting temperature of at least 55° C. in 10 mM NaHPO$_4$ to a hairpin comprising a duplex of at least 2 base pairs in length. A tetraloop may contain ribonucleotides, deoxyribonucleotides, modified nucleotides, and combinations thereof. Examples of RNA tetraloops include the UNCG family of tetraloops (e.g., UUCG), the GNRA family of tetraloops (e.g., GAAA), and the CUUG tetraloop. (Woese et al., Proc Natl Acad Sci USA. 1990 November; 87(21):8467-71; Antao et al., Nucleic Acids Res. 1991 Nov. 11; 19(21):5901-5). Examples of DNA tetraloops include the d(GNNA) family of tetraloops (e.g., d(GTTA), the d(GNRA)) family of tetraloops, the d(GNAB) family of tetraloops, the d(CNNG) family of tetraloops, the d(TNCG) family of tetraloops (e.g., d(TTCG)). (Nakano et al. Biochemistry, 41 (48), 14281-14292, 2002; Shinji et al. Nippon Kagakkai Koen Yokoshu vol. 78th; no. 2; page. 731 (2000).)

In certain embodiments of the invention, tetraloop- and modified nucleotide-containing dsNAs are contemplated as described, e.g., as described in U.S. Patent Publication No. 2011/0288147, the entire contents of which are incorporated by reference herein. In certain such embodiments, a dsNA of the invention possesses a first strand and a second strand, where the first strand and the second strand form a duplex region of 19-25 nucleotides in length, wherein the first strand comprises a 3' region that extends beyond the first strand-second strand duplex region and comprises a tetraloop, and the dsNA comprises a discontinuity between the 3' terminus of the first strand and the 5' terminus of the second strand.

Optionally, the discontinuity is positioned at a projected Dicer cleavage site of the tetraloop-containing double stranded nucleic acid (dsNA). It is contemplated that, as for any of the other duplexed oligonucleotides of the invention, tetraloop-containing duplexes of the invention can possess any range of modifications disclosed herein or otherwise known in the art, including, e.g., 2'-O-methyl, 2'-fluoro, inverted base, GalNAc moieties, etc. Typically, every nucleotide on both strands of the tetraloop-containing dsNA is chemically modified if the tetraloop-containing dsNA is going to be delivered without using lipid nanoparticles or some other delivery method that protects the dsNA from degradation during the delivery process. However, in certain embodiments, one or more nucleotides are not modified.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

A dsRNA as described herein can further include one or more single-stranded nucleotide overhangs e.g., 1, 2, 3, or 4 nucleotides. dsRNAs having at least one nucleotide overhang can have unexpectedly superior inhibitory properties relative to their blunt-ended counterparts. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA. In certain embodiments, longer, extended overhangs are possible.

A dsRNA can be synthesized by standard methods known in the art. iRNA compounds of the invention may be prepared using a two-step procedure. First, the individual strands of the double stranded RNA molecule are prepared separately. Then, the component strands are annealed. The individual strands of the siRNA compound can be prepared using solution-phase or solid-phase organic synthesis or both. In certain embodiments, the iRNA compound is produced from an expression vector delivered into a cell.

In one aspect, a dsRNA of the invention includes at least two nucleotide sequences, a sense sequence and an antisense sequence. The sense strand is selected from the group of sequences provided in any one of the Tables in Appendix A, and the corresponding antisense strand of the sense strand is selected from the group of sequences of any one of the Tables in Appendix A.

In some embodiments, the sense strand is selected from the group of sequences provided in any one of the Tables in Appendix A, and the corresponding antisense strand of the sense strand is selected from the group of sequences of any one of the Tables in Appendix A. In this aspect, one of the two sequences is complementary to the other of the two sequences, with one of the sequences being substantially complementary to a sequence of an mRNA generated in the expression of an HBV gene. As such, in this aspect, a dsRNA will include two oligonucleotides, where one oligonucleotide is described as the sense strand in any one of the Tables in Appendix A and the second oligonucleotide is described as the corresponding antisense strand of the sense strand in any one of the Tables in Appendix A. In one embodiment, the substantially complementary sequences of the dsRNA are contained on separate oligonucleotides. In another embodiment, the substantially complementary sequences of the dsRNA are contained on a single oligonucleotide.

It is understood that, although some of the sequences in the Tables in Appendix A are described as modified or conjugated sequences, the RNA of the iRNA of the invention e.g., a dsRNA of the invention, may comprise any one of the sequences set forth in the Tables in Appendix A that is un-modified, unconjugated, or modified or conjugated differently than described therein. Additional target sites are provided, for example, in PCT Publication Nos. WO 2016/077321, WO 2012/024170, WO 2017/027350, and WO 2013/003520; and in Michler, 2016, the entire contents of each of which are incorporated herein by reference.

The skilled person is well aware that dsRNAs having a duplex structure of about 20 to 23 base pairs, e.g., 21, base pairs have been hailed as particularly effective in inducing RNA interference (Elbashir et al., EMBO 2001, 20:6877-6888). However, others have found that shorter or longer RNA duplex structures can also be effective (Chu and Rana (2007) RNA 14:1714-1719; Kim et al. (2005) Nat Biotech 23:222-226). In the embodiments described above, by virtue of the nature of the oligonucleotide sequences provided in any one of the Tables in Appendix A, dsRNAs described herein can include at least one strand of a length of minimally 21 nucleotides. It can be reasonably expected that shorter duplexes having one of the sequences of any one of the Tables in Appendix A minus only a few nucleotides on one or both ends can be similarly effective as compared to the dsRNAs described above. Hence, dsRNAs having a sequence of at least 15, 16, 17, 18, 19, 20, or more contiguous nucleotides derived from one of the sequences of any one of the Tables in Appendix A and differing in their ability to inhibit the expression of an HBV gene by not more than 5, 10, 15, 20, 25, or 30% inhibition from a dsRNA comprising the full sequence.

An iRNA as described herein can contain one or more mismatches to the target sequence, or to one or more HBV target sequences due, e.g., to sequence variations among the HBV genotypes. In one embodiment, an iRNA as described herein contains no more than 3 mismatches. If the antisense strand of the iRNA contains mismatches to a target sequence, it is preferable that the area of mismatch is not located in the center of the region of complementarity. If the antisense strand of the iRNA contains mismatches to the target sequence, it is preferable that the mismatch be restricted to be within the last 5 nucleotides from either the 5'- or 3'-end of the region of complementarity. For example, for a 23 nucleotide iRNA agent the strand which is complementary to a region of an HBV gene, generally does not contain any mismatch within the central 13 nucleotides. The methods described herein or methods known in the art can be used to determine whether an iRNA containing a mismatch to a target sequence is effective in inhibiting the expression of an HBV gene. Consideration of the efficacy of iRNAs with mismatches in inhibiting expression of an HBV gene is important, especially if the particular region of complementarity in an HBV gene is known to have polymorphic sequence variation within various genotypes and the population.

i. Modified iRNAs for Use in the Methods of the Invention

In some embodiments, the RNA of the iRNA for use in the invention e.g., a dsRNA, is un-modified, and does not comprise, e.g., chemical modifications or conjugations known in the art and described herein, e.g., when produced from an expression vector. In other embodiments, the RNA of an iRNA of the invention, e.g., a dsRNA, is chemically modified to enhance stability or other beneficial characteristics. In certain embodiments of the invention, substantially all of the nucleotides of an iRNA of the invention are modified. In other embodiments of the invention, all of the nucleotides of an iRNA of the invention are modified. iRNAs of the invention in which "substantially all of the nucleotides are modified" are largely but not wholly modified and can include not more than 5, 4, 3, 2, or 1 unmodified nucleotides.

The nucleic acids featured in the invention can be synthesized or modified by methods well established in the art, such as those described in "Current protocols in nucleic acid chemistry," Beaucage, S. L. et al. (Edrs.), John Wiley & Sons, Inc., New York, N.Y., USA, which is incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative US patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. No. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative US patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in iRNAs, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative US patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., Science, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O-$CH_2CH_2OCH_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_3$)$_2$.

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative US patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

The RNA of an iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as deoxy-thymine (dT). 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative US patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12): 3185-3193).

In some embodiments, the iRNA of the invention comprises one or more monomers that are UNA (unlocked nucleic acid) nucleotides. UNA is unlocked acyclic nucleic acid, wherein any of the bonds of the sugar has been removed, forming an unlocked "sugar" residue. In one example, UNA also encompasses monomer with bonds between C1'-C4' have been removed (i.e. the covalent carbon-oxygen-carbon bond between the C1' and C4' carbons). In another example, the C2'-C3' bond (i.e. the covalent carbon-carbon bond between the C2' and C3' carbons) of the sugar has been removed (see *Nuc. Acids Symp. Series*, 52, 133-134 (2008) and Fluiter et al., *Mol. Biosyst.*, 2009, 10, 1039 hereby incorporated by reference).

The RNA of an iRNA can also be modified to include one or more bicyclic sugar moities. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an agent of the invention may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-CH2-O-2' bridge. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. Et al., (2007) *Mol Canc Ther* 6(3):833-843; Grunweller, A. et al., (2003) *Nucleic Acids Research* 31(12): 3185-3193). Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-(CH2)-O-2' (LNA); 4'-(CH2)-S-2; 4'-(CH2)$_2$-O-2' (ENA); 4'-CH(CH3)-O-2' (also referred to as "constrained ethyl" or "cEt") and 4'-CH(CH2OCH3)-O-2' (and analogs thereof; see, e.g., U.S. Pat. No. 7,399,845); 4'-C(CH3)(CH3)-O-2' (and analogs thereof; see e.g., U.S. Pat. No. 8,278,283); 4'-CH2-N(OCH3)-2' (and analogs thereof; see e.g., U.S. Pat. No. 8,278,425); 4'-CH2-O—N (CH3)-2' (see, e.g., US20040171570); 4'-CH2-N(R)—O-2', wherein R is H, C1-C12 alkyl, or a protecting group (see, e.g., U.S. Pat. No. 7,427,672); 4'-CH2-C(H)(CH3)-2' (see, e.g., Chattopadhyaya et al., *J. Org. Chem.*, 2009, 74, 118-134); and 4'-CH2-C(=CH2)-2' (and analogs thereof; see, e.g., U.S. Pat. No. 8,278,426). The entire contents of each of the foregoing are hereby incorporated herein by reference.

Additional representative US patents and US patent publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 20080039618; and US 20090012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

The RNA of an iRNA can also be modified to include one or more constrained ethyl nucleotides. As used herein, a "constrained ethyl nucleotide" or "cEt" is a locked nucleic acid comprising a bicyclic sugar moiety comprising a 4'-CH (CH3)-O-2' bridge. In one embodiment, a constrained ethyl nucleotide is in the S conformation referred to herein as "S-cEt."

An iRNA of the invention may also include one or more "conformationally restricted nucleotides" ("CRN"). CRN are nucleotide analogs with a linker connecting the C2' and C4' carbons of ribose or the C3 and -C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US 20130190383 and WO 2013036868, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in WO 2011005861.

Other modifications of the nucleotides of an iRNA of the invention include a 5' phosphate or 5' phosphate mimic, e.g., a 5'-terminal phosphate or phosphate mimic on the antisense strand of an RNAi agent. Suitable phosphate mimics are disclosed in, for example US20120157511, the entire contents of which are incorporated herein by reference.

In certain specific embodiments, the RNAi agent for use in the methods of the invention is an agent selected from the group of agents listed in any one of the Tables in Appendix A. These agents may further comprise a ligand.

ii. iRNAs Conjugated to Ligands

Another modification of the RNA of an iRNA of the invention involves chemically linking to the RNA one or more ligands, moieties or conjugates that enhance the activity, cellular distribution, or cellular uptake of the iRNA. Such moieties include but are not limited to lipid moieties such as a cholesterol moiety (Letsinger et al., *Proc. Natl. Acad. Sci. USA*, 1989, 86: 6553-6556), cholic acid (Manoharan et al., *Biorg. Med. Chem. Let.*, 1994, 4:1053-1060), a thioether, e.g., beryl-S-tritylthiol (Manoharan et al., *Ann. N.Y. Acad. Sci.*, 1992, 660:306-309; Manoharan et al., *Biorg. Med. Chem. Let.*, 1993, 3:2765-2770), a thiocholesterol (Oberhauser et al., *Nucl. Acids Res.*, 1992, 20:533-538), an aliphatic chain, e.g., dodecandiol or undecyl residues (Saison-Behmoaras et al., *EMBO J*, 1991, 10:1111-1118; Kabanov et al., *FEBS Lett.*, 1990, 259:327-330; Svinarchuk et al., *Biochimie*, 1993, 75:49-54), a phospholipid, e.g., di-hexadecyl-rac-glycerol or triethyl-ammonium 1,2-di-O-hexadecyl-rac-glycero-3-phosphonate (Manoharan et al., *Tetrahedron Lett.*, 1995, 36:3651-3654; Shea et al., *Nucl. Acids Res.*, 1990, 18:3777-3783), a polyamine or a polyethylene glycol chain (Manoharan et al., *Nucleosides & Nucleotides*, 1995, 14:969-973), or adamantane acetic acid (Manoharan et al., *Tetrahedron Lett.*, 1995, 36:3651-3654), a palmityl moiety (Mishra et al., *Biochim. Biophys. Acta*, 1995, 1264:229-237), or an octadecylamine or hexylaminocarbonyloxycholesterol moiety (Crooke et al., *J. Pharmacol. Exp. Ther.*, 1996, 277:923-937).

In one embodiment, a ligand alters the distribution, targeting, or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid, or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, monovalent or multivalent galactose, N-acetyl-galactosamine, N-acetyl-gulucoseamine multivalent mannose, multivalent fucose, glycosylated polyaminoacids, transferrin, bisphosphonate, polyglutamate, polyaspartate, a lipid, cholesterol, a steroid, bile acid, folate, vitamin B12, vitamin A, biotin, or an RGD peptide or RGD peptide mimetic. In certain embodiments, ligands include monovalent or multivalent galactose. In certain embodiments, ligands include cholesterol.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, monovalent or multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated oligonucleotides of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

1. Lipid Conjugates

In one embodiment, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

2. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 33). An RFGF analogue (e.g., amino acid sequence AALLPVL-LAAP (SEQ ID NO: 34) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 35) and the *Drosophila* Antennapedia protein (RQIKIWFQNRRMKWKK (SEQ ID NO: 36) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to a dsRNA agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

3. Carbohydrate Conjugates

In some embodiments of the compositions and methods of the invention, an iRNA oligonucleotide further comprises a carbohydrate. The carbohydrate conjugated iRNA are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In one embodiment, a carbohydrate conjugate for use in the compositions and methods of the invention is a monosaccharide. In another embodiment, a carbohydrate conjugate for use in the compositions and methods of the invention is selected from the group consisting of:

Formula II

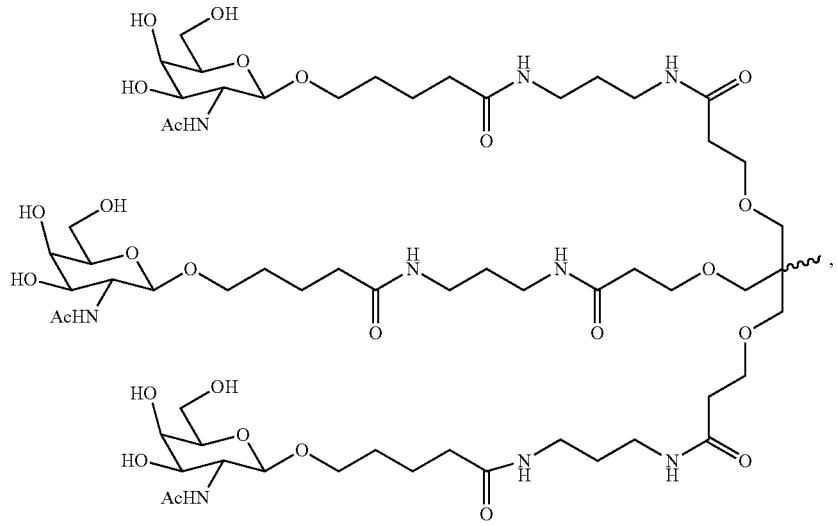

-continued
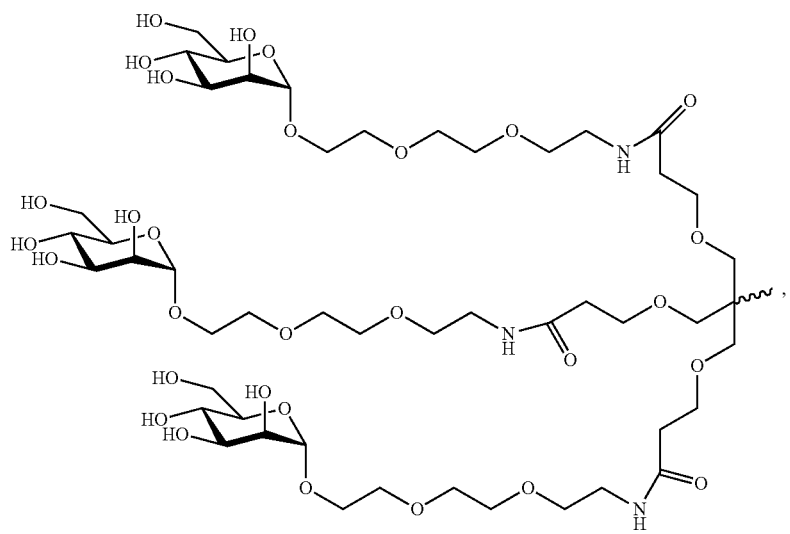
Formula III
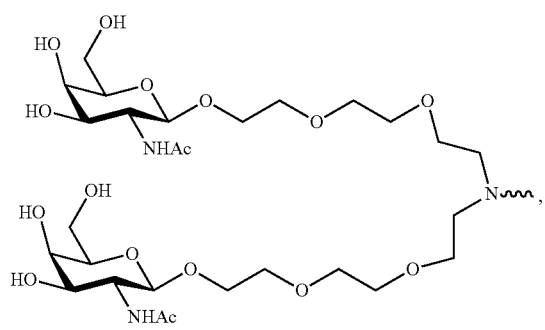
Formula IV
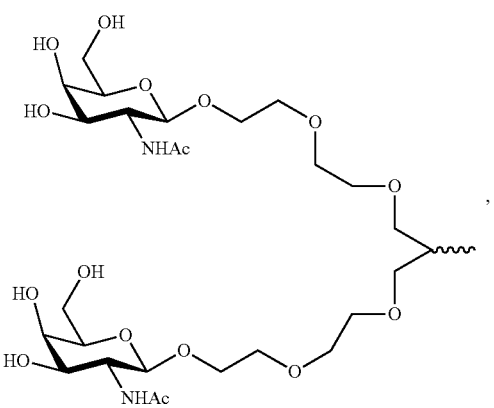
Formula V
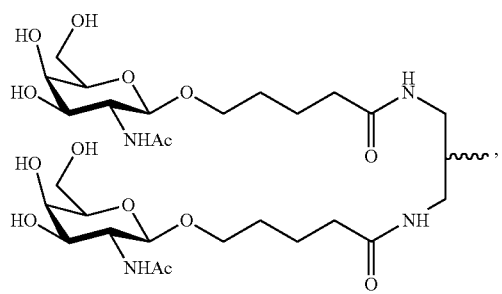
Formula VI
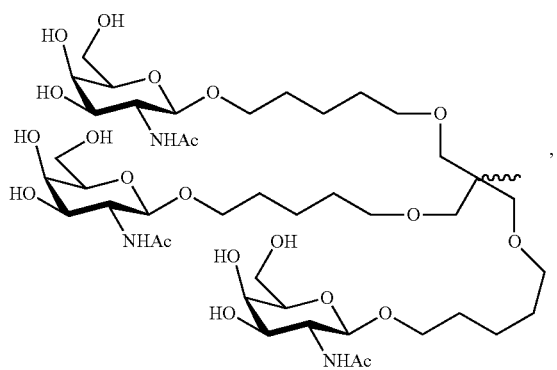
Formula VII
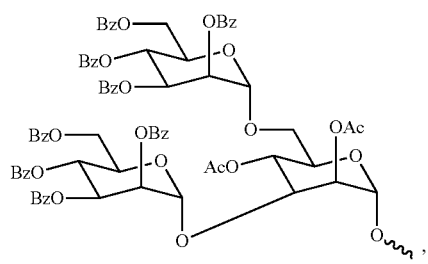
Formula VIII Formula IX
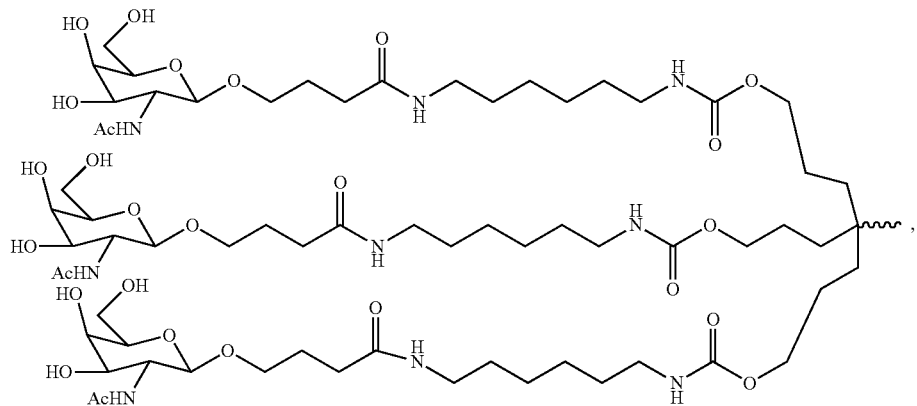
Formula X
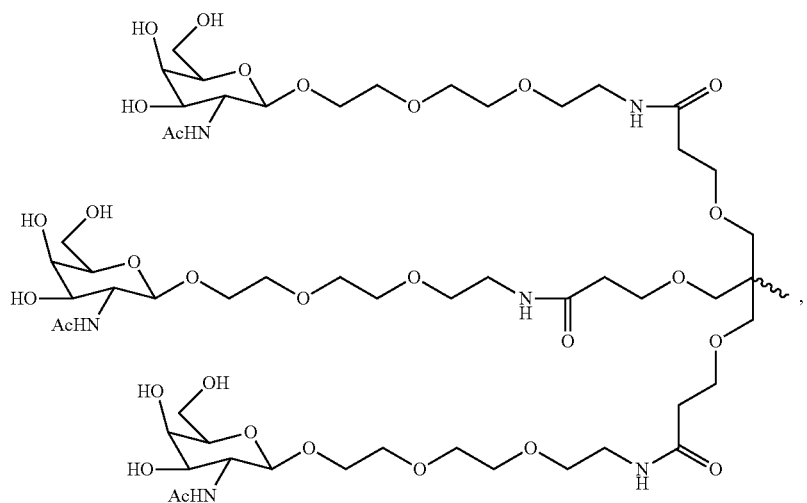
Formula XI
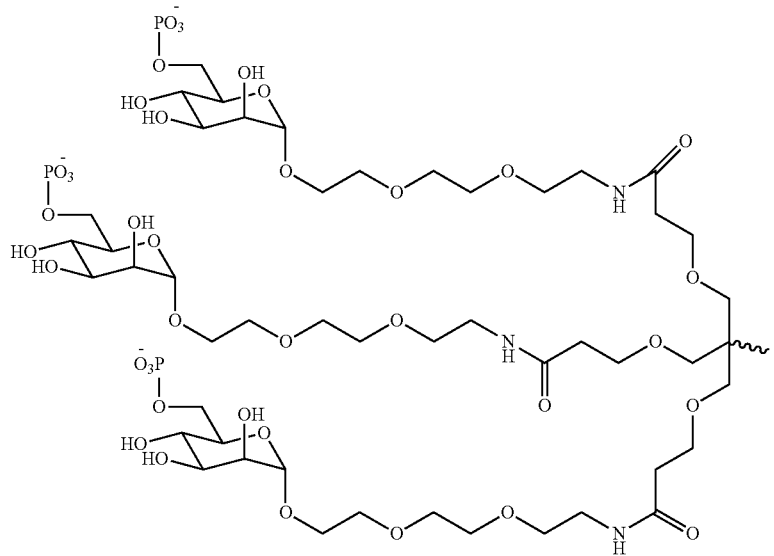

Formula XII
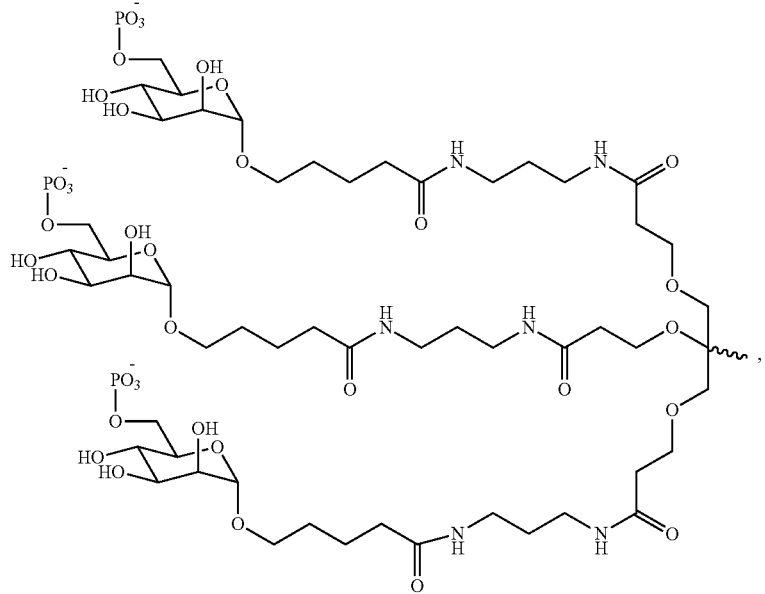
Formula XIII
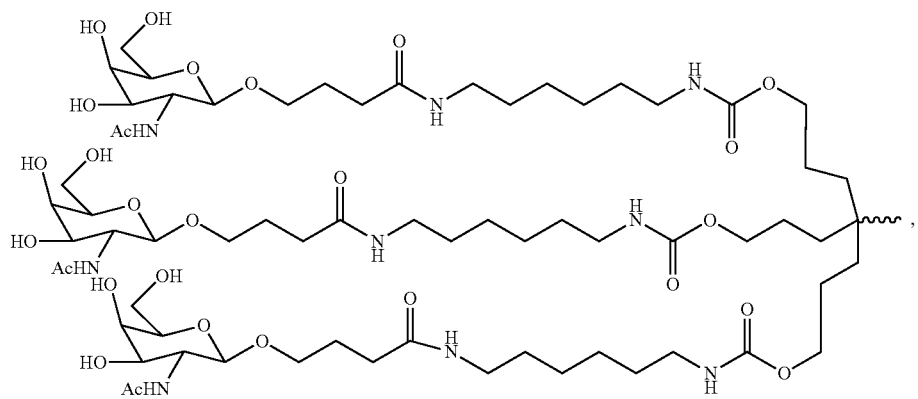
Formula XIV
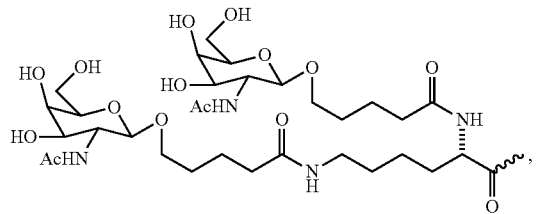
Formula XV
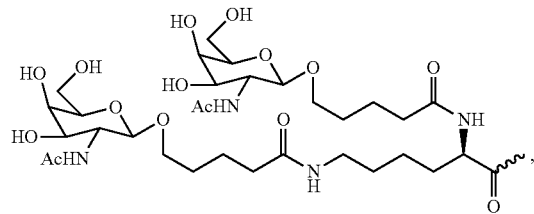
Formula XVI
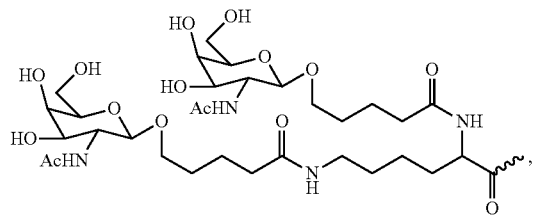
Formula XVII
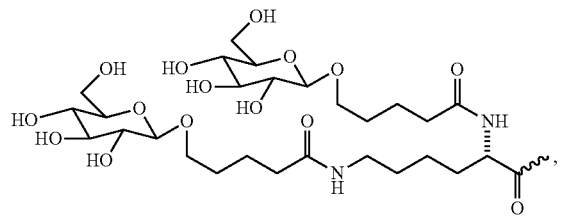

-continued
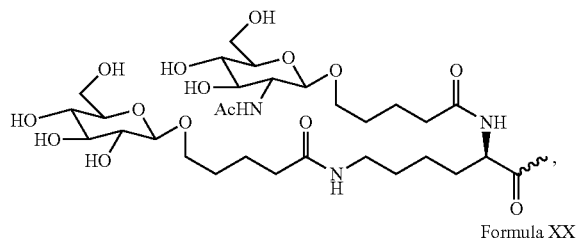
Formula XVIII
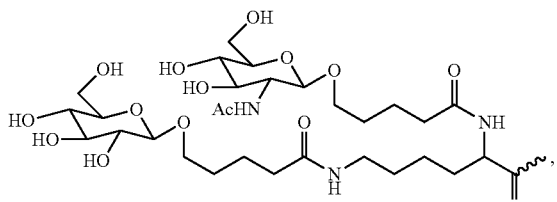
Formula XIX
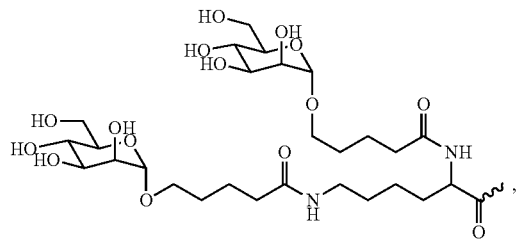
Formula XX
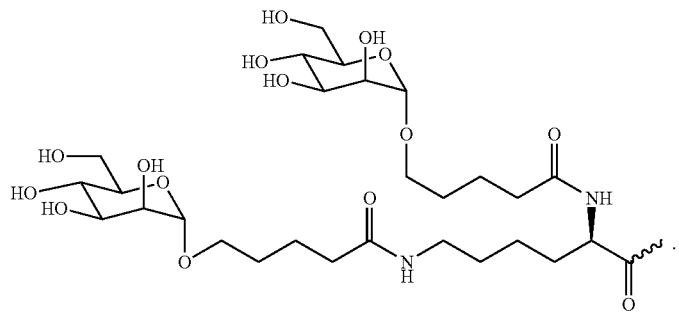
Formula XXI
Formula XXII
In one embodiment, the monosaccharide is an N-acetyl-galactosamine, such as
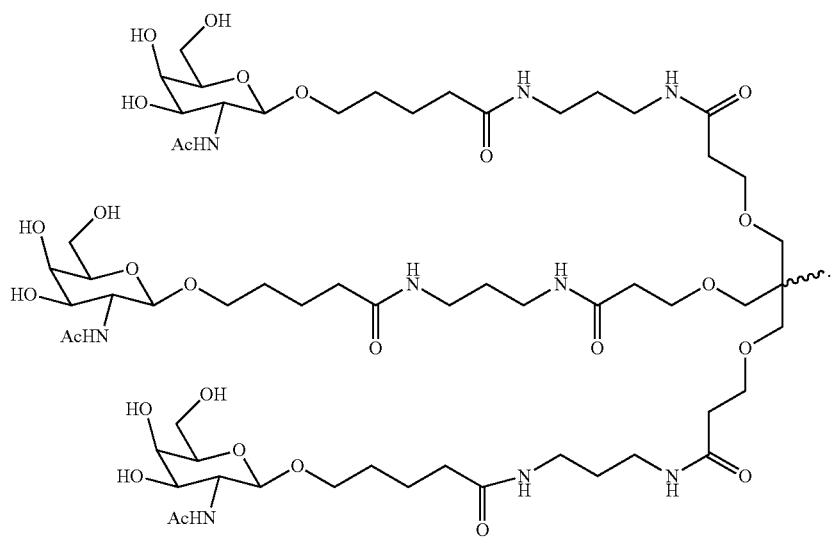
Formula II
Another representative carbohydrate conjugate for use in the embodiments described herein includes, but is not limited to,

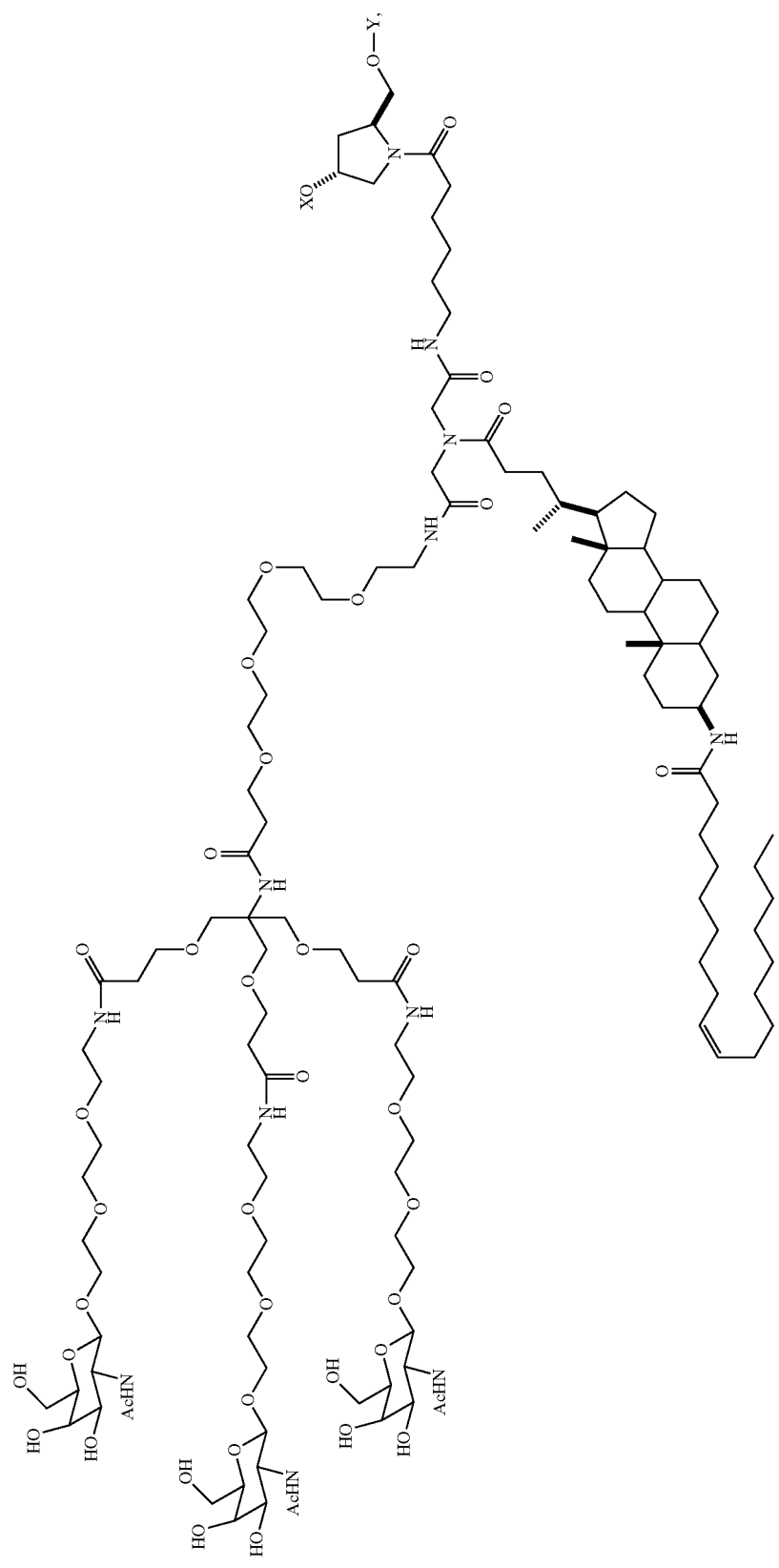
(Formula XXIII)

when one of X or Y is an oligonucleotide, the other is a hydrogen.

In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker.

In one embodiment, the double stranded RNAi agents of the invention comprise one GalNAc or GalNAc derivative attached to the iRNA agent. In another embodiment, the double stranded RNAi agents of the invention comprise a plurality (e.g., 2, 3, 4, 5, or 6) GalNAc or GalNAc derivatives, each independently attached to a plurality of nucleotides of the double stranded RNAi agent through a plurality of monovalent linkers.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker. The hairpin loop may also be formed by an extended overhang in one strand of the duplex.

In some embodiments, the carbohydrate conjugate further comprises one or more additional ligands as described above, such as, but not limited to, a PK modulator or a cell permeation peptide.

Additional carbohydrate conjugates suitable for use in the present invention include those described in WO 2014179620 and WO 2014179627, the entire contents of each of which are incorporated herein by reference.

4. Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2$NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(R8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is about 1-24 atoms, 2-24, 3-24, 4-24, 5-24, 6-24, 6-18, 7-18, 8-18 atoms, 7-17, 8-17, 6-16, 7-16, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

a. Redox Cleavable Linking Groups

In one embodiment, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

b. Phosphate-Based Cleavable Linking Groups

In another embodiment, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, —O—P(S)(H)—S—. A preferred embodiment is —O—P(O)(OH)—O—. These candidates can be evaluated using methods analogous to those described above.

c. Acid Cleavable Linking Groups

In another embodiment, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

d. Ester-Based Linking Groups

In another embodiment, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

e. Peptide-Based Cleaving Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In one embodiment, an iRNA of the invention is conjugated to a carbohydrate through a linker. Non-limiting examples of iRNA carbohydrate conjugates with linkers of the compositions and methods of the invention include, but are not limited to,

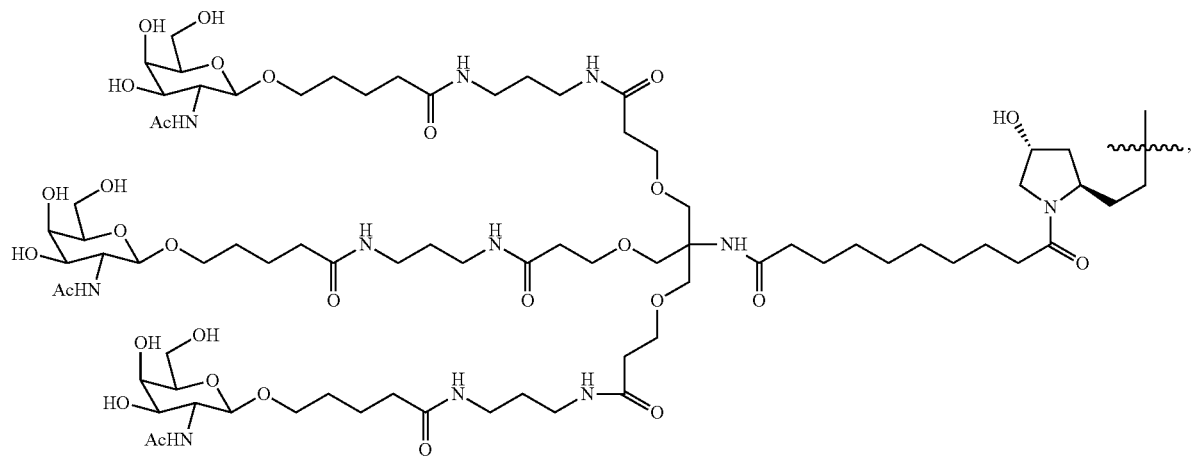
(Formula XXIV)
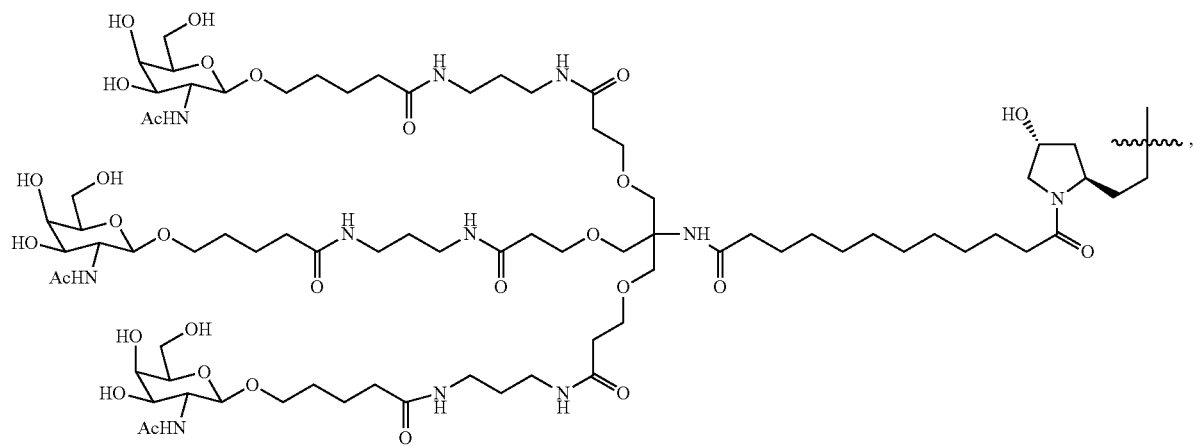
(Formula XXV)
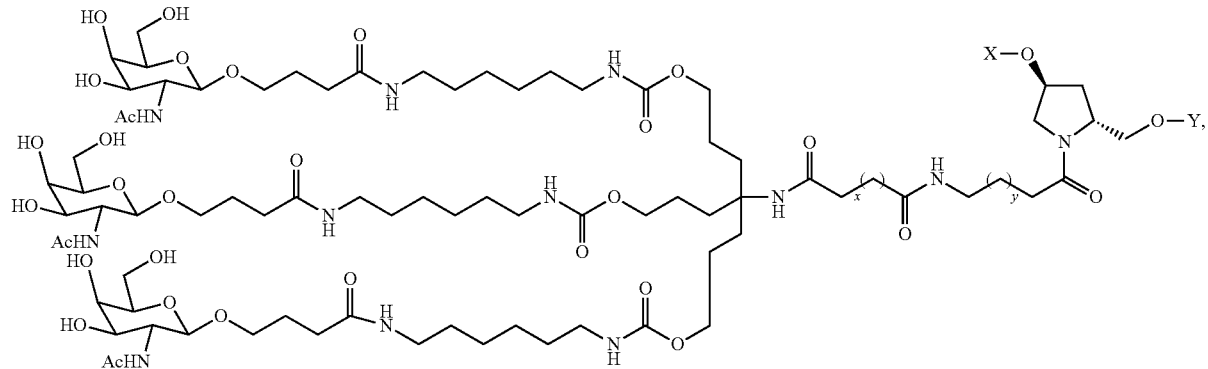
x = 1-30
y = 1-15

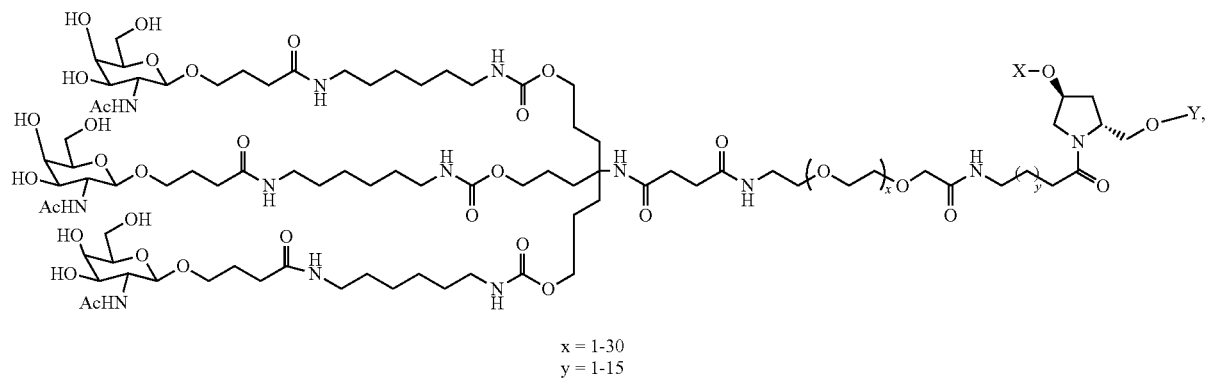
(Formula XXVII)
x = 1-30
y = 1-15
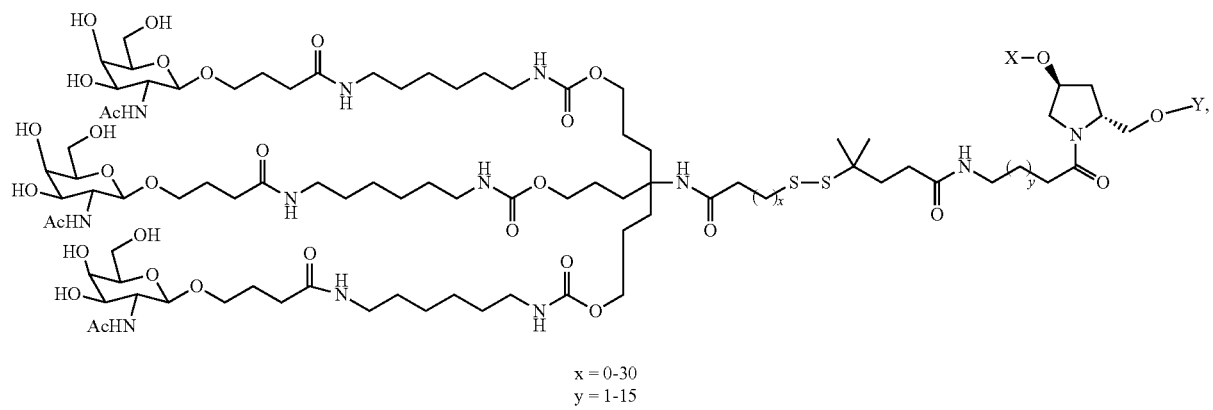
(Formula XXVIII)
x = 0-30
y = 1-15
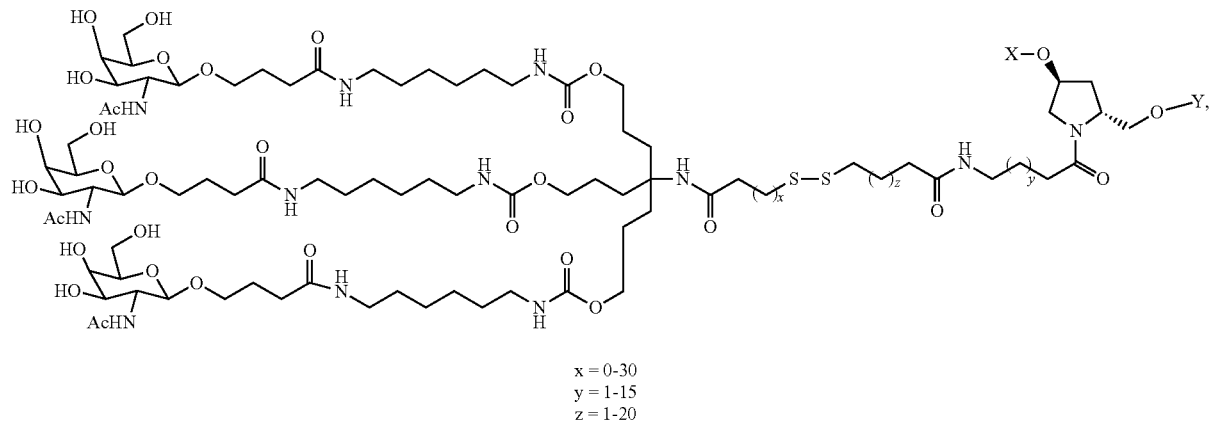
(Formula XXIX)
x = 0-30
y = 1-15
z = 1-20

(Formula XXX)

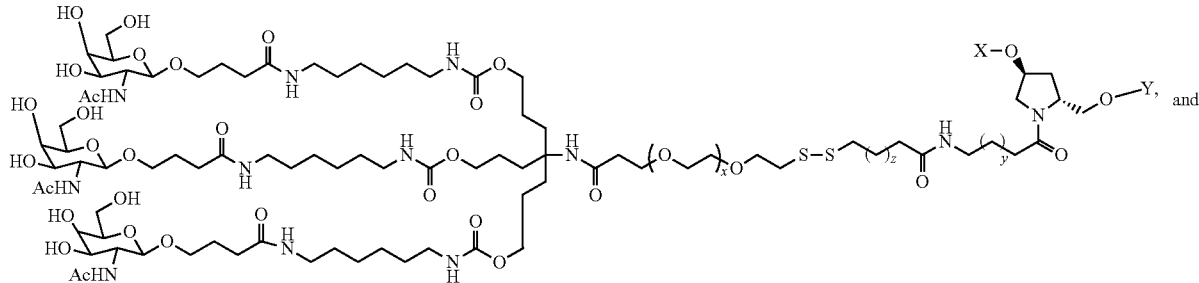

x = 1-30
y = 1-15
z = 1-20

(Formula XXXI)

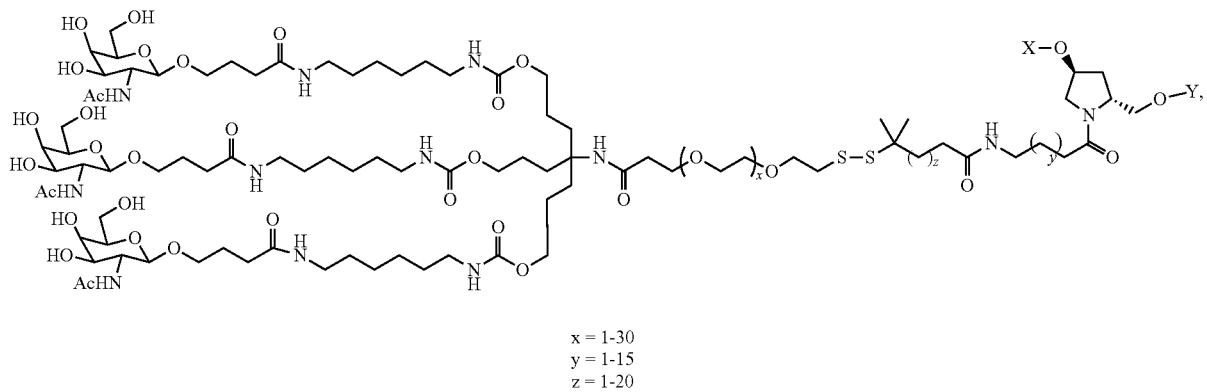

x = 1-30
y = 1-15
z = 1-20 when one of X or Y is an oligonucleotide, the other is a hydrogen.

In certain embodiments of the compositions and methods of the invention, a ligand is one or more "GalNAc" (N-acetylgalactosamine) derivatives attached through a bivalent or trivalent branched linker.

In one embodiment, a dsRNA of the invention is conjugated to a bivalent or trivalent branched linker selected from the group of structures shown in any of formula (XXXII)-(XXXV):

Formula XXXII

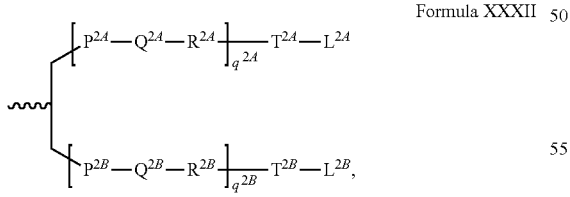

Formula XXXIII

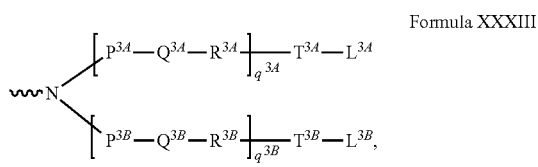

Formula XXXIV

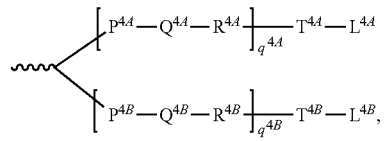

Formula XXXV

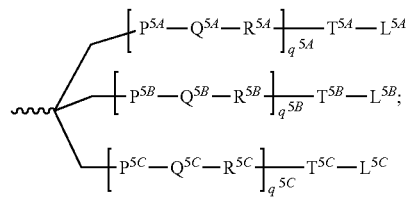

wherein:

q2A, q2B, q3A, q3B, q4A, q4B, q5A, q5B and q5C represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), CH$_2$, CH$_2$NH or CH$_2$O;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), SO$_2$, N(R$^N$), C(R')=C(R"), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, CH$_2$, C(O)O, C(O)NH, NHCH(R$^a$)C(O), —C(O)—CH(R$^a$)—NH—, CO, CH=N—O,

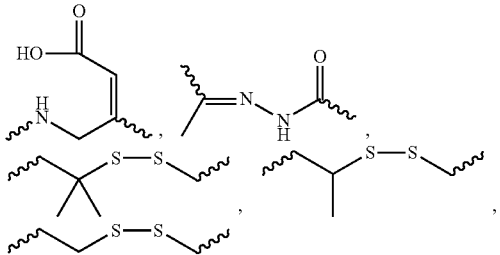

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and R$^a$ is H or amino acid side chain. Trivalent conjugating GalNAc derivatives are particularly useful for use with RNAi agents for inhibiting the expression of a target gene, such as those of formula (XXXV):

Formula XXXV

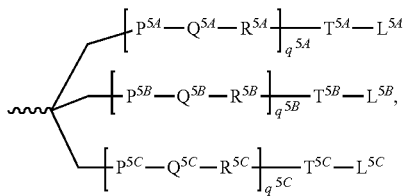

wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

Representative US patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNAs, which contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, or increased binding affinity for the target nucleic acid. An additional region of the iRNA can serve as a substrate for enzymes capable of cleaving RNa:DNA or RNA:RNA hybrids. By way of example, RNase H is a cellular endonuclease which cleaves the RNa strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., *Biochem. Biophys. Res. Comm.*, 2007, 365(1):54-61; Letsinger et al., *Proc. Natl. Acad. Sci. USA*, 1989, 86:6553), cholic acid (Manoharan et al., *Bioorg. Med. Chem. Lett.*, 1994, 4:1053), a thioether, e.g., hexyl-S-tritylthiol (Manoharan et al., *Ann. N.Y. Acad. Sci.*, 1992, 660:306; Manoharan et al., *Bioorg. Med. Chem. Let.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO J.*, 1991, 10:111; Kabanov et al., *FEBS Lett.*, 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36:3651; Shea et al., *Nucl. Acids Res.*, 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.*, 1995, 36:3651), a palmityl moiety (Mishra et al., *Biochim. Biophys. Acta*, 1995, 1264:229), or an octadecylamine or hexylamino-carbonyl-oxycholesterol moiety (Crooke et al., *Pharmacol. Exp. Ther.*, 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

iii. Delivery of an iRNA of the Invention

The delivery of an iRNA of the invention to a cell e.g., a cell within a subject, such as a human subject infected with HBV can be achieved in a number of different ways.

Delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian R L. (1992) Trends Cell. Biol. 2(5):139-144 and WO9402595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) *J. Mol. Biol* 327:761-766; Verma, U N., et al (2003) *Clin. Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) *Nature* 441:111-114), cardiolipin (Chien, P Y., et al (2005) *Cancer Gene Ther.* 12:321-328; Pal, A., et al (2005) *Int J. Oncol.* 26:1087-1091), polyethyleneimine (Bonnet M E., et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A., et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety. In certain embodiments, the iRNA agents can be administered with amphipathic peptides to facilitate pH-dependent endosomal escape (see, e.g., Bartz et al., 2011. Biochem. J. 435:475-87, incorporated herein by reference)

1. Vector Encoded iRNAs for Use in the Invention iRNA targeting an HBV gene can be expressed from transcription units inserted into DNA or RNA vectors (see, e.g., Couture, A, et al., *TIG.* (1996), 12:5-10; Skillern, A., et al., WO 00/22113, WO 00/22114, and U.S. Pat. No. 6,054, 299). Exemplary expression vectors for expression of shRNA targeted to HBV are provided in Michler et al., 2016 which discloses adeno-associated virus (AAV) 8 vectors for delivery included (i) embedded the shRNA in an artificial mi(cro)RNA under a liver-specific promoter; (ii) co-expressed Argonaute-2, a rate limiting cellular factor whose saturation with excess RNAi triggers can be toxic; or (iii) co-delivered a decoy ("TuD") directed against the shRNA sense strand to curb off-target gene regulation. The plasmids expressing shRNAs shHBV4 to 7 that were used in the cell culture studies were cloned by direct insertion of the respective shRNA-encoding oligonucleotides into a self-complementary AAV vector plasmid previously reported by Grimm et al, 2006 (Nature 441: 537-541), containing an H1 promoter followed by two BbsI sites for oligonucleotide insertion as well as an RSV promoter. Such constructs can also be used for the expression of vaccine antigens if appropriately sized for the expression vector.

Expression can be transient (on the order of days to weeks) or sustained (weeks to months, or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by subcutaneous, intravenous, or intramuscular administration. Such vectors can also be used for expression of viral antigens from nucleic acid-based vaccines.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors including modified vaccinia virus Ankara vector or avipox, e.g. canary pox or fowl pox; and (j) a helper-dependent or gutless adenovirus. Replication-defective viruses can also be advantageous.

Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA or HBV antigen will generally require regulatory elements, e.g., promoters, enhancers, etc., to ensure the expression of the iRNA in target cells. Other aspects to consider for vectors and constructs are further described below.

Such constructs and vectors can also be used for the expression of vaccine antigens if appropriately sized for the expression vector. Such limitations are well understood by those of skill in the art.

B. Therapeutic HBV Vaccines for Use in the Methods of the Invention

Therapeutic HBV vaccines for use in the regimens and methods of the invention can be a peptide vaccine, a DNA vaccine including a vector-based vaccine, or cell-based vaccine that induces an immune response, preferably an effector T cell induced response, against one or more HBV proteins. Preferably the vaccine is a multi-epitope vaccine that is cross-reactive with multiple HBV serotypes, preferably all HBV serotypes.

A therapeutic vaccine is designed to activate the patient's immune system to recognize and control or eliminate an already established pathogen infection. This is clearly distinct from a prophylactic vaccination which is designed to promote rapid antibody-mediated neutralization of an invading pathogen. Control and elimination of persistent viruses such as hepatitis, herpes, or papilloma viruses requires multi-specific and poly-functional effector T cell responses. These T cell responses are ideally directed against continuously expressed viral antigens to keep the pathogen in check. Therapeutic vaccines are under development for a number of chronic infections. Hepatitis B virus infection is a candidate for treatment by therapeutic vaccination since a spontaneous, immune-mediated recovery of chronic hepatitis B and an elimination of the virus has been observed in very rare cases.

Robust T cell responses seem to be essential to achieve HBV cure. While HBV-specific CD4+ and CD8+ T cell responses are readily detectable in patients resolving HBV infection, HBV-specific T cells are scarce and functionally impaired in chronic hepatitis B most likely due to high amounts of circulating viral HBeAg and HBsAg. T cells eliminate HBV infected cells by their cytotoxic activity but also control HBV gene expression and replication in a non-cytolytic fashion.

To overcome immune tolerance in chronic hepatitis B different approaches have been investigated in preclinical models using DNA or peptide vaccines, or vector- or cell-based vaccines to induce an effector T cell response. Multi-epitope therapeutic vaccine candidates that cover sufficient different HBV genotypes and most frequent HLA types have been developed. Although proper peptide presentation was demonstrated, immunogenicity was limited and the approach was not translated into the clinics. A non-exhaustive list is provided in the table below.

Therapeutic HBV Vaccine Tables

| Vaccine Name | Proteins/ coding sequences | Vaccine type/ Composition | Results available | Sponsor | Development Stage | Clinical Trial Reference No. | References (the entire contents of each of which are incorporated herein by reference) |
|---|---|---|---|---|---|---|---|
| HB-110 | HBsAg,, HBcAg, human IL-12 | 3 Plasmid based DNA vaccine | Study completed, results not reported | Genexine | Phase I | NCT01813487 NCT01641536 NCT00513968 | Kim et al., 2008. Exp Mol Med. 40: 669-676 |
| HB-100 | pGX10 S +pGX10 S1/S2/X +pGX10 core +pGX10 Pol +pGX10 hIL-12N222L | 5 Plasmid based DNA vaccine – 4 antigens + human IL-12 | | | | | Yang et al., 2006. Gene Therapy. 13: 1110-1117 |
| ppdpSC18 | | DNA vaccine adjuvanted with particle mediated epidermal delivery | Study completed, results not reported | PowderMed | Phase I | NCT00277576 | |
| INO-1800 | HbsAg, HBcAg | DNA plasmid | Recruiting | Inovio Pharmaceuticals | Phase I | NCT02431312 | |
| HB02 VAC-ADN | HB preS/S | pCMV-S2.S DNA vaccine; CMV promoter, plasmid vector | Well tolerated; No change in relapse rate in HBV treated patients or decrease in virological breakthrough | ANRS | Phase I/II | NCT00536627 | Mancini-Bourgine et al., 2006. Vaccine 24: 4482-4489 |
| CVI-HBV-002 | HbsAg | DNA + L-pampo | Recruiting | CHA Vaccine Institute Co., Ltd. | Phase I/II | NCT02693652 | |
| Theravax (DV-601) | HBsAg, HBcAg | Protein + adjuvant | Well tolerated; anti-viral response observed in all patients | Dynavax Technologies Corp. | Phase Ib | NCT01023230 | |
| HepTcell ™ | | IC31 ® adjuvanted peptide | Recruiting | Altimmune, Inc. | Phase I | NCT02496897 | US 20130330382 US 20120276138 US 20150216967 |

Therapeutic HBV Vaccine Tables

| Vaccine Name | Proteins/ coding sequences | Vaccine type/ Composition | Results available | Sponsor | Development Stage | Clinical Trial Reference No. | References (the entire contents of each of which are incorporated herein by reference) |
|---|---|---|---|---|---|---|---|
| HBsAg/HBcAg | HBsAg HBcAg | protein | | | Research | | Li et al., 2015, Vaccine. 33: 4247-4254 |
| GS-4774 | Fusion protein HBsAg, HBcAg, HBxAg | Protein + Tamogen T cell stimulator | Phase II naïve group ongoing; no significant viral decrease in treatment-experience patients | Gilead | Phase II | NCT01943799 NCT01779505 NCT02174276 | Gaggar et al., 2014. Vaccine. 32: 4925-4931. |
| εPA-44 | | Multi-peptide vaccine | Some seroconversion observed in all groups, no statistical analysis | Chongqing Jaichen Biotechnology, Ltd. | Phase II | NCT00869778 NCT02862106 | |
| ABX 203 | HBsAg, HBcAg | HBsAg, HBcAg | Ongoing | ABIVAX S.A. | Phase II/III | NCT02249988 | |
| pSG2.HBs/ MVA.HBs | | Protein prime-viral vector boost | Well tolerated, but did not control HBV infection | Oxxon Therapeutics | Phase IIa | ISRCTN 67270384 | Cavenaugh et al., 2011. PLoS ONE 6: e14626. |
| | HBsAg, HBcAg | Adjuvanted protein prime-viral vector boost | | | Research | | Backes, 2016, Vaccine; WO2017121791 |

Existing prophylactic vaccines have been used to restore HBV-specific immunity in chronically infected patients, but have failed to provide a functional cure. These subviral particle-based vaccines were able to reduce HBV replication in animal models of chronic hepadnaviral infection, but have not been successful in patients with chronic hepatitis B. An antigen-antibody (HBsAg-HBIG) immunogenic complex therapeutic vaccine candidate with alum as adjuvant first showed promising results in a double-blind, placebo controlled, phase IIb clinical trial, but results of a phase III clinical trial including 450 patients were disappointing. This is most likely due to the fact that subviral particle vaccines with alum-based adjuvants are designed as prophylactic vaccines and preferentially induce antibodies but not cytotoxic T cell responses that would be required for therapeutic efficacy.

Alternatively, DNA vaccines encoding HBV envelope proteins were designed to induce HBV-specific T cells but also had limited success. Since DNA-based vaccines hardly induce antibody responses, they failed to achieve HBeAg or HBsAg seroconversion. An alternative DNA prime, poxvirus-boost vaccine encompassing the HBV preS/S region encoding for the HBV envelope proteins showed promising results in chimpanzees, but also failed in a clinical phase IIa trial neither inducing sustained T cell responses nor reducing viremia in chronic HBV carriers. They may have failed to induce T cell help or broad enough, multi-specific immune responses.

Any vaccines known in the art can be used in the methods and regimens provided herein. Preferred embodiments include the prime-boost vaccination scheme with protein antigens administered twice and a nucleic acid vaccine administered once as provided in the Examples and provided in PCT Publication No. WO 2017/121791 (the entire contents of which are incorporated herein by reference). As discussed above, the sequence of the protein antigen in the vaccine and the amino acid sequence encoded by nucleic acid-based vaccine need not be identical. They simply must share at least one epitope, preferably multiple epitopes, so that the sequential administration of the vaccines has the desired prime-boost effect. Further, as discussed herein, in preferred embodiments, the treatment regimen provided herein would provide a treatment regimen effective across multiple, if not all, HBV serotypes. Therefore, it is understood that the antigen delivered to the subject may not have antigen sequences identical to the antigens expressed by the HBV virus that infected the subject.

It is known in the art that some portions of HBV antigens are the main targets of antibodies generated during the initial immune response to infection with HBV known as determinants. For example the HBsAg includes the "a" determinant epitope that is located at amino acids 124 to 147 within the major hydrophilic region (MHR, amino acids 100 to 169) of the 226 amino acid S gene (SEQ ID NO: 8 or 22). This "a" determinant is one of the main targets of anti-HBs antibodies during the course of the initial immune response in acute hepatitis B. In certain embodiments, an immunogenic fragment of HBsAg comprises compared to the full length protein at least amino acids 99 to 168 corresponding to the amino acid positons of the small envelope protein (SEQ ID NO: 23) (see, e.g., Lada et al., J. Virol. (2006) 80:2968-2975, the entire contents of which are incorporated herein by reference).

Similarly, determinants have been identified in HBcAg (see, e.g., Salfeld et al., J. Virol. (1989) 63:798-808, the entire contents of which are incorporated herein by reference). The full-length core protein is 183 amino acids in length and consists of an assembly domain (amino acids 1 to 149) and a nucleic acid-binding domain (amino acids 150 to 183). Three distinct major determinants have been characterized. The single conformational determinant responsible for HBc antigenicity in the assembled core (HBc) and a linear HBe-related determinant (HBe1) were both mapped to an overlapping hydrophilic sequence around amino acid 80; a second HBe determinant (HBe2) was assigned to a location in the vicinity of amino acid 138 but found to require for its antigenicity the intramolecular participation of the extended sequence between amino acids 10 and 140. Typically, such an immunogenic fragment comprises, compared to the full length core protein, at least amino acids 18 to 143 corresponding to the sequence positions set forth in SEQ ID NO: 24. Analogous sequences can be identified in SEQ ID NO: 10.

In preferred embodiments, the vaccines include an amino acid sequence or encode an amino acid sequence that includes at least one determinant of HBsAg or HBcAg. Specifically, in certain embodiments, a vaccine targeted to HBsAg includes at least the amino acid sequence of amino acids 127 to 147 of HBsAg, e.g., includes at least amino acids 99 to 168 of the amino acid sequence of the small envelope protein (SEQ ID NO: 23). In certain embodiments, a vaccine targeted to a hydrophilic sequence at least around amino acid 80 of HBcAg or an amino acid sequence at least around amino acid 138, e.g., at least a 40 amino acid portion, at least a 50 amino acid portion, at least a 60 amino acid portion, at least a 70 amino acid portion, at least an 80 amino acid portion, at least a 90 amino acid portion, or at least a 100 amino acid portion of SEQ ID NO: 43 including amino acid 80 or amino acid 138, or a coding sequence therefor. In preferred embodiments, the antigen amino sequence of the antigen targeted to HBcAg includes at least 20 amino acids N-terminal and C-terminal to amino acid 80 or 138 of SEQ ID NO: 24. In certain embodiments, a vaccine targeted to HBcAg includes at least the amino acid sequence of amino acids 10 to 140 or 18 to 143 of HBsAg.

In certain embodiments, the vaccine may comprise the entire amino acid sequence or encode the entire amino acid sequence of any one or more of SEQ ID NO: 22, 23, or 24.

It is understood that there are multiple serotypes of HBV with different nucleic acid sequences that encode different amino acid sequences. Therefore, it is understood that the amino acid sequence of a protein-based vaccine or the amino acid sequence encoded by a nucleic acid-based vaccine may not be 100% identical to the sequences provided in the SEQ ID NOs. In certain embodiments of the invention, the amino acid sequence of a protein-based vaccine or the amino acid sequence encoded by a nucleic acid-based vaccine is at least 90% identical, at least 91% identical, at least 92% identical, at least 93% identical, at least 94% identical, at least 95% identical, at least 96% identical, at least 97% identical, or at least 98% identical to the portion of SEQ ID NO: 22, 23, or 24. Additional exemplary HBsAg and HBcAg amino acid sequences are provided in the sequence listing. Alignment methods to identify appropriate sequences corresponding to the HBsAg and HBcAg determinants in the sequences indicated above are known in the art.

The vaccine preferably comprises MVA viruses in a concentration range of $10^4$ to $10^9$ tissue-culture infectious dose $(TCID)_{50}$/ml, preferably in a concentration range of $10^5$ to $5 \times 10^8$ $TCID_{50}$/ml, more preferably in a concentration range of $10^6$ to $10^8$ $TCID_{50}$/ml, and most preferably in a concentration range of $10^7$ to $10^8$ $TCID_{50}$/ml.

A preferred vaccination dose for humans comprises $10^6$ to $10^9$ $TCID_{50}$, most preferably a dose of $10^6$ $TCID_{50}$ or $10^7$ $TCID_{50}$ or $10^8$ $TCID_{50}$.

The preferred methods of the invention include administration of both a protein-based vaccine and a nucleic acid-based vaccine. However, other methods include administration of only protein antigens. Less preferred embodiments include administration of only nucleic acids encoding antigens.

i. Adjuvants

As used herein "adjuvant" is understood as an agent that promotes (e g., enhances, accelerates, or prolongs) an immune response to an antigen with which it is administered to elicit long-term protective immunity. No substantial immune response is directed at the adjuvant itself. Adjuvants include, but are not limited to, pathogen components, particulate adjuvants, and combination adjuvants (see, e.g., www.niaid.nih.gov/research/vaccine-adjuvants-types).

Pathogen components (e.g., monophosphoryl lipid A (MPL), poly(I:C), CpG DNA, emulsions such as poly[di(sodiumcarboxylatoethylphenoxy)phosphazene] (PCEP)) can help trigger early non-specific, or innate, immune responses to vaccines by targeting various receptors inside or on the surface of innate immune cells. The innate immune system influences adaptive immune responses, which provide long-lasting protection against the pathogen that the vaccine targets. Particulate adjuvants (e.g., alum, virosomes, cytokines, e.g., IL-12) form very small particles that can stimulate the immune system and also may enhance delivery of antigen to immune cells. Combination adjuvants (e.g., AS02, AS03 and AS04 (GSK); MF59 (Novartis); and IC31® (Altimmune) elicit multiple protective immune responses. Adjuvants that have a modest effect when used alone may induce a more potent immune response when used together. In certain embodiments, preferred adjuvants include c-di-AMP, c-di-GMP, c-di-CMP, PolyICLC, CpG, ISCOMATRIX®, AS02, AS03, AS04, or a RIG-I ligand such as 5' 3P-RNA. In certain embodiments, a viral capsid, with or without a nucleic acid expressing an HBV antigen can be used as an adjuvant. For example, a vaccine that preferentially stimulates T cells such as an MVA-only or a DNA prime, MVA boost or an adenovirus vector prime-MVA boost can be used in the methods of the invention.

In preferred embodiments of the invention, adjuvants for use in the invention promote a humoral and a cellular immune response as discussed above. In certain embodiments, adjuvants provide a balanced Th1/Th2 response.

ii. Non-Adjuvant Immune Stimulators and Additional Agents

Methods of the invention can further include administration of additional agents used in the treatment of HBV or to stimulate an immune response. Such agents can include an immune stimulator (e.g., pegylated interferon alfa 2a (PEG-IFN-α2a), Interferon alfa-2b, a recombinant human interleukin-7, and aToll-like receptor 3, 7, 8, or 9 (TLR3, TLR7, TLR8, or TLR9) agonist), a viral entry inhibitor (e.g., Myrcludex), an oligonucleotide that inhibits the secretion or release of HBsAg (e.g., REP 9AC), a capsid inhibitor (e.g., Bay41-4109 and NVR-1221), a cccDNA inhibitor (e.g., IHVR-25), a Rig-I-ligand, a STING agonist, an antibody based immune therapy against HBV (mono-, bi-, or trispecific antibody against HBV), or an immune checkpoint regulator. Such agents are known in the art.

C. Nucleotide and Nucleoside Analogs for Use in the Methods of the Invention

Nucleotide and nucleoside analogs are considered to be the standard of care for HBV infection as they are generally considered safe and inexpensive. However, nucleotide and nucleoside analogs cannot cure HBV infection, may cause the development of resistance, and must be taken indefinitely. Nucleotide analog and nucleoside analogs include, but are not limited to, Tenofovir disoproxil fumarate (TDF), Tenofovir alafenamide, Lamivudine, Adefovir dipivoxil, Entecavir (ETV), Telbivudine, AGX-1009, emtricitabine, clevudine, ritonavir, dipivoxil, lobucavir, famvir, FTC, N-Acetyl-Cysteine (NAC), PC1323, theradigm-HBV, thymosin-alpha, ganciclovir, Besifovir (ANA-380/LB-80380), and Tenofvir-Exalidex (TXL/CMX157). In certain embodiments, the nucelot(s)ide analog is Entecavir (ETV) or Tenofovir or a derivative thereof. In certain embodiments, the nucleot(s)ide analog is not Lamivudine. Nucleot(s)ide analogs are commercially available from a number of sources and are used in the methods provided herein according to their label indication (e.g., typically orally administered at a specific dose) or as determined by a skilled practitioner in the treatment of HBV.

III. Antisense Oligonucleotides Targeting HBV

The present invention includes the use of iRNAs which promote cleavage of at least one HBV transcript, and preferably three or four HBV transcripts. Antisense oligonucleotides can similarly be used to promote cleavage of at least one HBV transcript, preferably three or four HBV transcripts, in the methods of the invention provided here. Exemplary antisense oligonucleotides targeted to HBV are provided, for example, in U.S. Patent Publication Nos. 2013/0035366, 2012/0207709, and 2004/0127446, the contents of each of which is incorporated by reference herein in its entirety.

It is understood by those of skill in the art that conjugates, linkers, and formulations for the delivery of siRNAs as provided above can be used for the formulation and delivery of antisense oligonucleotide therapeutic agents to subjects.

IV. Pharmaceutical Compositions of the Invention

The present invention also includes pharmaceutical compositions and formulations which include the iRNAs or vaccines for use in the invention. It is understood that approved therapeutic agents are formulated and administered by the route indicated on their package instructions.

In some embodiments, provided herein are pharmaceutical compositions containing an iRNA or a vaccine, as described herein, and a pharmaceutically acceptable carrier. The pharmaceutical compositions containing the iRNA or vaccine are useful for treating subject with an HBV infection. Such pharmaceutical compositions are formulated based on the mode of delivery, e.g., for systemic administration via parenteral delivery, e.g., by subcutaneous (SC), intramuscular (IM), or intravenous (IV) delivery.

The pharmaceutical RNAi compositions for use in the invention may be administered in dosages sufficient to significantly reduce the level of at least one HBV transcript. In general, a suitable dose of an iRNA of the invention will be in the range of about 0.001 to about 200.0 milligrams per kilogram body weight of the recipient per day, generally in the range of about 1 to 50 mg per kilogram body weight per day. Typically, a suitable dose of an iRNA of the invention will be in the range of about 0.1 mg/kg to about 5.0 mg/kg, preferably about 0.3 mg/kg and about 3.0 mg/kg. A repeat-dose regimen may include administration of a therapeutic amount of iRNA on a regular basis, such as every other week or once a year. In certain embodiments, the iRNA is administered about once per month to about once per quarter (i.e., about once every three months). In preferred embodiments, the RNAi agent is administered subcutaneously.

Formulation and dosing of the vaccine will depend on the nature of the vaccine administered. In a protein prime-expression vector boost vaccination strategy, the protein-based priming vaccines are administered about 2, 3, or 4 weeks apart with the expression vector vaccine boost being administered about 2, 3, or 4 weeks after the second protein-based vaccine dose. In certain embodiments, it is about two weeks between the first and second doses of the protein-based vaccine. In certain embodiments, it is about two weeks between the second dose of the protein based vaccine and the DNA expression vector vaccine boost. In certain embodiments, the prime and boost vaccinations are administered by routes independently selected from intramuscularly, intradermally, or subcutaneously.

The pharmaceutical nucleic acid-based vaccines for use in the invention may be administered in dosages sufficient to promote an immune response, as either a prime agent or a boost agent. The amount of nucleic acid-based vaccine to be administered will depend, for example, on the design of the vaccine. As the regimens provided herein can include the use of existing nucleic acid-based vaccines, knowledge regarding appropriate dosages based on therapeutic efficacy and safety should be based on the specific agent used.

The pharmaceutical protein-based vaccines for use in the invention may be administered in dosages sufficient to promote an immune response, as either a prime or a boost agent. The amount of protein-based vaccine to be administered will depend, for example, on the adjuvant used. Protein-based vaccines can be dosed, for example, at about 5-100 mg/kg/dose, about 10-50 mg/kg/dose, or about 20-40 mg/kg/dose. As the regimens provided herein can include the use of existing protein-based vaccines, knowledge regarding appropriate dosages based on therapeutic efficacy and safety should be based on the specific agent used.

After an initial treatment regimen, the treatments can be administered on a less frequent basis. In preferred embodiments, the treatment regimens and methods provided herein result in a functional cure allowing for discontinuation of treatment after completion of the regimen or after diagnostic criteria indicate a functional cure, e.g., decreased HBsAg levels preferably to below the level of detection of the methods provided herein and a detectable immune response to HBsAg.

The skilled artisan will appreciate that certain factors can influence the dosage and timing required to effectively treat a subject, including but not limited to the severity of the disease or disorder, previous treatments, the general health or age of the subject, and other diseases present. Moreover, treatment of a subject with a therapeutically effective amount of a composition can include a single treatment or a series of treatments. Estimates of effective dosages and in vivo half-lives for the individual therapeutic agent used in the methods and regimens invention can be made using conventional methodologies or on the basis of in vivo testing using an appropriate animal model, as described elsewhere herein and known in the art.

A. iRNA Formulations Comprising Membranous Molecular Assemblies

An iRNA for use in the compositions and methods of the invention can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the iRNA composition. The lipophilic material isolates the aqueous interior from an aqueous exterior, which typically does not include the iRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the iRNA are delivered into the cell where the iRNA can specifically bind to a target RNA and can mediate iRNA. In some cases the liposomes are also specifically targeted, e.g., to direct the iRNA to particular cell types.

A liposome containing an iRNA agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The iRNA agent preparation is then added to the micelles that include the lipid component. The cationic groups on the lipid interact with the iRNA agent and condense around the iRNA agent to form a liposome. After condensation, the detergent is removed, e.g., by dialysis, to yield a liposomal preparation of the iRNA agent.

If necessary a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Methods for producing stable polynucleotide delivery vehicles, which incorporate a polynucleotide/cationic lipid complex as structural components of the delivery vehicle, are further described in, e.g., WO 9637194, the entire contents of which are incorporated herein by reference. Liposome formation can also include one or more aspects of exemplary methods described in Felgner, P. L. et al., *Proc. Natl. Acad. Sci., USA* 8:7413-7417, 1987; U.S. Pat. Nos. 4,897,355; 5,171,678; Bangham, et al. *M. Mol. Biol.* 23:238, 1965; Olson, et al. *Biochim. Biophys. Acta* 557:9, 1979; Szoka, et al. *Proc. Natl. Acad. Sci. USA* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986). Microfluidization can be used when consistently small (50 to 200 nm) and relatively uniform aggregates are desired (Mayhew, et al. *Biochim. Biophys. Acta* 775:169, 1984). These methods are readily adapted to packaging iRNA agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980-985).

Liposomes which are pH-sensitive or negatively-charged, entrap nucleic acids rather than complex with it. Since both the nucleic acid and the lipid are similarly charged, repulsion rather than complex formation occurs. Nevertheless, some nucleic acid is entrapped within the aqueous interior of these liposomes. pH-sensitive liposomes have been used to deliver nucleic acids encoding the thymidine kinase gene to cell monolayers in culture. Expression of the exogenous gene was detected in the target cells (Zhou et al., *Journal of Controlled Release*, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC and egg PC. Another type is formed from mixtures of phospholipid or phosphatidylcholine or cholesterol.

Examples of other methods to introduce liposomes into cells in vitro and in vivo include U.S. Pat. Nos. 5,283,185 and 5,171,678; WO 94/00569; WO 93/24640; WO 91/16024; Felgner, *J. Biol. Chem.* 269:2550, 1994; Nabel, *Proc. Natl. Acad. Sci. USA* 90:11307, 1993; Nabel, *Human Gene Ther.* 3:649, 1992; Gershon, Biochem. 32:7143, 1993; and Strauss *EMBO J.* 11:417, 1992.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al. *S.T.P. Pharma. Sci.*, 1994, 4(6) 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. USA*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 discloses liposomes comprising sphingomyelin. Liposomes comprising 1,2-sn-dimyristoylphosphatidylcholine are disclosed in WO 9713499 (Lim et al).

Cationic liposomes possess the advantage of being able to fuse to the cell membrane. Non-cationic liposomes, although not able to fuse as efficiently with the plasma membrane, are taken up by macrophages in vivo and can be used to deliver iRNA agents to macrophages.

Further advantages of liposomes include: liposomes obtained from natural phospholipids are biocompatible and biodegradable; liposomes can incorporate a wide range of water and lipid soluble drugs; liposomes can protect encapsulated iRNA agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of iRNA agent (see, e.g., Felgner, P. L. et al., Proc. Natl. Acad. Sci., USA 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., Biochim. Biophys. Res. Commun. 179:280, 1991). Lipopolylysine, made by conjugating polylysine to DOPE, has been reported to be effective for transfection in the presence of serum (Zhou, X. et al., Biochim. Biophys. Acta 1065:8, 1991). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration. Liposomes present several advantages over other formulations. Such advantages include reduced side effects related to high systemic absorption of the administered drug, increased accumulation of the administered drug at the desired target, and the ability to administer iRNA agent into the skin. In some implementations, liposomes are used for delivering iRNA agent to epidermal cells and also to enhance the penetration of iRNA agent into dermal tissues, e.g., into skin. For example, the liposomes can be applied topically. Topical delivery of drugs formulated as liposomes to the skin has been documented (see, e.g., Weiner et al., Journal of Drug Targeting, 1992, vol. 2, 405-410 and du Plessis et al., Antiviral Research, 18, 1992, 259-265; Mannino, R. J. and Fould-Fogerite, S., Biotechniques 6:682-690, 1988; Itani, T. et al. Gene 56:267-276. 1987; Nicolau, C. et al. Meth. Enz. 149:157-176, 1987; Straubinger, R. M. and Papahadjopoulos, D. Meth. Enz. 101:512-527, 1983; Wang, C. Y. and Huang, L., Proc. Natl. Acad. Sci. USA 84:7851-7855, 1987).

Liposomes that include iRNA can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include iRNA agent can be delivered, for example, subcutaneously by infection in order to deliver iRNA agent to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present invention are described in WO 2008042973.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in "Pharmaceutical Dosage Forms", Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms", Marcel Dekker, Inc., New York, N.Y., 1988, p. 285).

The iRNA for use in the methods of the invention can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

B. Lipid Particles iRNAs, e.g., dsRNAs of in the invention may be fully encapsulated in a lipid formulation, e.g., a LNP, or other nucleic acid-lipid particle. Expression vectors or RNAs containing coding sequences for viral antigens under the control of an appropriate promoter can be formulated in lipid particles for delivery.

As used herein, the term "LNP" refers to a stable nucleic acid-lipid particle. LNPs typically contain a cationic lipid, a non-cationic lipid, and a lipid that prevents aggregation of the particle (e.g., a PEG-lipid conjugate). LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in WO 0003683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; and 6,815,432; US20100324120 and WO 9640964.

In some embodiments, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the invention.

The cationic lipid can be, for example, N,N-dioleyl-N,N-dimethylammonium chloride (DODAC), N,N-distearyl-N,N-dimethylammonium bromide (DDAB), N-(I-(2,3-dioleoyloxy)propyl)-N,N,N-trimethylammonium chloride (DOTAP), N-(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (Dlin-DAC), 1,2-Dilinoleyoxy-3-morpholinopropane (DLin-MA), 1,2-Dilinoleoyl-3-dimethylaminopropane (DLinDaP), 1,2-Dilinoleylthio-3-dimethylaminopropane (DLin-S-DMA), 1-linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPz), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1), or a mixture thereof. The cationic lipid can comprise from about 20 mol % to about 50 mol % or about 40 mol % of the total lipid present in the particle. In other embodiments, the compound 2,2-Dilinoleyl-4-dimethylaminoethyl-[1,3]-dioxolane can be used to prepare lipid-siRNA nanoparticles.

In some embodiments, the lipid-siRNA particle includes 40% 2,2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($Ci_2$), a PEG-dimyristyloxypropyl ($Ci_4$), a PEG-dipalmityloxypropyl ($C_{16}$), or a PEG-distearyloxypropyl ($C]_8$). The conjugated lipid that prevents aggregation of particles can be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98.4HCl (MW 1487) (see US20090023673, which is incorporated herein by reference), Cholesterol (Sigma-Aldrich), and PEG-Ceramide C16 (Avanti Polar Lipids) can be used to prepare lipid-dsRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

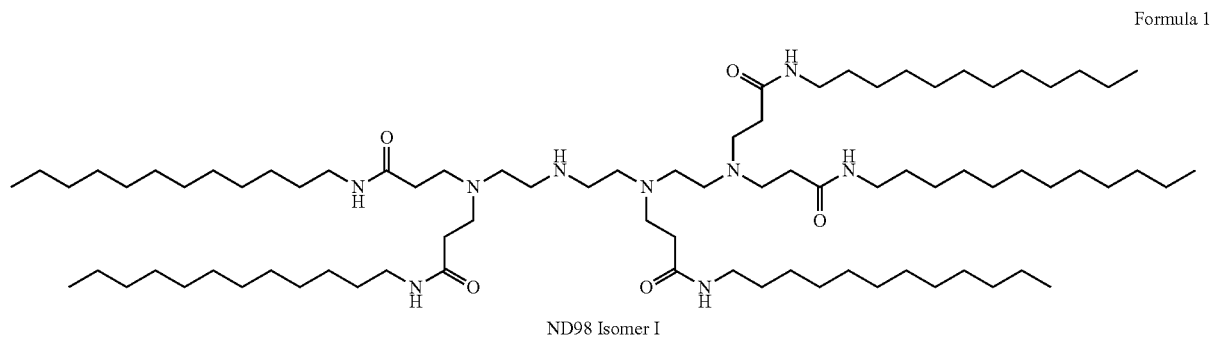 [SMILES: CCCCCCCCCCCCNC(=O)CCN(CCNCCN(CCC(=O)NCCCCCCCCCCCC)CCN(CCC(=O)NCCCCCCCCCCCC)CCC(=O)NCCCCCCCCCCCC)CCC(=O)NCCCCCCCCCCCC]

ND98 Isomer I

LNP01 formulations are described, e.g., in WO 2008042973, which is hereby incorporated by reference.

Additional exemplary lipid-dsRNA formulations are described in Table 1.

TABLE 1

|  | Ionizable/Cationic Lipid | cationic lipid/non-cationic lipid/cholesterol/PEG-lipid conjugate Lipid:siRNA ratio |
|---|---|---|
| SNALP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA ~7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA ~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |

TABLE 1-continued

| | Ionizable/Cationic Lipid | cationic lipid/non-cationic lipid/cholesterol/PEG-lipid conjugate Lipid:siRNA ratio |
|---|---|---|
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |
| LNP21 | C12-200 | C12-200/DSPC/Chol/PEG-DSG 50/10/38.5/1.5 Lipid:siRNA: 7:1 |
| LNP22 | XTC | XTC/DSPC/Chol/PEG-DSG 50/10/38.5/1.5 Lipid:siRNA: 10:1 |

DSPC: distearoylphosphatidylcholine
DPPC: dipalmitoylphosphatidylcholine
PEG-DMG: PEG-didimyristoyl glycerol (C14-PEG, or PEG-C14) (PEG with avg mol wt of 2000)
PEG-DSG: PEG-distyryl glycerol (C18-PEG, or PEG-C18) (PEG with avg mol wt of 2000)
PEG-cDMA: PEG-carbamoyl-1,2-dimyristyloxypropylamine (PEG with avg mol wt of 2000)
SNALP (1,2-Dilinolenyloxy-N,N-dimethylaminopropane (DLinDMA)) comprising formulations are described in International Publication No. WO 2009/127060, filed Apr. 15, 2009, which is hereby incorporated by reference.
XTC comprising formulations are described in PCT Publication No. WO 2010/088537, the entire contents of which are hereby incorporated herein by reference.
MC3 comprising formulations are described, e.g., in U.S. Publication No. 2010/0324120, the entire contents of which are hereby incorporated by reference.
ALNY-100 comprising formulations are described in PCT Publication No. WO 2010/054406, the entire contents of which are hereby incorporated herein by reference.
C12-200 comprising formulations are described in PCT Publication No. WO 2010/129709, the entire contents of which are hereby incorporated herein by reference.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the invention are administered in conjunction with one or more penetration enhancer surfactants and chelators. Suitable surfactants include fatty acids or esters or salts thereof, bile acids or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention can be delivered orally, in granular form including sprayed dried particles, or complexed to form micro or nanoparticles. DsRNA complexing agents include poly-amino acids; polyimines; polyacrylates; poly-alkylacrylates, polyoxethanes, polyalkylcyanoacrylates; cationized gelatins, albumins, starches, acrylates, polyethyleneglycols (PEG) and starches; polyalkylcyanoacrylates;

DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly (ethylcyanoacrylate), poly(butylcyanoacrylate), poly (isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. Nos. 6,887,906 and 6,747,014, and US 20030027780, each of which is incorporated herein by reference.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient (s). In general, the formulations are prepared by uniformly and intimately bringing into association the active ingredients with liquid carriers or finely divided solid carriers or both, and then, if necessary, shaping the product.

V. Uses of the Methods of the Invention

The invention sets forth various methods and treatment regimens. It is understood that the methods can be provided as uses of the RNAi agents and vaccines provided herein. That is, the invention provides a) an RNAi agent that targets at least three HBV transcripts, wherein the RNAi agent comprises a sense strand and an antisense strand;

b) a protein-based vaccine comprising an HBV core antigen (HBcAg) and an HBV surface antigen (HBsAg); and c) a nucleic acid-based vaccine comprising an expression vector construct encoding an HBcAg or an HBsAg, wherein the construct encodes a protein that shares an epitope with the protein-based vaccine; thereby treating the subject for use in methods of treating a subject having a hepatitis B infection.

The uses include all of the variations and exemplary RNAi agents, protein-based vaccines, and nucleic acid-based vaccines provided herein.

VI. Kits for Practicing the Methods of the Invention

The invention sets forth various methods, treatment regimensm and uses of agents for the treatment of a subject having a hepatitis B infection. It is understood that agents for practicing the methods of the invention can be prepared based in the disclosure provided herein. Such a kit would include, a) an RNAi agent that targets at least three HBV transcripts, wherein the RNAi agent comprises a sense strand and an antisense strand;

b) a protein-based vaccine comprising an HBV core antigen (HBcAg) and an HBV surface antigen (HBsAg);

c) a nucleic acid-based vaccine comprising an expression vector construct encoding an HBcAg or an HBsAg, wherein the construct encodes a protein that shares an epitope with the protein-based vaccine; thereby treating the subject; and d) instructions for use in methods of treating a subject having a hepatitis B infection.

The uses include all of the variations and exemplary RNAi agents, protein-based vaccines, and nucleic acid-based vaccines provided herein. The components of the kit may be provided together, e.g., in a box. In certain embodiments, the components of the invention may be provided separately, e.g., due to different storage requirements, but be provided for use together, e.g., based on package instructions for use.

This invention is further illustrated by the following examples which should not be construed as limiting. The entire contents of all references, patents and published patent applications cited throughout this application, as well as the Figures, Appendix A, and the Sequence Listing, are hereby incorporated herein by reference.

EXAMPLES

Example 1. Materials and Methods

Exemplary iRNAs

Exemplary iRNA target sites and unmodified and modified siRNA sequences are provided in the tables in Appendix A.

The chemically modified HBV-siRNA duplexes used in the experiments below have the following sequences:

Unmodified Sequences:

| DuplexID | Sense Sequence Unmodified (5' to 3') | SEQ ID: | Antisense Sequence Umodified (5' to 3') | SEQ ID: |
|---|---|---|---|---|
| AD-66810 | GUGUGCACUUC GCUUCACA | 27 | UGUGAAGCGAAG UGCACACUU | 25 |
| AD-66816 | CACCAUGCAAC UUUUUCACCU | 28 | AGGUGAAAAAGU UGCAUGGUGUU | 26 |

Modified Sequences:

| DuplexID | Sense Sequence Modified (5' to 3') | SEQ ID: | Antisense Sequence Modified (5' to 3') | SEQ ID: |
|---|---|---|---|---|
| AD-66810 | gsusguGfcA fCfUfucgcu ucacaL96 | 37 | usGfsugaAf gCfGfaaguG fcAfcacsus u | 30 |
| AD-66816 | csasccauGf cAfAfCfuuu uucaccuL96 | 38 | asGfsgugAf aAfAfaguuG fcAfuggugs usu | 32 |

Abbreviations for nucleotide monomers in modified nucleic acid sequences are provided in Table 1 of Appendix A.

The target site of AD-66810 is GTGTGCACTTCGCTT-CACA (SEQ ID NO: 39) which is nucleotides 1579-1597 of NC 003977.1 (SEQ ID NO: 1).

The target site of AD-66816 is CACCATGCAACTTTTT-CACCT (SEQ ID NO: 40) which is nucleotides 1812-1832 of NC 003977.1 (SEQ ID NO: 1).

Cell Culture Evaluation of HBV-siRNA hNTCP-expressing HepG2 cells were infected (100 multiplicity of infection (MOI)) HBV particles/cell (subtype ayw)) in duplicate. At day 4 after infection, cells were trypsinized and reseeded into multiwell plates and transfected with control or HBV-siRNAs AD-66810 (having the chemical modifications shown in the table above and sense and antisense sequences as set forth in SEQ ID NOs: 37 and 30, respectively) or AD-66816 (having the chemical modifications shown in the table above and sense and antisense sequences as set forth in SEQ ID NOs: 38 and 32, respectively) each delivered at 100 nM, 10 nM, or 1 nM using Lipofectamine® RNAiMax. Supernatant was harvested at days 3, 6, 10, 13, and 17 after reseeding and HBeAg and HBsAg levels were determined relative to non-transfected control. HBsAg and HBeAg levels were determined using a chemiluminescent microparticle immunoassay (CMIA) measured in an Abbott Architect immunoassay analyzer (Abbott Laboratories, Abbott Park, Ill., USA).

Mice, siRNA Administration, and Vaccinations

HBV-transgenic mice (StrainHBV1.3xfs (HBV genotype D, subtype ayw)), were derived from in-house breeding under specific pathogen-free conditions following institutional guidelines.

For siRNA administration, mice were subcutaneously administered a 3 mg/kg or 9 mg/kg dose of control siRNA or HBV-siRNA (modified AD-66810 or modified AD-66816); or intravenously administered by tail vein injection $1\times10^{11}$ AAV particles for expression of the HBV-shRNA as indicated in the Figures and Examples below.

For protein vaccinations, mice were immunized subcutaneously with recombinant yeast HBsAg and *Escherichia coli* HBcAg (APP Latvijas Biomedicinas, Riga, Latvia) mixed with 31.91 µg of synthetic phosphorothioated CpG ODN 1668 and 25 µg poly[di(sodiumcarboxylatoethyl-phenoxy)phosphazene] (PCEP) in 50 µl PBS.

Recombinant MVA were generated by homologous recombination and host range selection as described previously (Staib et al., 2003. *Biotechniques*. 34:694-700). The entire HBcAg (genotype D, subtype ayw) and HBsAg open reading frames (genotype A, subtype ayw or adw) were cloned into MVA transfer plasmids pIIIΔHR-PH5 or pIIIΔHR-P7.5, thereby placing the HBV proteins under the control of the early/late Vaccinia virus-specific promoters PH5 (HBcAg ayw/HBsAg ayw/HBsAg adw) or P7.5 (HBsAg ayw). After construction of each virus, gene expression, sequence of inserted DNA, and viral purity were verified. For generation of vaccine preparations, MVA were routinely propagated in CEF, purified by ultracentrifugation through sucrose, reconstituted in 1 mM Tris-HCl pH 9.0 and titrated following standard methodology (Staib et al., 2004. *Methods Mol Biol*. 269:77-100). For MVA vaccination, mice were vaccinated intraperitoneally with $1\times10^8$ infectious units of respective recombinant MVA in 500 µl PBS.

Figure 3:
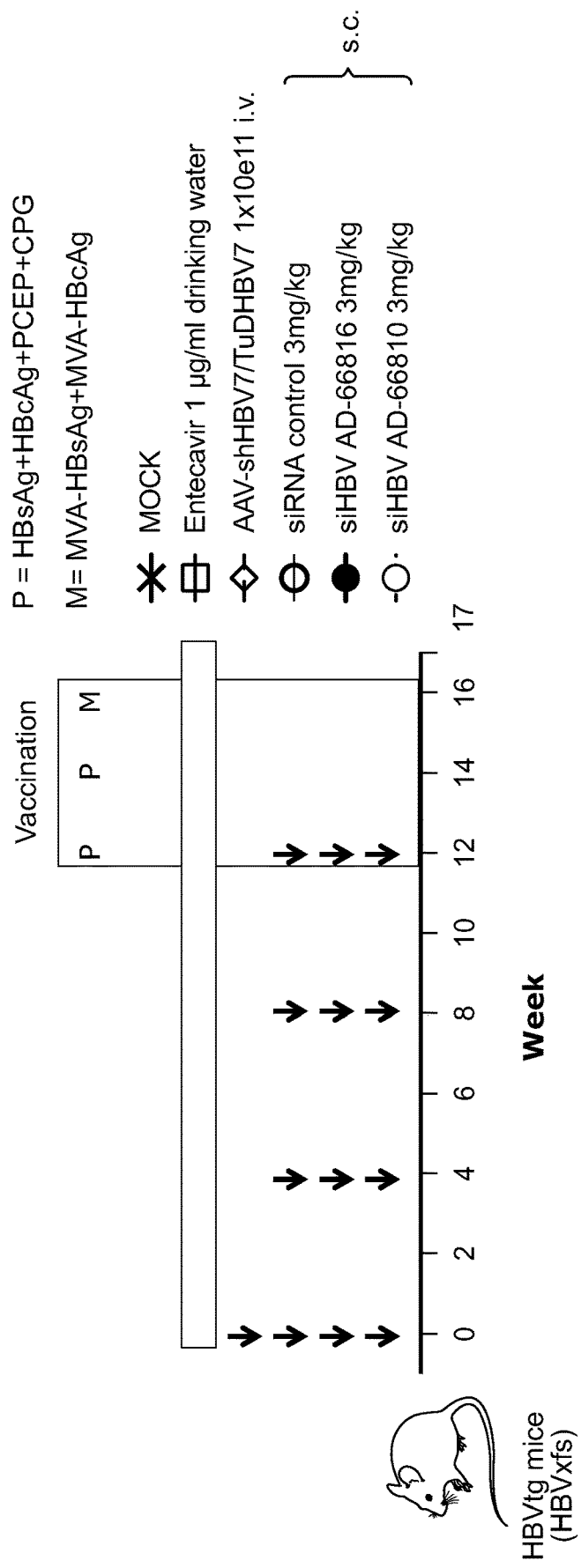
FIG. 3 is a schematic showing a dosing regimen for an experiment assaying the effect of pretreatment of HBV1.3-xfs mice with the nucleoside inhibitor, Entecavir, an HBV-shRNA, a control GalNAc-siRNA, AD-66816, or AD-66810 prior to administration of a therapeutic vaccine against HBV.
Figure 7:
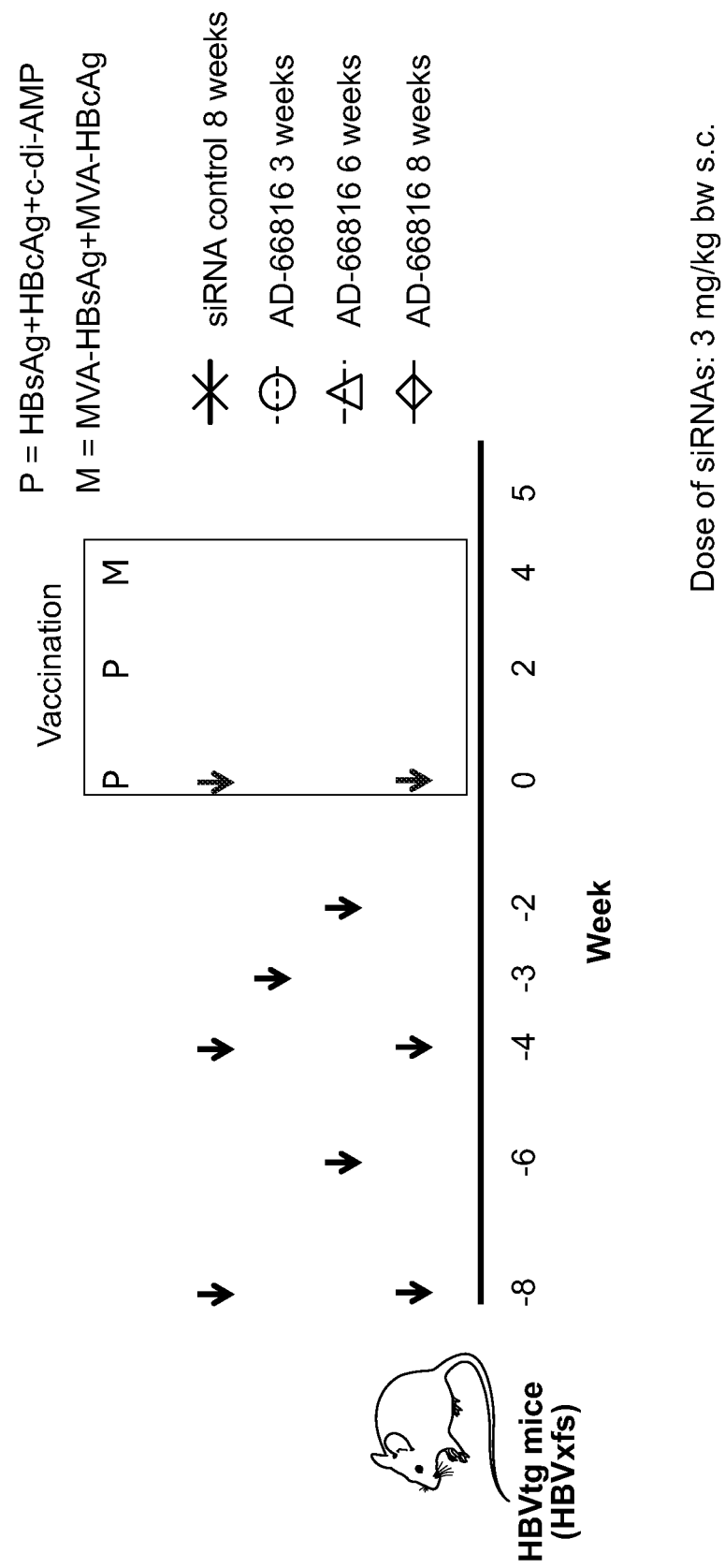
FIG. 7 is a schematic showing a dosing regimen for the experiment assaying the effect of pretreatment of HBV1.3-xfs mice with control siRNA or AD-66816 prior to administration of a therapeutic vaccine against HBV.

Specific dosing regimens are provided in the Examples below and in FIGS. 3, 7, and 12.

Serological Analysis

Serum levels of HBsAg and HBeAg were determined in 1:33 dilutions; and anti-HBs levels were determined in a 1:100 dilution using chemiluminescent microparticle immunoassay (CMIA) measured in an Abbott Architect immunoassay analyzer (Abbott Laboratories, Abbott Park, Ill., USA). Quantification of serum HBV titers by real-time polymerase chain reaction and determination of HBV DNA levels in serum was performed as described in Untergasser et al., 2006 (Hepatology. 43:539-47). The amount of HBV DNA was normalized to DNA level prior to treatment.

Levels of anti-HBc antibodies were determined in 1:20 dilution using the Enzgnost anti-HBc monoclonal test on the BEPIII platform (Both Siemens Healthcare, Eschborn, Germany). If a sample was measured outside the linear range, higher or lower dilutions were used as appropriate.

Quantification of serum HBV titers by real-time polymerase chain reaction and determination of HBV DNA levels in serum was performed as described in Untergasser et al., 2006 (Hepatology. 43:539-47). The amount of HBV DNA was normalized to DNA level prior to treatment.

ALT activity was measured at the day of bleeding in a 1:4 dilution in phosphate buffered saline (PBS) using the Reflotron GPT/ALT test (Roche Diagnostics, Mannheim, Germany).

Lymphocyte Stimulation Assay

Liver-associated lymphocytes (LAL) were isolated as described in Stross et al., 2012 (Hepatology 56:873-83) and stimulated with H2-kb- or H-2Db-restricted peptides (see Backes, 2016) for 12 hours in the presence of 1 mg/ml Brefeldin A (Sigma-Aldrich, Taufkirchen, Germany). Cells were live/dead-stained with ethidium monoazidebromide (Invitrogen®, Karlsruhe, Germany) and blocked with anti-CD16/CD32-Fc-Block (BD Biosciences, Heidelberg, Germany). Surface markers were stained with PB-conjugated anti-CD8-alpha and PE-conjugated anti-CD4 (eBiosciences, Eching, Germany). Intracellular cytokine staining (ICS) was performed with FITC anti-IFN-gamma (XMG1.2), PE-Cy7 anti-TNF-alpha and APC anti-IL-2 (eBiosciences, Ech-ing, Germany) using the Cytofix/Cytoperm kit (BD Biosciences, Heidelberg, Germany) according to the manufacturer's recommendations. The same data were analyzed twice, the second time with a more rigorous exclusion of dead cells.

Immunohistochemical Stainings for HBc-Expressing Hepatocytes

Livers were harvested, fixed in 4% paraformaldehyde, and paraffin-embedded. The liver was sectioned (2 µm) and sections were stained with rabbit anti-HBcAg as the primary antibody (Diagnostic Biosystems, Pleasanton, Calif.; #RP 017; 1:50 dilution; retrieval at 100° C. for 30 min with EDTA) and a horseradish peroxide coupled secondary antibody. Incubation in Ventana buffer and staining were performed on a NEXES immunohistochemistry robot (Ventana Instruments) using an IVIEW DAB Detection Kit (Ventana Instruments) or on a Bond MAX (Leica Biosystems). For analysis, slides were scanned using a SCN 400 slide scanner and positive cells were counted using the integrated Tissue AI software (both Leica Biosystems).

HBV Transcripts from Liver Lysate

For analysis of HBV RNA from liver lysate, RNA was extracted from 30 mg liver tissue with the RNeasy mini kit (Qiagen) and cDNA was synthesized with the Superscript III kit (Thermo Fisher Scientific). HBV transcripts were amplified with primers specific for only the 3.5 kb transcripts (forward primer 5'-GAGTGTGGATTCGCACTCC-3' (SEQ ID NO: 41); reverse primer 5'-GAGGCGAGG-GAGTTCTTCT-3' (SEQ ID NO: 42)), or with primers binding to the common 3' end of all HBV transcripts (forward primer 5'-TCACCAGCACCATGCAAC-3' (SEQ ID NO: 43); reverse primer 5'-AAGCCACC-CAAGGCACAG-3' (SEQ ID NO: 44)) (Denaturation: 95° C. 5 min; Amplification: 95° C. 3 s, 60° C. 30 s (40 cycles))

(Yan et al., 2012). Results were normalised to murine GAPDH expression (forward primer 5'-ACCAACTGCT-TAGCCC-3' (SEQ ID NO: 45); reverse primer 5'-CCACGACGGACACATT-3' (SEQ ID NO: 46)) (Denaturation: 95° C. 5 min; Amplification: 95° C. 15 s, 60 C° 10 s, 72° C. 25 s (45 cycles)). All PCR reactions were performed on a LightCycler 480 (Roche Diagnostics).

AAV-HBV Mouse Model

For the AAV mouse model, wildtype C57/Bl6 mice (9 weeks of age; 6 animals per treatment group) were injected i.v. with $2 \times 10^{10}$ genome equivalents (geq) of Adeno-Associated-Virus Serotype 8 (AAV8) carrying a 1.2-fold overlength HBV genome of genotype D (AAV-HBV1.2) (day −28) (see, e.g., Yang, et al. (2014) Cell and Mol Immunol 11:71). Starting 4 weeks after AAV-transduction (day 0), animals were treated with 3 injections (3 mg/kg bw, n=12 per group) of either a control siRNA, or HBV siRNA (AD-66816 or AD-66810) (days 0, 29, and 57). Each siRNA treatment group was divided into two groups (n=6 per group) to be not treated or treated with the vaccine regimen consisting of recombinant HBsAg, HBcAg (15 µg of each) and 10 µg c-di-AMP given at day 57 and 70 and boosted with MVA-HBs and MVA-HBc ($5 \times 10^7$ geq of each) at day 84. A schematic showing the treatment regimen is provided in FIG. 12.

Example 2—Evaluation of HBV-siRNA in HepG2-NTCP Cell Culture and Dose Finding Experiments in HBVxfs Mice Anti-HBV siRNAs were evaluated for efficient knockdown of HBV antigens and DNA in an in vitro infection model using HBV-infected HepG2-NTCP cells treated with 1 nM, 10 nM, or 100 nM of one of modified AD-66810 or modified AD-66816 HBV-siRNA, or a control siRNA as provided above. Supernatants were collected at days 3, 6, 10, 13, and 17 days after siRNA treatment and assayed for HBeAg and HBsAg levels as compared to untransfected control. Both HBV-siRNAs were demonstrated to effectively knockdown expression of both HBeAg and HBsAg with the highest levels of knockdown observed at days 13 and 17. No significant knockdown was observed with the control siRNA. These data demonstrate that the AD-66810 or AD-66816 HBV-siRNAs are effective at knocking down expression of HBV antigens in a sustained manner in an in vitro system of HBV infection.

The HBV and control siRNAs were then tested in the HBVxfs transgenic model of chronic hepatitis B. The HBVxfs mice include an integrated HBV genome that is expressed under the control of a liver-specific promoter. At about 10 weeks of age, mice were administered a 3 or 9 mg/kg dose of one of AD-66810 or AD-66816 HBV-siRNA or a control siRNA (n=6 per group). Blood samples were collected at days 6, 13, and 21 after siRNA treatment and serum was prepared. HBeAg, HBsAg, and HBV DNA levels in serum (FIGS. 2A-2C) were determined as provided above. Further, RNA was isolated from liver and total HBV RNA and HBV 3.5 kB transcript levels were detected using the method of Yan, 2012 and normalized to GAPDH expression (FIGS. 2D and 2E).

Figure 2A:
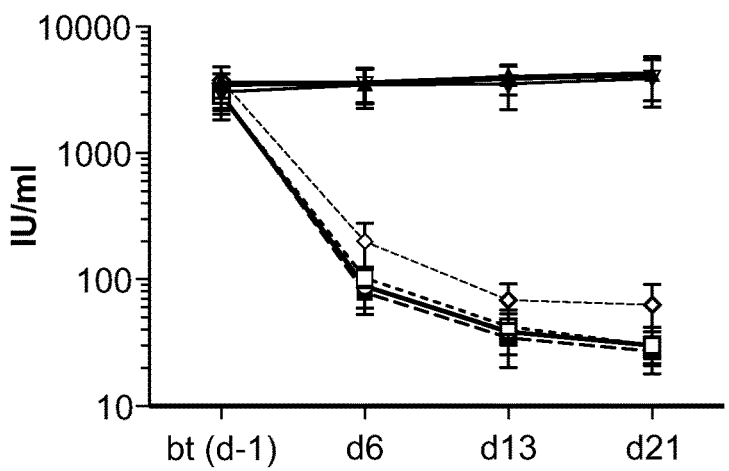
FIGS. 2A-2E are graphs showing suppression of HBV by siRNA in a transgenic mouse model. The level of (2A) HBsAg, (2B) HBeAg, and (2C) HBV-DNA in serum of HBV1.3-xfs mice (n=6 per group) after a single subcutaneous 3 mg/kg or 9 mg/kg dose of a control GalNAc-siRNA (an siRNA that does not target HBV), AD-66814, or AD-66810. The level of (2D) total HBV RNA and (2E) 3.5 kb HBV transcripts from liver lysates determined via RT-qPCR and normalized to expression of Glyceraldehyde 3-phosphate dehydrogenase (GAPDH).
Figure 2B:
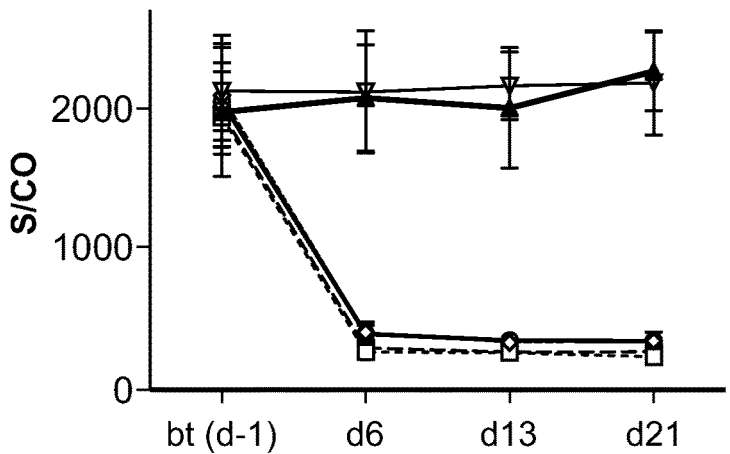
Figure 2C:
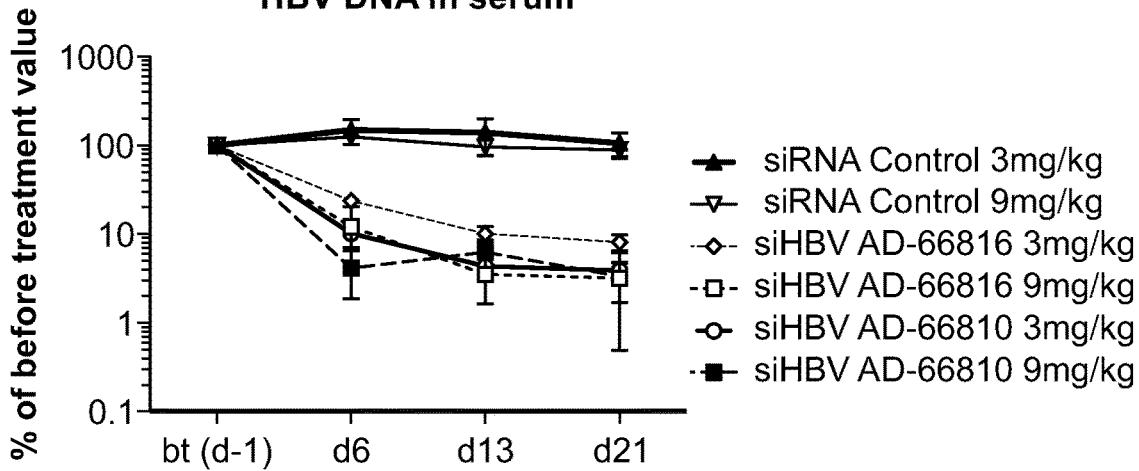
Figure 2D:
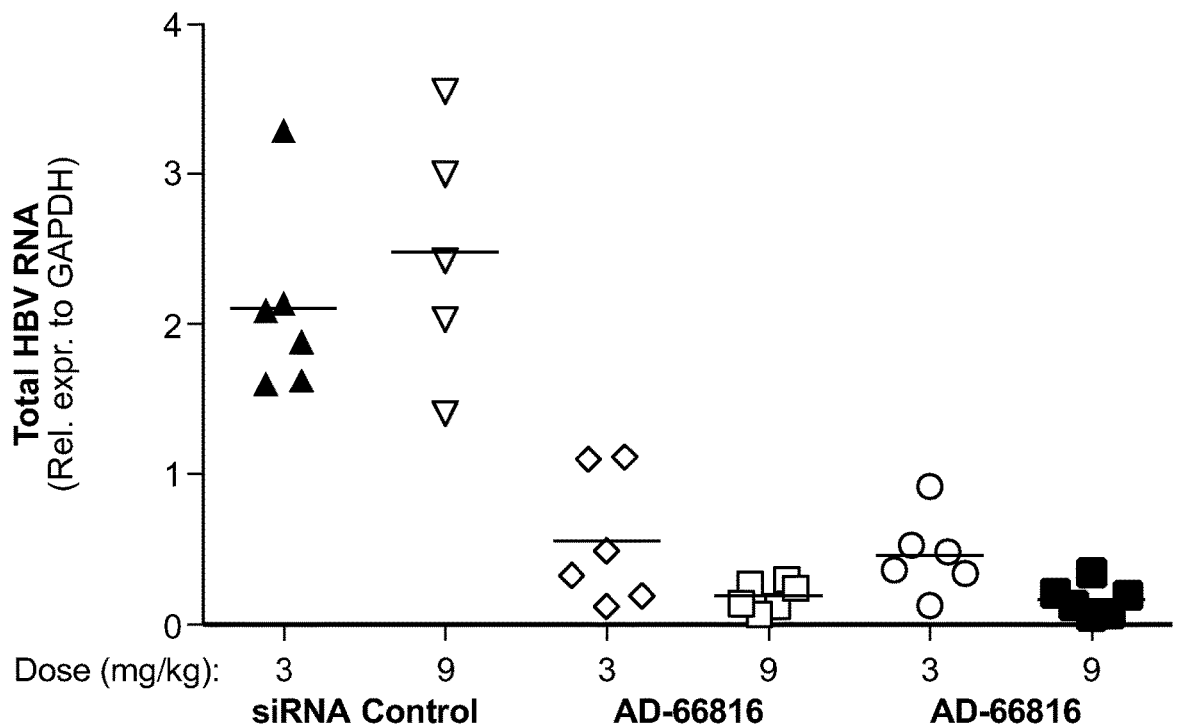
Figure 2E:
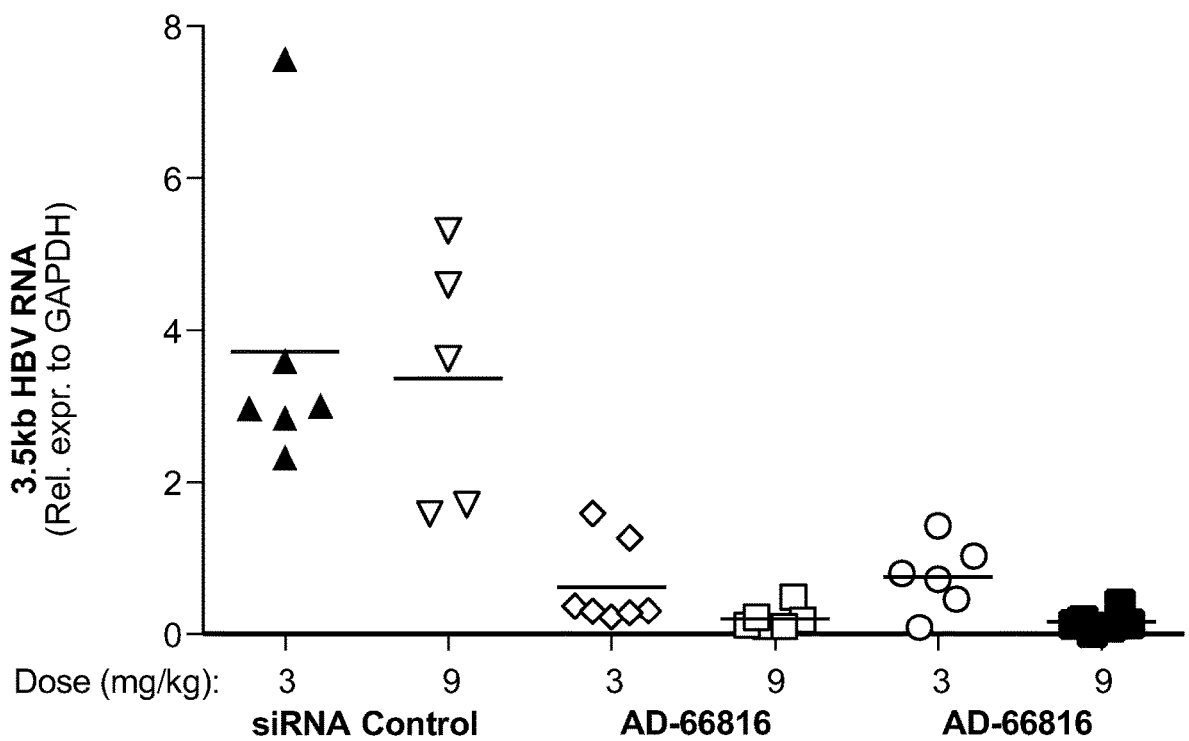

Both of the HBV-siRNAs at both doses were demonstrated to effectively knockdown expression of HBsAg and HBeAg and to decrease HBV DNA levels in serum as compared to control levels (see FIGS. 2A-2C). Further, total liver HBV RNA relative to GAPDH DNA and 3.5 kb HBV RNA relative to GAPDH RNA levels were strongly decreased by both doses of the HBV siRNAs as compared to control levels (FIGS. 2D and 2E). Based on these results, the 3 mg/kg dose was selected for use in further experiments.

Example 3—Comparison of Reducing Antigen Load with siRNA to Nucleot(s)ide Analogs Prior to Therapeutic Vaccine Administration in an HBV Transgenic Mouse Model Having demonstrated that siRNA targeted to HBV can effectively knockdown expression of HBsAg and HBeAg and decrease HBV DNA levels in serum in the HBVxfs mouse model, the effect of treatment of mice with the nucleoside analog Entecavir or HBV-siRNA prior to therapeutic vaccine administration using a prime-boost regimen was tested. The treatment scheme is shown in FIG. 3.

Mice were pretreated with one of six treatment regimens prior to vaccination using a prime-boost regimen (n=6 per group):

(1) No pretreatment;

(2) Entecavir at 1 µg/ml in water throughout the course of the study beginning on the first day of Week 0 (expected dose of about 4 mg/day based on calculations provided in Lütgehetmann et al., 2011, Gastroenterology. 140:2074-83);

(3) A 3 mg/kg dose on the first day of Weeks 0, 4, 8, and 12 of the control iRNA agent.

(4) A single dose on the first day of Week 0 with an expression vector encoding an shRNA targeted to HBV (HBV-shRNA) (Michler et al., 2016); or (5-6) A 3 mg/kg dose on the first day of Weeks 0, 4, 8, and 12 of modified AD-66816 or modified AD-86610 (generically HBV-siRNA).

On the first day of Weeks 12 and 14, a mixture of recombinantly expressed yeast HBsAg (15 µg) and E. coli expressed HBcAg (15 µg) adjuvanted with 31.9 µg synthetic phosphorothioated CpGODN 1668 (CpG) and 25 µg poly [di(sodiumcarboxylatoethyl-phenoxy)phosphazene] (PCEP) was subcutaneously administered to all mice as a protein-prime vaccination (Backes, 2016).

On the first day of week 16, a mixture of modified vaccinia viruses Ankara expressing HBsAg or HBcAg ($5 \times 10^7$ particles of each virus) was subcutaneously administered to all mice as a boost vaccination (Backes, 2016).

Blood samples were obtained on the first days of Week 0, 2, 4, 8, 12, 16, and 17 and serum samples prepared therefrom were assayed for levels of HBsAg, HBeAg, and HBV DNA. Results are shown in FIG. 4.

HBsAg and HBeAg levels mice in groups 1, 2, and 3 (mock, Entecavir, control iRNA agent) were similar. The HBV-shRNA or HBV-siRNAs (AD-66816 or AD-86610) alone caused a significant decrease in HBsAg, HBeAg, and HBV DNA in serum (FIGS. 4A-4C). The three dose prime-boost vaccination scheme resulted in a further decrease in HBsAg in all groups, and reduced the level of HBsAg in at least some animals in the HBV-shRNA and HBV-siRNA groups to below the level of detection. However, vaccine treatment did not decrease HBeAg levels in any of the groups. Without being bound by mechanism, it is proposed that the decrease in HBsAg, but not HBeAg, results from the immune response induced by the vaccine against the s antigen, but not the e antigen, which is produced by proteolytic processing of the C protein (see FIG. 5 discussed below).

HBV DNA levels were decreased to about the lower limit of quantitation with Entecavir alone so no effect of the three dose prime-boost vaccine could be detected (FIG. 4C). Mock treatment and treatment with the HBV-shRNA, the HBV-siRNAs, and control siRNA all decreased HBV DNA levels and the level of HBV-DNA was further decreased by the prime-boost vaccine in all groups. It is unclear why the mock treatment and control siRNA decreased HBV DNA levels in this experiment. No decrease in HBV DNA was observed in response to treatment with control siRNA in other experiments (see, e.g., FIGS. 2C and 8C). These data demonstrate that RNAi is superior to nucleot(s)ide analog therapy in reducing viral antigens. Also, RNAi and subsequent vaccination have a combined effect on HBsAg and HBV DNA levels greater than either agent alone.

On the final day of the experiment (first day of Week 17), mice were sacrificed and their livers harvested. Liver associated lymphocytes were isolated from liver and after peptide stimulation CD8+ T cell responses measured via intracellular cytokine staining. Specifically, intrahepatic CD8+ T cell responses were assessed for response to HBsAg, HBcAg, and the MVA virus particle using the method provided in Backes, 2016. The data were analyzed twice using two different thresholds for the exclusion of dead immune cells as the exclusion of dead immune cells in the first analysis provided in FIGS. 5A-5C was determined to be insufficient. The second analysis is presented in FIGS. 5D-5F. The second analysis confirmed the conclusions from the first analysis.

Figure 5F:
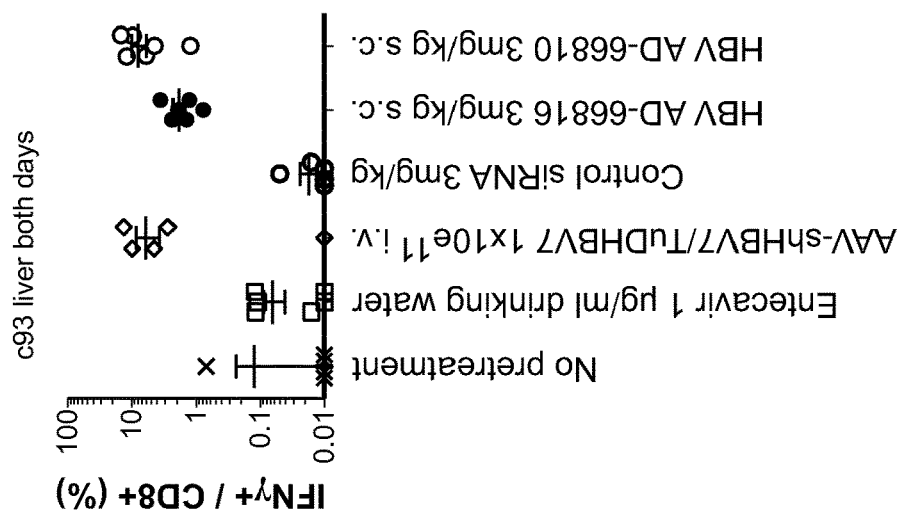
Figure 5E:
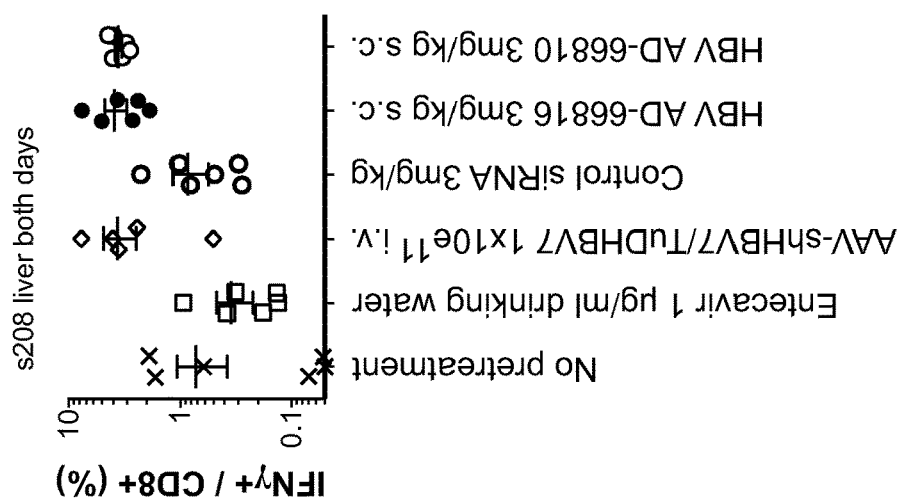
Figure 5D:
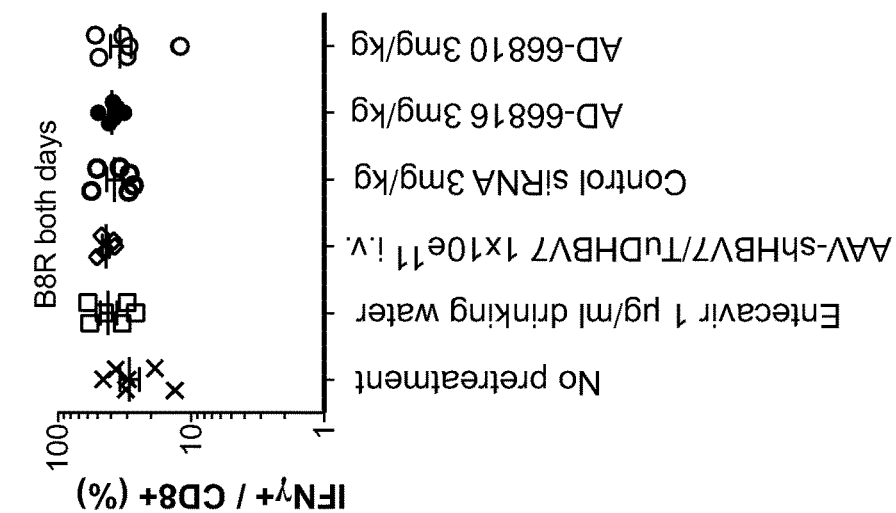

Mice pretreated with the HBV-shRNA or the HBV-siRNAs before vaccination were able to generate a CD8+ T cell immune response against the HBsAg and HBcAg (FIGS. 5A, 5B, 5D, and 5E) indicating that cytotoxic T cells able to clear HBV infection are induced when HBV antigen levels are suppressed prior to vaccination. No significant CD8+ T cell immune response against the HBV antigens was observed in the mock, Entecavir, or control siRNA groups. A significant and similar CD8+ T cell immune response against the MVA virus in all animals, independent of pretreatment or viral antigen levels, demonstrated that vaccination had worked equally well in all animals and was not influenced by HBV antigen levels, thereby demonstrating the presence of a competent immune system (FIGS. 5C and 5F). No significant differences in antibody production were observed between mock treated animals and any of the other groups indicating that high HBV antigen levels may induce T cell tolerance.

These data demonstrate that RNAi treatment, in contrast to the current standard of care treatment with a nucleoside analog, can restore HBV-specific T cell immunity in the liver and enable the induction of HBV-specific CD8+ T cell responses after therapeutic vaccination. A robust CD8+ effector T cell response has been associated with viral clearance and functional cure (see, e.g., Thimme et al., 2003. J Vivol. 77:68-76, and Backes et al., 2016. Vaccine. 34:923-932).

RNA was also isolated from liver and total HBV RNA and HBV 3.5 kB transcript levels were detected using the method of Yan, 2012 and normalized to GAPDH expression. Treatment of mice with HBV-siRNA or HBV-shRNA prior to vaccine administration resulted in a significant decrease in HBV total RNA and HBV 3.5 kb transcript as compared to the mock treated control (FIGS. 6A and 6B). No significant change in HBV total RNA and HBV 3.5 kb transcript was observed in the mice treated with Entecavir or the control siRNA prior to vaccination as compared to the mock treated control. These data demonstrate that both HBV siRNAs and the shRNA, in contrast to the control and Entecavir groups, successfully led to a decrease in HBV transcript levels.

Further, expression of HBV antigens in the liver was analyzed by immunohistochemical staining for HBc of liver sections and counting of HBc positive cells per mm$^2$ (FIG. 6C). Only groups of animals pre-treated with HBV siRNA or shRNA, but not Entecavir or the control siRNA, showed reduced HBc expression following vaccination.

Throughout the experiment, body weight and ALT levels were monitored. No significant differences were observed in any of the treatment groups as compared to mock treated control.

Example 4—Evaluation of the Effect of Duration of HBV Antigen Knockdown on Response to Immunization in an HBV Transgenic Mouse Model Having demonstrated that suppression of expression of HBV antigens using shRNA or siRNA is effective at potentiating an immune response to an HBV vaccine regimen, a study was designed to determine if the length of time of HBV antigen suppression had an effect on potentiation of an HBV immune response. A treatment scheme is shown in FIG. 7.

Using the HBV1.3xfs mouse model, mice were treated for eight, six, or three weeks with HBV-siRNA AD-66816 (modified) or the control siRNA for 8 weeks, administered subcutaneously at 3 mg/kg/dose. siRNA administration was followed by administration of the prime-boost vaccine regimen as set forth above with the exception that c-di-AMP was used as an adjuvant with protein administration rather than PCEP+CPG (n=6 per group). Therefore, mice in the 8 week group (n=6) received three doses of siRNA with the third dose being administered on the first day of vaccine administration. The mice in the 6 week group (n=12) received two doses of siRNA with the second dose being administered two weeks prior to the first day of vaccine administration. Finally, the mice in the 3 week group (n=6) received one dose of siRNA with the dose being administered three weeks prior to the first day of vaccine administration.

Blood samples were collected on the first day of −8 weeks, −6 weeks, −4 weeks, −2 weeks, 0 weeks, 2 weeks, 4 weeks, and 6 weeks, before (negative numbers) and after the first dose of vaccine administration on the first day of Week 0. Serum was prepared and HBsAg, HBeAg, and HBV DNA levels were assessed as provided above.

A significant decrease in each HBsAg, HBeAg, and HBV DNA was observed after the first administration of AD-66816 (FIGS. 8A-8C). A further significant decrease in HBsAg was observed after treatment with the vaccine boost, with the greatest decrease observed in the 8 week pretreatment group to below the level of detection of the assay, representing a greater than 5 log 10 decrease in HBsAg level in all treated animals. Immunization caused only slight further reductions (<0.5 log 10) of HBV DNA which had been significantly decreased by the siRNA treatment. No further decrease in HBeAg levels was observed in response to the vaccination regimen.

These data demonstrate that efficacy of therapeutic vaccination correlates with duration of antigen suppression before start of vaccination. Reconstitution of HBV-specific CD8+ T cell responses takes several weeks, with a 6 or preferably 8 week pretreatment rather than a 3 week pretreatment.

On the final day of the experiment, on the first day of Week 6 after the start of immunization, mice were sacrificed and their livers harvested for six mice from each group. Liver associated lymphocytes were isolated and a lymphocyte stimulation assay was performed as provided above. Specifically, intrahepatic CD8+ T cell responses were assessed for response to HBsAg, HBcAg, and the MVA virus particle using the method provided in Backes, 2016. T-cell responses against HBsAg and HBcAg in liver corresponded with the duration of HBV antigen knockdown, with a trend of higher levels of immune response observed with longer duration of HBV antigen resulting in greater T-cell response (see FIGS. 9A-9C). Similar responses to MVA virus antigens were observed across all groups, independent of pretreatment, showing that vaccination had worked equally well in all animals and was not influenced by HBV antigen levels demonstrating the presence of a competent immune system (FIG. 9D). No significant differences in antibody production were observed between control siRNA treated animals and any of the other groups. This demonstrates, that reconstitution of HBV-specific CD8+ T cell responses does not occur immediately, with stronger responses seen after therapeutic vaccination if animals had lowered HBV antigen titers for at least 6 or 8 weeks compared to only 3 weeks. It further confirms the previous finding that, in contrast to T cell responses, B cell immunity does not seem to be significant influenced by HBV antigen titers.

RNA was also isolated from liver and total HBV RNA and HBV 3.5 kB transcript levels were detected using the method of Yan, 2012 and normalized to GAPDH expression. Treatment of mice with HBV-siRNA AD-66816 prior to vaccine administration resulted in a significant decrease in HBV total RNA and HBV 3.5 kb transcript in liver lysates as compared to the control siRNA treated control (FIGS. 10A and 10B). Further, HBV antigen expression in the liver was analyzed by immunohistochemical staining and counting of HBc positive cells per mm$^2$ (FIG. 10C). Correlating the observed increase in HBV-specific CD8 responses with increased duration of siRNA pretreatment, decreased numbers of HBc expressing cells where observed in the liver. These results demonstrate that the CD8+ T cell responses did prevent antigen expression in the liver.

To assess the durability of response, blood samples were collected from mice pretreated with the AD-66816 HBV-siRNA using the six week treatment regimen at 2 and 3 weeks after administration of the boost vaccination (FIGS. 11A-11D). In three of the six mice, HBsAg levels continued to drop to below the level of detection of the assay (FIG. 11A). No similar decrease in HBeAg levels were observed during the course of the experiment (FIG. 11B). These data show that the maximum effect by the siRNA-vaccination combinatorial therapy provided herein is later than 1 week after the MVA vaccination, which was chosen as termination time point to best assess CD8+ T cell responses. Anti-HBs antibody response (FIG. 11C) and T cell immune response in the liver against HBs(5208) (FIG. 11D) at week 7 after the first vaccine dose after the 6 week regimen in the dosing regimen. The antibody response varied among animals.

These data demonstrate that a functional cure is possible using the treatment regimens provided herein. Further, these data suggest that a lower HBsAg and HBeAg burden can result in a greater level of immune clearance of HB antigens and potentiate an immune response, at least within the short time course of the experiment.

Throughout the experiment, body weight and ALT levels were monitored. No significant differences were observed in any of the treatment groups as compared to mock treated control.

Example 5—Evaluation of the Effect of Duration of HBV Antigen Knockdown on Response to Immunization in an AAV-HBV Mouse Model Having demonstrated the efficacy of the siRNA-vaccine combination treatment regimen in a transgenic mouse model, an AAV-HBV infection mouse model was used to study the efficacy of the treatment regimen in acquired infection model (see, e.g., Yang, et al. (2014) Cell Mol Immunol 11:71). This mouse model exhibits sustained HBV viremia after infection with a recombinant adeno-associated virus (AAV) carrying a replicable HBV genome.

There are a number of differences between the HBV-transgenic and AAV-HBV mouse models. The HBV transgenic mice can express HBV antigens essentially from birth, whereas the AAV-HBV model allows for the introduction of the HBV genome at a later time in the life of the mice. This may have an effect on immune tolerance. Further, the HBV transgenic mice carry the transgene in every cell of the body, providing the possibility of "leaky" extrahepatic expression. Although the AAV8 serotype could infect cells outside of the liver, it has a strong liver tropism. Moreover, it is not possible to clear an HBV infection in a transgenic mouse. When a transgenic HBV expressing liver cell is killed, it is replaced by a new HBV expressing cell. In the infection model, if the infected cells are killed, the newly dividing cells are not infected at the time of cell division.

Nine week old C57/Bl6 mice were infected with AAV-HBV (−28 days). Mice were then treated with one of control siRNA, or one of two HBV-siRNAs, modified AD-66816 or modified AD-66810 at 3 mg/kg administered subcutaneously on days 0, 29, and 57 (i.e., 0 weeks, 4 weeks, 8 weeks) (n=12 per group). Each siRNA treatment group was divided into two groups (n=6 per group). One group was treated with the HBV vaccine protocol (protein prime on days 57 and 70, and MVA boost on day 84, i.e., weeks 8, 10, and 12, respectively) and one group was not. A schematic showing the dosing regimen is provided in FIG. 12. Mice were monitored throughout the experiment for serum HBsAg, HBeAg, anti-HBs antibodies, body weight, and ALT. Anti-HBe antibody levels were also periodically tested.

FIGS. 13A and 13B show an increase in HBsAg and HBeAg levels comparable to that seen in transgenic mice within two weeks of transduction with the AAV-HBV virus. Mice treated only with the control siRNA replicated HBV for greater than 8 months at levels comparable to chronically infected humans (HBsAg levels around 2,000 IU/ml, HBV viremia $10^6$-$10^7$ IU/ml). HBV siRNAs AD-66816 and AD-66810 reduced HBsAg by 2 and 2.5 $\log_{10}$, respectively, and HBeAg by >1 $\log_{10}$. The effect persisted for at least 4 weeks after stopping siRNA treatment before antigenemia slowly rebounded to baseline levels after 18 weeks (FIGS. 13A and 13B).

Figure 13C:
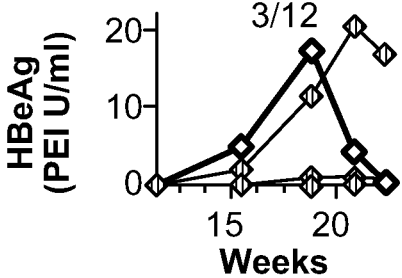
Figures 13D, 13E:
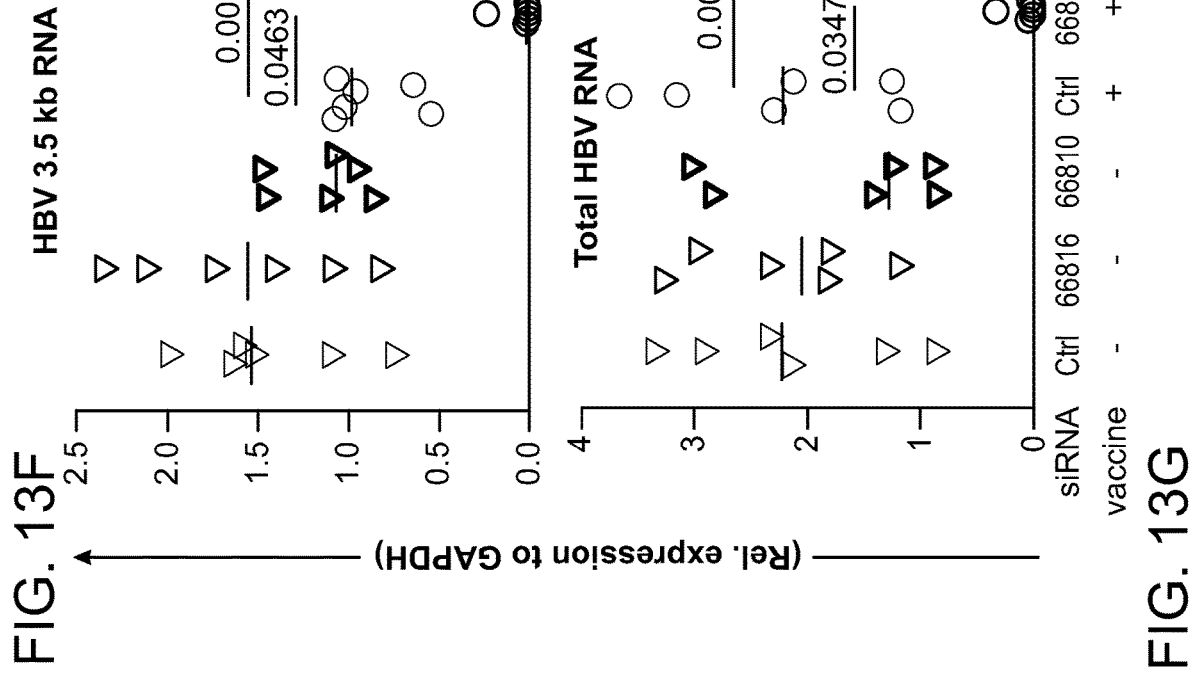
Figures 13F, 13G:
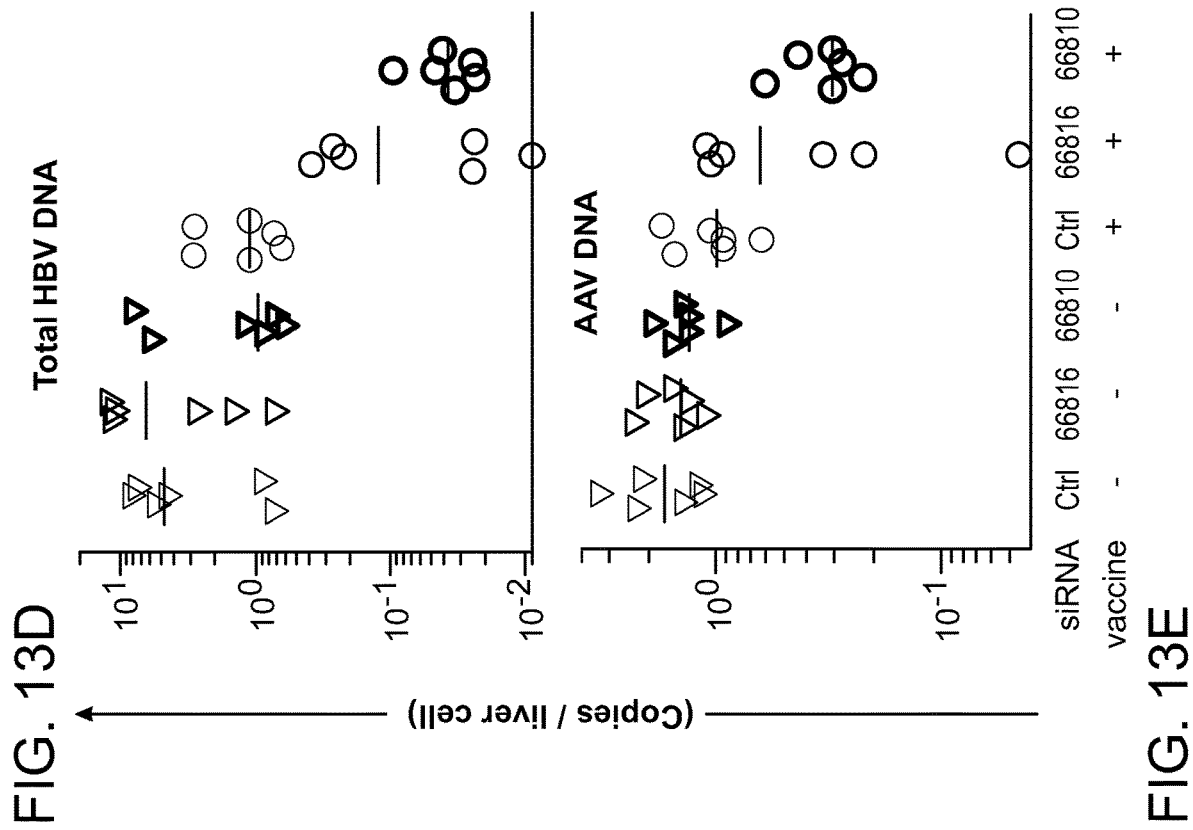

Intrahepatic HBV DNA (FIG. 13D) and AAV DNA (FIG. 13E) levels were determined at week 22 by qPCR as described above. The relative expression in liver of HBV 3.5 RNA relative to GAPDH RNA (FIG. 13F) and total HBV RNA relative to GAPDH RNA (FIG. 13G) were determined using rtPCR. Mice treated with the combined siRNA-vaccine protocol demonstrated a significant decrease in total HBV DNA and AAV DNA as compared to untreated control or siRNA or vaccine treatment alone at the 22 week time point (FIGS. 13D and 13E). Notably, total HBV DNA levels dropped to less than one copy per cell as a result of the combination treatment (FIG. 13D). Mice treated with the combined siRNA-vaccine protocol also demonstrated a significant decrease level of HBV 3.5 kb RNA expression relative to GAPDH RNA expression as compared to all other treatment regimens (FIG. 13F). A significant decrease in total HBV RNA relative to GAPDH RNA expression was observed as compared to treatment with vaccine or siRNA alone (FIG. 13G). These data suggest that a short course of administration of siRNA alone or a therapeutic vaccine against HBV is insufficient to durably suppress HBV infection. Immune mediated control of HBV after siRNA knockdown of HBV expression is long lasting. At 22 weeks after the last siRNA dose, the effect of the siRNA was waning as seen in the groups which had only received the HBV siRNAs without vaccination. Mice treated with the siRNA-vaccine protocol maintained HBV DNA and RNA suppression long after the end of siRNA administration.

No immune responses were observed in these fully immune competent mice under siRNA treatment alone, but vaccine treatment resulted in anti-HBs seroconversion in all vaccinated animals (FIGS. 14A and 14B). siRNA-pretreated animals, however, developed 10-fold higher and more constant anti-HBs titers and were able to completely and persistently clear serum HBsAg and HBeAg. In contrast, anti-HBe seroconversion was only observed in antimals pretreated with HBV siRNAs. Interestingly, three of the 12 mice vaccinated after HBV siRNA treatment showed a transient relapse of HBeAg between week 15 and 22 coinciding with decreased levels of anti-HBe (FIG. 13C). Without being bound by mechanism, it is proposed that theHBeAg relapse was controlled by a memory immune response induced by the vaccine. Taken together, suppression of HBV antigen expression by an siRNA in combination with a heterologous prime-boost vaccine is sufficient to break immune tolerance to HBV antigens. The sequential therapy achieved long-term functional cure in a mouse model of persistent HBV infection without causing significant liver damage.

FIGS. 14A and 14B show that animals treated with HBV siRNA plus the vaccine regimen developed high titers of anti-HBs antibodies and anti-HBe antibodies. The level of anti-HBs antibodies continued to increase after the last vaccine dose. Although anti-HBs antibodies could also be measured in animals that received the control siRNA plus the vaccine regimen, the levels were significantly lower. Further, only animals that received HBV siRNA plus the vaccine regimen developed anti-HBe antibodies and achieved anti-HBe seroconversion. The combinatorial therapy using siRNA and vaccine appeared to be well tolerated. All mice equally gained weight and only a mild ALT elevation (<2-fold upper limit of normal) was observed (FIGS. 15A and 15B). The loss of antigenemia coincided with slight increases of ALT activity seen in treatment groups which had received HBV siRNA in conjunction with the vaccination regimen (FIG. 15A). These groups showed significant but mild increases (both $p > 0.05$ or smaller by repeated measure two-way ANOVA; only comparing time points after start of vaccination) as compared to all other treatment groups that did not receive the combination HBV-siRNA-vaccine regimen. There was a steady increase in body weight in all animals throughout the experiment independent of siRNA treatment. Animals that were vaccinated showed a slight and transient decrease (approximately 5%) of body weight after vaccination, but rebounded to normal levels within nine days and subsequently gained weight comparable to the control groups (FIG. 15B).

Without being bound by mechanism, the data provided herein strongly suggest that the high level of HBV antigen expression routinely detected as circulating HBsAg and HBeAg prevents HBV-specific CD8+ T cell responses, which has far reaching consequences for future immune therapy of chronic hepatitis B. Using 2 different mouse models for chronic hepatitis B, it is proposed that HBV-specific immunomodulation can be reverted by suppressing HBV protein expression in hepatocytes using an RNAi-based therapy. Such reduction of HBV antigens by RNAi, in contrast to standard-of-care nucleo(t)side analogues, allows for induction of strong HBV-specific CD8+ T cell responses by therapeutic vaccination that are required for control of HBV infection.

APPENDIX A

TABLE 1

Abbreviations of nucleotide monomers used in nucleic acid sequence representation. It will be understood that, unless otherwise indicated, these monomers, when present in an oligonucleotide, are mutually linked by 5'-3'-phosphodiester bonds.

| Abbreviation | Nucleotide(s) |
|---|---|
| A | Adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amidodecanoyl)]-4-hydroxyprolinol Hyp-(GalNAc-alkyl)3 |
| (dT) | 2'-deoxythymidine-3'-phosphate |
| Y34 | 2-hydroxymethyl-tetrahydrofurane-4-methoxy-3-phosphate (abasic 2'-OMe furanose) |
| Y44 | 2-hydroxymethyl-tetrahydrofurane-5-phosphate |
| (Agn) | Adenosine-glycol nucleic acid (GNA) |
| (Tgn) | Thymidine-glycol nucleic acid (GNA) S-Isomer |
| (Cgn) | Cytidine-glycol nucleic acid (GNA) |
| P | Phosphate |
| VP | Vinyl-phosphate |

TABLE 2

Exemplary Unmodified Sense and Antisense Strand Sequences of HBV dsRNAs (Activity data available in WO2016/077321, incorporated herein by reference)

| Duplex Name | Sense Oligo Name | Sense Sequence (5' to 3') | SEQ ID NO | Antisense Oligo Name | Antisense Sequence (5' to 3') | SEQ ID NO: | Position in NC_003977.1 |
|---|---|---|---|---|---|---|---|
| AD-61522 | A-123463 | AGUUAUAUGGAUGAUGUGGUA | 47 | A-123464 | UACCACAUCAUCCAUAUAACUGA | 263 | 731_753 |
| AD-61547 | A-123487 | GGAUGUGUCUGCGGCGUUUUA | 48 | A-123488 | UAAAACGCCGCAGACACAUCCAG | 264 | 373_395 |
| AD-63938 | A-127896 | ACUCGUGGUGGACUUCUCUCA | 49 | A-127897 | UGAGAGAAGUCCACCACGAGUCU | 265 | 250_272 |
| AD-63939 | A-127909 | ACUCGUGGUGGACUUCUCUCA | 50 | A-127906 | UGAGAGAAGUCCACCACGAGUCU | 266 | 250_272 |
| AD-63940 | A-127917 | ACUCGUGGUGGACUUCTCUCA | 51 | A-127906 | UGAGAGAAGUCCACCACGAGUCU | 267 | 250_272 |
| AD-63941 | A-127905 | ACUCGUGGUGGACUUCUCUCA | 52 | A-127925 | UGAGAGAAGUCCACCACGAGUCU | 268 | 250_272 |
| AD-63942 | A-127933 | UCGUGGUGGACUUCUCUCA | 53 | A-127934 | UGAGAGAAGUCCACCACGAGU | 269 | 252_274 |
| AD-63943 | A-127944 | ACUCGUGGUGGACUUCUCUCA | 54 | A-127942 | UGAGAGAAGUCCACCACGAGUCU | 270 | 250_272 |
| AD-63945 | A-127910 | ACUCGUGGUGGACUUCUCUCA | 55 | A-127906 | UGAGAGAAGUCCACCACGAGUCU | 271 | 250_272 |
| AD-63946 | A-127918 | ACUCGUGGUGGACUUCUCUCA | 56 | A-127906 | UGAGAGAAGUCCACCACGAGUCU | 272 | 250_272 |
| AD-63947 | A-127905 | ACUCGUGGUGGACUUCUCUCA | 57 | A-127926 | UGAGAGAAGUCCACCACGAGUCU | 273 | 250_272 |
| AD-63948 | A-127935 | GUGGUGGACUUCUCUCA | 58 | A-127936 | UGAGAGAAGUCCACCACGA | 274 | 254_276 |
| AD-63949 | A-127944 | ACUCGUGGUGGACUUCUCUCA | 59 | A-127906 | UGAGAGAAGUCCACCACGAGUCU | 275 | 250_272 |
| AD-63950 | A-127900 | UCGUGGUGGACUUCUCUCAUU | 60 | A-127901 | UGAGAGAAGUCCACCACGAUU | 276 | 252_274 |
| AD-63951 | A-127911 | ACUCGUGGUGGACUUCUCUCA | 61 | A-127906 | UGAGAGAAGUCCACCACGAGUCU | 277 | 250_272 |
| AD-63952 | A-127905 | ACUCGUGGUGGACUUCUCUCA | 62 | A-127919 | UGAGAGAAGUCCACCACGAGUCU | 278 | 250_272 |
| AD-63953 | A-127905 | ACUCGUGGUGGACUUCUCUCA | 63 | A-127927 | UGAGAGAAGUCCACCACGAGUCU | 279 | 250_272 |
| AD-63955 | A-127945 | ACUCGUGGUGGACUUCUCUCA | 64 | A-127940 | UGAGAGAAGUCCACCACGAGUCU | 280 | 250_272 |
| AD-63956 | A-127902 | UCGUGGUGGACUUCUCUCA | 65 | A-127903 | UGAGAGAAGUCCACCACGAUU | 281 | 252_274 |
| AD-63957 | A-127912 | ACUCGUGGUGGACUUCUCUCA | 66 | A-127906 | UGAGAGAAGUCCACCACGAGUCU | 282 | 250_272 |
| AD-63958 | A-127905 | ACUCGUGGUGGACUUCUCUCA | 67 | A-127920 | UGAGAGAAGUCCACCACGAGUCU | 283 | 250_272 |
| AD-63959 | A-127905 | ACUCGUGGUGGACUUCUCUCA | 68 | A-127928 | UGAGAGAAGUCCACCACGAGUCU | 284 | 250_272 |
| AD-63960 | A-126619 | UAUUUCCUAGGGUACAA | 69 | A-127938 | UGAGAGAAGUCCACCACGA | 285 | 254_276 |
| AD-63961 | A-127945 | ACUCGUGGUGGACUUCUCUCA | 70 | A-127942 | UGAGAGAAGUCCACCACGAGUCU | 286 | 250_272 |
| AD-63962 | A-127902 | UCGUGGUGGACUUCUCUCA | 71 | A-127904 | UGAGAGAAGUCCACCACGAUU | 287 | 252_274 |
| AD-63963 | A-127913 | ACUCGUGGUGGACUUCUCUCA | 72 | A-127906 | UGAGAGAAGUCCACCACGAGUCU | 288 | 250_272 |
| AD-63964 | A-127905 | ACUCGUGGUGGACUUCUCUCA | 73 | A-127921 | UGAGAGAAGUCCACCACGAGUCU | 289 | 250_272 |
| AD-63965 | A-127905 | ACUCGUGGUGGACUUCUCUCA | 74 | A-127929 | UGAGAGAAGUCCACCACGAGUCU | 290 | 250_272 |
| AD-63966 | A-127939 | ACUCGUGGUGGACUUCUCUCA | 75 | A-127940 | UGAGAGAAGUCCACCACGAGUCU | 291 | 250_272 |
| AD-63967 | A-127945 | ACUCGUGGUGGACUUCUCUCA | 76 | A-127906 | UGAGAGAAGUCCACCACGAGUCU | 292 | 250_272 |
| AD-63968 | A-127905 | ACUCGUGGUGGACUUCUCUCA | 77 | A-127906 | UGAGAGAAGUCCACCACGAGUCU | 293 | 250_272 |
| AD-63968 | A-127905 | ACUCGUGGUGGACUUCUCUCA | 78 | A-127906 | UGAGAGAAGUCCACCACGAGUCU | 294 | 250_272 |
| AD-63968 | A-127905 | ACUCGUGGUGGACUUCUCUCA | 79 | A-127906 | UGAGAGAAGUCCACCACGAGUCU | 295 | 250_272 |
| AD-63969 | A-127914 | ACUCGUGGUGGACUUCUCUCA | 80 | A-127906 | UGAGAGAAGUCCACCACGAGUCU | 296 | 250_272 |
| AD-63970 | A-127905 | ACUCGUGGUGGACUUCUCUCA | 81 | A-127922 | UGAGAGAAGUCCACCACGAGUCU | 297 | 250_272 |
| AD-63971 | A-127905 | ACUCGUGGUGGACUUCUCUCA | 82 | A-127930 | UGAGAGAAGUCCACCACGAGUCU | 298 | 250_272 |

TABLE 2-continued

Exemplary Unmodified Sense and Antisense Strand Sequences of HBV dsRNAs (Activity data available in WO2016/077321, incorporated herein by reference)

| Duplex Name | Sense Oligo Name | Sense Sequence (5' to 3') | SEQ ID NO | Antisense Oligo Name | Antisense Sequence (5' to 3') | SEQ ID NO: | Position in NC_003977.1 |
|---|---|---|---|---|---|---|---|
| AD-63972 | A-127941 | ACUCGUGGUGGACUUCUCUCA | 83 | A-127942 | UGAGAGAAGUCCACCACGAGUCU | 299 | 250_272 |
| AD-63973 | A-127946 | ACUCGUGGUGGACUUCUCUCA | 84 | A-127947 | UGAGAGAAGTCCACCACGAGUCU | 300 | 250_272 |
| AD-63975 | A-127915 | ACUCGUGGUGGACUUCUCUCA | 85 | A-127906 | UGAGAGAAGUCCACCACGAGUCU | 301 | 250_272 |
| AD-63976 | A-127905 | ACUCGUGGUGGACUUCUCUCA | 86 | A-127923 | UGAGAGAAGUCCACCACGAGUCU | 302 | 250_272 |
| AD-63977 | A-127917 | ACUCGUGGUGGACUUCUCUCA | 87 | A-127931 | UGAGAGAAGUCCACCACGAGUCU | 303 | 250_272 |
| AD-63978 | A-127943 | ACUCGUGGUGGACUUCUCUCA | 88 | A-127906 | UGAGAGAAGUCCACCACGAGUCU | 304 | 250_272 |
| AD-63979 | A-127908 | ACUCGUGGUGGACUUCUCUCA | 89 | A-127906 | UGAGAGAAGUCCACCACGAGUCU | 305 | 250_272 |
| AD-63980 | A-127916 | ACUCGUGGUGGACUUCUCUCA | 90 | A-127906 | UGAGAGAAGUCCACCACGAGUCU | 306 | 250_272 |
| AD-63981 | A-127905 | ACUCGUGGUGGACUUCUCUCA | 91 | A-127924 | UGAGAGAAGUCCACCACGAGUCU | 307 | 250_272 |
| AD-63982 | A-127917 | ACUCGUGGUGGACUUCUCUCA | 92 | A-127932 | UGAGAGAAGUCCACCACGAGUCU | 308 | 250_272 |
| AD-63983 | A-127944 | ACUCGUGGUGGACUUCUCUCA | 93 | A-127940 | UGAGAGAAGUCCACCACGAGUCU | 309 | 250_272 |
| AD-63985 | A-127961 | GUGGUGGACUUCUCUCAAUUU | 94 | A-127956 | AAAUUGAGAGAAGUCCACCACGA | 310 | 254_276 |
| AD-63986 | A-127969 | GUGGUGGACUUCUCUCAAUUU | 95 | A-127956 | AAAUUGAGAGAAGUCCACCACGA | 311 | 254_276 |
| AD-63987 | A-127955 | GUGGUGGACUUCUCUCAAUUU | 96 | A-127977 | AAAUUGAGAGAAGUCCACCACGA | 312 | 254_276 |
| AD-63988 | A-127986 | UGGACUUCUCUCAAUUU | 97 | A-127987 | AAAUUGAGAGAAGUCCACC | 313 | 258_280 |
| AD-63989 | A-127996 | GUGGUGGACUUCUCUCAAUUU | 98 | A-127992 | AAAUUGAGAGAAGUCCACCACGA | 314 | 254_276 |
| AD-63990 | A-127950 | GGUGGACUUCUCUCAAUUUUU | 99 | A-127951 | AAAUUGAGAGAAGUCCACCUU | 315 | 256_278 |
| AD-63991 | A-127962 | GUGGUGGACUUCUCUCAAUUU | 100 | A-127956 | AAAUUGAGAGAAGUCCACCACGA | 316 | 254_276 |
| AD-63992 | A-127955 | GUGGUGGACUUCUCUCAAUUU | 101 | A-127970 | AAAUUGAGAGAAGUCCACCACGA | 317 | 254_276 |
| AD-63993 | A-127955 | GUGGUGGACUUCUCUCAAUUU | 102 | A-127978 | AAAUUGAGAGAAGUCCACCACGA | 318 | 254_276 |
| AD-63994 | A-127984 | GGUGGACUUCUCUCAAUUU | 103 | A-127988 | AAAUUGAGAGAAGUCCACCAC | 319 | 256_278 |
| AD-63995 | A-127996 | GUGGUGGACUUCUCUCAAUUU | 104 | A-127993 | AAAUUGAGAGAAGUCCACCACGA | 320 | 254_276 |
| AD-63996 | A-127952 | GGUGGACUUCUCUCAAUUU | 105 | A-127953 | AAAUUGAGAGAAGUCCACCUU | 321 | 256_278 |
| AD-63997 | A-127963 | GUGGUGGACUUCUCUCAAUUU | 106 | A-127956 | AAAUUGAGAGAAGUCCACCACGA | 322 | 254_276 |
| AD-63999 | A-127955 | GUGGUGGACUUCUCUCAAUUU | 107 | A-127979 | AAAUUGAGAGAAGUCCACCACGA | 323 | 254_276 |
| AD-64000 | A-127986 | UGGACUUCUCUCAAUUU | 108 | A-127989 | AAAUUGAGAGAAGUCCACC | 324 | 258_280 |
| AD-64001 | A-127996 | GUGGUGGACUUCUCUCAAUUU | 109 | A-127994 | AAAUUGAGAGAAGUCCACCACGA | 325 | 254_276 |
| AD-64002 | A-127952 | GGUGGACUUCUCUCAAUUU | 110 | A-127954 | AAAUUGAGAGAAGUCCACCUU | 326 | 256_278 |
| AD-64003 | A-127964 | GUGGUGGACUUCUCUCAAUUU | 111 | A-127956 | AAAUUGAGAGAAGUCCACCACGA | 327 | 254_276 |
| AD-64004 | A-127955 | GUGGUGGACUUCUCUCAAUUU | 112 | A-127972 | AAAUUGAGAGAAGUCCACCACGA | 328 | 254_276 |
| AD-64005 | A-127955 | GUGGUGGACUUCUCUCAAUUU | 113 | A-127980 | AAAUUGAGAGAAGUCCACCACGA | 329 | 254_276 |
| AD-64006 | A-127990 | GUGGUGGACUUCUCUCAAUUU | 114 | A-127991 | AAAUUGAGAGAAGUCCACCACGA | 330 | 254_276 |
| AD-64007 | A-127996 | GUGGUGGACUUCUCUCAAUUU | 115 | A-127995 | AAAUUGAGAGAAGUCCACCACGA | 331 | 254_276 |
| AD-64008 | A-127955 | GUGGUGGACUUCUCUCAAUUU | 116 | A-127956 | AAAUUGAGAGAAGUCCACCACGA | 332 | 254_276 |
| AD-64008 | A-127955 | GUGGUGGACUUCUCUCAAUUU | 117 | A-127956 | AAAUUGAGAGAAGUCCACCACGA | 333 | 254_276 |
| AD-64009 | A-127965 | GUGGUGGACUUCUCUCAAUUU | 118 | A-127956 | AAAUUGAGAGAAGUCCACCACGA | 334 | 254_276 |

TABLE 2-continued

Exemplary Unmodified Sense and Antisense Strand Sequences
of HBV dsRNAs (Activity data available in WO2016/077321,
incorporated herein by reference)

| Duplex Name | Sense Oligo Name | Sense Sequence (5' to 3') | SEQ ID NO | Antisense Oligo Name | Antisense Sequence (5' to 3') | SEQ ID NO | Position in NC_003977.1 |
|---|---|---|---|---|---|---|---|
| AD-64010 | A-127955 | GUGGUGGACUUCUCUCAAUUU | 119 | A-127973 | AAAUUGAGAGAAGUCCACCACGA | 335 | 254_276 |
| AD-64011 | A-127955 | GUGGUGGACUUCUCUCAAUUU | 120 | A-127981 | AAAUUGAGAGAAGUCCACCACGA | 336 | 254_276 |
| AD-64012 | A-127990 | GUGGUGGACUUCUCUCAAUUU | 121 | A-127992 | AAAUUGAGAGAAGUCCACCACGA | 337 | 254_276 |
| AD-64013 | A-127997 | GUGGUGGACTTCUCUCAAUUU | 122 | A-127998 | AAAUUGAGAGAAGTCCACCACGA | 338 | 254_276 |
| AD-64014 | A-127957 | GUGGUGGACUUCUCUCAAUUU | 123 | A-127958 | AAAUUGAGAGAAGUCCACCACGA | 339 | 254_276 |
| AD-64015 | A-127966 | GUGGUGGACUUCUCUCAAUUU | 124 | A-127956 | AAAUUGAGAGAAGUCCACCACGA | 340 | 254_276 |
| AD-64016 | A-127955 | GUGGUGGACUUCUCUCAAUUU | 125 | A-127974 | AAAUUGAGAGAAGUCCACCACGA | 341 | 254_276 |
| AD-64017 | A-127968 | GUGGUGGACUTCUCUCAAUUU | 126 | A-127982 | AAAUUGAGAGAAGUCCACCACGA | 342 | 254_276 |
| AD-64018 | A-127990 | GUGGUGGACUUCUCUCAAUUU | 127 | A-127993 | AAAUUGAGAGAAGUCCACCACGA | 343 | 254_276 |
| AD-64019 | A-127959 | GUGGUGGACUUCUCUCAAUUU | 128 | A-127956 | AAAUUGAGAGAAGUCCACCACGA | 344 | 254_276 |
| AD-64020 | A-127967 | GUGGUGGACUUCUCUCAAUUU | 129 | A-127956 | AAAUUGAGAGAAGUCCACCACGA | 345 | 254_276 |
| AD-64021 | A-127955 | GUGGUGGACUUCUCUCAAUUU | 130 | A-127975 | AAAUUGAGAGAAGUCCACCACGA | 346 | 254_276 |
| AD-64022 | A-127968 | GUGGUGGACUTCUCUCAAUUU | 131 | A-127983 | AAAUUGAGAGAAGTCCACCACGA | 347 | 254_276 |
| AD-64023 | A-127990 | GUGGUGGACUUCUCUCAAUUU | 132 | A-127994 | AAAUUGAGAGAAGUCCACCACGA | 348 | 254_276 |
| AD-64024 | A-127960 | GUGGUGGACUUCUCUCAAUUU | 133 | A-127956 | AAAUUGAGAGAAGUCCACCACGA | 349 | 254_276 |
| AD-64025 | A-127968 | GUGGUGGACUTCUCUCAAUUU | 134 | A-127956 | AAAUUGAGAGAAGUCCACCACGA | 350 | 254_276 |
| AD-64026 | A-127955 | GUGGUGGACUUCUCUCAAUUU | 135 | A-127976 | AAAUUGAGAGAAGUCCACCACGA | 351 | 254_276 |
| AD-64027 | A-127984 | GGUGGACUUCUCUCAAUUU | 136 | A-127985 | AAAUUGAGAGAAGUCCACCAC | 352 | 256_278 |
| AD-64028 | A-127990 | GUGGUGGACUUCUCUCAAUUU | 137 | A-127995 | AAAUUGAGAGAAGUCCACCACGA | 353 | 254_276 |
| AD-64272 | A-128001 | GUGCACUUCGCUUCACCUCUG | 138 | A-128002 | CAGAGGUGAAGCGAAGUGCACAC | 354 | 1577_1599 |
| AD-64274 | A-128363 | GUUGACAAAAAUCCUCACAAU | 139 | A-128364 | AUUGUGAGGAUUUUUGUCAACAA | 355 | 215_237 |
| AD-64275 | A-128377 | UGUUGACAAAAAUCCUCACAA | 140 | A-128378 | UUGUGAGGAUUUUUGUCAACAAG | 356 | 214_236 |
| AD-64276 | A-128393 | GGUGGACUUCUCUCAAUUUUA | 141 | A-128394 | UAAAAUUGAGAGAAGUCCACCAC | 357 | 256_278 |
| AD-64277 | A-128407 | UCUUUUGGAGUGUGGAUUCGA | 142 | A-128408 | UCGAAUCCACACUCCAAAAGACA | 358 | 2259_2281 |
| AD-64277 | A-128407 | UCUUUUGGAGUGUGGAUUCGA | 143 | A-128408 | UCGAAUCCACACUCCAAAAGACA | 359 | 2259_2281 |
| AD-64278 | A-128423 | ACUGUUCAAGCCUCCAAGCUA | 144 | A-128424 | UAGCUUGGAGGCUUGAACAAGAC | 360 | 1857_1879 |
| AD-64279 | A-128435 | UCUGCCGAUCCAUACUGCGGA | 145 | A-128436 | UCCGCAGUAUGGAUCGGCAGAGG | 361 | 1255_1277 |
| AD-64280 | A-128379 | AUGUGUCUGCGGCGUUUUAUA | 146 | A-128380 | UAUAAAACGCCGCAGACACAUCC | 362 | 375_397 |
| AD-64281 | A-128395 | CCCCGUCUGUGCCUUCUCAUA | 147 | A-128396 | UAUGAGAAGGCACAGACGGGAG | 363 | 1545_1567 |
| AD-64282 | A-128409 | GCCUAAUCAUCUCUUGUUCAU | 148 | A-128410 | AUGAACAAGAGAUGAUUAGCGAG | 364 | 1831_1853 |
| AD-64283 | A-128425 | UCUAGACUCUGGUGGACUUC | 149 | A-128426 | GAAGUCCACCACGAGUCUAGACU | 365 | 245_267 |
| AD-64284 | A-128437 | CUGCCGAUCCAUACUGCGGAA | 150 | A-128438 | UUCCGCAGUAUGGAUCGGCAGAG | 366 | 1256_1278 |
| AD-64285 | A-128365 | UUUUUCUUGUUGACAAAAAUA | 151 | A-128366 | UAUUUUUGUCAACAAGAAAAACC | 367 | 207_229 |
| AD-64286 | A-128381 | AUCUUCUUGUUGGUUCUUCUA | 152 | A-128382 | UAGAAGAACCAACAAGAAGAUGA | 368 | 426_448 |
| AD-64289 | A-128367 | GUUUUUCUUGUUGACAAAAAU | 153 | A-128368 | AUUUUUGUCAACAAGAAAAACCC | 369 | 206_228 |
| AD-64290 | A-128383 | CUGCCUAAUCAUCUCUUGUUA | 154 | A-128384 | UAACAAGAGAUGAUUAGGCAGAG | 370 | 1829_1851 |

TABLE 2-continued

Exemplary Unmodified Sense and Antisense Strand Sequences
of HBV dsRNAs (Activity data available in WO2016/077321,
incorporated herein by reference)

| Duplex Name | Sense Oligo Name | Sense Sequence (5' to 3') | SEQ ID NO | Antisense Oligo Name | Antisense Sequence (5' to 3') | SEQ ID NO: | Position in NC_003977.1 |
|---|---|---|---|---|---|---|---|
| AD-64291 | A-128399 | UCCUCACAAUACCACAGAGUA | 155 | A-128400 | UACUCUGUGGUAUUGUGAGGAUU | 371 | 226_248 |
| AD-64292 | A-128413 | CUUGUUGACAAAAAUCCUCAA | 156 | A-128414 | UUGAGGAUUUUUGUCAACAAGAA | 372 | 212_234 |
| AD-64293 | A-128439 | GCAACUUUUCACCUCUGCCU | 157 | A-128440 | AGGCAGAGGUGAAAAGUUGCAU | 373 | 1814_1836 |
| AD-64294 | A-128369 | GGGAACAAGAGCUACAGCAUA | 158 | A-128370 | UAUGCUGUAGCUCUUGUUCCCAA | 374 | 2828_2850 |
| AD-64295 | A-128385 | CGUGGUGGACUUCUCUCAAUU | 159 | A-128386 | AAUUGAGAGAAGUCCACCAGCAG | 375 | 253_275 |
| AD-64297 | A-128415 | CUGCUGCUAUGCCUCAUCUUA | 160 | A-128416 | UAAGAUGAGGCAUAGCAGCAGGA | 376 | 411_433 |
| AD-64298 | A-128427 | GUUGGAUGUGUCUGCGGCGUU | 161 | A-128428 | AACGCCGCAGACACAUCCAACGA | 377 | 370_392 |
| AD-64299 | A-128441 | UUCAUCCUGCUGCUAUGCCUA | 162 | A-128442 | UAGGCAUAGCAGCAGGAUGAAGA | 378 | 405_427 |
| AD-64300 | A-128371 | UUCUUGUUGACAAAAAUCCUA | 163 | A-128372 | UAGGAUUUUUGUCAACAAGAAAA | 379 | 210_232 |
| AD-64302 | A-128417 | UAUAUGGAUGAUGUGGUAUUA | 164 | A-128418 | UAAUACCACAUCAUCCAUAUAAC | 380 | 734_756 |
| AD-64303 | A-128429 | UUCAUCCUGCUGCUAUGCCUC | 165 | A-128430 | GAGGCAUAGCAGCAGGAUGAAGA | 381 | 405_427 |
| AD-64304 | A-128443 | GUGCACUUCGCUUCACCUCUA | 166 | A-128444 | UAGAGGUGAAGCGAAGUGCACAC | 382 | 1577_1599 |
| AD-64305 | A-128373 | UUGACAAAAAUCCUCACAAUA | 167 | A-128374 | UAUUGUGAGGAUUUUUGUCAACA | 383 | 216_238 |
| AD-64307 | A-128403 | AAGCCUCCAAGCUGUGCCUUA | 168 | A-128404 | UAAGGCACAGCUUGGAGGCUUGA | 384 | 1864_1886 |
| AD-64308 | A-128419 | CCUCUUCAUCCUGCUGCUAUA | 169 | A-128420 | UAUAGCAGCAGGAUGAAGAGGAA | 385 | 401_423 |
| AD-64309 | A-128431 | CCUGCUGCUAUGCCUCAUCUU | 170 | A-128432 | AAGAUGAGGCAUAGCAGCAGGAU | 386 | 410_432 |
| AD-64310 | A-128375 | CAUCUUCUUGUUGGUUCUUCU | 171 | A-128376 | AGAAGAACCAACAAGAAGAUGAG | 387 | 425_447 |
| AD-64311 | A-128391 | CCGUCUGUGCCUUCUCAUCUA | 172 | A-128392 | UAGAUGAGAAGGCACAGACGGGG | 388 | 1547_1569 |
| AD-64312 | A-128405 | CCUCAUCUUCUUGUUGGUUCU | 173 | A-128406 | AGAACCAACAAGAAGAUGAGGCA | 389 | 422_444 |
| AD-64313 | A-128421 | CCACCAAAUGCCCCUAUCUUA | 174 | A-128422 | UAAGAUAGGGGCAUUUGGUGGUC | 390 | 2298_2320 |
| AD-64314 | A-128433 | GCUCCUCUGCCGAUCCAUACU | 175 | A-128434 | AGUAUGGAUCGGCAGAGGAGCCA | 391 | 1250_1272 |
| AD-64315 | A-128363 | GUUGACAAAAAUCCUCACAAU | 176 | A-128445 | AUUGUGAGGAUUUUUGUCAACAA | 392 | 215_237 |
| AD-64316 | A-128377 | UGUUGACAAAAAUCCUCACAA | 177 | A-128453 | UUGUGAGGAUUUUUGUCAACAAG | 393 | 214_236 |
| AD-64317 | A-128393 | GGUGGACUUCUCUCAAUUUUA | 178 | A-128461 | UAAAAUUGAGAGAAGUCCACCAC | 394 | 256_278 |
| AD-64318 | A-128407 | UCUUUUGGAGUGUGGAUUCGA | 179 | A-128469 | UCGAAUCCACACUCCAAAAGACA | 395 | 2259_2281 |
| AD-64318 | A-128407 | UCUUUUGGAGUGUGGAUUCGA | 180 | A-128469 | UCGAAUCCACACUCCAAAAGACA | 396 | 2259_2281 |
| AD-64319 | A-128423 | ACUGUUCAAGCCUCCAAGCUA | 181 | A-128477 | UAGCUUGGAGGCUUGAACAAGAC | 397 | 1857_1879 |
| AD-64320 | A-128435 | UCUGCCGAUCCAUACUGCGGA | 182 | A-128483 | UCCGCAGUAUGGAUCGGCAGAGG | 398 | 1255_1277 |
| AD-64321 | A-123463 | AGUUAUAUGGAUGAUGUGGUA | 183 | A-128446 | UACCACAUCAUCCAUAUAACUGA | 399 | 731_753 |
| AD-64322 | A-128379 | AUGUGUCUGCGGCGUUUUAUA | 184 | A-128454 | UAUAAAACGCCGCAGACACAUCC | 400 | 375_397 |
| AD-64323 | A-128395 | CCCCGUCUGUGCCUUCUCAUA | 185 | A-128462 | UAUGAGAAGGCACAGACGGGAG | 401 | 1545_1567 |
| AD-64324 | A-128409 | GCCUAAUCAUCUCUUGUUCAU | 186 | A-128470 | AUGAACAAGAGAUGAUUAGCGAG | 402 | 1831_1853 |
| AD-64325 | A-128425 | UCUAGACUCUGGUGGACUUC | 187 | A-128478 | GAAGUCCACCACGAGUCUAGACU | 403 | 245_267 |
| AD-64326 | A-128437 | CUGCCGAUCCAUACUGCGGAA | 188 | A-128484 | UUCCGCAGUAUGGAUCGGCAGAG | 404 | 1256_1278 |
| AD-64328 | A-128381 | AUCUUCUUGUUGGUUCUUCUA | 189 | A-128455 | UAGAAGAACCAACAAGAAGAUGA | 405 | 426_448 |
| AD-64330 | A-128411 | UUCUCUCAAUUUUCUAGGGGA | 190 | A-128471 | UCCCCUAGAAAAUUGAGAGAAGU | 406 | 263_285 |

TABLE 2-continued

Exemplary Unmodified Sense and Antisense Strand Sequences
of HBV dsRNAs (Activity data available in WO2016/077321,
incorporated herein by reference)

| Duplex Name | Sense Oligo Name | Sense Sequence (5' to 3') | SEQ ID NO | Antisense Oligo Name | Antisense Sequence (5' to 3') | SEQ ID NO | Position in NC_003977.1 |
|---|---|---|---|---|---|---|---|
| AD-64331 | A-127905 | ACUCGUGGUGGACUUCUCUCA | 191 | A-127907 | UGAGAGAAGUCCACCACGAGUCU | 407 | 250_272 |
| AD-64332 | A-128001 | GUGCACUUCGCUUCACCUCUG | 192 | A-128485 | CAGAGGUGAAGCGAAGUGCACAC | 408 | 1577_1599 |
| AD-64333 | A-128367 | GUUUUUCUUGUUGACAAAAAU | 193 | A-128448 | AUUUUUGUCAACAAGAAAAACCC | 409 | 206_228 |
| AD-64334 | A-128383 | CUGCCUAAUCAUCUCUUGUUA | 194 | A-128456 | UAACAAGAGAUGAUUAGGCAGAG | 410 | 1829_1851 |
| AD-64335 | A-128399 | UCCUCACAAUACCACAGAGUA | 195 | A-128464 | UACUCUGUGGUAUUGUGAGGAUU | 411 | 226_248 |
| AD-64336 | A-128413 | CUUGUUGACAAAAAUCCUCAA | 196 | A-128472 | UUGAGGAUUUUUGUCAACAAGAA | 412 | 212_234 |
| AD-64337 | A-127955 | GUGGUGGACUUCUCUCAAUUU | 197 | A-127958 | AAAUUGAGAGAAGUCCACCACGA | 413 | 254_276 |
| AD-64338 | A-128439 | GCAACUUUUCACCUCUGCCU | 198 | A-128486 | AGGCAGAGGUGAAAAAGUUGCAU | 414 | 1814_1836 |
| AD-64339 | A-128369 | GGGAACAAGAGCUACAGCAUA | 199 | A-128449 | UAUGCUGUAGCUCUUGUUCCCAA | 415 | 2828_2850 |
| AD-64341 | A-128401 | UCAUCUUCUUGUUGGUUCUUA | 200 | A-128465 | UAAGAACCAACAAGAAGAUGAGG | 416 | 424_446 |
| AD-64342 | A-128415 | CUGCUGCUAUGCCUCAUCUUA | 201 | A-128473 | UAAGAUGAGGCAUAGCAGCAGGA | 417 | 411_433 |
| AD-64343 | A-128427 | GUUGGAUGUGUCUGCGGCGUU | 202 | A-128479 | AACGCCGCAGACACAUCCAACGA | 418 | 370_392 |
| AD-64344 | A-128441 | UUCAUCCUGCUGCUAUGCCUA | 203 | A-128487 | UAGGCAUAGCAGCAGGAUGAAGA | 419 | 405_427 |
| AD-64345 | A-128371 | UUCUUGUUGACAAAAAUCCUA | 204 | A-128450 | UAGGAUUUUUGUCAACAAGAAAA | 420 | 210_232 |
| AD-64347 | A-123487 | GGAUGUGUCUGCGGCGUUUUA | 205 | A-128466 | UAAAACGCCGCAGACACAUCCAG | 421 | 373_395 |
| AD-64348 | A-128417 | UAUAUGGAUGAUGUGGUAUUA | 206 | A-128474 | UAAUACCACAUCAUCCAUAUAAC | 422 | 734_756 |
| AD-64349 | A-128429 | UUCAUCCUGCUGCUAUGCCUC | 207 | A-128480 | GAGGCAUAGCAGCAGGAUGAAGA | 423 | 405_427 |
| AD-64350 | A-128443 | GUGCACUUCGCUUCACCUCUA | 208 | A-128488 | UAGAGGUGAAGCGAAGUGCACAC | 424 | 1577_1599 |
| AD-64351 | A-128373 | UUGACAAAAAUCCUCACAAUA | 209 | A-128451 | UAUUGUGAGGAUUUUUGUCAACA | 425 | 216_238 |
| AD-64352 | A-128389 | CCAAGUGUUUGCUGACGCAAA | 210 | A-128459 | UUUGCGUCAGCAAACACUUGGCA | 426 | 1174_1196 |
| AD-64352 | A-128389 | CCAAGUGUUUGCUGACGCAAA | 211 | A-128459 | UUUGCGUCAGCAAACACUUGGCA | 427 | 1174_1196 |
| AD-64353 | A-128403 | AAGCCUCCAAGCUGUGCCUUA | 212 | A-128467 | UAAGGCACAGCUUGGAGGCUUGA | 428 | 1864_1886 |
| AD-64354 | A-128419 | CCUCUUCAUCCUGCUGCUAUA | 213 | A-128475 | UAUAGCAGCAGGAUGAAGAGGAA | 429 | 401_423 |
| AD-64355 | A-128431 | CCUGCUGCUAUGCCUCAUCUU | 214 | A-128481 | AAGAUGAGGCAUAGCAGCAGGAU | 430 | 410_432 |
| AD-64356 | A-128375 | CAUCUUCUUGUUGGUUCUUCU | 215 | A-128452 | AGAAGAACCAACAAGAAGAUGAG | 431 | 425_447 |
| AD-64357 | A-128391 | CCGUCUGUGCCUUCUCAUCUA | 216 | A-128460 | UAGAUGAGAAGGCACAGACGGGG | 432 | 1547_1569 |
| AD-64358 | A-128405 | CCUCAUCUUCUUGUUGGUUCU | 217 | A-128468 | AGAACCAACAAGAAGAUGAGGCA | 433 | 422_444 |
| AD-64359 | A-128421 | CCACCAAAUGCCCCUAUCUUA | 218 | A-128476 | UAAGAUAGGGGCAUUUGGUGGUC | 434 | 2298_2320 |
| AD-64360 | A-128433 | GCUCCUCUGCCGAUCCAUACU | 219 | A-128482 | AGUAUGGAUCGGCAGAGGAGCCA | 435 | 1250_1272 |
| AD-64700 | A-129379 | ACUCGUGGUGUACUUCUCUCA | 220 | A-127906 | UGAGAGAAGUCCACCACGAGUCU | 436 | 250_272 |
| AD-64701 | A-127905 | ACUCGUGGUGGACUUCUCUCA | 221 | A-129387 | UGAGAGAAGTCCACCACGAGUCU | 437 | 250_272 |
| AD-64702 | A-127905 | ACUCGUGGUGGACUUCUCUCA | 222 | A-129395 | UGAGAGAAGUCCACCACGAGUCU | 438 | 250_272 |
| AD-64703 | A-129376 | ACUCGUGGUGGACUUCACUCA | 223 | A-129385 | UGAGAGAAGTCCACCACGAGUCU | 439 | 250_272 |
| AD-64704 | A-129381 | ACUCGUGGUGTACUUCACUCA | 224 | A-129389 | UGAGAGAAGUCCACCACGAGUCU | 440 | 250_272 |
| AD-64705 | A-129380 | ACUCGUGGUGTACUUCACUCA | 225 | A-127906 | UGAGAGAAGUCCACCACGAGUCU | 441 | 250_272 |
| AD-64706 | A-127905 | ACUCGUGGUGGACUUCUCUCA | 226 | A-129388 | UGAGAGAAGUCCACCACGAGUCU | 442 | 250_272 |

TABLE 2-continued

Exemplary Unmodified Sense and Antisense Strand Sequences of HBV dsRNAs (Activity data available in WO2016/077321, incorporated herein by reference)

| Duplex Name | Sense Oligo Name | Sense Sequence (5' to 3') | SEQ ID NO | Antisense Oligo Name | Antisense Sequence (5' to 3') | SEQ ID NO | Position in NC_003977.1 |
|---|---|---|---|---|---|---|---|
| AD-64707 | A-127905 | ACUCGUGGUGGACUUCUCUCA | 227 | A-129396 | UGAGAGAAGTCCACCACGAGUCU | 443 | 250_272 |
| AD-64708 | A-129382 | ACUCGUGGTGGACUUCTCUCA | 228 | A-129385 | UGAGAGAAGTCCACCACGAGUCU | 444 | 250_272 |
| AD-64709 | A-129373 | ACUCGUGGUGGACUUCUCUCA | 229 | A-129391 | UGAGAGAAGTCCACCACGAGUCU | 445 | 250_272 |
| AD-64710 | A-129373 | ACUCGUGGUGGACUUCUCUCA | 230 | A-127906 | UGAGAGAAGUCCACCACGAGUCU | 446 | 250_272 |
| AD-64711 | A-129381 | ACUCGUGGTGTACUUCACUCA | 231 | A-127906 | UGAGAGAAGUCCACCACGAGUCU | 447 | 250_272 |
| AD-64712 | A-127905 | ACUCGUGGUGGACUUCUCUCA | 232 | A-129389 | UGAGAGAAGUCCACCACGAGUCU | 448 | 250_272 |
| AD-64713 | A-127905 | ACUCGUGGUGGACUUCUCUCA | 233 | A-129397 | UGAGAGAAGTCCACCACGAGUCU | 449 | 250_272 |
| AD-64714 | A-129384 | ACUCGUGGTGGACUUCACUCA | 234 | A-129385 | UGAGAGAAGTCCACCACGAGUCU | 450 | 250_272 |
| AD-64715 | A-129376 | ACUCGUGGUGGACUUCACUCA | 235 | A-129391 | UGAGAGAAGTCCACCACGAGUCU | 451 | 250_272 |
| AD-64716 | A-129374 | ACUCGUGGUGGACUUCUCUCA | 236 | A-127906 | UGAGAGAAGUCCACCACGAGUCU | 452 | 250_272 |
| AD-64717 | A-129382 | ACUCGUGGTGGACUUCTCUCA | 237 | A-127906 | UGAGAGAAGUCCACCACGAGUCU | 453 | 250_272 |
| AD-64718 | A-127905 | ACUCGUGGUGGACUUCUCUCA | 238 | A-129390 | UGAGAGAAGUCCACCACGAGUCU | 454 | 250_272 |
| AD-64719 | A-127917 | ACUCGUGGUGGACUUCTCUCA | 239 | A-129385 | UGAGAGAAGTCCACCACGAGUCU | 455 | 250_272 |
| AD-64720 | A-129381 | ACUCGUGGTGTACUUCACUCA | 240 | A-129385 | UGAGAGAAGTCCACCACGAGUCU | 456 | 250_272 |
| AD-64721 | A-129382 | ACUCGUGGTGGACUUCTCUCA | 241 | A-129391 | UGAGAGAAGTCCACCACGAGUCU | 457 | 250_272 |
| AD-64722 | A-129375 | ACUCGUGGUGGACUUCCUCA | 242 | A-127906 | UGAGAGAAGUCCACCACGAGUCU | 458 | 250_272 |
| AD-64723 | A-129383 | ACUCGUGGUGGACUUCTCUCA | 243 | A-127906 | UGAGAGAAGUCCACCACGAGUCU | 459 | 250_272 |
| AD-64725 | A-127917 | ACUCGUGGUGGACUUCUCUCA | 244 | A-129398 | UGAGAGAAGTCCACCACGAGUCU | 460 | 250_272 |
| AD-64726 | A-129373 | ACUCGUGGUGGACUUCUCUCA | 245 | A-129389 | UGAGAGAAGUCCACCACGAGUCU | 461 | 250_272 |
| AD-64727 | A-129384 | ACUCGUGGTGGACUUCACUCA | 246 | A-129391 | UGAGAGAAGTCCACCACGAGUCU | 462 | 250_272 |
| AD-64728 | A-129376 | ACUCGUGGUGGACUUCACUCA | 247 | A-127906 | UGAGAGAAGUCCACCACGAGUCU | 463 | 250_272 |
| AD-64729 | A-129384 | ACUCGUGGTGGACUUCACUCA | 248 | A-127906 | UGAGAGAAGUCCACCACGAGUCU | 464 | 250_272 |
| AD-64730 | A-127905 | ACUCGUGGUGGACUUCUCUCA | 249 | A-129392 | UGAGAGAAGTCCACCACGAGUCU | 465 | 250_272 |
| AD-64731 | A-129399 | ACUCGUGGUGGACUUCUCUCA | 250 | A-129385 | UGAGAGAAGTCCACCACGAGUCU | 466 | 250_272 |
| AD-64732 | A-129376 | ACUCGUGGUGGACUUCACUCA | 251 | A-129389 | UGAGAGAAGUCCACCACGAGUCU | 467 | 250_272 |
| AD-64733 | A-129381 | ACUCGUGGTGTACUUCACUCA | 252 | A-129391 | UGAGAGAAGTCCACCACGAGUCU | 468 | 250_272 |
| AD-64734 | A-129377 | ACUCGUGGUGGACUUCCCUCA | 253 | A-127906 | UGAGAGAAGUCCACCACGAGUCU | 469 | 250_272 |
| AD-64735 | A-127905 | ACUCGUGGUGGACUUCUCUCA | 254 | A-129385 | UGAGAGAAGTCCACCACGAGUCU | 470 | 250_272 |
| AD-64736 | A-127905 | ACUCGUGGUGGACUUCUCUCA | 255 | A-129393 | UGAGAGAAGTCCACCACGAGUCU | 471 | 250_272 |
| AD-64737 | A-129399 | ACUCGUGGUGGACUUCTCUCA | 256 | A-129398 | UGAGAGAAGTCCACCACGAGUCU | 472 | 250_272 |
| AD-64738 | A-129382 | ACUCGUGGTGGACUUCTCUCA | 257 | A-129389 | UGAGAGAAGUCCACCACGAGUCU | 473 | 250_272 |
| AD-64739 | A-129378 | ACUCGUGGUGGACUUCGCUCA | 258 | A-127906 | UGAGAGAAGUCCACCACGAGUCU | 474 | 250_272 |
| AD-64740 | A-127905 | ACUCGUGGUGGACUUCUCUCA | 259 | A-129386 | UGAGAGAAGTCCACCACGAGUCU | 475 | 250_272 |
| AD-64741 | A-127905 | ACUCGUGGUGGACUUCUCUCA | 260 | A-129394 | UGAGAGAAGTCCACCACGAGUCU | 476 | 250_272 |
| AD-64742 | A-129373 | ACUCGUGGUGGACUUCUCUCA | 261 | A-129385 | UGAGAGAAGTCCACCACGAGUCU | 477 | 250_272 |
| AD-64743 | A-129384 | ACUCGUGGTGGACUUCACUCA | 262 | A-129389 | UGAGAGAAGUCCACCACGAGUCU | 478 | 250_272 |

TABLE 3

Exemplary Modified Sense and Antisense Strand Sequences
of HBV dsRNAs (Activity data available in WO2016/077321,
incorporated herein by reference)

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-61522 | A-123463 | AfsgsUfuAfuAfuGfGfAfuGfaUfgUfgGfuAfuL96 | 479 | A-123464 | usAfscCfaCfaUfcAfuccAfuAfuAfaCfusgsa | 694 |
| AD-61547 | A-123487 | GfsgsAfuGfuGfuCfUfGfcGfgCfgUfuUfuAfuL96 | 480 | A-123488 | usAfsaAfaCfgCfcGfcagAfcAfcAfuCfcsasg | 695 |
| AD-63938 | A-127896 | Y44ACUCGUGGUGGACUUCUCUCA | 481 | A-127897 | UGAGAGAAGUCCACCACGAGUCU | 696 |
| AD-63939 | A-127909 | ascsucGfuGfgUfGfGfaCfuucUfcucaL96 | 482 | A-127906 | usGfsaGfaGfaAfgUfccaCfcAfcGfaGfuscsu | 697 |
| AD-63940 | A-127917 | ascsucguggugdGacuuc(Tgn)cucaL96 | 483 | A-127906 | usGfsaGfaGfaAfgUfccaCfcAfcGfaGfuscsu | 698 |
| AD-63941 | A-127905 | AfscsUfcGfuGfgUfGfGfaCfuUfcUfcUfcAfL96 | 484 | A-127925 | usGfsaGfagaAfguccaCfcAfcgaGfuscsu | 699 |
| AD-63942 | A-127933 | uscsGfuGfgUfGfGfaCfuUfcUfcUfcAfL96 | 485 | A-127934 | usGfsaGfaGfaAfgUfccaCfcAfcGfasgsu | 700 |
| AD-63943 | A-127944 | ascsucGfuGfguGfGfaCfuucucucaL96 | 486 | A-127942 | usGfsAfgaGfaAfgUfccaCfcAfcGfaguscsu | 701 |
| AD-63945 | A-127910 | ascsucguGfgUfGfGfaCfuucUfcucaL96 | 487 | A-127906 | usGfsaGfaGfaAfgUfccaCfcAfcGfaGfuscsu | 702 |
| AD-63946 | A-127918 | ascsucguGfgUfGfGfacuuCfucucaL96 | 488 | A-127906 | usGfsaGfaGfaAfgUfccaCfcAfcGfaGfuscsu | 703 |
| AD-63947 | A-127905 | AfscsUfcGfuGfgUfGfGfaCfuUfcUfcUfcAfL96 | 489 | A-127926 | usGfsaGfagaagUfccaCfcAfcgaGfuscsu | 704 |
| AD-63948 | A-127935 | gsusGfuGfGfaCfuUfcUfcUfcAfL96 | 490 | A-127936 | usGfsaGfaGfaAfgUfccaCfcAfcsgsa | 705 |
| AD-63949 | A-127944 | ascsucGfuGfguGfGfaCfuucucucaL96 | 491 | A-127906 | usGfsaGfaGfaAfgUfccaCfcAfcGfaGfuscsu | 706 |
| AD-63950 | A-127900 | Y44UfcGfuGfgUfgGfaCfuUfcUfcUfcAfusuY44 | 492 | A-127901 | usGfsasGfaGfaAfgUfccCfaCfcAfcGfausu | 707 |
| AD-63951 | A-127911 | ascsucguGfgUfGfGfaCfuucucucaL96 | 493 | A-127906 | usGfsaGfaGfaAfgUfccaCfcAfcGfaGfuscsu | 708 |
| AD-63952 | A-127905 | AfscsUfcGfuGfgUfGfGfaCfuUfcUfcUfcAfL96 | 494 | A-127919 | usGfsaGfaGfaagUfccaCfcAfcGfaGfuscsu | 709 |
| AD-63953 | A-127905 | AfscsUfcGfuGfgUfGfGfaCfuUfcUfcUfcAfL96 | 495 | A-127927 | usGfsagagaAfgUfccaCfcAfcgaguscsu | 710 |
| AD-63955 | A-127945 | ascsucgugguGfGfacuucucucaL96 | 496 | A-127940 | usGfsAfgAfgAfaGfuccaCfCfaCfgAfguscsu | 711 |
| AD-63956 | A-127902 | Y44uscsGfuGfgUfgGfaCfuUfcUfcUfcAfY44 | 497 | A-127903 | usGfsaGfaGfaAfgUfcCfaCfcAfcGfasusu | 712 |
| AD-63957 | A-127912 | ascsucguGfgUfGfGfacuucucucaL96 | 498 | A-127906 | usGfsaGfaGfaAfgUfccaCfcAfcGfaGfuscsu | 713 |
| AD-63958 | A-127905 | AfscsUfcGfuGfgUfGfGfaCfuUfcUfcUfcAfL96 | 499 | A-127920 | usGfsagaGfaAfgUfccaCfcAfcgaGfuscsu | 714 |
| AD-63959 | A-127905 | AfscsUfcGfuGfgUfGfGfaCfuUfcUfcUfcAfL96 | 500 | A-127928 | usGfsaGfagaAfguccaCfcAfcgaguscsu | 715 |
| AD-63960 | A-126619 | usasUfuUfCfCfuAfgGfgUfaCfaAfL96 | 501 | A-127938 | PusGfsaGfaGfaAfgUfccaCfcAfcsgsa | 716 |
| AD-63961 | A-127945 | ascsucgugguGfGfacuucucucaL96 | 502 | A-127942 | usGfsAfgaGfaAfgUfccaCfcAfcGfaguscsu | 717 |

TABLE 3-continued

Exemplary Modified Sense and Antisense Strand Sequences of HBV dsRNAs (Activity data available in WO2016/077321, incorporated herein by reference)

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-63962 | A-127902 | Y44uscsGfuGfuGfgUfgGfaCfuUfcUfcUfcAfY44 | 503 | A-127904 | PusGfsaGfaGfaAfgUfcCfaCfcAfcGfasusu | 718 |
| AD-63963 | A-127913 | ascsucguggUfgGfacuucucucaL96 | 504 | A-127906 | usGfsaGfaGfaAfgUfccaCfcAfcGfaGfuscsu | 719 |
| AD-63964 | A-127905 | AfscsUfcGfuGfgUfGfGfaCfuUfcUfcUfcAfL96 | 505 | A-127921 | usGfsaGfaGfaAfgUfccaCfcAfcgaguscsu | 720 |
| AD-63965 | A-127905 | AfscsUfcGfuGfgUfGfGfaCfuUfcUfcUfcAfL96 | 506 | A-127929 | usGfsagaGfaaGfuccaCfcAfcgaguscsu | 721 |
| AD-63966 | A-127939 | ascsUfcGfugguGfGfaCfuCfuCfucaL96 | 507 | A-127940 | usGfsAfgAfgAfaGfuccaCfCfaCfgAfguscsu | 722 |
| AD-63967 | A-127945 | ascsucgugguGfGfacuucucucaL96 | 508 | A-127906 | usGfsaGfaGfaAfgUfccaCfcAfcGfaGfuscsu | 723 |
| AD-63968 | A-127905 | AfscsUfcGfuGfgUfGfGfaCfuUfcUfcUfcAfL96 | 509 | A-127906 | usGfsaGfaGfaAfgUfccaCfcAfcGfaGfuscsu | 724 |
| AD-63968 | A-127905 | AfscsUfcGfuGfgUfGfGfaCfuUfcUfcUfcAfL96 | 510 | A-127906 | usGfsaGfaGfaAfgUfccaCfcAfcGfaGfuscsu | 725 |
| AD-63968 | A-127905 | AfscsUfcGfuGfgUfGfGfaCfuUfcUfcUfcAfL96 | 511 | A-127906 | usGfsaGfaGfaAfgUfccaCfcAfcGfaGfuscsu | 726 |
| AD-63969 | A-127914 | ascsucguggugGfacuucucucaL96 | 512 | A-127906 | usGfsaGfaGfaAfgUfccaCfcAfcGfaGfuscsu | 727 |
| AD-63970 | A-127905 | AfscsUfcGfuGfgUfGfGfaCfuUfcUfcUfcAfL96 | 513 | A-127922 | usGfsagaGfaagUfccaCfcAfcgaGfuscsu | 728 |
| AD-63971 | A-127905 | AfscsUfcGfuGfgUfGfGfaCfuUfcUfcUfcAfL96 | 514 | A-127930 | usGfsagaGfaaguccaCfcAfcgaguscsu | 729 |
| AD-63972 | A-127941 | ascsUfcGfuGfguGfGfaCfuuCfuCfucaL96 | 515 | A-127942 | usGfsAfgaGfaAfgUfccaCfcAfcGfaguscsu | 730 |
| AD-63973 | A-127946 | ascsucguggudGdGacuucucucaL96 | 516 | A-127947 | usdGsaGfaGfaAfgdTccadCcAfcGfaguscsu | 731 |
| AD-63975 | A-127915 | ascsucguggUfgGfacuuc(Tgn)cucaL96 | 517 | A-127906 | usGfsaGfaGfaAfgUfccaCfcAfcGfaGfuscsu | 732 |
| AD-63976 | A-127905 | AfscsUfcGfuGfgUfGfGfaCfuUfcUfcUfcAfL96 | 518 | A-127923 | usGfsagaGfaAfgUfccaCfcAfcgaguscsu | 733 |
| AD-63977 | A-127917 | ascsucguggugdGacuuc(Tgn)cucaL96 | 519 | A-127931 | usdGsagagaaguccadCcacgaguscsu | 734 |
| AD-63978 | A-127943 | ascsUfcGfuGfuGfguGfgaCfuUfcUfcUfcaL96 | 520 | A-127906 | usGfsaGfaGfaAfgUfccaCfcAfcGfaGfuscsu | 735 |
| AD-63979 | A-127908 | ascsucGfuGfgUfGfGfaCfuucUfcucAfL96 | 521 | A-127906 | usGfsaGfaGfaAfgUfccaCfcAfcGfaGfuscsu | 736 |
| AD-63980 | A-127916 | ascsucgugguGfacuuc(Tgn)cucaL96 | 522 | A-127906 | usGfsaGfaGfaAfgUfccaCfcAfcGfaGfuscsu | 737 |
| AD-63981 | A-127905 | AfscsUfcGfuGfgUfGfGfaCfuUfcUfcUfcAfL96 | 523 | A-127924 | usGfsaGfagaAfgUfccaCfcAfcgaGfuscsu | 738 |
| AD-63982 | A-127917 | ascsucguggugdGacuuc(Tgn)cucaL96 | 524 | A-127932 | PusdGsagagaaguccadCcacgaguscsu | 739 |
| AD-63983 | A-127944 | ascsucGfuGfguGfGfaCfuucucucaL96 | 525 | A-127940 | usGfsAfgAfgAfaGfuccaCfCfaCfgAfguscsu | 740 |
| AD-63985 | A-127961 | gsusggugGfaCfUfUfcUfcucAfauuuL96 | 526 | A-127956 | asAfsaUfuGfaGfaGfaagUfcCfaCfcAfcsgsa | 741 |

TABLE 3-continued

Exemplary Modified Sense and Antisense Strand Sequences of HBV dsRNAs (Activity data available in WO2016/077321, incorporated herein by reference)

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-63986 | A-127969 | gsusggugGfaCfUfUfcucuCfaauuuL96 | 527 | A-127956 | asAfsaUfuGfaGfaGfaagUfcCfaCfcAfcsgsa | 742 |
| AD-63987 | A-127955 | GfsusGfgUfgGfaCfUfUfcUfcUfcAfaUfuUfL96 | 528 | A-127977 | asAfsaUfugagaGfaagUfcCfaccAfcsgsa | 743 |
| AD-63988 | A-127986 | usgsGfaCfUfUfcUfcUfcAfaUfuUfL96 | 529 | A-127987 | asAfsaUfuGfaGfaGfaagUfcCfascsc | 744 |
| AD-63989 | A-127996 | gsusgguggacUfUfcucucaauuUL96 | 530 | A-127992 | asAfsAfUfuGfaGfaGfaagUfcCfaCfcacsgsa | 745 |
| AD-63990 | A-127950 | Y44GfgUfgGfaCfuUfcUfcUfcAfaUfuUfusuY44 | 531 | A-127951 | asAfsasUfuGfaGfaGfaAfgUfcCfaCfcusu | 746 |
| AD-63991 | A-127962 | gsusggugGfaCfUfUfcUfcucaauuUL96 | 532 | A-127956 | asAfsaUfuGfaGfaGfaagUfcCfaCfcAfcsgsa | 747 |
| AD-63992 | A-127955 | GfsusGfgUfgGfaCfUfUfcUfcUfcAfaUfuUfL96 | 533 | A-127970 | asAfsaUfuGfagaGfaagUfcCfaCfcAfcsgsa | 748 |
| AD-63993 | A-127955 | GfsusGfgUfgGfaCfUfUfcUfcUfcAfaUfuUfL96 | 534 | A-127978 | asAfsauugaGfaGfaagUfcCfaccacsgsa | 749 |
| AD-63994 | A-127984 | gsgUfgGfaCfUfUfcUfcUfcAfaUfuUfL96 | 535 | A-127988 | PasAfsaUfuGfaGfaGfaagUfcCfaCfcsasc | 750 |
| AD-63995 | A-127996 | gsusgguggacUfUfcucucaauuUL96 | 536 | A-127993 | asAfsAfuuGfaGfaGfaagUfCfcaCfcacsgsa | 751 |
| AD-63996 | A-127952 | Y44gsgsUfgGfaCfuUfcUfcUfcAfaUfuUfY44 | 537 | A-127953 | asAfsaUfuGfaGfaGfaAfgUfcCfaCfcsusu | 752 |
| AD-63997 | A-127963 | gsusggugGfaCfUfUfcUfcucaauuUL96 | 538 | A-127956 | asAfsaUfuGfaGfaGfaagUfcCfaCfcAfcsgsa | 753 |
| AD-63999 | A-127955 | GfsusGfgUfgGfaCfUfUfcUfcUfcAfaUfuUfL96 | 539 | A-127979 | asAfsaUfugaGfagaagUfcCfaccacsgsa | 754 |
| AD-64000 | A-127986 | usgsGfaCfUfUfcUfcUfcAfaUfuUfL96 | 540 | A-127989 | PasAfsaUfuGfaGfaGfaagUfcCfascsc | 755 |
| AD-64001 | A-127996 | gsusgguggacUfUfcucucaauuUL96 | 541 | A-127994 | asAfsAfUfuGfaGfaGfaagUfCfcaCfcacsgsa | 756 |
| AD-64002 | A-127952 | Y44gsgsUfgGfaCfuUfcUfcUfcAfaUfuUfY44 | 542 | A-127954 | PasAfsaUfuGfaGfaGfaAfgUfcCfaCfcsusu | 757 |
| AD-64003 | A-127964 | gsusgguggaCfuUfcucucaauuUL96 | 543 | A-127956 | asAfsaUfuGfaGfaGfaagUfcCfaCfcAfcsgsa | 758 |
| AD-64004 | A-127955 | GfsusGfgUfgGfaCfUfUfcUfcUfcAfaUfuUfL96 | 544 | A-127972 | asAfsaUfuGfaGfaGfaagUfcCfaccacsgsa | 759 |
| AD-64005 | A-127955 | GfsusGfgUfgGfaCfUfUfcUfcUfcAfaUfuUfL96 | 545 | A-127980 | asAfsauuGfagAfgaagUfcCfaccacsgsa | 760 |
| AD-64006 | A-127990 | gsusGfgugGfaCfUfUfcUfcUfcAfaUfuuL96 | 546 | A-127991 | asAfsaUfuGfaGfaGfaagUfcCfaCfcacsgsa | 761 |
| AD-64007 | A-127996 | gsusgguggacUfUfcucucaauuUL96 | 547 | A-127995 | asAfsAfUfugaGfaGfaagUfcCfaCfcacsgsa | 762 |
| AD-64008 | A-127955 | GfsusGfgUfgGfaCfUfUfcUfcUfcAfaUfuUfL96 | 548 | A-127956 | asAfsaUfuGfaGfaGfaagUfcCfaCfcAfcsgsa | 763 |
| AD-64008 | A-127955 | GfsusGfgUfgGfaCfUfUfcUfcUfcAfaUfuUfL96 | 549 | A-127956 | asAfsaUfuGfaGfaGfaagUfcCfaCfcAfcsgsa | 764 |
| AD-64009 | A-127965 | gsusgguggacuUfcucucaauuUL96 | 550 | A-127956 | asAfsaUfuGfaGfaGfaagUfcCfaCfcAfcsgsa | 765 |

TABLE 3-continued

Exemplary Modified Sense and Antisense Strand Sequences of HBV dsRNAs (Activity data available in WO2016/077321, incorporated herein by reference)

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-64010 | A-127955 | GfsusGfgUfgGfaCfUfUfcUfcUfcAfaUfuUfL96 | 551 | A-127973 | asAfsauuGfagaGfaagUfcCfaccAfcsgsa | 766 |
| AD-64011 | A-127955 | GfsusGfgUfgGfaCfUfUfcUfcUfcAfaUfuUfL96 | 552 | A-127981 | asAfsauuGfagagaagUfcCfaccacsgsa | 767 |
| AD-64012 | A-127990 | gsusGfgugGfaCfUfUfcUfcUfcAfaUfuuL96 | 553 | A-127992 | asAfsAfUfuGfaGfaGfaagUfcCfaCfcacsgsa | 768 |
| AD-64013 | A-127997 | gsusggugg acdTdTcucucaauuL96 | 554 | A-127998 | asdAsAfuugaGfaGfaagdTdCcaCfcacsgsa | 769 |
| AD-64014 | A-127957 | Y44GfsusGfgUfgGfaCfUfUfcUfcUfcAfaUfuUfL96 | 555 | A-127958 | PasAfsaUfuGfaGfaGfaagUfcCfaCfcAfcsgsa | 770 |
| AD-64015 | A-127966 | gsusggugg aCfuUfcucuc(Agn)auuuL96 | 556 | A-127956 | asAfsaUfuGfaGfaGfaagUfcCfaCfcAfcsgsa | 771 |
| AD-64016 | A-127955 | GfsusGfgUfgGfaCfUfUfcUfcUfcAfaUfuUfL96 | 557 | A-127974 | asAfsauuGfaGfaGfaagUfcCfaccacsgsa | 772 |
| AD-64017 | A-127968 | gsusggugg acudTcucuc(Agn)auuuL96 | 558 | A-127982 | asdAsauugagagaagdTccaccacsgsa | 773 |
| AD-64018 | A-127990 | gsusGfgugGfaCfUfUfcUfcUfcAfaUfuuL96 | 559 | A-127993 | asAfsAfuuGfaGfaGfaagUfCfcaCfcacsgsa | 774 |
| AD-64019 | A-127959 | gsusggUfgGfaCfUfUfcUfcucAfauuUfL96 | 560 | A-127956 | asAfsaUfuGfaGfaGfaagUfcCfaCfcAfcsgsa | 775 |
| AD-64020 | A-127967 | gsusggugg acuUfcucuc(Agn)auuuL96 | 561 | A-127956 | asAfsaUfuGfaGfaGfaagUfcCfaCfcAfcsgsa | 776 |
| AD-64021 | A-127955 | GfsusGfgUfgGfaCfUfUfcUfcUfcAfaUfuUfL96 | 562 | A-127975 | asAfsaUfugaGfaGfaagUfcCfaccAfcsgsa | 777 |
| AD-64022 | A-127968 | gsusggugg acudTcucuc(Agn)auuuL96 | 563 | A-127983 | PasdAsauugagagaagdTccaccacsgsa | 778 |
| AD-64023 | A-127990 | gsusGfgugGfaCfUfUfcUfcUfcAfaUfuuL96 | 564 | A-127994 | asAfsAfUfuGfaGfaGfaagUfCfcaCfcacsgsa | 779 |
| AD-64024 | A-127960 | gsusggUfgGfaCfUfUfcUfcucAfauuuL96 | 565 | A-127956 | asAfsaUfuGfaGfaGfaagUfcCfaCfcAfcsgsa | 780 |
| AD-64025 | A-127968 | gsusggugg acudTcucuc(Agn)auuuL96 | 566 | A-127956 | asAfsaUfuGfaGfaGfaagUfcCfaCfcAfcsgsa | 781 |
| AD-64026 | A-127955 | GfsusGfgUfgGfaCfUfUfcUfcUfcAfaUfuUfL96 | 567 | A-127976 | asAfsaUfugaGfagaagUfcCfaccAfcsgsa | 782 |
| AD-64027 | A-127984 | gsgUfgGfaCfUfUfcUfcUfcAfaUfuUfL96 | 568 | A-127985 | asAfsaUfuGfaGfaGfaagUfcCfaCfcsasc | 783 |
| AD-64028 | A-127990 | gsusGfgugGfaCfUfUfcUfcUfcAfaUfuuL96 | 569 | A-127995 | asAfsAfUfugaGfaGfaagUfCfcaCfcacsgsa | 784 |
| AD-64272 | A-128001 | GfsusGfcAfcUfuCfGfCfuUfcAfcCfuCfuGfL96 | 570 | A-128002 | csAfsgAfgGfuGfaAfgcgAfaGfuGfcAfcsasc | 785 |
| AD-64274 | A-128363 | GfsusUfgAfcAfaAfAfAfuCfcUfcAfcAfaUfL96 | 571 | A-128364 | asUfsuGfuGfaGfgAfuuuUfuGfuCfaAfcsasa | 786 |
| AD-64275 | A-128377 | UfsgsUfuGfaCfaAfAfAfaUfcCfuCfaCfaAfL96 | 572 | A-128378 | usUfsgUfgAfgGfaUfuuuUfgUfcAfaCfasasg | 787 |
| AD-64276 | A-128393 | GfsgsUfgGfaCfuUfCfUfcUfcAfaUfuUfuAfL96 | 573 | A-128394 | usAfsaAfaUfuGfaGfagaAfgUfcCfaCfcsasc | 788 |
| AD-64277 | A-128407 | UfscsUfuUfuGfgAfGfUfgUfgGfaUfuCfgAfL96 | 574 | A-128408 | usCfsgAfaUfcCfaCfacuCfcAfaAfaGfascsa | 789 |

TABLE 3-continued

Exemplary Modified Sense and Antisense Strand Sequences of HBV dsRNAs (Activity data available in WO2016/077321, incorporated herein by reference)

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-64277 | A-128407 | UfscsUfuUfuGfgAfgAfUfg UfgGfaUfuCfgAfUfL96 | 575 | A-128408 | usCfsgAfaUfcCfaCfacuCfcAfaAfaGfascsa | 790 |
| AD-64278 | A-128423 | AfscsUfgUfuCfaAfgCfCfc UfcCfaAfgCfuAfUfL96 | 576 | A-128424 | usAfsgCfuUfgGfaGfgcuUfgAfaCfaAfgsasc | 791 |
| AD-64279 | A-128435 | UfscsUfgCfcGfaUfCfCfa UfaCfuGfcGfgAfUfL96 | 577 | A-128436 | usCfscGfcAfgUfaUfggaUfcGfgCfaGfasgsg | 792 |
| AD-64280 | A-128379 | AfsusGfuGfuCfuGfCfgGfg CfgUfuUfuAfuAfUfL96 | 578 | A-128380 | usAfsuAfaAfaCfgCfcgcAfgAfcAfcAfuscsc | 793 |
| AD-64281 | A-128395 | CfscsCfcGfuCfuGfuUfGfc CfuUfcUfcAfuAfUfL96 | 579 | A-128396 | usAfsuGfaGfaAfgGfcacAfgAfcGfgGfgsasg | 794 |
| AD-64282 | A-128409 | GfscsCfuAfaUfcAfUfCfu CfuUfgUfuCfaUfUfL96 | 580 | A-128410 | asUfsgAfaCfaAfgAfgauGfaUfuAfgCfgsasg | 795 |
| AD-64283 | A-128425 | UfscsUfaGfaCfuCfgUfgUfg GfuGfgAfcUfuCfL96 | 581 | A-128426 | gsAfsaGfuCfcAfcCfacgAfgUfcUfaGfascsu | 796 |
| AD-64284 | A-128437 | CfsusGfcCfgAfuCfCfAfu AfcUfgCfgGfaAfUfL96 | 582 | A-128438 | usUfscCfgCfaGfuAfuggAfuCfgGfcAfgsasg | 797 |
| AD-64285 | A-128365 | UfsusUfuUfcUfuGfUfUfg AfcAfaAfaUfuAfUfL96 | 583 | A-128366 | usAfsuUfuUfgUfcCfaacAfaGfaAfaAfascsc | 798 |
| AD-64286 | A-128381 | AfsusCfuUfcUfuGfUfUfg GfuUfcUfuCfuAfUfL96 | 584 | A-128382 | usAfsgAfaGfaAfcCfaacAfaGfaAfgAfusgsa | 799 |
| AD-64289 | A-128367 | GfsusUfuUfcUfuGfUfuUfu GfaCfaAfaAfaUfL96 | 585 | A-128368 | asUfsuUfuUfgUfcAfacaAfgAfaAfaAfcscsc | 800 |
| AD-64290 | A-128383 | CfsusGfcCfuAfaUfCfAfu CfuCfuUfgUfuAfUfL96 | 586 | A-128384 | usAfsaCfaAfgAfgAfugaUfuAfgGfcAfgsasg | 801 |
| AD-64291 | A-128399 | UfscsCfuCfaCfaAfUfAfc CfaCfaGfaGfuAfUfL96 | 587 | A-128400 | usAfscUfcUfgUfgGfuauUfgUfgAfgGfasusu | 802 |
| AD-64292 | A-128413 | CfsusUfgUfuGfaCfAfAfa AfaUfcCfuCfaAfUfL96 | 588 | A-128414 | usUfsgAfgGfaUfuUfuugUfcAfaCfaAfgsasa | 803 |
| AD-64293 | A-128439 | GfscsAfaCfuUfuUfCfCfa CfcCfuCfgCfcUfUfL96 | 589 | A-128440 | asGfsgCfaGfaGfgUfgaaAfaAfgUfuGfcsasu | 804 |
| AD-64294 | A-128369 | GfsgsGfaAfcAfaGfAfGfc UfaCfaGfcAfuAfUfL96 | 590 | A-128370 | usAfsuGfcUfgUfaGfcucUfuGfuUfcCfcsasa | 805 |
| AD-64295 | A-128385 | CfsgsUfgGfuGfgAfCfUfu CfuCfuCfaAfuUfUfL96 | 591 | A-128386 | asAfsuUfgAfgAfgAfaguCfcAfcCfaGfcsasg | 806 |
| AD-64297 | A-128415 | CfsusGfcUfgCfuAfUfGfc CfuCfaUfcUfuAfUfL96 | 592 | A-128416 | usAfsaGfaUfgAfgGfcauAfgCfaGfcAfgsgsa | 807 |
| AD-64298 | A-128427 | GfsusUfgGfaUfgUfGfUfc UfgCfgGfcGfuUfUfL96 | 593 | A-128428 | asAfscGfcCfgCfaGfacaCfaUfcCfaAfcsgsa | 808 |
| AD-64299 | A-128441 | UfsusCfaUfcCfuGfCfUfg CfuAfuGfcCfuAfUfL96 | 594 | A-128442 | usAfsgGfcAfuAfgCfagcAfgGfaUfgAfasgsa | 809 |
| AD-64300 | A-128371 | UfsusCfuUfgUfgAfCffa AfaAfaUfcCfuAfUfL96 | 595 | A-128372 | usAfsgGfaUfuUfuUfgucAfaCfaAfgAfasasa | 810 |
| AD-64302 | A-128417 | UfsasUfaUfgGfaUfGffu GfuGfgUfaUfuAfUfL96 | 596 | A-128418 | usAfsaUfaCfcAfcAfucaUfcCfaUfaUfasasc | 811 |
| AD-64303 | A-128429 | UfsusCfaUfcCfuGfCfUfg CfuAfuGfcCfuCfCfL96 | 597 | A-128430 | gsAfsgGfcAfuAfgCfagcAfgGfaUfgAfasgsa | 812 |
| AD-64304 | A-128443 | GfsusGfcAfcCfuGfCfCfu UfcAfcCfuCfuAfUfL96 | 598 | A-128444 | usAfsgAfgGfuGfaAfgcgAffaGfuGfcAfcscsasc | 813 |

TABLE 3-continued

Exemplary Modified Sense and Antisense Strand Sequences of HBV dsRNAs (Activity data available in WO2016/077321, incorporated herein by reference)

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-64305 | A-128373 | UfsusGfaCfaAfaAfAfAfUfc CfuCfaCfaAfuAfAfL96 | 599 | A-128374 | usAfsuUfgUfgAfgGfauuUfuUfgUfcAfascsa | 814 |
| AD-64307 | A-128403 | AfsasGfcCfuCfcAfAfGfc UfgUfgCfcUfuAfAfL96 | 600 | A-128404 | usAfsaGfgCfaCfaGfcuuGfgAfgGfcUfusgsa | 815 |
| AD-64308 | A-128419 | CfscsUfcUfuCfaUfCfCfu GfcUfgCfuAfuAfAfL96 | 601 | A-128420 | usAfsuAfgCfaGfcAfggaUfgAfaGfaGfgsasa | 816 |
| AD-64309 | A-128431 | CfscsUfgCfuGfcUfAfUfg CfcUfcAfuCfuUfUfL96 | 602 | A-128432 | asAfsgAfuGfaGfgCfauaGfcAfgCfaGfgsasu | 817 |
| AD-64310 | A-128375 | CfsasUfcUfuCfuUfGfUfu GfgUfcCfuUfcUfUfL96 | 603 | A-128376 | asGfsaAfgAfaCfcAfacaAfgAfaGfaUfgsasg | 818 |
| AD-64311 | A-128391 | CfscsGfuCfuGfuGfCfCfu UfcUfcAfuCfuAfAfL96 | 604 | A-128392 | usAfsgAfuGfaGfaAfggcAfcAfgAfcGfgsgsg | 819 |
| AD-64312 | A-128405 | CfscsUfcAfuCfuUfcUfUfu GfuUfgGfuUfcUfAfL96 | 605 | A-128406 | asGfsaAfcCfaAfcAfagaAfgAfuGfaGfgscsa | 820 |
| AD-64313 | A-128421 | CfscsAfcCfaAfaUfGfCfc CfcUfaUfcUfuAfAfL96 | 606 | A-128422 | usAfsa TABLE 3-continued Exemplary Modified Sense and Antisense Strand Sequences of HBV dsRNAs (Activity data available in WO2016/077321, incorporated herein by reference)

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-64332 | A-128001 | GfsusGfcAfcUfuCfgCfcUfu UfcAfcCfuCfuGfL96 | 623 | A-128485 | PcsAfsgAfgGfuGfaAfgcgAfaGfuGfcAfcsasc | 838 |
| AD-64333 | A-128367 | GfsusUfuUfuCfuUfgUfuUfu GfaCfaAfaAfaUfL96 | 624 | A-128448 | PasUfsuUfuUfgUfcAfacaAfgAfaAfaAfcscsc | 839 |
| AD-64334 | A-128383 | CfsusGfcCfuAfaUfCfAfu CfuCfuUfgUfuAfL96 | 625 | A-128456 | PusAfsaCfaAfgAfgAfugaUfuAfgGfcAfgsasg | 840 |
| AD-64335 | A-128399 | UfscsCfuCfaCfaAfuUfAfc CfaCfaGfaGfuAfL96 | 626 | A-128464 | PusAfscUfcUfgUfgGfuauUfgUfgAfgGfasusu | 841 |
| AD-64336 | A-128413 | CfsusUfgUfuGfaCfAfAfa AfaUfcCfuCfaAfL96 | 627 | A-128472 | PusUfsgAfgGfaUfuUfuugUfcAfaCfaAfgsasa | 842 |
| AD-64337 | A-127955 | GfsusGfgUfgGfaCfUfUfc UfcUfcAfaUfuUfL96 | 628 | A-127958 | PasAfsaUfgGfaGfaAfgaagUfcCfaCfcAfcsgsa | 843 |
| AD-64338 | A-128439 | GfscsAfaCfuUfuUfUfCfa CfcUfcUfgCfcUfL96 | 629 | A-128486 | PasGfsgCfaGfaGfgUfgaaAfaAfgUfuGfcsasu | 844 |
| AD-64339 | A-128369 | GfsgsGfaAfcAfaGfAfgGfc UfaCfaGfcAfuAfL96 | 630 | A-128449 | PusAfsuGfcUfgUfaGfcucUfuGfuUfcCfcsasa | 845 |
| AD-64341 | A-128401 | UfscsAfuCfuUfcUfUfGfu UfgGfuUfcUfuAfL96 | 631 | A-128465 | PusAfsaGfaAfcCfaAfcaaGfaAfgAfuGfasgsg | 846 |
| AD-64342 | A-128415 | CfsusGfcUfgCfuAfUfGfc CfuCfaUfcUfuAfL96 | 632 | A-128473 | PusAfsaGfaUfgAfgGfcauAfgCfaGfcAfgsgsa | 847 |
| AD-64343 | A-128427 | GfsusUfgGfaUfgUfGfUfc UfgCfgGfcGfuUfL96 | 633 | A-128479 | PasAfscGfcCfgCfaGfacaCfaUfcCfaAfcsgsa | 848 |
| AD-64344 | A-128441 | UfsusCfaUfcCfuGfCfUfg CfaUfuGfcCfuAfL96 | 634 | A-128487 | PusAfsgGfcAfuAfgCfagcAfgGfaUfgAfasgsa | 849 |
| AD-64345 | A-128371 | UfsusCfuUfgUfuGfAfCfa AfaAfaUfcCfuAfL96 | 635 | A-128450 | PusAfsgGfaUfuUfuUfgucAfaCfaAfgAfasasa | 850 |
| AD-64347 | A-123487 | GfsgsAfuGfuGfuCfUfGfc GfgCfgUfuUfuAfL96 | 636 | A-128466 | PusAfsaAfaCfgCfcGfcagAfcAfcAfuCfcsasg | 851 |
| AD-64348 | A-128417 | UfsasUfaUfgGfaUfGfAfu GfuGfgUfaUfuAfL96 | 637 | A-128474 | PusAfsaUfaCfcAfcAfucaUfcCfaUfaUfasasc | 852 |
| AD-64349 | A-128429 | UfsusCfaUfcCfuGfCfUfg CfaUfuGfcCfuCfL96 | 638 | A-128480 | PgsAfsgGfcAfuAfgCfagcAfgGfaUfgAfasgsa | 853 |
| AD-64350 | A-128443 | GfsusGfcAfcUfuCfgCffu UfcAfcCfuCfuAfL96 | 639 | A-128488 | PusAfsgAfgGfuGfaAfgcgAfaGfuGfcAfcsasc | 854 |
| AD-64351 | A-128373 | UfsusGfaCfaAfaAfAfUfc CfuCfaCfaAfuAfL96 | 640 | A-128451 | PusAfsuUfgUfgAfgGfauuUfuUfgUfcAfascsa | 855 |
| AD-64352 | A-128389 | CfscsAfaGfuGfuUfUfGfc UfgAfcGfcAfaAfL96 | 641 | A-128459 | PusUfsuGfcGfuCfaGfcaaAfcAfcUfuGfscsa | 856 |
| AD-64352 | A-128389 | CfscsAfaGfuGfuUfUfGfc UfgAfcGfcAfaAfL96 | 642 | A-128459 | PusUfsuGfcGfuCfaGfcaaAfcAfcUfuGfscsa | 857 |
| AD-64353 | A-128403 | AfsasGfcCfuCfcAfAfGfc UfgUfgCfcUfuAfL96 | 643 | A-128467 | PusAfsaGfcAfcAfgCfcuuGfaGfgCfufusgsa | 858 |
| AD-64354 | A-128419 | CfscsUfcUfuCfaUfCfCfu GfcUfgCfuAfuAfL96 | 644 | A-128475 | PusAfsuAfgCfaGfcAfggaUfgAfaGfaGfgsasa | 859 |
| AD-64355 | A-128431 | CfscsUfgCfuGfcUfAfUfg CfcUfcAfuCfuUfL96 | 645 | A-128481 | PasAfsgAfuGfaGfgCfauaGfcAfgCfaGfgsasu | 860 |
| AD-64356 | A-128375 | CfsasUfcUfuCfuUfgUfu GfgUfuCfuUfcUfL96 | 646 | A-128452 | PasGfsaAfgAfaCfcAfacaAfgAfaGfaUfgsasg | 861 |

TABLE 3-continued

Exemplary Modified Sense and Antisense Strand Sequences
of HBV dsRNAs (Activity data available in WO2016/077321,
incorporated herein by reference)

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-64357 | A-128391 | CfscsGfuCfuGfuGfCfCfuUfcUfcAfuCfuAfuL96 | 647 | A-128460 | PusAfsgAfuGfaGfaAfggcAfcAfgAfcGfgsgsg | 862 |
| AD-64358 | A-128405 | CfscsUfcAfuCfuUfCfUfuGfuUfgGfuUfcUfL96 | 648 | A-128468 | PasGfsaAfcCfaAfcAfagaAfgAfuGfaGfgscsa | 863 |
| AD-64359 | A-128421 | CfscsAfcCfaAfaUfGfCfcCfcUfaUfcUfuAfL96 | 649 | A-128476 | PusAfsaGfaUfaGfgGfgcaUfuUfgGfuGfgsusc | 864 |
| AD-64360 | A-128433 | GfscsUfcCfuCfuGfCfCfgAfuCfcAfuAfcUfL96 | 650 | A-128482 | PasGfsuAfuGfaAfuCfggcAfgAfgGfaGfcscsa | 865 |
| AD-64700 | A-129379 | ascsucguggugdTacuu(Cgn)ucucaL96 | 651 | A-127906 | usGfsaGfaGfaAfgUfccaCfcAfcGfaGfuscsu | 866 |
| AD-64701 | A-127905 | AfscsUfcGfuGfgUfGfGfaCfuUfcUfcUfcAfL96 | 652 | A-129387 | PusgsagagaagdTccadCcacgaguscsu | 867 |
| AD-64702 | A-127905 | AfscsUfcGfuGfgUfGfGfaCfuUfcUfcUfcAfL96 | 653 | A-129395 | usGsagadGaaguccaCcacgaguscsu | 868 |
| AD-64703 | A-129376 | ascsucguggugdGacuucdAcucaL96 | 654 | A-129385 | usdGsagagaagdTccadCcacgaguscsu | 869 |
| AD-64704 | A-129381 | ascsucguggdTgdTacuucdAcucaL96 | 655 | A-129389 | usdGsagadGaaguccadCcacgaguscsu | 870 |
| AD-64705 | A-129380 | ascsucguggugdTacuucdAcucaL96 | 656 | A-127906 | usGfsaGfaGfaAfgUfccaCfcAfcGfaGfuscsu | 871 |
| AD-64706 | A-127905 | AfscsUfcGfuGfgUfGfGfaCfuUfcUfcUfcAfL96 | 657 | A-129388 | usdGsadGagaaguccadCcacgaguscsu | 872 |
| AD-64707 | A-127905 | AfscsUfcGfuGfgUfGfGfaCfuUfcUfcUfcAfL96 | 658 | A-129396 | usgsagadGaagdTccadCcacgaguscsu | 873 |
| AD-64708 | A-129382 | ascsucguggdTgdGacuuc(Tgn)cucaL96 | 659 | A-129385 | usdGsagagaagdTccadCcacgaguscsu | 874 |
| AD-64709 | A-129373 | ascsucguggugdGacuu(Cgn)ucucaL96 | 660 | A-129391 | usdGsagadGaagdTccadCcacgaguscsu | 875 |
| AD-64710 | A-129373 | ascsucguggugdGacuu(Cgn)ucucaL96 | 661 | A-127906 | usGfsaGfaGfaAfgUfccaCfcAfcGfaGfuscsu | 876 |
| AD-64711 | A-129381 | ascsucguggdTgdTacuucdAcucaL96 | 662 | A-127906 | usGfsaGfaGfaAfgUfccaCfcAfcGfaGfuscsu | 877 |
| AD-64712 | A-127905 | AfscsUfcGfuGfgUfGfGfaCfuUfcUfcUfcAfL96 | 663 | A-129389 | usdGsagadGaaguccadCcacgaguscsu | 878 |
| AD-64713 | A-127905 | AfscsUfcGfuGfgUfGfGfaCfuUfcUfcUfcAfL96 | 664 | A-129397 | PusgsagadGaagdTccadCcacgaguscsu | 879 |
| AD-64714 | A-129384 | ascsucguggdTgdGacuucdAcucaL96 | 665 | A-129385 | usdGsagagaagdTccadCcacgaguscsu | 880 |
| AD-64715 | A-129376 | ascsucguggugdGacuucdAcucaL96 | 666 | A-129391 | usdGsagadGaagdTccadCcacgaguscsu | 881 |
| AD-64716 | A-129374 | ascsucguggugdGacuucu(Cgn)ucaL96 | 667 | A-127906 | usGfsaGfaGfaAfgUfccaCfcAfcGfaGfuscsu | 882 |
| AD-64717 | A-129382 | ascsucguggdTgdGacuuc(Tgn)cucaL96 | 668 | A-127906 | usGfsaGfaGfaAfgUfccaCfcAfcGfaGfuscsu | 883 |
| AD-64718 | A-127905 | AfscsUfcGfuGfgUfGfGfaCfuUfcUfcUfcAfL96 | 669 | A-129390 | usdGsagagadAguccadCcacgaguscsu | 884 |
| AD-64719 | A-127917 | ascsucguggugdGacuuc(Tgn)cucaL96 | 670 | A-129385 | usdGsagagaagdTccadCcacgaguscsu | 885 |

TABLE 3-continued

Exemplary Modified Sense and Antisense Strand Sequences of HBV dsRNAs (Activity data available in WO2016/077321, incorporated herein by reference)

| Duplex Name | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-64720 | A-129381 | ascsucguggdTgdTacuucdAcucaL96 | 671 | A-129385 | usdGsagadGaagdTccadCcacgaguscsu | 886 |
| AD-64721 | A-129382 | ascsucguggdTgdGacuuc(Tgn)cucaL96 | 672 | A-129391 | usdGsagadGaagdTccadCcacgaguscsu | 887 |
| AD-64722 | A-129375 | ascsucguggugdGacuucY34cucaL96 | 673 | A-127906 | usGfsaGfaGfaAfgUfccaCfcAfcGfaGfuscsu | 888 |
| AD-64723 | A-129383 | ascsucguggugGdAcuuc(Tgn)cucaL96 | 674 | A-127906 | usGfsaGfaGfaAfgUfccaCfcAfcGfaGfuscsu | 889 |
| AD-64725 | A-127917 | ascsucguggugdGacuuc(Tgn)cucaL96 | 675 | A-129398 | PusdGsagagaaagdTccadCcacgaguscsu | 890 |
| AD-64726 | A-129373 | ascsucguggugdGacuu(Cgn)ucucaL96 | 676 | A-129389 | usdGsagadGaaguccadCcacgaguscsu | 891 |
| AD-64727 | A-129384 | ascsucguggdTgdGacuucdAcucaL96 | 677 | A-129391 | usdGsagadGaagdTccadCcacgaguscsu | 892 |
| AD-64728 | A-129376 | ascsucguggugdGacuucdAcucaL96 | 678 | A-127906 | usGfsaGfaGfaAfgUfccaCfcAfcGfaGfuscsu | 893 |
| AD-64729 | A-129384 | ascsucguggdTgdGacuucdAcucaL96 | 679 | A-127906 | usGfsaGfaGfaAfgUfccaCfcAfcGfaGfuscsu | 894 |
| AD-64730 | A-127905 | AfscsUfcGfuGfgUfGfGfaCfuUfcUfcUfcAfL96 | 680 | A-129392 | usGsagagaaagdTccadCcacgaguscsu | 895 |
| AD-64731 | A-129399 | Y34ascsucguggugdGacuuc(Tgn)cucaL96 | 681 | A-129385 | usdGsagadGaagdTccadCcacgaguscsu | 896 |
| AD-64732 | A-129376 | ascsucguggugdGacuucdAcucaL96 | 682 | A-129389 | usdGsagadGaaguccadCcacgaguscsu | 897 |
| AD-64733 | A-129381 | ascsucguggdTgdTacuucdAcucaL96 | 683 | A-129391 | usdGsagadGaagdTccadCcacgaguscsu | 898 |
| AD-64734 | A-129377 | ascsucguggugdGacuucdCcucaL96 | 684 | A-127906 | usGfsaGfaGfaAfgUfccaCfcAfcGfaGfuscsu | 899 |
| AD-64735 | A-127905 | AfscsUfcGfuGfgUfGfGfaCfuUfcUfcUfcAfL96 | 685 | A-129385 | usdGsagadGaagdTccadCcacgaguscsu | 900 |
| AD-64736 | A-127905 | AfscsUfcGfuGfgUfGfGfaCfuUfcUfcUfcAfL96 | 686 | A-129393 | usdGsagagaagdTccaCcacgaguscsu | 901 |
| AD-64737 | A-129399 | Y34ascsucguggugdGacuuc(Tgn)cucaL96 | 687 | A-129398 | PusdGsagagaaagdTccadCcacgaguscsu | 902 |
| AD-64738 | A-129382 | ascsucguggdTgdGacuuc(Tgn)cucaL96 | 688 | A-129389 | usdGsagadGaaguccadCcacgaguscsu | 903 |
| AD-64739 | A-129378 | ascsucguggugdGacuucdGcucaL96 | 689 | A-127906 | usGfsaGfaGfaAfgUfccaCfcAfcGfaGfuscsu | 904 |
| AD-64740 | A-127905 | AfscsUfcGfuGfgUfGfGfaCfuUfcUfcUfcAfL96 | 690 | A-129386 | usgsagagaagdTccadCcacgaguscsu | 905 |
| AD-64741 | A-127905 | AfscsUfcGfuGfgUfGfGfaCfuUfcUfcUfcAfL96 | 691 | A-129394 | usGsagagaagdTccaCcacgaguscsu | 906 |
| AD-64742 | A-129373 | ascsucguggugdGacuu(Cgn)ucucaL96 | 692 | A-129385 | usdGsagadGaagdTccadCcacgaguscsu | 907 |
| AD-64743 | A-129384 | ascsucguggdTgdGacuucdAcucaL96 | 693 | A-129389 | usdGsagadGaaguccadCcacgaguscsu | 908 |

TABLE 4

Unmodified Sense and Antisense Strand Sequences of HBV dsRNAs (Activity data available in WO2016/077321, incorporated herein by reference)

| Duplex ID | Sense Sequence (5' to 3') | SEQ ID NO: | Antisense Sequence (5' to 3') | SEQ ID NO: |
|---|---|---|---|---|
| AD-65369 | UCGUGGUGGACUUCUCUCA | 909 | UGAGAGAAGUCCACCACGAUU | 938 |
| AD-65381 | UCGUGGUGGACUUCUCUCA | 910 | UGAGAGAAGUCCACCACGAUU | 939 |
| AD-63962 | UCGUGGUGGACUUCUCUCA | 911 | UGAGAGAAGUCCACCACGAUU | 940 |
| AD-63938 | ACUCGUGGUGGACUUCUCUCA | 912 | UGAGAGAAGUCCACCACGAGUCU | 941 |
| AD-65561 | UCGUGGUGGACUUCUCUCA | 913 | UGAGAGAAGUCCACCACGAUU | 942 |
| AD-65566 | UCGUGGUGGACUUCUCUCA | 914 | UGAGAGAAGUCCACCACGAUU | 943 |
| AD-63944 | UCGUGGUGGACUUCUCUCAUU | 915 | UGAGAGAAGUCCACCACGAUU | 944 |
| AD-63968 | ACUCGUGGUGGACUUCUCUCA | 916 | UGAGAGAAGUCCACCACGAGUCU | 945 |
| AD-65406 | UCGUGGUGGACUUCUCUCA | 917 | UGAGAGAAGUCCACCACGAUU | 946 |
| AD-65396 | ACUCGUGGUGGACUUCUCUCA | 918 | UGAGAGAAGUCCACCACGAGUUU | 947 |
| AD-65427 | GUGCACUUCGCUUCACCUCUA | 919 | UAGAGGUGAAGCGAAGUGCACUU | 948 |
| AD-65573 | GUGCACUUCGCUUCACCUCUA | 920 | UAGAGGUGAAGCGAAGUGCACAC | 949 |
| AD-65432 | GCACUUCGCUUCACCUCUA | 921 | UAGAGGUGAAGCGAAGUGCAC | 950 |
| AD-64332 | GUGCACUUCGCUUCACCUCUG | 922 | CAGAGGUGAAGCGAAGUGCACAC | 951 |
| AD-64322 | AUGUGUCUGCGGCGUUUUAUA | 923 | UAUAAAACGCCGCAGACACAUCC | 952 |
| AD-64272 | GUGCACUUCGCUUCACCUCUG | 924 | CAGAGGUGAAGCGAAGUGCACAC | 953 |
| AD-65583 | GCACUUCGCUUCACCUCUA | 925 | UAGAGGUGAAGCGAAGUGCUU | 954 |
| AD-63994 | GGUGGACUUCUCUCAAUUU | 926 | AAAUUGAGAGAAGUCCACCAC | 955 |
| AD-65370 | CGUGGUGGACUUCUCUCAAUU | 927 | AAUUGAGAGAAGUCCACCAGCAG | 956 |
| AD-65265 | GUGGUGGACUUCUCUCAAUUU | 928 | AAAUUGAGAGAAGUCCACCACGA | 957 |
| AD-65407 | CGUGGUGGACUUCUCUCAAUU | 929 | AAUUGAGAGAAGUCCACCAGCAG | 958 |
| AD-64027 | GGUGGACUUCUCUCAAUUU | 930 | AAAUUGAGAGAAGUCCACCAC | 959 |
| AD-65266 | GUGGUGGACUUCUCUCAAUUU | 931 | AAAUUGAGAGAAGUCCACCACGA | 960 |
| AD-65389 | UGGUGGUCUUCUCUAAAUU | 932 | AAUUGAGAGAAGUCCACCAUU | 961 |
| AD-64008 | GUGGUGGACUUCUCUCAAUUU | 933 | AAAUUGAGAGAAGUCCACCACGA | 962 |
| AD-65377 | CGUGGUGGUCUUCUCUAAAUU | 934 | AAUUGAGAGAAGUCCACCAGCUU | 963 |
| AD-65409 | GGUGGACUUCUCUCAAUUUUA | 935 | UAAAAUUGAGAGAAGUCCACCAC | 964 |
| AD-65403 | GGUGGACUUCUCUCAAUUUUA | 936 | UAAAAUUGAGAGAAGUCCACCAC | 965 |
| AD-65385 | UGGACUACUCUCAAAUUUA | 937 | UAAAAUUGAGAGAAGUCCAUU | 966 |

TABLE 5

Exemplary Modified Sense and Antisense Strand Sequences of HBV dsRNAs (Activity data available in WO2016/077321, incorporated herein by reference)

| DuplexID | Sense Sequence (5' to 3') | SEQ ID NO: | Antisense Sequence (5' to 3') | SEQ ID NO: |
|---|---|---|---|---|
| AD-65369 | uscsguGfgUfGfGfacuuCfUfcucaL96 | 967 | PusGfsagaGfaAfGfuccaCfcAfcgasusu | 996 |
| AD-65381 | uscsguGfgUfGfGfacuucucucaL96 | 968 | PusGfsagaGfaAfGfuccaCfcAfcgasusu | 997 |
| AD-63962 | Y44uscsGfuGfgUfgGfaCfuUfcUfcUfcAfY44 | 969 | PusGfsaGfaGfaAfgUfcCfaCfcAfcGfasusu | 998 |
| AD-63938 | Y44ACUCGUGGUGGACUUCUCUCA | 970 | UGAGAGAAGUCCACCACGAGUCU | 999 |
| AD-65561 | uscsguGfgUfGfGfacuuCfUfcucaL96 | 971 | UfsGfsagaGfaAfGfuccaCfcAfcgasusu | 1000 |
| AD-65566 | uscsguGfgUfGfGfacuucucucaL96 | 972 | UfsGfsagaGfaAfGfuccaCfcAfcgasusu | 1001 |
| AD-63944 | Y44ucGuGGuGGAcuucucucAusuY44 | 973 | UfGfagAfgAfAfGUfccaCfCAfcgAusu | 1002 |
| AD-63968 | AfscsUfcGfuGfgUfGfGfaCfuUfcUfcUfcAfL96 | 974 | usGfsaGfaGfaAfgUfccaCfcAfcGfaGfuscsu | 1003 |
| AD-65406 | uscsguGfgUfGfGfacuuCfUfcucaL96 | 975 | usGfsagaGfaAfGfuccaCfcAfcgasusu | 1004 |
| AD-65396 | ascsucguGfgUfGfGfacuucucucaL96 | 976 | usGfsagaGfaaguccaCfcAfcgagususu | 1005 |
| AD-65427 | gsusgcacUfuCfGfCfuucaccucuaL96 | 977 | PusAfsgagGfugaagegAfaGfugcacsusu | 1006 |
| AD-65573 | gsusgcacUfuCfGfCfuucaCfCfucuaL96 | 978 | UfsAfsgagGfuGfAfagegAfaGfugcacsasc | 1007 |
| AD-65432 | gscsacUfucGfCfuucacCfucuaL96 | 979 | PusAfsgagGfuGfAfagegAfaGfugcsasc | 1008 |
| AD-64332 | GfsusGfcAfcUfuCfGfCfuUfcAfcCfuCfuGfL96 | 980 | PcsAfsgAfgGfuGfaAfgcgAfaGfuGfcAfcsasc | 1009 |
| AD-64322 | AfsusGfuGfuCfuGfCfGfgCfgUfuUfuAfuAfL96 | 981 | PusAfsuAfaAfaCfgCfcgcAfgAfcAfcAfuscsc | 1010 |
| AD-64272 | GfsusGfcAfcUfuCfGfCfuUfcAfcCfuCfuGfL96 | 982 | csAfsgAfgGfuGfaAfgcgAfaGfuGfcAfcsasc | 1011 |
| AD-65583 | gscsacuucgdCuucac(Cgn)ucuaL96 | 983 | usdAsgagdGugaagcgdAagugcsusu | 1012 |
| AD-63994 | gsgsUfgGfaCfUfUfcUfcUfcAfaUfuUfL96 | 984 | PasAfsaUfuGfaGfaGfaagUfcCfaCfcsasc | 1013 |
| AD-65370 | csgsugguGfgAfCfUfucucUfCfaauuL96 | 985 | asAfsuugAfgAfGfaaguCfcAfccagcsasg | 1014 |
| AD-65265 | gsusggugGfaCfUfUfcUfcucaauuuL96 | 986 | asAfsaUfugagaGfaagUfcCfaccAfcsgsa | 1015 |
| AD-65407 | csgsugguGfgAfCfUfucucUfCfaauuL96 | 987 | asAfsuugAfgAfgAfaguCfcAfccagcsasg | 1016 |
| AD-64027 | gsgsUfgGfaCfUfUfcUfcUfcAfaUfuUfL96 | 988 | asAfsaUfuGfaGfaGfaagUfcCfaCfcsasc | 1017 |
| AD-65266 | gsusggugGfaCfUfUfcucuCfaauuuL96 | 989 | asAfsaUfugagaGfaagUfcCfaccAfcsgsa | 1018 |
| AD-65389 | usgsgudGgucdTucucuaaauuL96 | 990 | asdAsuugagagdAagudCcaccasusu | 1019 |
| AD-64008 | GfsusGfgUfgGfaCfUfUfcUfcUfcAfaUfuUfL96 | 991 | asAfsaUfuGfaGfaGfaagUfcCfaCfcAfcsgsa | 1020 |
| AD-65377 | csgsuggudGgucdTucucuaaauuL96 | 992 | asdAsuugagagdAagudCcaccagcsusu | 1021 |
| AD-65409 | gsgsuggaCfuUfCfUfcucaAfUfuuuaL96 | 993 | PusAfsaaaUfuGfAfgagaAfgUfccaccsasc | 1022 |
| AD-65403 | gsgsuggaCfuUfCfUfcucaAfUfuuuaL96 | 994 | usAfsaaaUfuGfAfgagaAfgUfccaccsasc | 1023 |
| AD-65385 | usgsgacuacdTcucaaauuuaL96 | 995 | usdAsaaauugadGagadAguccasusu | 1024 |

TABLE 6

Exemplary Unmodified Sense and Antisense Strand Sequences of HBV dsRNAs (Activity data available in WO2016/077321, incorporated herein by reference)

| Duplex ID | Sense ID | Sense Sequence Unmodified (5' to 3') | SEQ ID NO: | Antisense ID | Antisense Sequence Unmodified (5' to 3') | SEQ ID NO: |
|---|---|---|---|---|---|---|
| AD-65381 | A-130366 | UCGUGGUGGACUUCUCUCA | 1025 | A-131904 | UGAGAGAAGUCCACCACGAUU | 1036 |
| AD-66019 | A-130366 | UCGUGGUGGACUUCUCUCA | 1026 | A-131904 | UGAGAGAAGUCCACCACGAUU | 1037 |
| AD-65375 | A-130366 | UCGUGGUGGACUUCUCUCA | 1027 | A-130364 | UGAGAGAAGUCCACCACGAUU | 1038 |
| AD-65427 | A-130441 | GUGCACUUCGCUUCACCUCUA | 1028 | A-131905 | UAGAGGUGAAGCGAAGUGCACUU | 1039 |
| AD-66110 | A-130441 | GUGCACUUCGCUUCACCUCUA | 1029 | A-131905 | UAGAGGUGAAGCGAAGUGCACUU | 1040 |
| AD-65421 | A-130441 | GUGCACUUCGCUUCACCUCUA | 1030 | A-130442 | UAGAGGUGAAGCGAAGUGCACUU | 1041 |
| AD-65407 | A-130371 | CGUGGUGGACUUCUCUCAAUU | 1031 | A-130372 | AAUUGAGAGAAGUCCACCAGCAG | 1042 |
| AD-65377 | A-130384 | CGUGGUGGUCUUCUCUAAAUU | 1032 | A-130748 | AAUUGAGAGAAGUCCACCAGCUU | 1043 |
| AD-65409 | A-130388 | GGUGGACUUCUCUCAAUUUUA | 1033 | A-131906 | UAAAAUUGAGAGAAGUCCACCAC | 1044 |
| AD-66111 | A-130388 | GGUGGACUUCUCUCAAUUUUA | 1034 | A-131906 | UAAAAUUGAGAGAAGUCCACCAC | 1045 |
| AD-65403 | A-130388 | GGUGGACUUCUCUCAAUUUUA | 1035 | A-130389 | UAAAAUUGAGAGAAGUCCACCAC | 1046 |

TABLE 7

Exemplary Modified Sense and Antisense Strand Sequences of HBV dsRNAs (Activity data available in WO2016/077321, incorporated herein by reference)

| Duplex ID | Sense ID | Sense Sequence (5' to 3') | SEQ ID NO: | Antisense ID | Antisense Sequence (5' to 3') | SEQ ID NO: |
|---|---|---|---|---|---|---|
| AD-65381 | A-130366 | uscsguGfgUfGfGfacuucucucaL96 | 1047 | A-131904 | PusGfsagaGfaAfGfuccaCfcAfcgasusu | 1058 |
| AD-66019 | A-130366 | uscsguGfgUfGfGfacuucucucaL96 | 1048 | A-131904 | VPusGfsagaGfaAfGfuccaCfcAfcgasusu | 1059 |
| AD-65375 | A-130366 | uscsguGfgUfGfGfacuucucucaL96 | 1049 | A-130364 | usGfsagaGfaAfGfuccaCfcAfcgasusu | 1060 |
| AD-65427 | A-130441 | gsusgcacUfuCfGfCffuucaccucuaL96 | 1050 | A-131905 | PusAfsgagGfugaagcgAfaGfugcacsusu | 1061 |
| AD-66110 | A-130441 | gsusgcacUfuCfGfCffuucaccucuaL96 | 1051 | A-131905 | VPusAfsgagGfugaagcgAfaGfugcacsusu | 1062 |
| AD-65421 | A-130441 | gsusgcacUfuCfGfCffuucaccucuaL96 | 1052 | A-130442 | usAfsgagGfugaagcgAfaGfugcacsusu | 1063 |
| AD-65407 | A-130371 | csgsugguGfgAfCfUfucucUfCfaauuL96 | 1053 | A-130372 | asAfsuugAfgAfgAfaguCfcAfccagcsasg | 1064 |
| AD-65377 | A-130384 | csgsuggudGgucdTucucuaaauuL96 | 1054 | A-130748 | asdAsuugagagdAagudCcaccagcsusu | 1065 |
| AD-65409 | A-130388 | gsgsuggaCfuUfCfUfcucaAfUfuuuaL96 | 1055 | A-131906 | PusAfsaaaUfuGfAfgagaAfgUfccaccsasc | 1066 |
| AD-66111 | A-130388 | gsgsuggaCfuUfCfUfcucaAfUfuuuaL96 | 1056 | A-131906 | VPusAfsaaaUfuGfAfgagaAfgUfccaccsasc | 1067 |
| AD-65403 | A-130388 | gsgsuggaCfuUfCfUfcucaAfUfuuuaL96 | 1057 | A-130389 | usAfsaaaUfuGfAfgagaAfgUfccaccsasc | 1068 |

TABLE 8

Exemplary Unmodified Sense and Antisense Strand Sequences
of HBV dsRNAs (Activity data available in WO2016/077321,
incorporated herein by reference)

| DuplexID | Sense Oligo Name | Sense Sequence (5' to 3') | SEQ ID NO: | Antisense OligoName | Antisense Sequence (5' to 3') | SEQ ID NO: |
|---|---|---|---|---|---|---|
| AD-65776 | A-131859 | UGUGCACUUCGCUUCACCUCU | 1069 | A-131860 | AGAGGUGAAGCGAAGUGCACACG | 1115 |
| AD-65782 | A-131877 | UGCACUUCGCUUCACCUCUGA | 1070 | A-131878 | UCAGAGGUGAAGCGAAGUGCACA | 1116 |
| AD-65792 | A-131865 | GUGUGCACUUCGCUUCACCUA | 1071 | A-131866 | UAGGUGAAGCGAAGUGCACACGG | 1117 |
| AD-65781 | A-131861 | CGUGUGCACUUCGCUUCACCU | 1072 | A-131862 | AGGUGAAGCGAAGUGCACACGGU | 1118 |
| AD-64304 | A-128443 | GUGCACUUCGCUUCACCUCUA | 1073 | A-128444 | UAGAGGUGAAGCGAAGUGCACAC | 1119 |
| AD-65771 | A-131857 | CCGUGUGCACUUCGCUUCACA | 1074 | A-131858 | UGUGAAGCGAAGUGCACACGGUC | 1120 |
| AD-65758 | A-131867 | CACUUCGCUUCACCUCUGCAA | 1075 | A-131868 | UUGCAGAGGUGAAGCGAAGUGCA | 1121 |
| AD-65777 | A-131875 | ACUUCGCUUCACCUCUGCACA | 1076 | A-131876 | UGUGCAGAGGUGAAGCGAAGUGC | 1122 |
| AD-61567 | A-123525 | GGCUGUAGGCAUAAAUUGGUA | 1077 | A-123526 | UACCAAUUUAUGCCUACAGCCUC | 1123 |
| AD-65772 | A-131873 | UUCGCUUCACCUCUGCACGUA | 1078 | A-131874 | UACGUGCAGAGGUGAAGCGAAGU | 1124 |
| AD-65767 | A-131871 | UCGCUUCACCUCUGCACGUCA | 1079 | A-131872 | UGACGUGCAGAGGUGAAGCGAAG | 1125 |
| AD-65763 | A-131869 | CUUCGCUUCACCUCUGCACGU | 1080 | A-131870 | ACGUGCAGAGGUGAAGCGAAGUG | 1126 |
| AD-64281 | A-128395 | CCCCGUCUGUGCCUUCUCAUA | 1081 | A-128396 | UAUGAGAAGGCACAGACGGGGAG | 1127 |
| AD-64311 | A-128391 | CCGUCUGUGCCUUCUCAUCUA | 1082 | A-128392 | UAGAUGAGAAGGCACAGACGGGG | 1128 |
| AD-65790 | A-131837 | CCAGCACCAUGCAACUUUUUA | 1083 | A-131838 | UAAAAAGUUGCAUGGUGCUGGUG | 1129 |
| AD-65761 | A-131841 | CACCAGCACCAUGCAACUUUU | 1084 | A-131842 | AAAAGUUGCAUGGUGCUGGUGCG | 1130 |
| AD-65786 | A-131849 | CACCAUGCAACUUUUUCACCU | 1085 | A-131850 | AGGUGAAAAGUUGCAUGGUGCU | 1131 |
| AD-65785 | A-131835 | CAAUGUCAACGACCGACCUUA | 1086 | A-131836 | UAAGGUCGGUCGUUGACAUUGCA | 1132 |
| AD-65787 | A-131863 | CGCUUCACCUCUGCACGUCGA | 1087 | A-131864 | UCGACGUGCAGAGGUGAAGCGAA | 1133 |
| AD-65770 | A-131845 | ACCUUGAGGCAUACUUCAAAG | 1088 | A-131846 | CUUUGAAGUAUGCCUCAAGGUCG | 1134 |
| AD-65766 | A-131843 | CCGACCUUGAGGCAUACUUCA | 1089 | A-131844 | UGAAGUAUGCCUCAAGGUCGGUC | 1135 |
| AD-61555 | A-123521 | GACCUUGAGGCAUACUUCAAA | 1090 | A-123522 | UUUGAAGUAUGCCUCAAGGUCGG | 1136 |
| AD-65762 | A-131855 | ACCGACCUUGAGGCAUACUUA | 1091 | A-131856 | UAAGUAUGCCUCAAGGUCGGUCG | 1137 |
| AD-65755 | A-131827 | UCGCAUGGAGACCACCGUGAA | 1092 | A-131828 | UUCACGGUGGUCUCCAUGCGACG | 1138 |
| AD-65788 | A-131811 | UUACAUAAGAGGACUCUUGGA | 1093 | A-131812 | UCCAAGAGUCCUCUUAUGUAAGA | 1139 |
| AD-65768 | A-131803 | UCUUACAUAAGAGGACUCUUA | 1094 | A-131804 | UAAGAGUCCUCUUAUGUAAGACC | 1140 |
| AD-61561 | A-123523 | ACUUCAAAGACUGUUUGUUUA | 1095 | A-123524 | UAAACAAACAGUCUUUGAAGUAU | 1141 |
| AD-65764 | A-131801 | UACUUCAAAGACUGUUUGUUU | 1096 | A-131802 | AAACAAACAGUCUUUGAAGUAUG | 1142 |
| AD-65753 | A-131799 | AUACUUCAAAGACUGUUUGUU | 1097 | A-131800 | AACAAACAGUCUUUGAAGUAUGC | 1143 |
| AD-65765 | A-131817 | UUGUUUAAAGACUGGGAGGAA | 1098 | A-131818 | UUCCUCCCAGUCUUUAAACAAAC | 1144 |
| AD-65769 | A-131819 | GCAUACUUCAAAGACUGUUUA | 1099 | A-131820 | UAAACAGUCUUUGAAGUAUGCCU | 1145 |
| AD-65759 | A-131815 | CAAAGACUGUUUGUUUAAAGA | 1100 | A-131816 | UCUUUAAACAAACAGUCUUUGAA | 1146 |
| AD-65774 | A-131831 | AGACUGUUUGUUUAAAGACUA | 1101 | A-131832 | UAGUCUUUAAACAAACAGUCUUU | 1147 |
| AD-65778 | A-131807 | GUUUGUUUAAAGACUGGGAGA | 1102 | A-131808 | UCUCCCAGUCUUUAAACAAACAG | 1148 |
| AD-65773 | A-131805 | GGGGAGGAGAUUAGAUUAAAA | 1103 | A-131806 | UUUAAUCUAAUCUCCUCCCCAA | 1149 |
| AD-65789 | A-131825 | GGGGAGGAGAUUAGAUUAAAG | 1104 | A-131826 | CUUUAAUCUAAUCUCCUCCCCA | 1150 |

TABLE 8-continued

Exemplary Unmodified Sense and Antisense Strand Sequences of HBV dsRNAs (Activity data available in WO2016/077321, incorporated herein by reference)

| DuplexID | Sense Oligo Name | Sense Sequence (5' to 3') | SEQ ID NO: | Antisense OligoName | Antisense Sequence (5' to 3') | SEQ ID NO: |
|---|---|---|---|---|---|---|
| AD-65783 | A-131809 | GUUGGGGGAGGAGAUUAGAUU | 1105 | A-131810 | AAUCUAAUCUCCUCCCCCAACUC | 1151 |
| AD-65754 | A-131813 | UUGGGGGAGGAGAUUAGAUUA | 1106 | A-131814 | UAAUCUAAUCUCCUCCCCCAACU | 1152 |
| AD-65779 | A-131821 | GGGAGGAGAUUAGAUUAAAGA | 1107 | A-131822 | UCUUUAAUCUAAUCUCCUCCCCC | 1153 |
| AD-65791 | A-131851 | UUAGAUUAAAGGUCUUUGUAA | 1108 | A-131852 | UUACAAAGACCUUUAAUCUAAUC | 1154 |
| AD-65760 | A-131829 | UAGAUUAAAGGUCUUUGUACU | 1109 | A-131830 | AGUACAAAGACCUUUAAUCUAAU | 1155 |
| AD-65784 | A-131823 | AUUAGAUUAAAGGUCUUUGUA | 1110 | A-131824 | UACAAAGACCUUUAAUCUAAUCU | 1156 |
| AD-65757 | A-131853 | GAGGAGAUUAGAUUAAAGGUA | 1111 | A-131854 | UACCUUUAAUCUAAUCUCCUCCC | 1157 |
| AD-65775 | A-131847 | GGACUCUUGGACUCUCUGCAA | 1112 | A-131848 | UUGCAGAGAGUCCAAGAGUCCUC | 1158 |
| AD-65780 | A-131833 | ACUCUUGGACUCUCUGCAAUA | 1113 | A-131834 | UAUUGCAGAGAGUCCAAGAGUCC | 1159 |
| AD-65756 | A-131839 | AGAUUAAAGGUCUUUGUACUA | 1114 | A-131840 | UAGUACAAAGACCUUUAAUCUAA | 1160 |

TABLE 9

Exemplary Unmodified Sense and Antisense Strand Sequences of HBV dsRNAs (Activity data available in WO2016/077321, incorporated herein by reference)

| Duplex ID | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-65776 | A-131859 | UfsgsUfgCfaCfuUfCfGfcUfuCfaCfcUfcUfL96 | 1161 | A-131860 | asGfsaGfgUfgCfaAfaGfcgaAfgUfgCfaCfascsg | 1207 |
| AD-65782 | A-131877 | UfsgsCfaCfuUfcGfCfUfuCfaCfcUfcUfgAfL96 | 1162 | A-131878 | usCfsaGfaGfgUfgAfagcGfaAfgUfgCfascsa | 1208 |
| AD-65792 | A-131865 | GfsusGfuGfcAfcUfUfCfgCfuUfcAfcCfuAfL96 | 1163 | A-131866 | usAfsgGfuGfaAfgCfgaaGfuGfcAfcAfcsgsg | 1209 |
| AD-65781 | A-131861 | CfsgsUfgUfgCfaCfUfUffcGfcUfuCfaCfcUfL96 | 1164 | A-131862 | asGfsgUfgAfaGfcGfaagUfgCfaCfaCfgsgsu | 1210 |
| AD-64304 | A-128443 | GfsusGfcAfcUfuCfGfCffuUfcAfcCfuCfuAfL96 | 1165 | A-128444 | usAfsgAfgGfuGfaAfgcGfaAfgUfgCfaCfsasc | 1211 |
| AD-65771 | A-131857 | CfscsGfuGfuGfcAfCfUffuCfgCfuUfcAfcAfL96 | 1166 | A-131858 | usGfsuGfaAfgCfgAfaguGfcAfcAfcGfsusc | 1212 |
| AD-65758 | A-131867 | CfsasCfuUfcGfcUfUfCfaCfcUfcUfgCfaAfL96 | 1167 | A-131868 | usUfsgCfaGfaGfgUfgaaGfcGfaAfgUfgscsa | 1213 |
| AD-65777 | A-131875 | AfscsUfuCfgCfuUfCfCfAfcCfuCfuGfcAfcAfL96 | 1168 | A-131876 | usGfsuGfcAfgAfgGfugaAfgCfgAfaGfusgsc | 1214 |
| AD-61567 | A-123525 | GfsgsCfuGfuAfgGfCfAfuAfaAfuUfgGfuAfL96 | 1169 | A-123526 | usAfscCfaAfuUfUfAfugcCfuAfcAfgCfcsusc | 1215 |
| AD-65772 | A-131873 | UfsusCfgCfuUfcAfCfCffuCfuGfcAfcGfuAfL96 | 1170 | A-131874 | usAfscGfuGfcAfgAfgguGfaAfgCfgAfasgsu | 1216 |
| AD-65767 | A-131871 | UfscsGfcUfuCfaCfCfCfUfcUfgCfaCfgUfcAfL96 | 1171 | A-131872 | usGfsaCfgUfgCfaGfaggUfgAfaGfcGfasasg | 1217 |
| AD-65763 | A-131869 | CfsusUfcGfcUfuCfAfCfcUfcUfgCfaCfgUfL96 | 1172 | A-131870 | asCfsgUfgCfaGfaGfguGfaAfgCfgAfagsusg | 1218 |
| AD-64281 | A-128395 | CfscsCfcGfuCfuGfUfGfcCfuUfcUfcAfuAfL96 | 1173 | A-128396 | usAfsuGfaGfaAfgGfcacAfgAfcGfgGfgsasg | 1219 |

TABLE 9-continued

Exemplary Unmodified Sense and Antisense Strand Sequences of HBV dsRNAs (Activity data available in WO2016/077321, incorporated herein by reference)

| Duplex ID | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-64311 | A-128391 | CfscsGfuCfuGfuGfCfC fuUfcUfcAfuCfuAfL96 | 1174 | A-128392 | usAfsgAfuGfaGfaAfg gcAfcAfgAfcGfgsgsg | 1220 |
| AD-65790 | A-131837 | CfscsAfgCfaCfcAfUfG fcAfaCfuUfuUfuAfL96 | 1175 | A-131838 | usAfsaAfaAfgUfuGfc auGfuGfgCfuGfgsusg | 1221 |
| AD-65761 | A-131841 | CfsasCfcAfgCfaCfCfA fuGfcAfaCfuUfuUfL96 | 1176 | A-131842 | asAfsaAfgUfuGfcAfu ggUfgCfuGfgUfgscsg | 1222 |
| AD-65786 | A-131849 | CfsasCfcAfuGfcAfAfC fuUfuUfuCfaCfcUfL96 | 1177 | A-131850 | asGfsgUfgAfaAfaAfg uuGfcAfuGfgUfgscsu | 1223 |
| AD-65785 | A-131835 | CfsasAfuGfuCfaAfCfG faCfcGfaCfcUfuAfL96 | 1178 | A-131836 | usAfsaGfuUfcGfgUfc guUfgAfcAfuUfgscsa | 1224 |
| AD-65787 | A-131863 | CfsgsCfuUfcAfcCfUfC fuGfcAfcGfuCfgAfL96 | 1179 | A-131864 | usCfsgAfcGfuGfcAfg agGfuGfaAfgCfgsasa | 1225 |
| AD-65770 | A-131845 | AfscsCfuUfgAfgGfCfA fuAfcUfuCfaAfaGfL96 | 1180 | A-131846 | csUfsuUfgAfaGfuAfu gcCfuCfaAfgGfuscsg | 1226 |
| AD-65766 | A-131843 | CfscsGfaCfcUfuGfAfG fgCfaUfaCfuUfcAfL96 | 1181 | A-131844 | usGfsaAfgUfaUfgCfc ucAfaGfgUfcGfgsusc | 1227 |
| AD-61555 | A-123521 | GfsasCfcUfuGfaGfGfC faUfaCfuUfcAfaAfL96 | 1182 | A-123522 | usUfsuGfaAfgUfaUfg ccUfcAfaGfgUfcsgsg | 1228 |
| AD-65762 | A-131855 | AfscsCfgAfcCfuUfGfA fgGfcAfuAfcUfuAfL96 | 1183 | A-131856 | usAfsaGfuAfuGfcCfu caAfgGfuCfgGfuscsg | 1229 |
| AD-65755 | A-131827 | UfscsGfcAfuGfgAfGfA fcCfaCfcGfuGfaAfL96 | 1184 | A-131828 | usUfscAfcGfgUfgGfu cuCfcAfuGfcGfascsg | 1230 |
| AD-65788 | A-131811 | UfsusAfcAfuAfgAfAfG fgAfcUfcUfuGfgAfL96 | 1185 | A-131812 | usCfscAfaGfaGfuCfc ucUfuAfuGfuAfasgsa | 1231 |
| AD-65768 | A-131803 | UfscsUfuAfcAfuAfAfG faGfgAfcUfcUfuAfL96 | 1186 | A-131804 | usAfsaGfaGfuCfcUfc uuAfuGfuAfaGfascsc | 1232 |
| AD-61561 | A-123523 | AfscsUfuCfaAfaGfAfC fuGfuUfuGfuUfuAfL96 | 1187 | A-123524 | usAfsaAfcAfaAfcAfg ucUfuUfgAfaGfusasu | 1233 |
| AD-65764 | A-131801 | UfsasCfuUfcAfaAfGfA fcUfgUfuUfgUfuUfL96 | 1188 | A-131802 | asAfsaCfaAfaCfaGfu cuUfuGfaAfgUfasusg | 1234 |
| AD-65753 | A-131799 | AfsusAfcUfuCfaAfAfG faCfuGfuUfuGfuUfL96 | 1189 | A-131800 | asAfscAfaAfcAfgUfc uuUfgAfaGfuAfusgsc | 1235 |
| AD-65765 | A-131817 | UfsusGfuUfuAfaAfGfA fcUfgGfgAfgGfaAfL96 | 1190 | A-131818 | usUfscCfuCfcCfaGfu cuUfuAfaAfcAfasasc | 1236 |
| AD-65769 | A-131819 | GfscsAfuAfcUfuCfAfA faGfaCfuGfuUfuAfL96 | 1191 | A-131820 | usAfsaAfcAfgUfcUfu ugAfaGfuAfuGfcscsu | 1237 |
| AD-65759 | A-131815 | CfsasAfaGfaCfuGfUfU fuGfuUfuAfaAfgAfL96 | 1192 | A-131816 | usCfsuUfuAfaAfcAfa acAfgUfcUfuUfgsasa | 1238 |
| AD-65774 | A-131831 | AfsgsAfcUfgUfuUfGfU fuUfaAfaGfaCfuAfL96 | 1193 | A-131832 | usAfsgUfcUfuUfaAfa caAfaCfaGfuCfususu | 1239 |
| AD-65778 | A-131807 | GfsusUfgUfuUfaAfAfA fgAfcUfgGfgAfgAfL96 | 1194 | A-131808 | usCfsuCfcCfaGfuCfu uuAfaAfcAfaAfcsasg | 1240 |
| AD-65773 | A-131805 | GfsgsGfgGfaGfgAfGfA fuUfaGfaUfuAfaAfL96 | 1195 | A-131806 | usUfsuAfaUfcUfaAfu cuCfuCfcCfcCfcsasa | 1241 |
| AD-65789 | A-131825 | GfsgsGfgAfgGfaGfAfU fuAfgGfuUfaAfaGfL96 | 1196 | A-131826 | csUfsuUfaAfuCfuAfa ucUfcCfuCfcCfcscsa | 1242 |
| AD-65783 | A-131809 | GfsusUfgUfgGfgAfGfG faGfaUfuAfgGfuUfL96 | 1197 | A-131810 | asAfsuCfuAfaUfcUfc cuCfcCfcCfaAfcsusc | 1243 |

TABLE 9-continued

Exemplary Unmodified Sense and Antisense Strand Sequences of HBV dsRNAs (Activity data available in WO2016/077321, incorporated herein by reference)

| Duplex ID | Sense Oligo Name | Sense Sequence (5' to 3') | SEQ ID NO: | Antisense Oligo Name | Antisense Sequence (5' to 3') | SEQ ID NO: |
|---|---|---|---|---|---|---|
| AD-65754 | A-131813 | UfsusGfgGfgGfaGfGfA fgAfuUfaGfaUfuAfL96 | 1198 | A-131814 | usAfsaUfcUfaAfuCfu ccUfcCfcCfcAfascsu | 1244 |
| AD-65779 | A-131821 | GfsgsGfaGfgAfgAfUfU faGfaUfuAfaAfgAfL96 | 1199 | A-131822 | usCfsuUfuAfaUfcUfa auCfuCfcUfcCfcscsc | 1245 |
| AD-65791 | A-131851 | UfsusAfgAfuUfaAfAfG fgUfcUfuUfgUfaAfL96 | 1200 | A-131852 | usUfsaCfaAfaGfaCfc uuUfaAfuCfuAfasusc | 1246 |
| AD-65760 | A-131829 | UfsasGfaUfuAfaAfGfG fuCfuUfuGfuAfcUfL96 | 1201 | A-131830 | asGfsuAfcAfaAfgAfc cuUfaAfaUfcUfasasu | 1247 |
| AD-65784 | A-131823 | AfsusUfaGfaUfuAfAfA fgGfuCfuUfuGfuAfL96 | 1202 | A-131824 | usAfscAfaAfgAfcCfu uuAfaUfcUfaAfuscsu | 1248 |
| AD-65757 | A-131853 | GfsasGfgAfgAfuUfAfG faUfuAfaAfgGfuAfL96 | 1203 | A-131854 | usAfscCfuUfuAfaUfc uaAfuCfuCfcUfcscsc | 1249 |
| AD-65775 | A-131847 | GfsgsAfcUfcUfuGfGfA fcUfcUfcUfgCfaAfL96 | 1204 | A-131848 | usUfsgCfaGfaGfaGfu ccAfaGfaGfuCfcsusc | 1250 |
| AD-65780 | A-131833 | AfscsUfcUfuGfgAfCfU fcUfcUfgCfaAfuAfL96 | 1205 | A-131834 | usAfsuUfgCfaGfaGfa guCfcAfaGfaGfuscsc | 1251 |
| AD-65756 | A-131839 | AfsgsAfuUfaAfaGfGfU fcUfuUfgUfaCfuAfL96 | 1206 | A-131840 | usAfsgUfaCfaAfaGfa ccUfuUfaAfuCfsasa | 1252 |

TABLE 10

Exemplary Unmodified HBV X ORF Sense and Antisense Sequences. (Activity data available in WO2016/077321, incorporated herein by reference)

| DuplexID | Sense Sequence Unmodified (5' to 3') | SEQ ID NO: | Antisense Sequence Umodified (5' to 3') | SEQ ID NO: |
|---|---|---|---|---|
| AD-66808 | GUCUGUGCCUUCUCAUCUA | 1253 | UAGAUGAGAAGGCACAGACUU | 1263 |
| AD-66809 | GUCUGUGCCUUCUCAUCUA | 1254 | UAGAUGAGAAGGCACAGACUU | 1264 |
| AD-66810 | GUGUGCACUUCGCUUCACA | 1255 | UGUGAAGCGAAGUGCACACUU | 1265 |
| AD-66811 | GUGUGCACUUCGCUUCACA | 1256 | UGUGAAGCGAAGUGCACACUU | 1266 |
| AD-66812 | UGUGCACUUCGCUUCACCUCU | 1257 | AGAGGUGAAGCGAAGUGCACAUU | 1267 |
| AD-66813 | UGUGCACUUCGCUUCACCUCU | 1258 | AGAGGUGAAGCGAAGUGCACAUU | 1268 |
| AD-66814 | CACCAGCACCAUGCAACUUUU | 1259 | AAAAGUUGCAUGGUGCUGGUGUU | 1269 |
| AD-66815 | CACCAGCACCAUGCAACUUUU | 1260 | AAAAGUUGCAUGGUGCUGGUGUU | 1270 |
| AD-66816 | CACCAUGCAACUUUUUCACCU | 1261 | AGGUGAAAAGUUGCAUGGUGUU | 1271 |
| AD-66817 | CACCAUGCAACUUUUUCACCU | 1262 | AGGUGAAAAGUUGCAUGGUGUU | 1272 |

TABLE 11

Exemplary Modified HBV X ORF Sense and Antisense Sequences. (Activity data available in WO2016/077321, incorporated herein by reference)

| DuplexID | Sense Sequence Modified (5' to 3') | SEQ ID NO: | Antisense Sequence Modified (5' to 3') | SEQ ID NO: |
|---|---|---|---|---|
| AD-66808 | gsuscuGfuGfCfCfuucucaucuaL96 | 1273 | usAfsgauGfaGfAfaggcAfcAfgacsusu | 1283 |
| AD-66809 | gsuscuGfuGfCfCfuucucaucuaL96 | 1274 | UfsAfsgauGfaGfAfaggcAfcAfgacsusu | 1284 |
| AD-66810 | gsusguGfcAfCfUfucgcuucacaL96 | 1275 | usGfsugaAfgCfGfaaguGfcAfcacsusu | 1285 |
| AD-66811 | gsusguGfcAfCfUfucgcuucacaL96 | 1276 | UfsGfsugaAfgCfGfaaguGfcAfcacsusu | 1286 |
| AD-66812 | usgsugcaCfuUfCfGfcuucaccucuL96 | 1277 | asGfsaggUfgAfAfgcgaAfgUfgcacasusu | 1287 |
| AD-66813 | usgsugcaCfuUfCfGfcuucaccucuL96 | 1278 | AfsGfsaggUfgAfAfgcgaAfgUfgcacasusu | 1288 |
| AD-66814 | csasccagCfaCfCfAfugcaacuuuuL96 | 1279 | asAfsaagUfuGfCfauggUfgCfuggugsusu | 1289 |
| AD-66815 | csasccagCfaCfCfAfugcaacuuuuL96 | 1280 | AfsAfsaagUfuGfCfauggUfgCfuggugsusu | 1290 |
| AD-66816 | csasccauGfcAfAfCfuuuuucaccuL96 | 1281 | asGfsgugAfaAfAfaguuGfcAfuggugsusu | 1291 |
| AD-66817 | csasccauGfcAfAfCfuuuuucaccuL96 | 1282 | AfsGfsgugAfaAfAfaguuGfcAfuggugsusu | 1292 |

TABLE 12

HBV Target Sequences, noting target sites on Accession No. X02763.1. (Activity data and exemplary chemical modifications available at WO2012/024170, incorporated herein by reference)

| Target Sequence | Target Site | SEQ ID NO: |
|---|---|---|
| UCGUGGUGGACUUCUCUCA | 1663 | 1293 |
| GUGGUGGACUUCUCUCAAU | 1665 | 1294 |
| GCCGAUCCAUACUGCGGAA | 2669 | 1295 |
| CCGAUCCAUACUGCGGAAC | 2670 | 1296 |
| CAUCCUGCUGCUAUGCCUC | 1818 | 1297 |
| UGCUGCUAUGCCUCAUCUU | 1823 | 1298 |
| GGUGGACUUCUCUCAAUUU | 1667 | 1299 |
| UGGUGGACUUCUCUCAAUU | 1666 | 1300 |
| UAGACUCGUGGUGGACUUC | 1658 | 1301 |
| UCCUCUGCCGAUCCAUACU | 2663 | 1302 |
| UGCCGAUCCAUACUGCGGA | 2668 | 1303 |
| UGGAUGUGUCUGCGGCGUU | 1783 | 1304 |
| CGAUCCAUACUGCGGAACU | 2671 | 1305 |
| CGCACCUCUCUUUACGCGG | 2934 | 1306 |
| CUGCCGAUCCAUACUGCGG | 2667 | 1307 |
| CGUGGUGGACUUCUCUCAA | 1664 | 1308 |
| CUGCUGCUAUGCCUCAUCU | 1822 | 1309 |
| CCUGCUGCUAUGCCUCAUC | 1821 | 1310 |
| CUAGACUCGUGGUGGACUU | 1657 | 1311 |
| UCCUGCUGCUAUGCCUCAU | 1820 | 1312 |
| GACUCGUGGUGGACUUCUC | 1660 | 1313 |
| AUCCAUACUGCGGAACUCC | 2673 | 1314 |
| CUCUGCCGAUCCAUACUGC | 2665 | 1315 |
| GAUCCAUACUGCGGAACUC | 2672 | 1316 |
| GAAGAACUCCCUCGCCUCG | 567 | 1317 |
| AAGCCUCCAAGCUGUGCCU | 54 | 1318 |
| AGAAGAACUCCCUCGCCUC | 566 | 1319 |
| GGAGUGUGGAUUCGCACUC | 455 | 1320 |
| CCUCUGCCGAUCCAUACUG | 2664 | 1321 |
| CAAGCCUCCAAGCUGUGCC | 53 | 1322 |
| UCCAUACUGCGGAACUCCU | 2674 | 1323 |
| CAGAGUCUAGACUCGUGGU | 1651 | 1324 |
| AAGAAGAACUCCCUCGCCU | 565 | 1325 |
| GAGUGUGGAUUCGCACUCC | 456 | 1326 |
| UCUAGACUCGUGGUGGACU | 1656 | 1327 |
| GCUGCUAUGCCUCAUCUUC | 1824 | 1328 |
| AGUCUAGACUCGUGGUGGA | 1654 | 1329 |
| CUCCUCUGCCGAUCCAUAC | 2662 | 1330 |

TABLE 12-continued

HBV Target Sequences, noting target sites on Accession No. X02763.1. (Activity data and exemplary chemical modifications available at WO2012/024170, incorporated herein by reference)

| Target Sequence | Target Site | SEQ ID NO: |
|---|---|---|
| UGGCUCAGUUUACUAGUGC | 2077 | 1331 |
| GUCUAGACUCGUGGUGGAC | 1655 | 1332 |
| UUCAAGCCUCCAAGCUGUG | 51 | 1333 |
| CUAUGGGAGUGGGCCUCAG | 2047 | 1334 |
| CUCGUGGUGGACUUCUCUC | 1662 | 1335 |
| CCUAUGGGAGUGGGCCUCA | 2046 | 1336 |
| AAGAACUCCCUCGCCUCGC | 568 | 1337 |

TABLE 12-continued

HBV Target Sequences, noting target sites on Accession No. X02763.1. (Activity data and exemplary chemical modifications available at WO2012/024170, incorporated herein by reference)

| Target Sequence | Target Site | SEQ ID NO: |
|---|---|---|
| UCUGCCGAUCCAUACUGCG | 2666 | 1338 |
| AGAGUCUAGACUCGUGGUG | 1652 | 1339 |
| GAAGAAGAACUCCCUCGCC | 564 | 1340 |
| UCAAGCCUCCAAGCUGUGC | 52 | 1341 |
| AGCCUCCAAGCUGUGCCUU | 55 | 1342 |
| AGACUCGUGGUGGACUUCU | 1659 | 1343 |

TABLE 13

Various HBV siNA sense and antisense sequences corresponding to the identified target sequences in Table 1a. (Activity data and exemplary chemical modifications available at WO2012/024170, incorporated herein by reference)

| Target Site | SEQ ID NO: | Sense Sequence | Antisense Sequence | SEQ ID NO: |
|---|---|---|---|---|
| 1663 | 1344 | UCGUGGUGGACUUCUCUCA | UGAGAGAAGUCCACCACGA | 1395 |
| 1665 | 1345 | GUGGUGGACUUCUCUCAAU | AUUGAGAGAAGUCCACCAC | 1396 |
| 2669 | 1346 | GCCGAUCCAUACUGCGGAA | UUCCGCAGUAUGGAUCGGC | 1397 |
| 2670 | 1347 | CCGAUCCAUACUGCGGAAC | GUUCCGCAGUAUGGAUCGG | 1398 |
| 1818 | 1348 | CAUCCUGCUGCUAUGCCUC | GAGGCAUAGCAGCAGGAUG | 1399 |
| 1823 | 1349 | UGCUGCUAUGCCUCAUCUU | AAGAUGAGGCAUAGCAGCA | 1400 |
| 1667 | 1350 | GGUGGACUUCUCUCAAUUU | AAAUUGAGAGAAGUCCACC | 1401 |
| 1666 | 1351 | UGGUGGACUUCUCUCAAUU | AAUUGAGAGAAGUCCACCA | 1402 |
| 1658 | 1352 | UAGACUCGUGGUGGACUUC | GAAGUCCACCACGAGUCUA | 1403 |
| 2663 | 1353 | UCCUCUGCCGAUCCAUACU | AGUAUGGAUCGGCAGAGGA | 1404 |
| 2668 | 1354 | UGCCGAUCCAUACUGCGGA | UCCGCAGUAUGGAUCGGCA | 1405 |
| 1783 | 1355 | UGGAUGUGUCUGCGGCGUU | AACGCCGCAGACACAUCCA | 1406 |
| 2671 | 1356 | CGAUCCAUACUGCGGAACU | AGUUCCGCAGUAUGGAUCG | 1407 |
| 2934 | 1357 | CGCACCUCUCUUUACGCGG | CCGCGUAAAGAGAGGUGCG | 1408 |
| 2667 | 1358 | CUGCCGAUCCAUACUGCGG | CCGCAGUAUGGAUCGGCAG | 1409 |
| 1664 | 1359 | CGUGGUGGACUUCUCUCAA | UUGAGAGAAGUCCACCACG | 1410 |
| 1822 | 1360 | CUGCUGCUAUGCCUCAUCU | AGAUGAGGCAUAGCAGCAG | 1411 |
| 1821 | 1361 | CCUGCUGCUAUGCCUCAUC | GAUGAGGCAUAGCAGCAGG | 1412 |
| 1657 | 1362 | CUAGACUCGUGGUGGACUU | AAGUCCACCACGAGUCUAG | 1413 |
| 1820 | 1363 | UCCUGCUGCUAUGCCUCAU | AUGAGGCAUAGCAGCAGGA | 1414 |
| 1660 | 1364 | GACUCGUGGUGGACUUCUC | GAGAAGUCCACCACGAGUC | 1415 |
| 2673 | 1365 | AUCCAUACUGCGGAACUCC | GGAGUUCCGCAGUAUGGAU | 1416 |

TABLE 13-continued

Various HBV siNA sense and antisense sequences corresponding to the identified target sequences in Table 1a. (Activity data and exemplary chemical modifications available at WO2012/024170, incorporated herein by reference)

| Target Site | SEQ ID NO: | Sense Sequence | Antisense Sequence | SEQ ID NO: |
|---|---|---|---|---|
| 2665 | 1366 | CUCUGCCGAUCCAUACUGC | GCAGUAUGGAUCGGCAGAG | 1417 |
| 2672 | 1367 | GAUCCAUACUGCGGAACUC | GAGUUCCGCAGUAUGGAUC | 1418 |
| 567 | 1368 | GAAGAACUCCCUCGCCUCG | CGAGGCGAGGGAGUUCUUC | 1419 |
| 54 | 1369 | AAGCCUCCAAGCUGUGCCU | AGGCACAGCUUGGAGGCUU | 1420 |
| 566 | 1370 | AGAAGAACUCCCUCGCCUC | GAGGCGAGGGAGUUCUUCU | 1421 |
| 455 | 1371 | GGAGUGUGGAUUCGCACUC | GAGUGCGAAUCCACACUCC | 1422 |
| 2664 | 1372 | CCUCUGCCGAUCCAUACUG | CAGUAUGGAUCGGCAGAGG | 1423 |
| 53 | 1373 | CAAGCCUCCAAGCUGUGCC | GGCACAGCUUGGAGGCUUG | 1424 |
| 2674 | 1374 | UCCAUACUGCGGAACUCCU | AGGAGUUCCGCAGUAUGGA | 1425 |
| 1651 | 1375 | CAGAGUCUAGACUCGUGGU | ACCACGAGUCUAGACUCUG | 1426 |
| 565 | 1376 | AAGAAGAACUCCCUCGCCU | AGGCGAGGGAGUUCUUCUU | 1427 |
| 456 | 1377 | GAGUGUGGAUUCGCACUCC | GGAGUGCGAAUCCACACUC | 1428 |
| 1656 | 1378 | UCUAGACUCGUGGUGGACU | AGUCCACCACGAGUCUAGA | 1429 |
| 1824 | 1379 | GCUGCUAUGCCUCAUCUUC | GAAGAUGAGGCAUAGCAGC | 1430 |
| 1654 | 1380 | AGUCUAGACUCGUGGUGGA | UCCACCACGAGUCUAGACU | 1431 |
| 2662 | 1381 | CUCCUCUGCCGAUCCAUAC | GUAUGGAUCGGCAGAGGAG | 1432 |
| 2077 | 1382 | UGGCUCAGUUUACUAGUGC | GCACUAGUAAACUGAGCCA | 1433 |
| 1655 | 1383 | GUCUAGACUCGUGGUGGAC | GUCCACCACGAGUCUAGAC | 1434 |
| 51 | 1384 | UUCAAGCCUCCAAGCUGUG | CACAGCUUGGAGGCUUGAA | 1435 |
| 2047 | 1385 | CUAUGGGAGUGGGCCUCAG | CUGAGGCCCACUCCCAUAG | 1436 |
| 1662 | 1386 | CUCGUGGUGGACUUCUCUC | GAGAGAAGUCCACCACGAG | 1437 |
| 2046 | 1387 | CCUAUGGGAGUGGGCCUCA | UGAGGCCCACUCCCAUAGG | 1438 |
| 568 | 1388 | AAGAACUCCCUCGCCUCGC | GCGAGGCGAGGGAGUUCUU | 1439 |
| 2666 | 1389 | UCUGCCGAUCCAUACUGCG | CGCAGUAUGGAUCGGCAGA | 1440 |
| 1652 | 1390 | AGAGUCUAGACUCGUGGUG | CACCACGAGUCUAGACUCU | 1441 |
| 564 | 1391 | GAAGAAGAACUCCCUCGCC | GGCGAGGGAGUUCUUCUUC | 1442 |
| 52 | 1392 | UCAAGCCUCCAAGCUGUGC | GCACAGCUUGGAGGCUUGA | 1443 |

TABLE 13-continued

Various HBV siNA sense and antisense sequences corresponding to the identified target sequences in Table 1a. (Activity data and exemplary chemical modifications available at WO2012/024170, incorporated herein by reference)

| Target Site | SEQ ID NO: | Sense Sequence | Antisense Sequence | SEQ ID NO: |
|---|---|---|---|---|
| 55 | 1393 | AGCCUCCAAGCUGUGCCUU | AAGGCACAGCUUGGAGGCU | 1444 |
| 1659 | 1394 | AGACUCGUGGUGGACUUCU | AGAAGUCCACCACGAGUCU | 1445 |

EQUIVALENTS

Those skilled in the art will recognize, or be able to ascertain using no more than routine experimentation, many equivalents to the specific embodiments and methods described herein. Such equivalents are intended to be encompassed by the scope of the following claims.

We claim:

1. A method for treating a subject having an HBV infection, comprising sequentially administering to the subject having an HBV infection:
   a) an RNAi agent that inhibits expression of at least three HBV transcripts, wherein the RNAi agent comprises a sense strand and an antisense strand forming a double stranded region, and (i) the sense strand comprises the nucleotide sequence of 5'-GUGUGCACUUCGCUU-CACA-3' (SEQ ID NO: 27) and the antisense strand comprises the nucleotide sequence of 5'-UGUGAAGCGAAGUGCACACUU-3' (SEQ ID NO: 25), or (ii) the sense strand comprises the nucleotide sequence of 5'-CACCAUGCAACUUUUU-CACCU-3' (SEQ ID NO: 28) and the antisense strand comprises the nucleotide sequence of 5'-AG-GUGAAAAAGUUGCAUGGUGUU-3' (SEQ ID NO: 26);
   b) a protein-based HBV vaccine comprising a first HBV core antigen (HBcAg) polypeptide, or immunogenic fragment thereof, and a first HBV surface antigen (HBsAg) polypeptide, or immunogenic fragment thereof; and
   c) a nucleic acid-based HBV vaccine comprising an expression vector construct encoding a second HBcAg polypeptide, or immunogenic fragment thereof, and/or a second HBsAg polypeptide, or immunogenic fragment thereof,
   wherein the second HBcAg polypeptide, or immunogenic fragment thereof, and/or the second HBsAg polypeptide, or immunogenic fragment thereof, shares at least one epitope with at least one of the first HBcAg polypeptide, or immunogenic fragment thereof, and/or the first HBsAg polypeptide, or immunogenic fragment thereof;
   thereby treating the subject.

2. The method of claim 1, wherein at least two doses of the RNAi agent are administered to the subject.

3. The method of claim 1, wherein a dose of the RNAi agent is administered to the subject no more than once per week or no more than once every four weeks.

4. The method of claim 1, wherein the RNAi agent is administered to the subject at a dose of 0.01 mg/kg to 10 mg/kg; or 0.5 mg/kg to 50 mg/kg; or 10 mg/kg to 30 mg/kg.

5. The method of claim 1, wherein the RNAi agent is administered to the subject at a dose of 0.5 mg/kg, 1 mg/kg, 1.5 mg/kg, 3 mg/kg, 5 mg/kg, 10 mg/kg, or 30 mg/kg.

6. The method of claim 1, wherein the first and/or second HBsAg polypeptide, or immunogenic fragment thereof, comprises (a) an amino acid sequence at least 90% identical to amino acids 124 to 147 of SEQ ID NO: 22 or (b) an amino acid sequence at least 90% identical to amino acids 99 to 168 of SEQ ID NO: 23.

7. The method of claim 1, wherein the first and/or second HBcAg polypeptide, or immunogenic fragment thereof, comprises (a) an amino acid sequence comprising amino acid residue 80 of SEQ ID NO: 24, (b) an amino acid sequence at least 90% identical to at least amino acids 70 to 90 of SEQ ID NO: 24, (c) an amino acid sequence comprising amino acid residue 138 of SEQ ID NO: 24; (d) an amino acid sequence at least 90% identical to at least amino acids 128 to 143 of SEQ ID NO: 24; (e) an amino acid sequence at least 90% identical to at least 40, 50, 60, 70, 80, 90, or 100 contiguous amino acids of SEQ ID NO: 24; or (f) an amino acid sequence at least 90% identical to amino acids 18 to 143 of SEQ ID NO: 24.

8. The method of claim 1, wherein a dose of the protein-based HBV vaccine administered to the subject comprises about 0.1 µg to about 1.0 mg of the first HBcAg polypeptide, or immunogenic fragment thereof, and about 0.1 µg to about 1.0 mg of the first HBsAg polypeptide, or immunogenic fragment thereof.

9. The method of claim 1, wherein the first HBcAg polypeptide, or immunogenic fragment thereof, and the first HBsAg polypeptide, or immunogenic fragment thereof, are present in a single protein-based vaccine formulation.

10. The method of claim 9, wherein the protein-based HBV vaccine further comprises an adjuvant.

11. The method of claim 10, wherein the adjuvant is monophosphoryl lipid A (MPL), poly(I:C), polyICLC adjuvant, CpG DNA, a STING agonist, c-di-AMP, c-di-GMP, c-di-CMP; short, blunt-ended 5'-triphosphate dsRNA (3pRNA) Rig-I ligand, poly[di(sodiumcarboxylatoethylphenoxy)phosphazene] (PCEP)), alum, virosomes, cytokines, IL-12, AS02, AS03, AS04, MF59, ISCOMATRIX®, IC31®, or Rig-I ligand.

12. The method of claim 1, wherein a dose of the protein-based HBV vaccine is administered to the subject (a) at least two times; (b) no more than once every two weeks; (c) no sooner than the day on which a final dose of the RNAi agent has been administered to the subject; (d) on the same day as a final dose of the RNAi agent has been administered to the subject; (e) no later than one month after a final dose of the RNAi agent has been administered to the subject; (f) no later than three months after a final dose of the RNAi agent has been administered to the subject; (g) when the subject has a serum HBsAg level of 500 IU/ml or less, 200 IU/ml or less, or 100 IU/ml or less after administration of the RNAi agent and prior to administration of a first dose of the protein-based HBV vaccine; (h) when the subject has a serum HBeAg level of 500 IU/ml or less, 200 IU/ml or less, or 100 IU/ml or less after administration of the RNAi agent and prior to administration of a first dose of the protein-based HBV vaccine; or (i) when the subject has a serum HBsAg level of 500 IU/ml or less, 200 IU/ml or less, or 100 IU/ml or less and a serum HBeAg level of 500 IU/ml or less, 200 IU/ml or less, or 100 IU/ml or less after administration of the RNAi agent and prior to administration of a first dose of the protein-based HBV vaccine.

13. The method of claim 1, wherein the nucleic acid-based HBV vaccine comprises at least one expression vector construct encoding the second HBcAg polypeptide, or immunogenic fragment thereof, and the second HBsAg polypeptide, or immunogenic fragment thereof.

14. The method of claim 13, wherein the at least one expression vector construct comprises (a) a promoter that promotes expression of the second HBcAg polypeptide, or immunogenic fragment thereof, and the second HBsAg polypeptide, or immunogenic fragment thereof; or (b) a first and second promoter, the first promoter promoting expression of the second HBcAg polypeptide, or immunogenic fragment thereof, and the second promoter promoting expression of the second HBsAg polypeptide, or immunogenic fragment thereof.

15. The method of claim 1, wherein the expression construct comprises a viral vector.

16. The method of claim 1, wherein a dose of the nucleic acid-based HBV vaccine administered to the subject comprises a tissue-culture infectious dose ($TCID_{50}$) of $10^6$ to $10^{10}$ $TCID_{50}$; $10^6$ to $10^9$ $TCID_{50}$; or $10^6$ to $10^8$ $TCID_{50}$.

17. The method of claim 1, wherein (a) a dose of the nucleic acid-based HBV vaccine is administered to the subject no sooner than two weeks after administration of a final dose of the protein-based vaccine is administered to the subject; (b) a first dose of the nucleic acid-based HBV vaccine is administered to the subject when the level of HBsAg in the serum of the subject is decreased to at least 0.5 log 10 IU/ml following administration of at least one dose of the protein-based HBV vaccine; or (c) a single dose of the nucleic acid-based HBV vaccine is administered to the subject.

18. The method of claim 1, further comprising administering a nucleot(s)ide analog to the subject.

19. The method of claim 18, wherein at least one dose of the nucleot(s)ide analog is administered to the subject prior to administration of the RNAi agent to the subject; or multiple doses of the nucleot(s)ide analog are administered to the subject.

20. The method of claim 1, further comprising administering an immune stimulator to the subject.

21. The method of claim 1, wherein the subject is human.

22. The method of claim 1, wherein the antisense strand of the RNAi agent comprises the nucleotide sequence of 5'-UGUGAAGCGAAGUGCACACUU-3' (SEQ ID NO: 25) and the sense strand comprises the nucleotide sequence of 5'-GUGUGCACUUCGCUUCACA-3' (SEQ ID NO: 27).

23. The method of claim 1, wherein the antisense strand of the RNAi agent comprises the nucleotide sequence of 5'-AGGUGAAAAAGUUGCAUGGUGUU-3' (SEQ ID NO: 26) and the sense strand of the RNAi agent comprises the nucleotide sequence of 5'-CACCAUGCAACUUUUU-CACCU-3' (SEQ ID NO: 28).

24. The method of claim 1, wherein substantially all of the nucleotides of said sense strand and substantially all of the nucleotides of said antisense strand are modified nucleotides, and
wherein said sense strand is conjugated to a ligand attached at the 3'-terminus.

25. The method of claim 24, wherein the ligand is one or more GalNAc derivatives attached through a monovalent linker, bivalent branched linker, or trivalent branched linker.

26. The method of claim 25, wherein at least one of said modified nucleotides is a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a phosphorothioate group, a nucleotide comprising a methylphosphonate group, a nucleotide comprising a 5'-phosphate, or a nucleotide comprising a 5'-phosphate mimic.

27. The method of claim 1, wherein at least one strand of the RNAi agent comprises a 3' overhang of at least 1 nucleotide or at least 2 nucleotides.

28. The method of claim 1, wherein the double-stranded region of the RNAi agent is 19-21 or 21-23 nucleotide pairs in length.

29. The method of claim 1, wherein each strand of the RNAi agent has 19-30 nucleotides.

30. The method of claim 24, wherein the ligand is

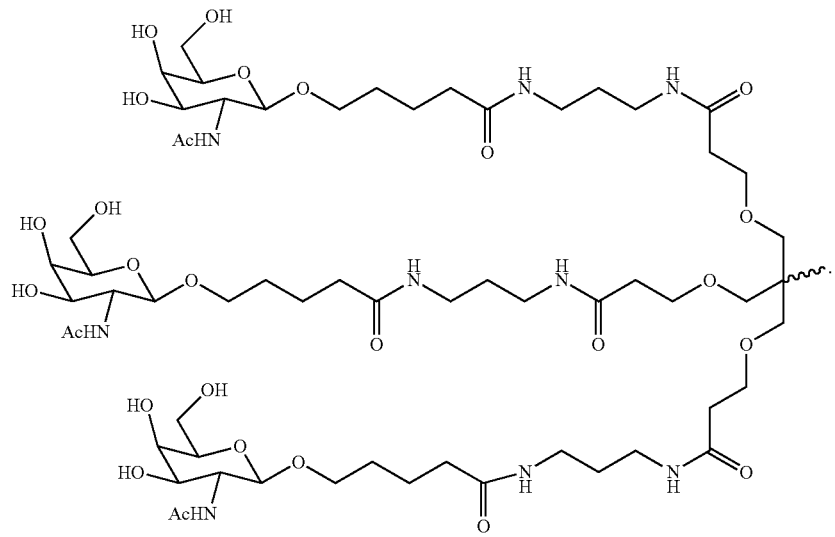 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

31. The method of claim 24, wherein the RNAi agent is conjugated to the ligand as shown in the following schematic

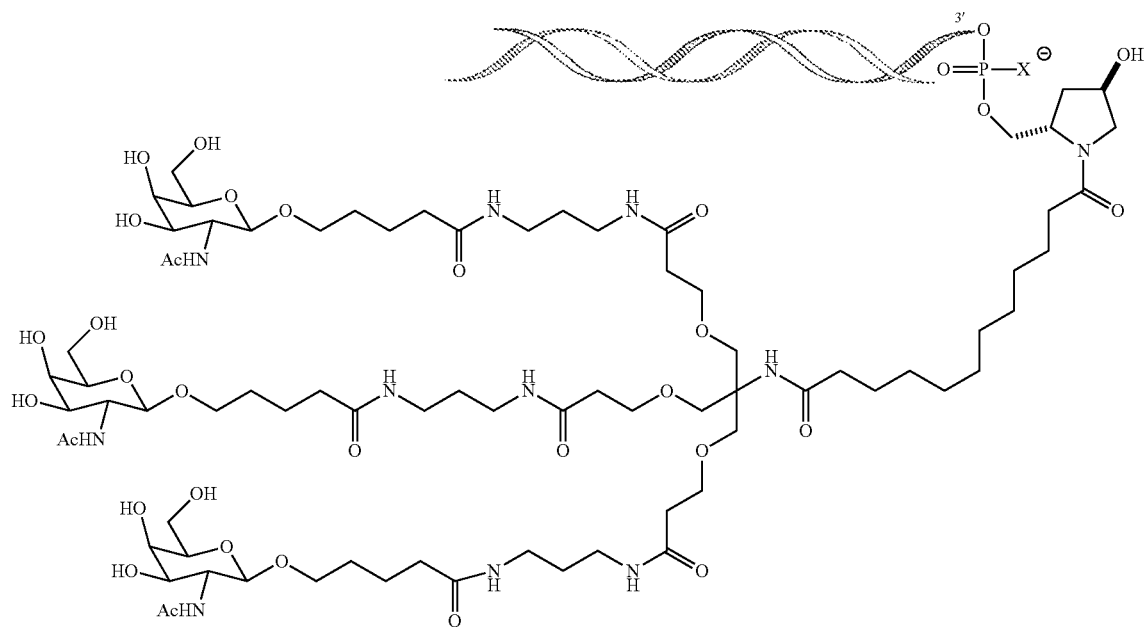

wherein X is O or S.

32. The method of claim 26, wherein (i) the sense strand comprises the nucleotide sequence of 5'-gsusguGfcAfCfU-fucgcuucacaL96-3' (SEQ ID NO: 37) and the antisense strand comprises the nucleotide sequence of 5'-usGfsugaAf-gCfGfaaguGfcAfcacsusu-3' (SEQ ID NO: 30), or (ii) the sense strand comprises the nucleotide sequence of 5'-csasccauGfcAfAfCfuuuuucaccuL96-3' (SEQ ID NO: 38) and the antisense strand comprises the nucleotide sequence of 5'-asGfsgugAfaAfAfaguuGfcAfuggugsusu-3' (SEQ ID NO: 32);

wherein a, c, g, and u are 2'-O-methyl (2'-OMe) A, 2'-OMe C, 2'-OMe G, and 2'-OMe U, respectively; Af, Cf, Gf, and Uf are 2'-fluoro A, 2'-fluoro C, 2'-fluoro G, and 2'-fluoro U, respectively; s is a phosphorothioate linkage; and L96 is N-[tris(GalNAc-alkyl)-amidodecanoyl)]-4-hydroxyprolinol.

33. The method of claim 1, wherein the first and/or second HBcAg polypeptide, or immunogenic fragment thereof, and/or the first and/or second HBsAg polypeptide, or immunogenic fragment thereof, comprise at least one determinant present in at least four, at least six, or at least seven genotypes of HBV.

34. A kit for treating a subject having an HBV infection, the kit comprising:
   a) an RNAi agent that inhibits expression of at least three HBV transcripts, wherein the RNAi agent comprises a sense strand and an antisense strand forming a double stranded region, and (i) the sense strand comprises the nucleotide sequence of 5'-GUGUGCACUUCGCUU-CACA-3' (SEQ ID NO: 27) and the antisense strand comprises the nucleotide sequence of 5'-UGUGAAGCGAAGUGCACACUU-3' (SEQ ID NO: 25), or (ii) the sense strand comprises the nucleotide sequence of 5'-CACCAUGCAACUUUUU-CACCU-3' (SEQ ID NO: 28) and the antisense strand comprises the nucleotide sequence of 5'-AG-GUGAAAAAGUUGCAUGGUGUU-3' (SEQ ID NO: 26);
   b) a protein-based HBV vaccine comprising a first HBV core antigen (HBcAg) polypeptide, or immunogenic fragment thereof, and a first HBV surface antigen (HBsAg) polypeptide, or immunogenic fragment thereof; and
   c) a nucleic acid-based HBV vaccine comprising an expression vector construct encoding a second HBcAg polypeptide, or immunogenic fragment thereof, and/or a second HBsAg polypeptide, or immunogenic fragment thereof,
   wherein the second HBcAg polypeptide, or immunogenic fragment thereof, and/or the second HBsAg polypeptide, or immunogenic fragment thereof, shares at least one epitope with at least one of the first HBcAg polypeptide, or immunogenic fragment thereof, and/or the first HBsAg polypeptide, or immunogenic fragment thereof; and
   d) instructions for use according to the method of claim 1.

* * * * *

SEQUENCE LISTING

<160> NUMBER OF SEQ ID NOS: 1445

<210> SEQ ID NO 1
<211> LENGTH: 3182
<212> TYPE: DNA
<213> ORGANISM: Hepatitis B virus

<400> SEQUENCE: 1
aattccacaa ccttccacca aactctgcaa gatcccagag tgagaggcct gtatttccct 60
gctggtggct ccagttcagg aacagtaaac cctgttctga ctactgcctc tcccttatcg 120
tcaatcttct cgaggattgg ggaccctgcg ctgaacatgg agaacatcac atcaggattc 180
ctaggacccc ttctcgtgtt acaggcgggg tttttcttgt tgacaagaat cctcacaata 240
ccgcagagtc tagactcgtg gtggacttct ctcaattttc tagggggaac taccgtgtgt 300
cttggccaaa attcgcagtc cccaacctcc aatcactcac caacctcttg tcctccaact 360
tgtcctggtt atcgctggat gtgtctgcgg cgttttatca tcttcctctt catcctgctg 420
ctatgcctca tcttcttgtt ggttcttctg gactatcaag gtatgttgcc cgtttgtcct 480
ctaattccag gatcctcaac aaccagcacg ggaccatgcc ggacctgcat gactactgct 540
caaggaacct ctatgtatcc ctcctgttgc tgtaccaaac cttcggacgg aaattgcacc 600
tgtattccca tcccatcatc ctgggctttc ggaaaattcc tatgggagtg ggcctcagcc 660
cgtttctcct ggctcagttt actagtgcca tttgttcagt ggttcgtagg gctttccccc 720
actgtttggc tttcagttat atggatgatg tggtattggg ggccaagtct gtacagcatc 780
ttgagtccct ttttaccgct gttaccaatt ttcttttgtc tttgggtata catttaaacc 840
ctaacaaaac aaagagatgg ggttactctc taaattttat gggttatgtc attggatgtt 900
atgggtcctt gccacaagaa cacatcatac aaaaaatcaa agaatgtttt agaaaacttc 960
ctattaacag gcctattgat tggaaagtat gtcaacgaat tgtgggtctt ttgggttttg 1020
ctgccccttt tacacaatgt ggttatcctg cgttgatgcc tttgtatgca tgtattcaat 1080
ctaagcaggc tttcactttc tcgccaactt acaaggcctt tctgtgtaaa caatacctga 1140
acctttaccc cgttgcccgg caacggccag gtctgtgcca agtgtttgct gacgcaaccc 1200
ccactggctg gggcttggtc atgggccatc agcgcatgcg tggaaccttt tcggctcctc 1260

```
tgccgatcca tactgcggaa ctcctagccg cttgttttgc tcgcagcagg tctggagcaa    1320
acattatcgg gactgataac tctgttgtcc tatcccgcaa atatacatcg tttccatggc    1380
tgctaggctg tgctgccaac tggatcctgc gcgggacgtc ctttgtttac gtcccgtcgg    1440
cgctgaatcc tgcggacgac ccttctcggg gtcgcttggg actctctcgt ccccttctcc    1500
gtctgccgtt ccgaccgacc acggggcgca cctctcttta cgcggactcc ccgtctgtgc    1560
cttctcatct gccggaccgt gtgcacttcg cttcacctct gcacgtcgca tggagaccac    1620
cgtgaacgcc caccaaatat tgcccaaggt cttacataag aggactcttg gactctcagc    1680
aatgtcaacg accgaccttg aggcatactt caaagactgt tgtttaaag actggagga     1740 gttgggggag gagattaggt taaaggtctt tgtactagga ggctgtaggc ataaattggt    1800
ctgcgcacca gcaccatgca acttttcac ctctgcctaa tcatctcttg ttcatgtcct     1860
actgttcaag cctccaagct gtgccttggg tggctttggg catggacat cgacccttat     1920 aaagaatttg gagctactgt ggagttactc tcgttttgc cttctgactt ctttccttca     1980
gtacgagatc ttctagatac cgcctcagct ctgtatcggg aagccttaga gtctcctgag    2040
cattgttcac ctcaccatac tgcactcagg caagcaattc tttgctgggg ggaactaatg    2100
actctagcta cctgggtggg tgttaatttg gaagatccag cgtctagaga cctagtagtc    2160
agttatgtca acactaatat gggcctaaag ttcaggcaac tcttgtggtt tcacatttct    2220
tgtctcactt ttggaagaga aacagttata gagtatttgg tgtctttcgg agtgtggatt    2280
cgcactcctc cagcttatag accaccaaat gcccctatcc tatcaacact tccggagact    2340
actgttgtta gacgacgagg caggtcccct agaagaagaa ctccctcgcc tcgcagacga    2400
aggtctcaat cgccgcgtcg cagaagatct caatctcggg aatctcaatg ttagtattcc    2460
ttggactcat aaggtgggga actttactgg gctttattct tctactgtac ctgtctttaa    2520
tcctcattgg aaaacaccat cttttcctaa tatacattta caccaagaca ttatcaaaaa    2580
atgtgaacag tttgtaggcc cactcacagt taatgagaaa agaagattgc aattgattat    2640
gcctgccagg ttttatccaa aggttaccaa atatttacca ttggataagg gtattaaacc    2700
ttattatcca gaacatctag ttaatcatta cttccaaact agacactatt tacacactct    2760
atggaaggcg ggtatattat ataagagaga acaacacat agcgcctcat tttgtgggtc     2820
accatattct tgggaacaag atctacagca tggggcagaa tctttccacc agcaatcctc    2880
tgggattctt tcccgaccac cagttggatc cagccttcag agcaaacacc gcaaatccag    2940
attgggactt caatcccaac aaggacacct ggccagacgc caacaaggta ggagctggag    3000
cattcgggct gggtttcacc ccaccgcacg gaggcctttt ggggtggagc cctcaggctc    3060
agggcatact acaaactttg ccagcaaatc cgcctcctgc ctccaccaat cgccagtcag    3120
gaaggcagcc taccccgctg tctccacctt tgagaaacac tcatcctcag gccatgcagt    3180
gg                                                                    3182
```

<210> SEQ ID NO 2
<211> LENGTH: 3182
<212> TYPE: DNA
<213> ORGANISM: Hepatitis B virus

<400> SEQUENCE: 2

```
ccactgcatg gcctgaggat gagtgttct caaaggtgga gacagcgggg taggctgcct       60
tcctgactgg cgattggtgg aggcaggagg cggatttgct ggcaaagttt gtagtatgcc     120
```

```
ctgagcctga gggctccacc ccaaaaggcc tccgtgcggt ggggtgaaac ccagcccgaa      180
tgctccagct cctaccttgt tggcgtctgg ccaggtgtcc ttgttgggat tgaagtccca      240
atctggattt gcggtgtttg ctctgaaggc tggatccaac tggtggtcgg␣gaaagaatcc     300 cagaggattg ctggtggaaa gattctgccc catgctgtag atcttgttcc caagaatatg      360
gtgacccaca aaatgaggcg ctatgtgttg tttctctctt atataatata cccgccttcc      420
atagagtgtg taaatagtgt ctagtttgga agtaatgatt aactagatgt␣tctgataat      480 aaggtttaat acccttatcc aatggtaaat atttggtaac ctttggataa aacctggcag      540
gcataatcaa ttgcaatctt cttttctcat taactgtgag tgggcctaca aactgttcac      600 atttttgat aatgtcttgg tgtaaatgta tattaggaaa agatggtgtt ttccaatgag       660
gattaaagac aggtacagta gaagaataaa gcccagtaaa gttccccacc ttatgagtcc      720
aaggaatact aacattgaga ttcccgagat tgagatcttc tgcgacgcgg cgattgagac      780
cttcgtctgc gaggcgaggg agttcttctt ctaggggacc tgcctcgtcg tctaacaaca      840
gtagtctccg gaagtgttga taggataggg gcatttggtg gtctataagc tggaggagtg      900
cgaatccaca ctccgaaaga caccaaatac tctataactg tttctcttcc aaaagtgaga      960
caagaaatgt gaaccacaa gagttgcctg aactttaggc ccatattagt gttgacataa      1020
ctgactacta ggtctctaga cgctggatct tccaaattaa cacccaccca ggtagctaga      1080
gtcattagtt ccccccagca aagaattgct tgcctgagtg cagtatggtg aggtgaacaa      1140
tgctcaggag actctaaggc ttccgatac agagctgagg cggtatctag aagatctcgt       1200
actgaaggaa agaagtcaga aggcaaaaac gagagtaact ccacagtagc tccaaattct      1260
ttataagggt cgatgtccat gccccaaagc cacccaaggc acagcttgga ggcttgaaca      1320
gtaggacatg aacaagagat gattaggcag aggtgaaaaa gttgcatggt gctggtgcgc      1380
agaccaattt atgcctacag cctcctagta caaagacctt taacctaatc tcctccccca      1440
actcctccca gtctttaaac aaacagtctt tgaagtatgc ctcaaggtcg gtcgttgaca      1500
ttgctgagag tccaagagtc ctcttatgta agaccttggg caatatttgg tgggcgttca      1560
cggtggtctc catgcgacgt gcagaggtga agcgaagtgc acacggtccg gcagatgaga      1620
aggcacagac ggggagtccg cgtaaagaga ggtgcgcccc gtggtcggtc ggaacggcag      1680
acggagaagg ggacgagaga gtcccaagcg accccgagaa gggtcgtccg caggattcag      1740
cgccgacggg acgtaaacaa aggacgtccc gcgcaggatc cagttggcag cacagcctag      1800
cagccatgga aacgatgtat atttgcggga taggacaaca gagttatcag tcccgataat      1860
gtttgctcca gacctgctgc gagcaaaaca agcggctagg agttccgcag tatggatcgg      1920
cagaggagcc gaaaaggttc cacgcatgcg ctgatggccc atgaccaagc cccagccagt      1980
gggggttgcg tcagcaaaca cttggcacag acctggccgt tgccgggcaa cggggtaaag      2040
gttcaggtat tgtttacaca gaaaggcctt gtaagttggc gagaaagtga aagcctgctt      2100
agattgaata catgcataca aaggcatcaa cgcaggataa ccacattgtg taaaaggggc      2160
agcaaaaccc aaaagaccca caattcgttg acatactttc caatcaatag gcctgttaat      2220
aggaagtttt ctaaaacatt cttgatttt ttgtatgatg tgttcttgtg gcaaggaccc       2280
ataacatcca atgacataac ccataaaatt tagagagtaa ccccatctct ttgttttgtt      2340
agggtttaaa tgtataccca aagacaaaag aaaattggta acagcggtaa aaagggactc      2400
aagatgctgt acagacttgg ccccaatac cacatcatcc atataactga aagccaaaca       2460
gtgggggaaa gccctacgaa ccactgaaca aatggcacta gtaaactgag ccaggagaaa      2520
```

```
cgggctgagg cccactccca taggaattt  ccgaaagccc aggatgatgg gatgggaata    2580
caggtgcaat ttccgtccga aggtttggta cagcaacagg agggatacat agaggttcct    2640
tgagcagtag tcatgcaggt ccggcatggt cccgtgctgg ttgttgagga tcctggaatt    2700
agaggacaaa cggcaacat  accttgatag tccagaagaa ccaacaagaa gatgaggcat    2760
agcagcagga tgaagaggaa gatgataaaa cgccgcagac acatccagcg ataaccagga    2820
caagttggag acaagaggt  tggtgagtga ttggaggttg gggactgcga atttggcca     2880
agacacacgg tagttccccc tagaaaattg agagaagtcc accacgagtc tagactctgc    2940
ggtattgtga ggattcttgt caacaagaaa accccgcct  gtaacacgag aagggtcct    3000
aggaatcctg atgtgatgtt ctccatgttc agcgcagggt ccccaatcct cgagaagatt    3060
gacgataagg gagaggcagt agtcagaaca gggtttactg ttcctgaact ggagccacca    3120
gcagggaaat acaggcctct cactctggga tcttgcagag tttggtggaa ggttgtggaa    3180
tt                                                                    3182
```

<210> SEQ ID NO 3
<211> LENGTH: 3215
<212> TYPE: DNA
<213> ORGANISM: Hepatitis B virus
<220> FEATURE:
<221> NAME/KEY: modified_base
<222> LOCATION: (2768)..(2768)
<223> OTHER INFORMATION: a, c, t, g, unknown or other

<400> SEQUENCE: 3

```
ctccaccaca ttccaccaag ctctgctaca ccccagagta aggggcctat actttcctgc     60
tggtggctcc agttccggaa cagtaaaccc tgttccgact actgcctctc ccatatcgtc    120
aatcttctcg aggactgggg accctgcacc gaacatggag aacacaacat caggattcct    180
aggaccctg  tcgtgttac  aggcggggtt tttcttgttg acaagaatcc tcacaatacc    240
acagagtcta gactcgtggt ggacttctct caattttcta gggggagcac ccacgtgtcc    300
tggccaaaat tcgcagtccc caacctccaa tcactcacca acctcttgtc ctccaatttg    360
tcctggctat cgctggatgt gtctgcggcg ttttatcata ttcctcttca tcctgctgct    420
atgcctcatc ttcttgttgg ttcttctgga ctaccaaggt atgttgcccg tttgtcctct    480
acttccagga acatcaacta ccagcacggg accatgcaag acctgcacga ttcctgctca    540
aggcacctct atgtttccct cttgttgctg tacaaaacct tcggacggaa actgcacttg    600
tattcccatc ccatcatcct gggctttcgc aagattccta tgggagtggg cctcagtccg    660
tttctcctgg ctcagtttac tagtgccatt tgttcagtgg ttcgtagggc tttcccccac    720
tgtttggctt tcagttatat ggatgatgtg gtattggggg ccaagtctgt acaacatctt    780
gagtcccttt ttaccgctgt taccaatttt cttttgtctt gggtataca  tttgaaccct    840
aataaaacca acgttgggg  ttactccctt aacttcatgg gatatgtaat ggaagttgg    900
ggtactttac cgcaagacca tattgtacta aaaatcaagc aatgtttcg  aaaactgcct    960
gtaaatagac ctattgattg gaaagtatgt cagagaattg tgggtctttt gggctttgct   1020
gccccttta  cacaatgtgg ctatcctgcc ttaatgcctt tatatgcatg tacaatct     1080
aagcaggctt tcactttctc gccaacttac aaggcctttc tgtgtaaaca atatctgaac   1140
ctttaccccg ttgcccggca acggtcaggt ctctgccaag tgtttgctga cgcaaccccc   1200
actggatggg gcttggctat tggccatcgc cgcatgcgtg gaacctttgt ggctcctctg   1260
```

```
ccgatccata ctgcggaact cctagcagct tgttttgctc gcagccggtc tggagcgaaa      1320
ctgatcggaa cggacaactc tgttgttctc tctcggaaat acacctcctt tccatggctg      1380
ctagggtgtg ctgccaactg gatcctgcgc gggacgtcct ttgtttacgt cccgtcggcg      1440
ctgaatcccg cggacgaccc atctcggggc cgtttgggtc tctaccgtcc ccttcttcat      1500
ctgccgttcc ggccgaccac ggggcgcacc tctctttacg cggtctcccc gtctgtgcct      1560
tctcatctgc cggaccgtgt gcacttcgct tcacctctgc acgtcgcatg gagaccaccg      1620
tgaacgccca ccaggtcttg cccaaggtct tatataagag gactcttgga ctctcagcaa      1680
tgtcaacgac cgaccttgag gcatacttca aagactgttt gtttaaggac tgggaggagt      1740
tggggggagga gattaggtta atgatctttg tactaggagg ctgtaggcat aaattggtct      1800
gttcaccagc accatgcaac ttttcaccct ctgcctaatc atctcatgtt catgtcctac      1860
tgttcaagcc tccaagctgt gccttgggtg gctttaggac atggacattg acccatataa      1920
agaatttgga gcttctgtgg agttactctc ttttttgcct tctgactttt ttccttctat      1980
tcgagatctc ctcgacaccg cctctgctct gtatcgggag gccttagagt ctccggaaca      2040
ttgttcacct caccatacag cactcagaca agccattctg tgttggggtg agttgatgaa      2100
tctggccacc tgggtgggaa gtaatttgga agacccagca tccagggaat tagtagtcag      2160
ctatgtcaat gttaatatgg gcctaaaaat cagacaacta ctgtggtttc acatttcctg      2220
tcttactttt ggaagagaaa ctgttcttga gtatttggtg tcttttggag tgtggattcg      2280
cactcctcct gcttacagac catcaaatgc ccctatctta tcaacacttc cggaaactac      2340
tgttgttaga cgacgaggca ggtcccctag aagaagaact ccctcgcctc gcagacgaag      2400
gtctcaatcg ccgcgtcgca gaagatctca atctcgggaa cctcaatgtt agtatccctt      2460
ggactcataa ggtgggaaac tttactgggc tttattcttc tactgtacct gtctttaatc      2520
ctgagtggca aactccctct tttcctcata ttcatttgca ggaggacatt attaatagat      2580
gtcaacaata tgtgggccct cttacagtta atgaaaaaag gagattaaaa ttaattatgc      2640
ctgctaggtt ctatcctaac cttaccaaat atttgccctt ggacaaaggc attaaaccat      2700
attatccgga acatgcagtt aatcattact caaaactag  gcattattta catactctgt      2760
ggaaggcngg cattctatat aagagagaaa ctacacgcag cgcctcattt tgtgggtcac      2820
catattcttg ggaacaagag ctacagcatg ggaggttggt cttccaaacc tcgacaaggc      2880
atggggacaa atctttctgt tcccaatcct ctgggattct ttcccgatca ccagttggac      2940
cctgcgttcg gagccaactc aaacaatcca gattgggact tcaacccaa  caaggatcac      3000
tggccagagg caaatcaggt aggagcggga gcattcgggc agggttcac  cccaccacac      3060
ggcggtcttt tggggtggag ccctcaggct cagggcacat tgacaacagt gccagtagca      3120
cctcctcctg cctccaccaa tcggcagtca ggaagacagc ctactcccat ctctccacct      3180
ctaagagaca gtcatcctca ggccatgcag tggaa                                3215
```

<210> SEQ ID NO 4
<211> LENGTH: 3215
<212> TYPE: DNA
<213> ORGANISM: Hepatitis B virus
<220> FEATURE:
<221> NAME/KEY: modified_base
<222> LOCATION: (448)..(448)
<223> OTHER INFORMATION: a, c, t, g, unknown or other

<400> SEQUENCE: 4

```
ttccactgca tggcctgagg atgactgtct cttagaggtg gagagatggg agtaggctgt       60
```

```
cttcctgact gccgattggt ggaggcagga ggaggtgcta ctggcactgt tgtcaatgtg      120
ccctgagcct gagggctcca ccccaaaaga ccgccgtgtg gtggggtgaa ccctggcccg      180
aatgctcccg ctcctacctg atttgcctct ggccagtgat ccttgttggg gttgaagtcc      240
caatctggat tgtttgagtt ggctccgaac gcagggtcca actggtgatc gggaaagaat      300
cccagaggat tgggaacaga aagatttgtc cccatgcctt gtcgaggttt ggaagaccaa      360
cctcccatgc tgtagctctt gttcccaaga atatggtgac ccacaaaatg aggcgctgcg      420
tgtagtttct ctcttatata gaatgccngc cttccacaga gtatgtaaat aatgcctagt      480
tttgaagtaa tgattaactg catgttccgg ataatatggt ttaatgcctt tgtccaaggg      540
caaatatttg gtaaggttag gatagaacct agcaggcata attaattta atctccttt      600 ttcattaact gtaagagggc ccacatattg ttgacatcta ttaataatgt cctcctgcaa      660
atgaatatga ggaaaagagg gagtttgcca ctcaggatta aagacaggta cagtagaaga      720
ataaagccca gtaaagtttc ccaccttatg agtccaaggg atactaacat tgaggttccc      780
gagattgaga tcttctgcga cgcggcgatt gagaccttcg tctgcgaggc gagggagttc      840
ttcttctagg ggacctgcct cgtcgtctaa aacagtagt ttccggaagt gttgataaga      900
taggggcatt tgatggtctg taagcaggag gagtgcgaat ccacactcca aaagacacca      960
aatactcaag aacagtttct cttccaaaag taagacagga aatgtgaaac cacagtagtt     1020
gtctgatttt taggcccata ttaacattga catagctgac tactaattcc ctggatgctg     1080
ggtcttccaa attacttccc acccaggtgg ccagattcat caactcaccc caacacagaa     1140
tggcttgtct gagtgctgta tggtgaggtg aacaatgttc cggagactct aaggcctccc     1200
gatacagagc agaggcggtg tcgaggagat ctcgaataga aggaaaaaag tcagaaggca     1260
aaaaagagag taactccaca gaagctccaa attctttata tgggtcaatg tccatgtcct     1320
aaagccaccc aaggcacagc ttggaggctt gaacagtagg acatgaacat gagatgatta     1380
ggcagaggtg aaaaagttgc atggtgctgg tgaacagacc aatttatgcc tacagcctcc     1440
tagtacaaag atcattaacc taatctcctc ccccaactcc tcccagtcct aaacaaaca     1500 gtctttgaag tatgcctcaa ggtcggtcgt tgacattgct gagagtccaa gagtcctctt     1560
atataagacc ttgggcaaga cctggtgggc gttcacggtg gtctccatgc gacgtgcaga     1620
ggtgaagcga agtgcacacg gtccggcaga tgagaaggca cagacgggga gaccgcgtaa     1680
agagaggtgc gccccgtggt cggccggaac ggcagatgaa gaagggacg gtagagaccc     1740 aaacggcccc gagatgggtc gtccgcggga ttcagcgccg acgggacgta aacaaaggac     1800
gtcccgcgca ggatccagtt ggcagcacac cctagcagcc atggaaagga ggtgtatttc     1860
cgagagagaa caacagagtt gtccgttccg atcagtttcg ctccagaccg gctgcgagca     1920
aaacaagctg ctaggagttc cgcagtatgg atcggcagag gagccacaaa ggttccacgc     1980
atgcggcgat ggccaatagc caagcccat ccagtggggg ttgcgtcagc aaacacttgg     2040
cagagacctg accgttgccg ggcaacgggg taaaggttca gatattgttt acacagaaag     2100
gccttgtaag ttggcgagaa agtgaaagcc tgcttagatt gtatacatgc atataaaggc     2160
attaaggcag gatagccaca ttgtgtaaaa ggggcagcaa agcccaaaag acccacaatt     2220
ctctgacata ctttccaatc aataggtcta tttacaggca gttttcgaaa acattgcttg     2280 attttttagta caatatggtc ttgcggtaaa gtacccaac ttccaattac atatcccatg     2340
aagttaaggg agtaaccca cgtttggtt ttattagggt tcaaatgtat acccaaagac     2400
```

```
aaaagaaaat tggtaacagc ggtaaaaagg gactcaagat gttgtacaga cttggccccc    2460
aataccacat catccatata actgaaagcc aaacagtggg ggaaagccct acgaaccact    2520
gaacaaatgg cactagtaaa ctgagccagg agaaacggac tgaggcccac tcccatagga    2580
atcttgcgaa agcccaggat gatgggatgg aatacaagt gcagtttccg tccgaaggtt    2640
ttgtacagca acaagaggga aacatagagg tgccttgagc aggaatcgtg caggtcttgc    2700
atggtcccgt gctggtagtt gatgttcctg gaagtagagg acaaacgggc aacataccct    2760
ggtagtccag aagaaccaac aagaagatga ggcatagcag caggatgaag aggaatatga    2820
taaaacgccg cagacacatc cagcgatagc caggacaaat tggaggacaa gaggttggtg    2880
agtgattgga ggttggggac tgcgaatttt ggccaggaca cgtgggtgct cccctagaa     2940 aattgagaga agtccaccac gagtctagac tctgtggtat tgtgaggatt cttgtcaaca    3000
agaaaaaccc cgcctgtaac acgagcaggg gtcctaggaa tcctgatgtt gtgttctcca    3060
tgttcggtgc agggtcccca gtcctcgaga agattgacga tatgggagag gcagtagtcg    3120
gaacagggtt tactgttccg gaactggagc caccagcagg aaagtatagg ccccttactc    3180
tggggtgtag cagagcttgg tggaatgtgg tggag                              3215
```

<210> SEQ ID NO 5
<211> LENGTH: 832
<212> TYPE: PRT
<213> ORGANISM: Hepatitis B virus

<400> SEQUENCE: 5

```
Met Pro Leu Ser Tyr Gln His Phe Arg Arg Leu Leu Leu Leu Asp Asp
1               5                   10                  15

Glu Ala Gly Pro Leu Glu Glu Glu Leu Pro Arg Leu Ala Asp Glu Gly
                20                  25                  30

Leu Asn Arg Arg Val Ala Glu Asp Leu Asn Leu Gly Asn Leu Asn Val
            35                  40                  45

Ser Ile Pro Trp Thr His Lys Val Gly Asn Phe Thr Gly Leu Tyr Ser
        50                  55                  60

Ser Thr Val Pro Val Phe Asn Pro His Trp Lys Thr Pro Ser Phe Pro
65                  70                  75                  80

Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
            100                 105                 110

Ala Arg Phe Tyr Pro Lys Val Thr Lys Tyr Leu Pro Leu Asp Lys Gly
        115                 120                 125

Ile Lys Pro Tyr Tyr Pro Glu His Leu Val Asn His Tyr Phe Gln Thr
    130                 135                 140

Arg His Tyr Leu His Thr Leu Trp Lys Ala Gly Ile Leu Tyr Lys Arg
145                 150                 155                 160

Glu Thr Thr His Ser Ala Ser Phe Cys Gly Ser Pro Tyr Ser Trp Glu
                165                 170                 175

Gln Asp Leu Gln His Gly Ala Glu Ser Phe His Gln Ser Ser Gly
            180                 185                 190

Ile Leu Ser Arg Pro Pro Val Gly Ser Ser Leu Gln Ser Lys His Arg
        195                 200                 205

Lys Ser Arg Leu Gly Leu Gln Ser Gln Gln Gly His Leu Ala Arg Arg
    210                 215                 220

Gln Gln Gly Arg Ser Trp Ser Ile Arg Ala Gly Phe His Pro Thr Ala
```

-continued

```
            225                 230                 235                 240
Arg Arg Pro Phe Gly Val Glu Pro Ser Gly Ser Gly His Thr Thr Asn
                    245                 250                 255
Phe Ala Ser Lys Ser Ala Ser Cys Leu His Gln Ser Pro Val Arg Lys
                    260                 265                 270
Ala Ala Tyr Pro Ala Val Ser Thr Phe Glu Lys His Ser Ser Ser Gly
                    275                 280                 285
His Ala Val Glu Phe His Asn Leu Pro Pro Asn Ser Ala Arg Ser Gln
                    290                 295                 300
Ser Glu Arg Pro Val Phe Pro Cys Trp Trp Leu Gln Phe Arg Asn Ser
305                 310                 315                 320
Lys Pro Cys Ser Asp Tyr Cys Leu Ser Leu Ile Val Asn Leu Leu Glu
                    325                 330                 335
Asp Trp Gly Pro Cys Ala Glu His Gly Glu His Ile Arg Ile Pro
                    340                 345                 350
Arg Thr Pro Ser Arg Val Thr Gly Gly Val Phe Leu Val Asp Lys Asn
                    355                 360                 365
Pro His Asn Thr Ala Glu Ser Arg Leu Val Val Asp Phe Ser Gln Phe
                    370                 375                 380
Ser Arg Gly Asn Tyr Arg Val Ser Trp Pro Lys Phe Ala Val Pro Asn
385                 390                 395                 400
Leu Gln Ser Leu Thr Asn Leu Leu Ser Ser Asn Leu Ser Trp Leu Ser
                    405                 410                 415
Leu Asp Val Ser Ala Ala Phe Tyr His Leu Pro Leu His Pro Ala Ala
                    420                 425                 430
Met Pro His Leu Leu Val Gly Ser Ser Gly Leu Ser Arg Tyr Val Ala
                    435                 440                 445
Arg Leu Ser Ser Asn Ser Arg Ile Leu Asn Asn Gln His Gly Thr Met
                    450                 455                 460
Pro Asp Leu His Asp Tyr Cys Ser Arg Asn Leu Tyr Val Ser Leu Leu
465                 470                 475                 480
Leu Leu Tyr Gln Thr Phe Gly Arg Lys Leu His Leu Tyr Ser His Pro
                    485                 490                 495
Ile Ile Leu Gly Phe Arg Lys Ile Pro Met Gly Val Gly Leu Ser Pro
                    500                 505                 510
Phe Leu Leu Ala Gln Phe Thr Ser Ala Ile Cys Ser Val Val Arg Arg
                    515                 520                 525
Ala Phe Pro His Cys Leu Ala Phe Ser Tyr Met Asp Asp Val Val Leu
                    530                 535                 540
Gly Ala Lys Ser Val Gln His Leu Glu Ser Leu Phe Thr Ala Val Thr
545                 550                 555                 560
Asn Phe Leu Leu Ser Leu Gly Ile His Leu Asn Pro Asn Lys Thr Lys
                    565                 570                 575
Arg Trp Gly Tyr Ser Leu Asn Phe Met Gly Tyr Val Ile Gly Cys Tyr
                    580                 585                 590
Gly Ser Leu Pro Gln Glu His Ile Ile Gln Lys Ile Lys Glu Cys Phe
                    595                 600                 605
Arg Lys Leu Pro Ile Asn Arg Pro Ile Asp Trp Lys Val Cys Gln Arg
                    610                 615                 620
Ile Val Gly Leu Leu Gly Phe Ala Ala Pro Phe Thr Gln Cys Gly Tyr
625                 630                 635                 640
Pro Ala Leu Met Pro Leu Tyr Ala Cys Ile Gln Ser Lys Gln Ala Phe
                    645                 650                 655
```

-continued

Thr Phe Ser Pro Thr Tyr Lys Ala Phe Leu Cys Lys Gln Tyr Leu Asn
            660                 665                 670

Leu Tyr Pro Val Ala Arg Gln Arg Pro Gly Leu Cys Gln Val Phe Ala
        675                 680                 685

Asp Ala Thr Pro Thr Gly Trp Gly Leu Val Met Gly His Gln Arg Met
690                 695                 700

Arg Gly Thr Phe Ser Ala Pro Leu Pro Ile His Thr Ala Glu Leu Leu
705                 710                 715                 720

Ala Ala Cys Phe Ala Arg Ser Arg Ser Gly Ala Asn Ile Ile Gly Thr
                725                 730                 735

Asp Asn Ser Val Val Leu Ser Arg Lys Tyr Thr Ser Phe Pro Trp Leu
            740                 745                 750

Leu Gly Cys Ala Ala Asn Trp Ile Leu Arg Gly Thr Ser Phe Val Tyr
        755                 760                 765

Val Pro Ser Ala Leu Asn Pro Ala Asp Asp Pro Ser Arg Gly Arg Leu
    770                 775                 780

Gly Leu Ser Arg Pro Leu Leu Arg Leu Pro Phe Arg Pro Thr Thr Gly
785                 790                 795                 800

Arg Thr Ser Leu Tyr Ala Asp Ser Pro Ser Val Pro Ser His Leu Pro
                805                 810                 815

Asp Arg Val His Phe Ala Ser Pro Leu His Val Ala Trp Arg Pro Pro
            820                 825                 830

<210> SEQ ID NO 6
<211> LENGTH: 389
<212> TYPE: PRT
<213> ORGANISM: Hepatitis B virus

<400> SEQUENCE: 6

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
        35                  40                  45

Ala Gly Ala Phe Gly Leu Gly Phe Thr Pro Pro His Gly Gly Leu Leu
    50                  55                  60

Gly Trp Ser Pro Gln Ala Gln Gly Ile Leu Gln Thr Leu Pro Ala Asn
65                  70                  75                  80

Pro Pro Pro Ala Ser Thr Asn Arg Gln Ser Gly Arg Gln Pro Thr Pro
                85                  90                  95

Leu Ser Pro Pro Leu Arg Asn Thr His Pro Gln Ala Met Gln Trp Asn
            100                 105                 110

Ser Thr Thr Phe His Gln Thr Leu Gln Asp Pro Arg Val Arg Gly Leu
        115                 120                 125

Tyr Phe Pro Ala Gly Gly Ser Ser Ser Gly Thr Val Asn Pro Val Leu
    130                 135                 140

Thr Thr Ala Ser Pro Leu Ser Ser Ile Phe Ser Arg Ile Gly Asp Pro
145                 150                 155                 160

Ala Leu Asn Met Glu Asn Ile Thr Ser Gly Phe Leu Gly Pro Leu Leu
                165                 170                 175

Val Leu Gln Ala Gly Phe Phe Leu Leu Thr Arg Ile Leu Thr Ile Pro
            180                 185                 190

Gln Ser Leu Asp Ser Trp Trp Thr Ser Leu Asn Phe Leu Gly Gly Thr

```
                195                 200                 205
Thr Val Cys Leu Gly Gln Asn Ser Gln Ser Pro Thr Ser Asn His Ser
    210                 215                 220
Pro Thr Ser Cys Pro Pro Thr Cys Pro Gly Tyr Arg Trp Met Cys Leu
225                 230                 235                 240
Arg Arg Phe Ile Ile Phe Leu Phe Ile Leu Leu Cys Leu Ile Phe
                    245                 250                 255
Leu Leu Val Leu Leu Asp Tyr Gln Gly Met Leu Pro Val Cys Pro Leu
                260                 265                 270
Ile Pro Gly Ser Ser Thr Thr Ser Thr Gly Pro Cys Arg Thr Cys Met
                275                 280                 285
Thr Thr Ala Gln Gly Thr Ser Met Tyr Pro Ser Cys Cys Cys Thr Lys
    290                 295                 300
Pro Ser Asp Gly Asn Cys Thr Cys Ile Pro Ile Pro Ser Ser Trp Ala
305                 310                 315                 320
Phe Gly Lys Phe Leu Trp Glu Trp Ala Ser Ala Arg Phe Ser Trp Leu
                    325                 330                 335
Ser Leu Leu Val Pro Phe Val Gln Trp Phe Val Gly Leu Ser Pro Thr
                340                 345                 350
Val Trp Leu Ser Val Ile Trp Met Met Trp Tyr Trp Gly Pro Ser Leu
                355                 360                 365
Tyr Ser Ile Leu Ser Pro Phe Leu Pro Leu Leu Pro Ile Phe Phe Cys
                370                 375                 380
Leu Trp Val Tyr Ile
385

<210> SEQ ID NO 7
<211> LENGTH: 281
<212> TYPE: PRT
<213> ORGANISM: Hepatitis B virus

<400> SEQUENCE: 7

Met Gln Trp Asn Ser Thr Thr Phe His Gln Thr Leu Gln Asp Pro Arg
1               5                   10                  15
Val Arg Gly Leu Tyr Phe Pro Ala Gly Gly Ser Ser Ser Gly Thr Val
                20                  25                  30
Asn Pro Val Leu Thr Thr Ala Ser Pro Leu Ser Ser Ile Phe Ser Arg
            35                  40                  45
Ile Gly Asp Pro Ala Leu Asn Met Glu Asn Ile Thr Ser Gly Phe Leu
        50                  55                  60
Gly Pro Leu Leu Val Leu Gln Ala Gly Phe Phe Leu Leu Thr Arg Ile
65                  70                  75                  80
Leu Thr Ile Pro Gln Ser Leu Asp Ser Trp Trp Thr Ser Leu Asn Phe
                85                  90                  95
Leu Gly Gly Thr Thr Val Cys Leu Gly Gln Asn Ser Gln Ser Pro Thr
            100                 105                 110
Ser Asn His Ser Pro Thr Ser Cys Pro Pro Thr Cys Pro Gly Tyr Arg
        115                 120                 125
Trp Met Cys Leu Arg Arg Phe Ile Ile Phe Leu Phe Ile Leu Leu Leu
    130                 135                 140
Cys Leu Ile Phe Leu Leu Val Leu Leu Asp Tyr Gln Gly Met Leu Pro
145                 150                 155                 160
Val Cys Pro Leu Ile Pro Gly Ser Ser Thr Thr Ser Thr Gly Pro Cys
                165                 170                 175
```

```
Arg Thr Cys Met Thr Thr Ala Gln Gly Thr Ser Met Tyr Pro Ser Cys
            180                 185                 190

Cys Cys Thr Lys Pro Ser Asp Gly Asn Cys Thr Cys Ile Pro Ile Pro
        195                 200                 205

Ser Ser Trp Ala Phe Gly Lys Phe Leu Trp Glu Trp Ala Ser Ala Arg
    210                 215                 220

Phe Ser Trp Leu Ser Leu Leu Val Pro Phe Val Gln Trp Phe Val Gly
225                 230                 235                 240

Leu Ser Pro Thr Val Trp Leu Ser Val Ile Trp Met Met Trp Tyr Trp
                245                 250                 255

Gly Pro Ser Leu Tyr Ser Ile Leu Ser Pro Phe Leu Pro Leu Leu Pro
                260                 265                 270

Ile Phe Phe Cys Leu Trp Val Tyr Ile
            275                 280

<210> SEQ ID NO 8
<211> LENGTH: 226
<212> TYPE: PRT
<213> ORGANISM: Hepatitis B virus

<400> SEQUENCE: 8

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Met Thr Thr Ala
        115                 120                 125

Gln Gly Thr Ser Met Tyr Pro Ser Cys Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Ile
        195                 200                 205

Leu Ser Pro Phe Leu Pro Leu Leu Pro Ile Phe Phe Cys Leu Trp Val
    210                 215                 220

Tyr Ile
225

<210> SEQ ID NO 9
<211> LENGTH: 154
<212> TYPE: PRT
<213> ORGANISM: Hepatitis B virus
```

<400> SEQUENCE: 9

```
Met Ala Ala Arg Leu Cys Cys Gln Leu Asp Pro Ala Arg Asp Val Leu
1               5                   10                  15

Cys Leu Arg Pro Val Gly Ala Glu Ser Cys Gly Arg Pro Phe Ser Gly
            20                  25                  30

Ser Leu Gly Thr Leu Ser Ser Pro Ser Pro Ser Ala Val Pro Thr Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Gln Ile Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Leu Phe Lys Asp Trp Glu Glu Leu Gly Glu Glu Ile Arg
        115                 120                 125

Leu Lys Val Phe Val Leu Gly Gly Cys Arg His Lys Leu Val Cys Ala
130                 135                 140

Pro Ala Pro Cys Asn Phe Phe Thr Ser Ala
145                 150
```

<210> SEQ ID NO 10
<211> LENGTH: 212
<212> TYPE: PRT
<213> ORGANISM: Hepatitis B virus

<400> SEQUENCE: 10

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205
```

Glu Ser Gln Cys
    210

<210> SEQ ID NO 11
<211> LENGTH: 843
<212> TYPE: PRT
<213> ORGANISM: Hepatitis B virus

<400> SEQUENCE: 11

Met Pro Leu Ser Tyr Gln His Phe Arg Lys Leu Leu Leu Leu Asp Asp
1               5                   10                  15

Glu Ala Gly Pro Leu Glu Glu Leu Pro Arg Leu Ala Asp Glu Gly
            20                  25                  30

Leu Asn Arg Arg Val Ala Glu Asp Leu Asn Leu Gly Asn Leu Asn Val
            35                  40                  45

Ser Ile Pro Trp Thr His Lys Val Gly Asn Phe Thr Gly Leu Tyr Ser
        50                  55                  60

Ser Thr Val Pro Val Phe Asn Pro Glu Trp Gln Thr Pro Ser Phe Pro
65                  70                  75                  80

His Ile His Leu Gln Glu Asp Ile Ile Asn Arg Cys Gln Gln Tyr Val
                85                  90                  95

Gly Pro Leu Thr Val Asn Glu Lys Arg Arg Leu Lys Leu Ile Met Pro
            100                 105                 110

Ala Arg Phe Tyr Pro Asn Leu Thr Lys Tyr Leu Pro Leu Asp Lys Gly
        115                 120                 125

Ile Lys Pro Tyr Tyr Pro Glu His Ala Val Asn His Tyr Phe Lys Thr
    130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Phe Gln Thr Ser Thr Arg His
            180                 185                 190

Gly Asp Lys Ser Phe Cys Ser Gln Ser Ser Gly Ile Leu Ser Arg Ser
        195                 200                 205

Pro Val Gly Pro Cys Val Arg Ser Gln Leu Lys Gln Ser Arg Leu Gly
    210                 215                 220

Leu Gln Pro Gln Gln Gly Ser Leu Ala Arg Gly Lys Ser Gly Arg Ser
225                 230                 235                 240

Gly Ser Ile Arg Ala Arg Val His Pro Thr Thr Arg Arg Ser Phe Gly
                245                 250                 255

Val Glu Pro Ser Gly Ser Gly His Ile Asp Asn Ser Ala Ser Ser Thr
            260                 265                 270

Ser Ser Cys Leu His Gln Ser Ala Val Arg Lys Thr Ala Tyr Ser His
        275                 280                 285

Leu Ser Thr Ser Lys Arg Gln Ser Ser Gly His Ala Val Glu Leu
    290                 295                 300

His His Ile Pro Pro Ser Ser Ala Thr Pro Gln Ser Lys Gly Pro Ile
305                 310                 315                 320

Leu Ser Cys Trp Trp Leu Gln Phe Arg Asn Ser Lys Pro Cys Ser Asp
                325                 330                 335

Tyr Cys Leu Ser His Ile Val Asn Leu Leu Glu Asp Trp Gly Pro Cys
            340                 345                 350

Thr Glu His Gly Glu His Asn Ile Arg Ile Pro Arg Thr Pro Ala Arg

```
                355                 360                 365
Val Thr Gly Gly Val Phe Leu Val Asp Lys Asn Pro His Asn Thr Thr
370                 375                 380
Glu Ser Arg Leu Val Val Asp Phe Ser Gln Phe Ser Arg Gly Ser Thr
385                 390                 395                 400
His Val Ser Trp Pro Lys Phe Ala Val Pro Asn Leu Gln Ser Leu Thr
                405                 410                 415
Asn Leu Leu Ser Ser Asn Leu Ser Trp Leu Ser Leu Asp Val Ser Ala
                420                 425                 430
Ala Phe Tyr His Ile Pro Leu His Pro Ala Ala Met Pro His Leu Leu
                435                 440                 445
Val Gly Ser Ser Gly Leu Pro Arg Tyr Val Ala Arg Leu Ser Ser Thr
                450                 455                 460
Ser Arg Asn Ile Asn Tyr Gln His Gly Thr Met Gln Asp Leu His Asp
465                 470                 475                 480
Ser Cys Ser Arg His Leu Tyr Val Ser Leu Leu Leu Leu Tyr Lys Thr
                485                 490                 495
Phe Gly Arg Lys Leu His Leu Tyr Ser His Pro Ile Ile Leu Gly Phe
                500                 505                 510
Arg Lys Ile Pro Met Gly Val Gly Leu Ser Pro Phe Leu Leu Ala Gln
                515                 520                 525
Phe Thr Ser Ala Ile Cys Ser Val Val Arg Arg Ala Phe Pro His Cys
                530                 535                 540
Leu Ala Phe Ser Tyr Met Asp Asp Val Val Leu Gly Ala Lys Ser Val
545                 550                 555                 560
Gln His Leu Glu Ser Leu Phe Thr Ala Val Thr Asn Phe Leu Leu Ser
                565                 570                 575
Leu Gly Ile His Leu Asn Pro Asn Lys Thr Lys Arg Trp Gly Tyr Ser
                580                 585                 590
Leu Asn Phe Met Gly Tyr Val Ile Gly Ser Trp Gly Thr Leu Pro Gln
                595                 600                 605
Asp His Ile Val Leu Lys Ile Lys Gln Cys Phe Arg Lys Leu Pro Val
                610                 615                 620
Asn Arg Pro Ile Asp Trp Lys Val Cys Gln Arg Ile Val Gly Leu Leu
625                 630                 635                 640
Gly Phe Ala Ala Pro Phe Thr Gln Cys Gly Tyr Pro Ala Leu Met Pro
                645                 650                 655
Leu Tyr Ala Cys Ile Gln Ser Lys Gln Ala Phe Thr Phe Ser Pro Thr
                660                 665                 670
Tyr Lys Ala Phe Leu Cys Lys Gln Tyr Leu Asn Leu Tyr Pro Val Ala
                675                 680                 685
Arg Gln Arg Ser Gly Leu Cys Gln Val Phe Ala Asp Ala Thr Pro Thr
                690                 695                 700
Gly Trp Gly Leu Ala Ile Gly His Arg Arg Met Arg Gly Thr Phe Val
705                 710                 715                 720
Ala Pro Leu Pro Ile His Thr Ala Glu Leu Leu Ala Ala Cys Phe Ala
                725                 730                 735
Arg Ser Arg Ser Gly Ala Lys Leu Ile Gly Thr Asp Asn Ser Val Val
                740                 745                 750
Leu Ser Arg Lys Tyr Thr Ser Phe Pro Trp Leu Leu Gly Cys Ala Ala
                755                 760                 765
Asn Trp Ile Leu Arg Gly Thr Ser Phe Val Tyr Val Pro Ser Ala Leu
                770                 775                 780
```

```
Asn Pro Ala Asp Asp Pro Ser Arg Gly Arg Leu Gly Leu Tyr Arg Pro
785                 790                 795                 800

Leu Leu His Leu Pro Phe Arg Pro Thr Thr Gly Arg Thr Ser Leu Tyr
            805                 810                 815

Ala Val Ser Pro Ser Val Pro Ser His Leu Pro Asp Arg Val His Phe
            820                 825                 830

Ala Ser Pro Leu His Val Ala Trp Arg Pro Pro
        835                 840
```

<210> SEQ ID NO 12
<211> LENGTH: 400
<212> TYPE: PRT
<213> ORGANISM: Hepatitis B virus

<400> SEQUENCE: 12

```
Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Ala Gly Ala Phe Gly
50                  55                  60

Pro Gly Phe Thr Pro Pro His Gly Gly Leu Leu Gly Trp Ser Pro Gln
65                  70                  75                  80

Ala Gln Gly Thr Leu Thr Thr Val Pro Val Ala Pro Pro Pro Ala Ser
            85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
            115                 120                 125

Gln Ala Leu Leu His Pro Arg Val Arg Gly Leu Tyr Phe Pro Ala Gly
        130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn Met Glu
                165                 170                 175

Asn Thr Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ala Pro Thr Cys Pro Gly
210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Leu Pro Gly Thr Ser
        275                 280                 285

Thr Thr Ser Thr Gly Pro Cys Lys Thr Cys Thr Ile Pro Ala Gln Gly
        290                 295                 300

Thr Ser Met Phe Pro Ser Cys Cys Cys Thr Lys Pro Ser Asp Gly Asn
```

```
                305                 310                 315                 320

Cys Thr Cys Ile Pro Ile Pro Ser Ser Trp Ala Phe Ala Arg Phe Leu
                325                 330                 335

Trp Glu Trp Ala Ser Val Arg Phe Ser Trp Leu Ser Leu Leu Val Pro
                340                 345                 350

Phe Val Gln Trp Phe Val Gly Leu Ser Pro Thr Val Trp Leu Ser Val
                355                 360                 365

Ile Trp Met Met Trp Tyr Trp Gly Pro Ser Leu Tyr Asn Ile Leu Ser
                370                 375                 380

Pro Phe Leu Pro Leu Leu Pro Ile Phe Phe Cys Leu Trp Val Tyr Ile
385                 390                 395                 400

<210> SEQ ID NO 13
<211> LENGTH: 210
<212> TYPE: PRT
<213> ORGANISM: Hepatitis B virus

<400> SEQUENCE: 13

Met Gly Leu Gly Tyr Trp Pro Ser Pro His Ala Trp Asn Leu Cys Gly
1               5                   10                  15

Ser Ser Ala Asp Pro Tyr Cys Gly Thr Pro Ser Ser Leu Phe Cys Ser
                20                  25                  30

Gln Pro Val Trp Ser Glu Thr Asp Arg Asn Gly Gln Leu Cys Cys Ser
                35                  40                  45

Leu Ser Glu Ile His Leu Leu Ser Met Ala Ala Arg Val Cys Cys Gln
                50                  55                  60

Leu Asp Pro Ala Arg Asp Val Leu Cys Leu Arg Pro Val Gly Ala Glu
65                  70                  75                  80

Ser Arg Gly Arg Pro Ile Ser Gly Pro Phe Gly Ser Leu Pro Ser Pro
                85                  90                  95

Ser Ser Ser Ala Val Pro Ala Asp His Gly Ala His Leu Ser Leu Arg
                100                 105                 110

Gly Leu Pro Val Cys Ala Phe Ser Ser Ala Gly Pro Cys Ala Leu Arg
                115                 120                 125

Phe Thr Ser Ala Arg Arg Met Glu Thr Thr Val Asn Ala His Gln Val
                130                 135                 140

Leu Pro Lys Val Leu Tyr Lys Arg Thr Leu Gly Leu Ser Ala Met Ser
145                 150                 155                 160

Thr Thr Asp Leu Glu Ala Tyr Phe Lys Asp Cys Leu Phe Lys Asp Trp
                165                 170                 175

Glu Glu Leu Gly Glu Gly Ile Arg Leu Met Ile Phe Val Leu Gly Gly
                180                 185                 190

Cys Arg His Lys Leu Val Cys Ser Pro Ala Pro Cys Asn Phe Phe Thr
                195                 200                 205

Ser Ala
    210

<210> SEQ ID NO 14
<211> LENGTH: 389
<212> TYPE: PRT
<213> ORGANISM: Hepatitis B virus

<400> SEQUENCE: 14

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
```

```
            20                  25                  30
Asp Phe Asn Pro Asn Lys Asp Thr Trp Pro Asp Ala Asn Lys Val Gly
         35                  40                  45

Ala Gly Ala Phe Gly Leu Gly Phe Thr Pro Pro His Gly Gly Leu Leu
 50                  55                  60

Gly Trp Ser Pro Gln Ala Gln Gly Ile Leu Gln Thr Leu Pro Ala Asn
 65                  70                  75                  80

Pro Pro Pro Ala Ser Thr Asn Arg Gln Ser Gly Arg Gln Pro Thr Pro
                 85                  90                  95

Leu Ser Pro Pro Leu Arg Asn Thr His Pro Gln Ala Met Gln Trp Asn
                100                 105                 110

Ser Thr Thr Phe His Gln Thr Leu Gln Asp Pro Arg Val Arg Gly Leu
                115                 120                 125

Tyr Phe Pro Ala Gly Gly Ser Ser Ser Gly Thr Val Asn Pro Val Leu
                130                 135                 140

Thr Thr Ala Ser Pro Leu Ser Ser Ile Phe Ser Arg Ile Gly Asp Pro
145                 150                 155                 160

Ala Leu Asn Met Glu Asn Ile Thr Ser Gly Phe Leu Gly Pro Leu Leu
                165                 170                 175

Val Leu Gln Ala Gly Phe Phe Leu Leu Thr Arg Ile Leu Thr Ile Pro
                180                 185                 190

Gln Ser Leu Asp Ser Trp Trp Thr Ser Leu Asn Phe Leu Gly Gly Thr
                195                 200                 205

Thr Val Cys Leu Gly Gln Asn Ser Gln Ser Pro Thr Ser Asn His Ser
                210                 215                 220

Pro Thr Ser Cys Pro Pro Thr Cys Pro Gly Tyr Arg Trp Met Cys Leu
225                 230                 235                 240

Arg Arg Phe Ile Ile Phe Leu Phe Ile Leu Leu Leu Cys Leu Ile Phe
                245                 250                 255

Leu Leu Val Leu Leu Asp Tyr Gln Gly Met Leu Pro Val Cys Pro Leu
                260                 265                 270

Ile Pro Gly Ser Ser Thr Thr Ser Thr Gly Pro Cys Arg Thr Cys Met
                275                 280                 285

Thr Thr Ala Gln Gly Thr Ser Met Tyr Pro Ser Cys Cys Cys Thr Lys
                290                 295                 300

Pro Ser Asp Gly Asn Cys Thr Cys Ile Pro Ile Pro Ser Ser Trp Ala
305                 310                 315                 320

Phe Gly Lys Phe Leu Trp Glu Trp Ala Ser Ala Arg Phe Ser Trp Leu
                325                 330                 335

Ser Leu Leu Val Pro Phe Val Gln Trp Phe Val Gly Leu Ser Pro Thr
                340                 345                 350

Val Trp Leu Ser Val Ile Trp Met Met Trp Tyr Trp Gly Pro Ser Leu
                355                 360                 365

Tyr Ser Ile Leu Ser Pro Phe Leu Pro Leu Leu Pro Ile Phe Phe Cys
                370                 375                 380

Leu Trp Val Tyr Ile
385

<210> SEQ ID NO 15
<211> LENGTH: 183
<212> TYPE: PRT
<213> ORGANISM: Hepatitis B virus

<400> SEQUENCE: 15
```

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 16
<211> LENGTH: 3182
<212> TYPE: DNA
<213> ORGANISM: Hepatitis B virus

<400> SEQUENCE: 16

```
aattccactg catggcctga ggatgagtgt ttctcaaagg tggagacagc ggggtaggct      60
gccttcctga ctggcgattg gtggaggcag gaggcggatt tgctggcaaa gtttgtagta     120
tgccctgagc ctgagggctc accccaaaa ggcctccgtg cggtggggtg aaacccagcc      180
cgaatgctcc agctcctacc ttgttggcgt ctggccaggt gtccttgttg ggattgaagt     240
cccaatctgg atttgcggtg tttgctctga aggctggatc caactggtgg tcgggaaaga     300
atcccagagg attgctggtg gaaagattct gccccatgct gtagatcttg ttcccaagaa     360
tatggtgacc cacaaaatga ggcgctatgt gttgtttctc tcttatataa atacccgcc      420
ttccatagag tgtgtaaata gtgtctagtt tggaagtaat gattaactag atgttctgga     480
taataaggtt taataccctt atccaatggt aaatatttgg taacctttgg ataaaacctg     540
gcaggcataa tcaattgcaa tcttcttttc tcattaactg tgagtgggcc tacaaactgt     600
tcacattttt tgataatgtc ttggtgtaaa tgtatattag gaaaagatgg tgttttccaa     660
tgaggattaa agacaggtac agtagaagaa taaagcccag taaagttccc caccttatga    720
gtccaaggaa tactaacatt gagattcccg agattgagat cttctgcgac gcggcgattg    780
agaccttcgt ctgcgaggcg agggagttct tcttctaggg gacctgcctc gtcgtctaac    840
aacagtagtc tccggaagtg ttgataggat aggggcattt ggtggtctat aagctggagg    900
agtgcgaatc cacactccga aagacaccaa atactctata actgtttctc ttccaaaagt    960
gagacaagaa atgtgaaacc acaagagttg cctgaacttt aggcccatat tagtgttgac   1020
ataactgact actaggtctc tagacgctgg atcttccaaa ttaacaccca cccaggtagc   1080
```

```
tagagtcatt agttccccec agcaaagaat tgcttgcctg agtgcagtat ggtgaggtga    1140
acaatgctca ggagactcta aggcttcccg atacagagct gaggcggtat ctagaagatc    1200
tcgtactgaa ggaaagaagt cagaaggcaa aaacgagagt aactccacag tagctccaaa    1260
ttctttataa gggtcgatgt ccatgcccca aagccaccca aggcacagct tggaggcttg    1320
aacagtagga catgaacaag agatgattag gcagaggtga aaaagttgca tggtgctggt    1380
gcgcagacca atttatgcct acagcctcct agtacaaaga cctttaacct aatctcctcc    1440
cccaactcct cccagtcttt aaacaaacag tctttgaagt atgcctcaag gtcggtcgtt    1500
gacattgctg agagtccaag agtcctctta tgtaagacct tgggcaatat ttggtgggcg    1560
ttcacggtgg tctccatgcg acgtgcagag gtgaagcgaa gtgcacacgg tccggcagat    1620
gagaaggcac agacggggag tccgcgtaaa gagaggtgcg ccccgtggtc ggtcggaacg    1680
gcagacggag aaggggacga gagagtccca agcgaccccg agaagggtcg tccgcaggat    1740
tcagcgccga cggacgtaa acaaaggacg tcccgcgcag gatccagttg gcagcacagc    1800
ctagcagcca tggaaacgat gtatatttgc gggataggac aacagagtta tcagtcccga    1860
taatgtttgc tccagacctg ctgcgagcaa acaagcggc taggagttcc gcagtatgga    1920
tcggcagagg agccgaaaag gttccacgca tgcgctgatg gcccatgacc aagccccagc    1980
cagtgggggt tgcgtcagca aacacttggc acagacctgg ccgttgccgg gcaacggggt    2040
aaaggttcag gtattgttta cacagaaagg ccttgtaagt tggcgagaaa gtgaaagcct    2100
gcttagattg aatacatgca tacaaaggca tcaacgcagg ataaccacat tgtgtaaaag    2160
gggcagcaaa acccaaaaga cccacaattc gttgacatac tttccaatca ataggcctgt    2220
taataggaag ttttctaaaa cattctttga ttttttgtat gatgtgttct tgtggcaagg    2280
acccataaca tccaatgaca taacccataa aatttagaga gtaaccccat ctctttgttt    2340
tgttagggtt taaatgtata cccaaagaca aagaaaatt ggtaacgcg gtaaaagggg    2400 actcaagatg ctgtacagac ttggccccca ataccacatc atccatataa ctgaaagcca    2460
aacagtgggg gaaagcccta cgaaccactg aacaaatggc actagtaaac tgagccagga    2520
gaaacgggct gaggcccact cccataggaa ttttccgaaa gcccaggatg atgggatggg    2580
aatacaggtg caatttccgt ccgaaggttt ggtacagcaa caggagggat acatagaggt    2640
tccttgagca gtagtcatgc aggtccggca tggtcccgtg ctggttgttg aggatcctgg    2700
aattagagga caaacgggca acataccttg atagtccaga agaaccaaca agaagatgag    2760
gcatagcagc aggatgaaga ggaagatgat aaaacgccgc agacacatcc agcgataacc    2820
aggacaagtt ggaggacaag aggttggtga gtgattggag gttggggact gcgaattttg    2880
gccaagacac acggtagttc cccctagaaa attgagagaa gtccaccacg agtctagact    2940
ctgcggtatt gtgaggattc ttgtcaacaa gaaaacccc gcctgtaaca cgagaagggg    3000
tcctaggaat cctgatgtga tgttctccat gttcagcgca gggtcccaa tcctcgagaa    3060 gattgacgat aagggagagg cagtagtcag aacagggttt actgttcctg aactggagcc    3120
accagcaggg aaatacaggc ctctcactct gggatcttgc agagtttggt ggaaggttgt    3180
gg                                                                   3182
```

<210> SEQ ID NO 17
<211> LENGTH: 3182
<212> TYPE: DNA
<213> ORGANISM: Hepatitis B virus

<400> SEQUENCE: 17

```
ccacaacctt ccaccaaact ctgcaagatc ccagagtgag aggcctgtat ttccctgctg      60
gtggctccag ttcaggaaca gtaaaccctg ttctgactac tgcctctccc ttatcgtcaa     120
tcttctcgag gattggggac cctgcgctga acatggagaa catcacatca ggattcctag     180
gaccccttct cgtgttacag gcggggtttt tcttgttgac aagaatcctc acaataccgc     240
agagtctaga ctcgtggtgg acttctctca attttctagg gggaactacc gtgtgtcttg     300
gccaaaattc gcagtcccca acctccaatc actcaccaac ctcttgtcct ccaacttgtc     360
ctggttatcg ctggatgtgt ctgcggcgtt ttatcatctt cctcttcatc ctgctgctat     420
gcctcatctt cttgttggtt cttctggact atcaaggtat gttgcccgtt tgtcctctaa     480
ttccaggatc ctcaacaacc agcacgggac catgccggac ctgcatgact actgctcaag     540
gaacctctat gtatccctcc tgttgctgta ccaaaccttc ggacggaaat tgcacctgta     600
ttcccatccc atcatcctgg gctttcggaa aattcctatg ggagtgggcc tcagcccgtt     660
tctcctggct cagtttacta gtgccatttg ttcagtggtt cgtagggctt ccccccactg     720
tttggctttc agttatatgg atgatgtggt attgggggcc aagtctgtac agcatcttga     780
gtcccttttt accgctgtta ccaattttct tttgtctttg ggtatacatt taaaccctaa     840
caaaacaaag agatggggtt actctctaaa ttttatgggt tatgtcattg gatgttatgg     900
gtccttgcca caagaacaca tcatacaaaa aatcaaagaa tgttttagaa aacttcctat     960
taacaggcct attgattgga aagtatgtca acgaattgtg ggtcttttgg gttttgctgc    1020
cccttttaca caatgtggtt atcctgcgtt gatgcctttg tatgcatgta ttcaatctaa    1080
gcaggctttc actttctcgc caacttacaa ggcctttctg tgtaaacaat acctgaacct    1140
ttaccccgtt gccggcaac ggccaggtct gtgccaagtg tttgctgacg caacccccac     1200
tggctggggc ttggtcatgg gccatcagcg catgcgtgga accttttcgg ctcctctgcc    1260
gatccatact gcggaactcc tagccgcttg ttttgctcgc agcaggtctg gagcaaacat    1320
tatcgggact gataactctg ttgtcctatc ccgcaaatat acatcgtttc catggctgct    1380
aggctgtgct gccaactgga tcctgcgcgg gacgtccttt gtttacgtcc cgtcggcgct    1440
gaatcctgcg gacgaccctt ctcggggtcg cttgggactc tctcgtcccc ttctccgtct    1500
gccgttccga ccgaccacgg ggcgcacctc tctttacgcg gactcccgt ctgtgccttc     1560
tcatctgccg gaccgtgtgc acttcgcttc acctctgcac gtcgcatgga gaccaccgtg    1620
aacgcccacc aaatattgcc caaggtctta cataagagga ctcttggact ctcagcaatg    1680
tcaacgaccg accttgaggc atacttcaaa gactgtttgt ttaaagactg ggaggagttg    1740
ggggaggaga ttaggttaaa ggtctttgta ctaggaggct gtaggcataa attggtctgc    1800
gcaccagcac catgcaactt tttcacctct gcctaatcat ctcttgttca gtccctactg    1860
ttcaagcctc caagctgtgc cttgggtggc tttggggcat ggacatcgac ccttataaag    1920
aatttggagc tactgtggag ttactctcgt ttttgccttc tgacttcttt ccttcagtac    1980
gagatcttct agataccgcc tcagctctgt atcgggaagc cttagagtct cctgagcatt    2040
gttcacctca ccatactgca ctcaggcaag caattctttg ctgggggaa ctaatgactc     2100
tagctacctg ggtgggtgtt aatttggaag atccagcgtc tagagaccta gtagtcagtt    2160
atgtcaacac taatatgggc ctaaagttca ggcaactctt gtggtttcac atttcttgtc    2220
tcactttgg aagagaaaca gttatagagt atttggtgtc tttcggagtg tggattcgca     2280
ctcctccagc ttatagacca ccaaatgccc ctatcctatc aacacttccg gagactactg    2340
```

-continued

```
ttgttagacg acgaggcagg tccctagaa gaagaactcc ctcgcctcgc agacgaaggt    2400
ctcaatcgcc gcgtcgcaga agatctcaat ctcgggaatc tcaatgttag tattccttgg    2460
actcataagg tggggaactt tactgggctt tattcttcta ctgtacctgt ctttaatcct    2520
cattggaaaa caccatcttt tcctaatata catttacacc aagacattat caaaaaatgt    2580
gaacagtttg taggcccact cacagttaat gagaaaagaa gattgcaatt gattatgcct    2640
gccaggtttt atccaaaggt taccaaatat ttaccattgg ataagggtat taaaccttat    2700
tatccagaac atctagttaa tcattacttc caaactagac actatttaca cactctatgg    2760
aaggcgggta tattatataa gagagaaaca acacatagcg cctcattttg tgggtcacca    2820
tattcttggg aacaagatct acagcatggg gcagaatctt tccaccagca atcctctggg    2880
attctttccc gaccaccagt tggatccagc cttcagagca acaccgcaa atccagattg    2940 ggacttcaat cccaacaagg acacctggcc agacgccaac aaggtaggag ctggagcatt    3000
cgggctgggt ttcaccccac cgcacggagg ccttttgggg tggagccctc aggctcaggg    3060
catactacaa actttgccag caaatccgcc tcctgcctcc accaatcgcc agtcaggaag    3120
gcagcctacc ccgctgtctc cacctttgag aaacactcat cctcaggcca tgcagtggaa    3180
tt                                                                   3182
```

<210> SEQ ID NO 18
<211> LENGTH: 389
<212> TYPE: PRT
<213> ORGANISM: Hepatitis B virus

<400> SEQUENCE: 18

```
Met Gly Thr Asn Leu Ser Val Pro Asn Pro Leu Gly Phe Leu Pro Asp
1               5                   10                  15

His Gln Leu Asp Pro Ala Phe Gly Ala Asn Ser Thr Asn Pro Asp Trp
            20                  25                  30

Asp Phe Asn Pro Ile Lys Asp His Trp Pro Ala Ala Asn Gln Val Gly
        35                  40                  45

Val Gly Ala Phe Gly Pro Gly Leu Thr Pro Pro His Gly Gly Ile Leu
    50                  55                  60

Gly Trp Ser Pro Gln Ala Gln Gly Ile Leu Thr Thr Val Ser Thr Ile
65                  70                  75                  80

Pro Pro Pro Ala Ser Thr Asn Arg Gln Ser Gly Arg Gln Pro Thr Pro
                85                  90                  95

Ile Ser Pro Pro Leu Arg Asp Ser His Pro Gln Ala Met Gln Trp Asn
            100                 105                 110

Ser Thr Ala Leu His Gln Ala Leu Gln Asp Pro Arg Val Arg Gly Leu
        115                 120                 125

Tyr Leu Pro Ala Gly Gly Ser Ser Gly Thr Val Asn Pro Ala Pro
    130                 135                 140

Asn Ile Ala Ser His Ile Ser Ser Ile Ser Ala Arg Thr Gly Asp Pro
145                 150                 155                 160

Val Thr Ile Met Glu Asn Ile Thr Ser Gly Phe Leu Gly Pro Leu Leu
                165                 170                 175

Val Leu Gln Ala Gly Phe Phe Leu Leu Thr Arg Ile Leu Thr Ile Pro
            180                 185                 190

Gln Ser Leu Asp Ser Trp Trp Thr Ser Leu Asn Phe Leu Gly Gly Ser
        195                 200                 205

Pro Val Cys Leu Gly Gln Asn Ser Gln Ser Pro Thr Ser Asn His Ser
```

```
            210                 215                 220
Pro Thr Ser Cys Pro Pro Ile Cys Pro Gly Tyr Arg Trp Met Cys Leu
225                 230                 235                 240

Arg Arg Phe Ile Ile Phe Leu Phe Ile Leu Leu Cys Leu Ile Phe
                    245                 250                 255

Leu Leu Val Leu Leu Asp Tyr Gln Gly Met Leu Pro Val Cys Pro Leu
                260                 265                 270

Ile Pro Gly Ser Thr Thr Thr Ser Thr Gly Pro Cys Lys Thr Cys Thr
                275                 280                 285

Thr Pro Ala Gln Gly Asn Ser Lys Phe Pro Ser Cys Cys Cys Thr Lys
290                 295                 300

Pro Thr Asp Gly Asn Cys Thr Cys Ile Pro Ile Pro Ser Ser Trp Ala
305                 310                 315                 320

Phe Ala Lys Tyr Leu Trp Glu Trp Ala Ser Val Arg Phe Ser Trp Leu
                    325                 330                 335

Ser Leu Leu Val Pro Phe Val Gln Trp Phe Val Gly Leu Ser Pro Thr
                340                 345                 350

Val Trp Leu Ser Ala Ile Trp Met Met Trp Tyr Trp Gly Pro Ser Leu
                355                 360                 365

Tyr Ser Ile Val Ser Pro Phe Ile Pro Leu Leu Pro Ile Phe Phe Cys
370                 375                 380

Leu Trp Val Tyr Ile
385

<210> SEQ ID NO 19
<211> LENGTH: 185
<212> TYPE: PRT
<213> ORGANISM: Hepatitis B virus

<400> SEQUENCE: 19

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Gln Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185
```

<210> SEQ ID NO 20
<211> LENGTH: 3200
<212> TYPE: DNA
<213> ORGANISM: Hepatitis B virus

<400> SEQUENCE: 20

```
ttccactgcc ttgcaccaag ctctgcagga tcccagagtc aggggtctgt atcttcctgc        60
tggtggctcc agttcaggaa cagtaaaccc tgctccgaat attgcctctc acatctcgtc       120
aatctccgcg aggactgggg accctgtgac gatcatggag aacatcacat caggattcct       180
aggacccctg ctcgtgttac aggcggggtt tttcttgttg acaagaatcc tcacaatacc       240
gcagagtcta gactcgtggt ggacttctct caattttcta ggggatcac ccgtgtgtct       300
tggccaaaat tcgcagtccc caacctccaa tcactcacca acctcctgtc ctccaatttg       360
tcctggttat cgctggatgt gtctgcggcg ttttatcata ttcctcttca tcctgctgct       420
atgcctcatc ttcttattgg ttcttctgga ttatcaaggt atgttgcccg tttgtcctct       480
aattccagga tcaacaacaa ccagtacggg accatgcaaa acctgcacga ctcctgctca       540
aggcaactct aagtttccct catgttgctg tacaaaacct acggatggaa attgcacctg       600
tattcccatc ccatcgtcct gggctttcgc aaaataccta tgggagtggg cctcagtccg       660
tttctcttgg ctcagtttac tagtgccatt tgttcagtgg ttcgtagggc tttcccccac       720
tgtttggctt tcagctatat ggatgatgtg gtattggggg ccaagtctgt acagcatcgt       780
gagtcccttt ataccgctgt taccaatttt cttttgtctc tgggtataca tttaaaccct       840
aacaaaacaa aaagatgggg ttattcccta aacttcatgg gctacataat ggaagttgg        900
ggaactttgc cacaggatca tattgtacaa aagatcaaac actgttttag aaaacttcct       960
gttaacaggc ctattgattg gaaagtatgt caaagaattg tgggtctttt gggctttgct      1020
gctccattta cacaatgtgg atatcctgcc ttaatgcctt tgtatgcatg tatacaagct      1080
aaacaggctt tcactttctc gccaacttac aaggcctttc taagtaaaca gtacatgaac      1140
ctttaccccg ttgctcggca acggcctggt ctgtgccaag tgtttgctga cgcaaccccc      1200
actggctggg gcttagccat aggccatcag cgcatgcgtg gaacctttgt ggctcctctg      1260
ccgatccata ctgcggaact cctagccgct tgttttgctc gcagccggtc tggagcaaag      1320
ctcatcggaa ctgacaattc tgtcgtcctc tcgcggaaat atacatcatt tccatggctg      1380
ctaggctgta ctgccaactg gatccttcgc gggacgtcct ttgtttacgt cccgtcggcg      1440
ctgaatcccg cggacgaccc ctctcggggc cgcttgggac tctctcgtcc ccttctccgt      1500
ctgccgttcc agccgaccac ggggcgcacc tctctttacg cggtctcccc gtctgtgcct      1560
tctcatctgc cggtccgtgt gcacttcgct tcacctctgc acgttgcatg gcgaccaccg      1620
tgaacgccca tcagatcctg cccaaggtct tacataagag gactcttgga ctcccagcaa      1680
tgtcaacgac cgaccttgag gcctacttca aagactgtgt gtttaaggac tgggaggagt      1740
tgggggagga gattaggtta atgatctttg tattaggagg ctgtaggcat aaattggtct      1800
gcgcaccagc accatgcaac ttttcacct ctgcctaatc atctcttgta catgtcccac      1860
tgttcaagcc tccaagctgt gccttgggtg gctttgggc atggacattg acccttataa      1920
agaatttgga gctactgtgg agttactctc gttttttgcct tctgacttct ttccttccgt      1980
acgagatctc ctagacaccg cctcagctct gtatcgagaa gccttagagt ctcctgagca      2040
ttgctcacct caccatactg cactcaggca agccattctc tgctgggggg aattgatgac      2100
tctagctacc tgggtgggta ataatttgca agatccagca tccagagatc tagtagtcaa      2160
```

```
ttatgttaat actaacatgg gtttaaagat caggcaacta ttgtggtttc atatatcttg    2220
ccttactttt ggaagagaga ctgtacttga atatttggtc tctttcggag tgtggattcg    2280
cactcctcca gcctatagac caccaaatgc cctatctta tcaacacttc cggaaactac     2340
tgttgttaga cgacgggacc gaggcaggtc cctagaaga gaactccct cgcctcgcag      2400
acgcagatct caatcgccgc gtcgcagaag atctcaatct cgggaatctc aatgttagta    2460
ttccttggac tcataaggtc ggaaacttta cggggcttta ttcctctaca gtacctatct    2520
ttaatcctga atggcaaact ccttcctttc ctaagattca tttacaagag gacattatta   2580
ataggtgtca acaatttgtg ggccctctca ctgtaaatga aaagagaaga ttgaaattaa    2640
ttatgcctgc tagattctat cctacccaca ctaaatattt gcccttagac aaaggaatta   2700
aaccttatta tccagatcag gtagttaatc attacttcca aaccagacat tatttacata   2760
ctctttggaa ggctggtatt ctatataaga gggaaaccac acgtagcgca tcattttgcg   2820
ggtcaccata ttcttgggaa caagagctac agcattcgca aaggcatggg gacgaatctt   2880
tctgttccca accctctggg attccttccc gatcatcagt tggaccctgc attcggagcc    2940
aactcaacaa atccagattg ggacttcaac cccatcaagg accactggcc agcagccaac    3000
caggtaggag tgggagcatt cgggccaggg ctcacccctc cacacggcgg tatttttgggg   3060
tggagccctc aggctcaggg catattgacc acagtgtcaa caattcctcc tcctgcctcc    3120
accaatcggc agtcaggaag gcagcctact cccatctctc cacctctaag agacagtcat    3180
cctcaggcca tgcagtggaa                                                3200

<210> SEQ ID NO 21
<211> LENGTH: 3200
<212> TYPE: DNA
<213> ORGANISM: Hepatitis B virus

<400> SEQUENCE: 21
ttccactgca tggcctgagg atgactgtct cttagaggtg gagagatggg agtaggctgc     60
cttcctgact gccgattggt ggaggcagga ggaggaattg ttgacactgt ggtcaatatg    120
ccctgagcct gagggctcca ccccaaaata ccgccgtgtg gaggggtgag ccctggcccg    180
aatgctccca ctcctacctg gttggctgct ggccagtggt ccttgatggg gttgaagtcc    240
caatctggat ttgttgagtt ggctccgaat gcagggtcca actgatgatc gggaaggaat    300
cccagagggt tgggaacaga aagattcgtc cccatgcctt tgcgaatgct gtagctcttg    360
ttcccaagaa tatggtgacc cgcaaaatga tgcgctacgt gtggtttccc tcttatatag    420
aataccagcc ttccaaagag tatgtaaata atgtctggtt tggaagtaat gattaactac    480
ctgatctgga taataaggtt taattccttt gtctaagggc aaatatttag tgtgggtagg    540
atagaatcta gcaggcataa ttaatttcaa tcttctcttt tcatttacag tgagagggcc    600
cacaaattgt tgacacctat taataatgtc tcttgtaaa tgaatcttag gaaggaagg     660
agtttgccat tcaggattaa agataggtac tgtagaggaa taaagccccg taaagtttcc    720
gaccttatga gtccaaggaa tactaacatt gagattcccg agattgagat cttctgcgac    780
gcggcgattg agatctgcgt ctgcgaggcg agggagttct tcttctaggg gacctgcctc    840
ggtcccgtcg tctaacaaca gtagtttccg gaagtgttga taagataggg gcatttggtg    900
gtctataggc tggaggagtg cgaatccaca ctccgaaaga gaccaaatat tcaagtacag    960
tctctcttcc aaaagtaagg caagatatat gaaaccacaa tagttgcctg atctttaaac    1020
```

```
ccatgttagt attaacataa ttgactacta gatctctgga tgctggatct tgcaaattat      1080
tacccaccca ggtagctaga gtcatcaatt cccccagca gagaatggct tgcctgagtg       1140
cagtatggtg aggtgagcaa tgctcaggag actctaaggc ttctcgatac agagctgagg      1200
cggtgtctag gagatctcgt acggaaggaa agaagtcaga aggcaaaaac gagagtaact      1260
ccacagtagc tccaaattct ttataagggt caatgtccat gccccaaagc cacccaaggc      1320
acagcttgga ggcttgaaca gtgggacatg tacaagagat gattaggcag aggtgaaaaa     1380
gttgcatggt gctggtgcgc agaccaattt atgcctacag cctcctaata caaagatcat      1440
taacctaatc cctcccca actcctccca gtccttaaac acacagtctt tgaagtaggc        1500
ctcaaggtcg gtcgttgaca ttgctgggag tccaagagtc ctcttatgta agaccttggg      1560
caggatctga tgggcgttca cggtggtcgc catgcaacgt gcagaggtga agcgaagtgc      1620
acacggaccg gcagatgaga aggcacagac ggggagaccg cgtaaagaga ggtgcgcccc     1680
gtggtcggct ggaacggcag acggagaagg ggacgagaga gtcccaagcg gccccgagag    1740
gggtcgtccg cgggattcag cgccgacggg acgtaaacaa aggacgtccc gcgaaggatc    1800
cagttggcag tacagcctag cagccatgga aatgatgtat atttccgcga gaggacgaca      1860
gaattgtcag ttccgatgag cttttgctcca gaccggctgc gagcaaaaca gcggctagg      1920 agttccgcag tatggatcgg cagaggagcc acaaaggttc cacgcatgcg ctgatggcct     1980
atggctaagc cccagccagt gggggttgcg tcagcaaaca cttggcacag accaggccgt    2040
tgccgagcaa cggggtaaag gttcatgtac tgtttactta gaaaggcctt gtaagttggc      2100
gagaaagtga aagcctgttt agcttgtata catgcataca aaggcattaa ggcaggatat      2160
ccacattgtg taaatggagc agcaaagccc aaaagaccca caattctttg acatactttc      2220 caatcaaatag gcctgttaac aggaagtttt ctaaaacagt gtttgatctt ttgtacaata    2280
tgatcctgtg gcaaagttcc ccaacttcca attatgtagc ccatgaagtt tagggaataa     2340 ccccatctttt ttgttttgtt agggtttaaa tgtatacccca gagacaaaag aaaattggta   2400
acagcggtat aaagggactc acgatgctgt acagacttgg cccccaatac cacatcatcc     2460
atatagctga aagccaaaca gtgggggaaa gccctacgaa ccactgaaca aatggcacta     2520
gtaaactgag ccaagagaaa cggactgagg cccactccca taggtatttt gcgaaagccc     2580
aggacgatgg gatgggaata caggtgcaat ttccatccgt aggttttgta cagcaacatg     2640
agggaaactt agagttgcct tgagcaggag tcgtgcaggt tttgcatggt cccgtactgg    2700
ttgttgttga tcctggaatt agaggacaaa cgggcaacat accttgataa tccagaagaa     2760
ccaataagaa gatgaggcat agcagcagga tgaagaggaa tatgataaaa cgccgcagac    2820
acatccagcg ataaccagga caaattggag gacaggaggt tggtgagtga ttggaggttg     2880
gggactgcga attttggcca agacacacgg gtgatccccc tagaaaattg agagaagtcc    2940
accacgagtc tagactctgc ggtattgtga ggattcttgt caacaagaaa aaccccgcct    3000
gtaacacgag caggggtcct aggaatcctg atgtgatgtt ctccatgatc gtcacagggt    3060
ccccagtcct cgcggagatt gacgagatgt gagaggcaat attcggagca gggtttactg    3120
ttcctgaact ggagccacca gcaggaagat acagacccct gactctggga tcctgcagag    3180
cttggtgcaa ggcagtggaa                                                 3200
```

<210> SEQ ID NO 22
<211> LENGTH: 226
<212> TYPE: PRT
<213> ORGANISM: Hepatitis B virus

<400> SEQUENCE: 22

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Ser Thr Thr Ser Thr Gly Pro Cys Arg Thr Cys Met Thr Thr Ala
        115                 120                 125

Gln Gly Thr Ser Met Tyr Pro Ser Cys Cys Thr Lys Pro Ser Asp
    130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Ile
        195                 200                 205

Leu Ser Pro Phe Leu Pro Leu Leu Pro Ile Phe Phe Cys Leu Trp Val
    210                 215                 220

Tyr Ile
225

<210> SEQ ID NO 23
<211> LENGTH: 247
<212> TYPE: PRT
<213> ORGANISM: Hepatitis B virus

<400> SEQUENCE: 23

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
        115                 120                 125

```
Gln Gly Asn Ser Met Phe Pro Ser Cys Cys Cys Thr Lys Pro Thr Asp
            130                 135                 140
Gly Asn Cys Thr Cys Ile Pro Ile Pro Ser Ser Trp Ala Phe Ala Lys
145                 150                 155                 160
Tyr Leu Trp Glu Trp Ala Ser Val Arg Phe Ser Trp Leu Ser Leu Leu
                165                 170                 175
Val Pro Phe Val Gln Trp Phe Val Gly Leu Ser Pro Thr Val Trp Leu
            180                 185                 190
Ser Ala Ile Trp Met Met Trp Tyr Trp Gly Pro Ser Leu Tyr Ser Ile
            195                 200                 205
Val Ser Pro Phe Ile Pro Leu Leu Pro Ile Phe Phe Cys Leu Trp Val
            210                 215                 220
Tyr Ile Gly Ser Gly Ala Thr Asn Phe Ser Leu Leu Lys Gln Ala Gly
225                 230                 235                 240
Asp Val Glu Glu Asn Pro Gly
                245

<210> SEQ ID NO 24
<211> LENGTH: 149
<212> TYPE: PRT
<213> ORGANISM: Hepatitis B virus

<400> SEQUENCE: 24

Met Asp Ile Asp Pro Tyr Lys Glu Phe Gly Ala Thr Val Glu Leu Leu
1               5                   10                  15
Ser Phe Leu Pro Ser Asp Phe Phe Pro Ser Val Arg Asp Leu Leu Asp
            20                  25                  30
Thr Ala Ser Ala Leu Tyr Arg Glu Ala Leu Glu Ser Pro Glu His Cys
        35                  40                  45
Ser Pro His His Thr Ala Leu Arg Gln Ala Ile Leu Cys Trp Gly Glu
    50                  55                  60
Leu Met Thr Leu Ala Thr Trp Val Gly Val Asn Leu Glu Asp Pro Ala
65                  70                  75                  80
Ser Arg Asp Leu Val Val Ser Tyr Val Asn Thr Asn Met Gly Leu Lys
                85                  90                  95
Phe Arg Gln Leu Leu Trp Phe His Ile Ser Cys Leu Thr Phe Gly Arg
            100                 105                 110
Glu Thr Val Ile Glu Tyr Leu Val Ser Phe Gly Val Trp Ile Arg Thr
        115                 120                 125
Pro Pro Ala Tyr Arg Pro Pro Asn Ala Pro Ile Leu Ser Thr Leu Pro
    130                 135                 140
Glu Thr Thr Val Val
145

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
ugugaagcga agugcacacu u                                              21

<210> SEQ ID NO 26
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
aggugaaaaa guugcauggu guu                                            23

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
gugugcacuu cgcuucaca                                                 19

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
caccaugcaa cuuuuucacc u                                              21

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gugugcacuu cgcuucaca                                                 19

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ugugaagcga agugcacacu u                                              21

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
caccaugcaa cuuuuucacc u                                              21

<210> SEQ ID NO 32
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 32
aggugaaaaa guugcauggu guu                                              23

<210> SEQ ID NO 33
<211> LENGTH: 16
<212> TYPE: PRT
<213> ORGANISM: Unknown
<220> FEATURE:
<223> OTHER INFORMATION: Description of Unknown:
      RFGF peptide

<400> SEQUENCE: 33

Ala Ala Val Ala Leu Leu Pro Ala Val Leu Leu Ala Leu Leu Ala Pro
1               5                   10                  15

<210> SEQ ID NO 34
<211> LENGTH: 11
<212> TYPE: PRT
<213> ORGANISM: Unknown
<220> FEATURE:
<223> OTHER INFORMATION: Description of Unknown:
      RFGF analogue peptide

<400> SEQUENCE: 34

Ala Ala Leu Leu Pro Val Leu Leu Ala Ala Pro
1               5                   10

<210> SEQ ID NO 35
<211> LENGTH: 13
<212> TYPE: PRT
<213> ORGANISM: Human immunodeficiency virus

<400> SEQUENCE: 35

Gly Arg Lys Lys Arg Arg Gln Arg Arg Arg Pro Pro Gln
1               5                   10

<210> SEQ ID NO 36
<211> LENGTH: 16
<212> TYPE: PRT
<213> ORGANISM: Drosophila sp.

<400> SEQUENCE: 36

Arg Gln Ile Lys Ile Trp Phe Gln Asn Arg Arg Met Lys Trp Lys Lys
1               5                   10                  15

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
gugugcacuu cgcuucaca                                                   19

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 38
caccaugcaa cuuuuucacc u                                              21

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gtgtgcactt cgcttcaca                                                 19

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
caccatgcaa cttttcacc t                                               21

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gagtgtggat tcgcactcc                                                 19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gaggcgaggg agttcttct                                                 19

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tcaccagcac catgcaac                                                  18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 44
aagccaccca aggcacag                                                   18

<210> SEQ ID NO 45
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
accaactgct tagccc                                                     16

<210> SEQ ID NO 46
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccacgacgga cacatt                                                     16

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
aguuauaugg augauguggu a                                               21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
ggaugugucu gcggcguuuu a                                               21

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
acucguggug gacuucucuc a                                               21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 50
acucguggug gacuucucuc a                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
acucguggug gacuuctcuc a                                              21

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
acucguggug gacuucucuc a                                              21

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
ucguggugga cuucucuca                                                 19

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
acucguggug gacuucucuc a                                              21

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
acucguggug gacuucucuc a                                              21

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 56
acucguggug gacuucucuc a                                              21

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
acucguggug gacuucucuc a                                              21

<210> SEQ ID NO 58
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
gugguggacu ucucuca                                                   17

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
acucguggug gacuucucuc a                                              21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
ucguggugga cuucucucau u                                              21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
acucguggug gacuucucuc a                                              21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
acucguggug gacuucucuc a                                             21

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
acucguggug gacuucucuc a                                             21

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
acucguggug gacuucucuc a                                             21

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
ucguggugga cuucucuca                                                19

<210> SEQ ID NO 66
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
acucguggug gacuucucuc a                                             21

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
acucguggug gacuucucuc a                                             21

<210> SEQ ID NO 68
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 68
acucguggug gacuucucuc a                                              21

<210> SEQ ID NO 69
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
uauuuccuag gguacaa                                                   17

<210> SEQ ID NO 70
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
acucguggug gacuucucuc a                                              21

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
ucguggugga cuucucuca                                                 19

<210> SEQ ID NO 72
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
acucguggug gacuucucuc a                                              21

<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
acucguggug gacuucucuc a                                              21

<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
```
acucguggug gacuucucuc a        21

<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
acucguggug gacuucucuc a        21

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
acucguggug gacuucucuc a        21

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
acucguggug gacuucucuc a        21

<210> SEQ ID NO 78
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
acucguggug gacuucucuc a        21

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
acucguggug gacuucucuc a        21

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
acucguggug gacuucucuc a                                           21

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
acucguggug gacuucucuc a                                           21

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
acucguggug gacuucucuc a                                           21

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
acucguggug gacuucucuc a                                           21

<210> SEQ ID NO 84
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
acucguggug gacuucucuc a                                           21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 85
acucguggug gacuuctcuc a                                           21

<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 86
acucguggug gacuucucuc a                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 87
acucguggug gacuuctcuc a                                              21

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
acucguggug gacuucucuc a                                              21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
acucguggug gacuucucuc a                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 90
acucguggug gacuuctcuc a                                              21

<210> SEQ ID NO 91
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
acucguggug gacuucucuc a                                              21

<210> SEQ ID NO 92
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 92
acucguggug gacuuctcuc a                                              21

<210> SEQ ID NO 93
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
acucguggug gacuucucuc a                                              21

<210> SEQ ID NO 94
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
gugguggacu ucucucaauu u                                              21

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
gugguggacu ucucucaauu u                                              21

<210> SEQ ID NO 96
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
gugguggacu ucucucaauu u                                              21

<210> SEQ ID NO 97
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
uggacuucuc ucaauuu                                                   17

<210> SEQ ID NO 98
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
gugguggacu ucucucaauu u                                          21

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
gguggacuuc ucucaauuuu u                                          21

<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
gugguggacu ucucucaauu u                                          21

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
gugguggacu ucucucaauu u                                          21

<210> SEQ ID NO 102
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
gugguggacu ucucucaauu u                                          21

<210> SEQ ID NO 103
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
gguggacuuc ucucaauuu                                             19

<210> SEQ ID NO 104
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
gugguggacu ucucucaauu u                                              21

<210> SEQ ID NO 105
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
gguggacuuc ucucaauuu                                                 19

<210> SEQ ID NO 106
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
gugguggacu ucucucaauu u                                              21

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
gugguggacu ucucucaauu u                                              21

<210> SEQ ID NO 108
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
uggacuucuc ucaauuu                                                   17

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
gugguggacu ucucucaauu u                                              21

<210> SEQ ID NO 110
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 110
gguggacuuc ucucaauuu                                                  19

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
gugguggacu ucucucaauu u                                               21

<210> SEQ ID NO 112
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
gugguggacu ucucucaauu u                                               21

<210> SEQ ID NO 113
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
gugguggacu ucucucaauu u                                               21

<210> SEQ ID NO 114
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
gugguggacu ucucucaauu u                                               21

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
gugguggacu ucucucaauu u                                               21

<210> SEQ ID NO 116
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 116
gugguggacu ucucucaauu u                                             21

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
gugguggacu ucucucaauu u                                             21

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
gugguggacu ucucucaauu u                                             21

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
gugguggacu ucucucaauu u                                             21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
gugguggacu ucucucaauu u                                             21

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
gugguggacu ucucucaauu u                                             21

<210> SEQ ID NO 122
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122
gugguggact tcucucaauu u                                              21

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
gugguggacu ucucucaauu u                                              21

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
gugguggacu ucucucaaauu u                                             21

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
gugguggacu ucucucaauu u                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 126
gugguggacu tcucucaauu u                                              21

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
gugguggacu ucucucaauu u                                              21
```

```
<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
gugguggacu ucucucaauu u                                              21

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
gugguggacu ucucucaauu u                                              21

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
gugguggacu ucucucaauu u                                              21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131
gugguggacu tcucucaauu u                                              21

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
gugguggacu ucucucaauu u                                              21

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
gugguggacu ucucucaauu u                                              21
```

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 134
gugguggacu tcucucaauu u                                              21

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
gugguggacu ucucucaauu u                                              21

<210> SEQ ID NO 136
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
gguggacuuc ucucaauuu                                                 19

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
gugguggacu ucucucaauu u                                              21

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
gugcacuucg cuucaccucu g                                              21

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
guugacaaaa auccucacaa u						21

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
uguugacaaa aauccucaca a						21

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
gguggacuuc ucucaauuuu a						21

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
ucuuuuggag uguggauucg a						21

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
ucuuuuggag uguggauucg a						21

<210> SEQ ID NO 144
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
acuguucaag ccuccaagcu a						21

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
ucugccgauc cauacugcgg a                                          21

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
augugucugc ggcguuuuau a                                          21

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
ccccgucugu gccuucucau a                                          21

<210> SEQ ID NO 148
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
gccuaaucau cucuuguuca u                                          21

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
ucuagacucg ugguggacuu c                                          21

<210> SEQ ID NO 150
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
cugccgaucc auacugcgga a                                          21

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
uuuuucuugu ugacaaaaau a                                          21

```
<210> SEQ ID NO 152
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
aucuucuugu ugguucuucu a                                              21

<210> SEQ ID NO 153
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
guuuuucuug uugacaaaaa u                                              21

<210> SEQ ID NO 154
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
cugccuaauc aucucuuguu a                                              21

<210> SEQ ID NO 155
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
uccucacaau accacagagu a                                              21

<210> SEQ ID NO 156
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
cuuguugaca aaaauccuca a                                              21

<210> SEQ ID NO 157
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
gcaacuuuuu caccucugcc u                                              21
```

<210> SEQ ID NO 158
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
gggaacaaga gcuacagcau a                                              21

<210> SEQ ID NO 159
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
cgugguggac uucucucaau u                                              21

<210> SEQ ID NO 160
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
cugcugcuau gccucaucuu a                                              21

<210> SEQ ID NO 161
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
guuggaugug ucugcggcgu u                                              21

<210> SEQ ID NO 162
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
uucauccugc ugcuaugccu a                                              21

<210> SEQ ID NO 163
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
uucuuguuga caaaaauccu a                                              21

```
<210> SEQ ID NO 164
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
uauauggaug augugguauu a                                              21

<210> SEQ ID NO 165
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
uucauccugc ugcuaugccu c                                              21

<210> SEQ ID NO 166
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
gugcacuucg cuucaccucu a                                              21

<210> SEQ ID NO 167
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
uugacaaaaa uccucacaau a                                              21

<210> SEQ ID NO 168
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
aagccuccaa gcugugccuu a                                              21

<210> SEQ ID NO 169
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
ccucuucauc cugcugcuau a                                              21

<210> SEQ ID NO 170
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
ccugcugcua ugccucaucu u                                              21

<210> SEQ ID NO 171
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
caucuucuug uugguucuuc u                                              21

<210> SEQ ID NO 172
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
ccgucugugc cuucucaucu a                                              21

<210> SEQ ID NO 173
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
ccucaucuuc uuguuggsuc u                                              21

<210> SEQ ID NO 174
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
ccaccaaaug ccccuaucuu a                                              21

<210> SEQ ID NO 175
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
gcuccucugc cgauccauac u                                              21

<210> SEQ ID NO 176
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
guugacaaaa auccucacaa u                                              21

<210> SEQ ID NO 177
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
uguugacaaa aauccucaca a                                              21

<210> SEQ ID NO 178
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
gguggacuuc ucucaauuuu a                                              21

<210> SEQ ID NO 179
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
ucuuuuggag uguggauucg a                                              21

<210> SEQ ID NO 180
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
ucuuuuggag uguggauucg a                                              21

<210> SEQ ID NO 181
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
acuguucaag ccuccaagcu a                                              21

<210> SEQ ID NO 182
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 182
ucugccgauc cauacugcgg a                                              21

<210> SEQ ID NO 183
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
aguuauaugg augauguggu a                                              21

<210> SEQ ID NO 184
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
augugucugc ggcguuuuau a                                              21

<210> SEQ ID NO 185
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
ccccgucugu gccuucucau a                                              21

<210> SEQ ID NO 186
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
gccuaaucau cucuuguuca u                                              21

<210> SEQ ID NO 187
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
ucuagacucg ugguggacuu c                                              21

<210> SEQ ID NO 188
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 188
cugccgaucc auacugcgga a                                              21

<210> SEQ ID NO 189
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
aucuucuugu ugguucuucu a                                              21

<210> SEQ ID NO 190
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
uucucucaau uuucuagggg a                                              21

<210> SEQ ID NO 191
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
acucguggug gacuucucuc a                                              21

<210> SEQ ID NO 192
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
gugcacuucg cuucaccucu g                                              21

<210> SEQ ID NO 193
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
guuuuucuug uugacaaaaa u                                              21

<210> SEQ ID NO 194
<211> LENGTH: 21
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 194
cugccuaauc aucucuuguu a                                              21

<210> SEQ ID NO 195
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
uccucacaau accacagagu a                                              21

<210> SEQ ID NO 196
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
cuuguugaca aaauccuca a                                               21

<210> SEQ ID NO 197
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
gugguggacu ucucucaauu u                                              21

<210> SEQ ID NO 198
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
gcaacuuuuu caccucugcc u                                              21

<210> SEQ ID NO 199
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
gggaacaaga gcuacagcau a                                              21

<210> SEQ ID NO 200
<211> LENGTH: 21
<212> TYPE: RNA
<213> ORGANISM: Artificial Sequence
<220> FEATURE:
<223> OTHER INFORMATION: Description of Artificial Sequence: Synthetic -continued oligonucleotide

<400> SEQUENCE: 200
ucaucuucuu guugguucuu a                                          21

<210> SEQ ID NO 201
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
cugcugcuau gccucaucuu a                                          21

<210> SEQ ID NO 202
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
guuggaugug ucugcggcgu u                                          21

<210> SEQ ID NO 203
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
uucauccugc ugcuaugccu a                                          21

<210> SEQ ID NO 204
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
uucuuguuga caaaaauccu a                                          21

<210> SEQ ID NO 205
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
ggaugugucu gcggcguuuu a                                          21

<210> SEQ ID NO 206
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
uauauggaug augugguauu a                                              21

<210> SEQ ID NO 207
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
uucauccugc ugcuaugccu c                                              21

<210> SEQ ID NO 208
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
gugcacuucg cuucaccucu a                                              21

<210> SEQ ID NO 209
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
uugacaaaaa uccucacaau a                                              21

<210> SEQ ID NO 210
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
ccaaguguuu gcugacgcaa a                                              21

<210> SEQ ID NO 211
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
ccaaguguuu gcugacgcaa a                                              21

<210> SEQ ID NO 212
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 212
aagccuccaa gcugugccuu a                                              21

<210> SEQ ID NO 213
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
ccucuucauc cugcugcuau a                                              21

<210> SEQ ID NO 214
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
ccugcugcua ugccucaucu u                                              21

<210> SEQ ID NO 215
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
caucuucuug uugguucuuc u                                              21

<210> SEQ ID NO 216
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
ccgucugugc cuucucaucu a                                              21

<210> SEQ ID NO 217
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
ccucaucuuc uuguugguuc u                                              21

<210> SEQ ID NO 218
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
```
ccaccaaaug ccccuaucuu a                                              21

<210> SEQ ID NO 219
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
gcuccucugc cgauccauac u                                              21

<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 220
acucguggug tacuucucuc a                                              21

<210> SEQ ID NO 221
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
acucguggug gacuucucuc a                                              21

<210> SEQ ID NO 222
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
acucguggug gacuucucuc a                                              21

<210> SEQ ID NO 223
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
acucguggug gacuucacuc a                                              21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 224
acucguggtg tacuucacuc a                                              21

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 225
acucguggug tacuucacuc a                                              21

<210> SEQ ID NO 226
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
acucguggug gacuucucuc a                                              21

<210> SEQ ID NO 227
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
acucguggug gacuucucuc a                                              21

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 228
acucguggtg gacuuctcuc a                                              21

<210> SEQ ID NO 229
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
acucguggug gacuucucuc a                                              21
```

<210> SEQ ID NO 230
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
acucguggug gacuucucuc a                                                21

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 231
acucguggtg tacuucacuc a                                                21

<210> SEQ ID NO 232
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
acucguggug gacuucucuc a                                                21

<210> SEQ ID NO 233
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
acucguggug gacuucucuc a                                                21

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 234
acucguggtg gacuucacuc a                                                21

<210> SEQ ID NO 235
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 235
acucguggug gacuucacuc a                                             21

<210> SEQ ID NO 236
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
acucguggug gacuucucuc a                                             21

<210> SEQ ID NO 237
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 237
acucguggtg gacuuctcuc a                                             21

<210> SEQ ID NO 238
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
acucguggug gacuucucuc a                                             21

<210> SEQ ID NO 239
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 239
acucguggug gacuuctcuc a                                             21

<210> SEQ ID NO 240
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 240
acucguggtg tacuucacuc a                                             21

<210> SEQ ID NO 241
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 241
acucguggtg gacuuctcuc a                                              21

<210> SEQ ID NO 242
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
acucguggug gacuuccuca                                                20

<210> SEQ ID NO 243
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 243
acucguggug gacuuctcuc a                                              21

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 244
acucguggug gacuuctcuc a                                              21

<210> SEQ ID NO 245
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
acucguggug gacuucucuc a                                              21

<210> SEQ ID NO 246
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 246
acucguggtg gacuucacuc a                                              21

<210> SEQ ID NO 247
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
acucguggug gacuucacuc a                                              21

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 248
acucguggtg gacuucacuc a                                              21

<210> SEQ ID NO 249
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
acucguggug gacuucucuc a                                              21

<210> SEQ ID NO 250
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 250
acucguggug gacuuctcuc a                                              21

<210> SEQ ID NO 251
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
```
acucguggug gacuucacuc a                                    21

<210> SEQ ID NO 252
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 252
acucguggtg tacuucacuc a                                    21

<210> SEQ ID NO 253
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
acucguggug gacuucccuc a                                    21

<210> SEQ ID NO 254
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
acucguggug gacuucucuc a                                    21

<210> SEQ ID NO 255
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
acucguggug gacuucucuc a                                    21

<210> SEQ ID NO 256
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 256
acucguggug gacuuctcuc a                                    21

<210> SEQ ID NO 257
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 257
acucguggtg gacuuctcuc a                                                21

<210> SEQ ID NO 258
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
acucguggug gacuucgcuc a                                                21

<210> SEQ ID NO 259
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
acucguggug gacuucucuc a                                                21

<210> SEQ ID NO 260
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
acucguggug gacuucucuc a                                                21

<210> SEQ ID NO 261
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
acucguggug gacuucucuc a                                                21

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 262
acucguggtg gacuucacuc a                                                21
```

```
<210> SEQ ID NO 263
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
uaccacauca uccauauaac uga                                            23

<210> SEQ ID NO 264
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
uaaaacgccg cagacacauc cag                                            23

<210> SEQ ID NO 265
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
ugagagaagu ccaccacgag ucu                                            23

<210> SEQ ID NO 266
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
ugagagaagu ccaccacgag ucu                                            23

<210> SEQ ID NO 267
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
ugagagaagu ccaccacgag ucu                                            23

<210> SEQ ID NO 268
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
ugagagaagu ccaccacgag ucu                                            23
```

```
<210> SEQ ID NO 269
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
ugagagaagu ccaccacgag u                                             21

<210> SEQ ID NO 270
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
ugagagaagu ccaccacgag ucu                                           23

<210> SEQ ID NO 271
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
ugagagaagu ccaccacgag ucu                                           23

<210> SEQ ID NO 272
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
ugagagaagu ccaccacgag ucu                                           23

<210> SEQ ID NO 273
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
ugagagaagu ccaccacgag ucu                                           23

<210> SEQ ID NO 274
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
ugagagaagu ccaccacga                                                19

<210> SEQ ID NO 275
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
ugagagaagu ccaccacgag ucu                                              23

<210> SEQ ID NO 276
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
ugagagaagu ccaccacgau u                                                21

<210> SEQ ID NO 277
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
ugagagaagu ccaccacgag ucu                                              23

<210> SEQ ID NO 278
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
ugagagaagu ccaccacgag ucu                                              23

<210> SEQ ID NO 279
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
ugagagaagu ccaccacgag ucu                                              23

<210> SEQ ID NO 280
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
ugagagaagu ccaccacgag ucu                                              23

<210> SEQ ID NO 281
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
ugagagaagu ccaccacgau u                                              21

<210> SEQ ID NO 282
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
ugagagaagu ccaccacgag ucu                                            23

<210> SEQ ID NO 283
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
ugagagaagu ccaccacgag ucu                                            23

<210> SEQ ID NO 284
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
ugagagaagu ccaccacgag ucu                                            23

<210> SEQ ID NO 285
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
ugagagaagu ccaccacga                                                 19

<210> SEQ ID NO 286
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
ugagagaagu ccaccacgag ucu                                            23

<210> SEQ ID NO 287
<211> LENGTH: 21
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 287
ugagagaagu ccaccacgau u                                              21

<210> SEQ ID NO 288
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
ugagagaagu ccaccacgag ucu                                            23

<210> SEQ ID NO 289
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
ugagagaagu ccaccacgag ucu                                            23

<210> SEQ ID NO 290
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
ugagagaagu ccaccacgag ucu                                            23

<210> SEQ ID NO 291
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
ugagagaagu ccaccacgag ucu                                            23

<210> SEQ ID NO 292
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
ugagagaagu ccaccacgag ucu                                            23

<210> SEQ ID NO 293
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
ugagagaagu ccaccacgag ucu                                                23

<210> SEQ ID NO 294
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
ugagagaagu ccaccacgag ucu                                                23

<210> SEQ ID NO 295
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
ugagagaagu ccaccacgag ucu                                                23

<210> SEQ ID NO 296
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
ugagagaagu ccaccacgag ucu                                                23

<210> SEQ ID NO 297
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
ugagagaagu ccaccacgag ucu                                                23

<210> SEQ ID NO 298
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
ugagagaagu ccaccacgag ucu                                                23

<210> SEQ ID NO 299
<211> LENGTH: 23
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 299
ugagagaagu ccaccacgag ucu                                              23

<210> SEQ ID NO 300
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 300
ugagagaagt ccaccacgag ucu                                              23

<210> SEQ ID NO 301
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
ugagagaagu ccaccacgag ucu                                              23

<210> SEQ ID NO 302
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
ugagagaagu ccaccacgag ucu                                              23

<210> SEQ ID NO 303
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
ugagagaagu ccaccacgag ucu                                              23

<210> SEQ ID NO 304
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
ugagagaagu ccaccacgag ucu                                              23

<210> SEQ ID NO 305
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 305
ugagagaagu ccaccacgag ucu                                           23

<210> SEQ ID NO 306
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
ugagagaagu ccaccacgag ucu                                           23

<210> SEQ ID NO 307
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
ugagagaagu ccaccacgag ucu                                           23

<210> SEQ ID NO 308
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
ugagagaagu ccaccacgag ucu                                           23

<210> SEQ ID NO 309
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
ugagagaagu ccaccacgag ucu                                           23

<210> SEQ ID NO 310
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
aaauugagag aaguccacca cga                                           23

<210> SEQ ID NO 311
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 311
aaauugagag aaguccacca cga                                                 23

<210> SEQ ID NO 312
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
aaauugagag aaguccacca cga                                                 23

<210> SEQ ID NO 313
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
aaauugagag aaguccacc                                                      19

<210> SEQ ID NO 314
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
aaauugagag aaguccacca cga                                                 23

<210> SEQ ID NO 315
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
aaauugagag aaguccaccu u                                                   21

<210> SEQ ID NO 316
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
aaauugagag aaguccacca cga                                                 23

<210> SEQ ID NO 317
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 317
aaauugagag aaguccacca cga                                              23

<210> SEQ ID NO 318
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
aaauugagag aaguccacca cga                                              23

<210> SEQ ID NO 319
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
aaauugagag aaguccacca c                                                21

<210> SEQ ID NO 320
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
aaauugagag aaguccacca cga                                              23

<210> SEQ ID NO 321
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
aaauugagag aaguccaccu u                                                21

<210> SEQ ID NO 322
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
aaauugagag aaguccacca cga                                              23

<210> SEQ ID NO 323
<211> LENGTH: 23
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 323
aaauugagag aaguccacca cga                                              23

<210> SEQ ID NO 324
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
aaauugagag aaguccacc                                                   19

<210> SEQ ID NO 325
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
aaauugagag aaguccacca cga                                              23

<210> SEQ ID NO 326
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
aaauugagag aaguccaccu u                                                21

<210> SEQ ID NO 327
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
aaauugagag aaguccacca cga                                              23

<210> SEQ ID NO 328
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
aaauugagag aaguccacca cga                                              23

<210> SEQ ID NO 329
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 329
aaauugagag aaguccacca cga                                              23

<210> SEQ ID NO 330
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
aaauugagag aaguccacca cga                                              23

<210> SEQ ID NO 331
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
aaauugagag aaguccacca cga                                              23

<210> SEQ ID NO 332
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
aaauugagag aaguccacca cga                                              23

<210> SEQ ID NO 333
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
aaauugagag aaguccacca cga                                              23

<210> SEQ ID NO 334
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
aaauugagag aaguccacca cga                                              23

<210> SEQ ID NO 335
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 335
aaauugagag aaguccacca cga                                              23

<210> SEQ ID NO 336
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
aaauugagag aaguccacca cga                                              23

<210> SEQ ID NO 337
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
aaauugagag aaguccacca cga                                              23

<210> SEQ ID NO 338
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 338
aaauugagag aagtccacca cga                                              23

<210> SEQ ID NO 339
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
aaauugagag aaguccacca cga                                              23

<210> SEQ ID NO 340
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
aaauugagag aaguccacca cga                                              23

<210> SEQ ID NO 341
<211> LENGTH: 23
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 341
aaauugagag aaguccacca cga					23

<210> SEQ ID NO 342
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 342
aaauugagag aagtccacca cga					23

<210> SEQ ID NO 343
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
aaauugagag aaguccacca cga					23

<210> SEQ ID NO 344
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
aaauugagag aaguccacca cga					23

<210> SEQ ID NO 345
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
aaauugagag aaguccacca cga					23

<210> SEQ ID NO 346
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
aaauugagag aaguccacca cga					23

<210> SEQ ID NO 347
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 347
aaauugagag aagtccacca cga                                          23

<210> SEQ ID NO 348
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
aaauugagag aaguccacca cga                                          23

<210> SEQ ID NO 349
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
aaauugagag aaguccacca cga                                          23

<210> SEQ ID NO 350
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
aaauugagag aaguccacca cga                                          23

<210> SEQ ID NO 351
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
aaauugagag aaguccacca cga                                          23

<210> SEQ ID NO 352
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
aaauugagag aaguccacca c                                            21

<210> SEQ ID NO 353
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
aaauugagag aaguccacca cga                                             23

<210> SEQ ID NO 354
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
cagaggugaa gcgaagugca cac                                             23

<210> SEQ ID NO 355
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
auugugagga uuuuugucaa caa                                             23

<210> SEQ ID NO 356
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
uugugaggau uuuugucaac aag                                             23

<210> SEQ ID NO 357
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
uaaaauugag agaaguccac cac                                             23

<210> SEQ ID NO 358
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
ucgaauccac acuccaaaag aca                                             23

<210> SEQ ID NO 359
<211> LENGTH: 23
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 359
ucgaauccac acuccaaaag aca                                                23

<210> SEQ ID NO 360
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
uagcuuggag gcuugaacaa gac                                                23

<210> SEQ ID NO 361
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
uccgcaguau ggaucggcag agg                                                23

<210> SEQ ID NO 362
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
uauaaaacgc cgcagacaca ucc                                                23

<210> SEQ ID NO 363
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
uaugagaagg cacagacggg gag                                                23

<210> SEQ ID NO 364
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
augaacaaga gaugauuagc gag                                                23

<210> SEQ ID NO 365
<211> LENGTH: 23
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 365
gaaguccacc acgagucuag acu                                              23

<210> SEQ ID NO 366
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
uuccgcagua uggaucggca gag                                              23

<210> SEQ ID NO 367
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367 uauuuuguc aacaagaaaa acc                                               23

<210> SEQ ID NO 368
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
uagaagaacc aacaagaaga uga                                              23

<210> SEQ ID NO 369
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
auuuuuguca acaagaaaaa ccc                                              23

<210> SEQ ID NO 370
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
uaacaagaga ugauuaggca gag                                              23

<210> SEQ ID NO 371
<211> LENGTH: 23
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 371
uacucugugg uauugugagg auu                                           23

<210> SEQ ID NO 372
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
uugaggauuu uugucaacaa gaa                                           23

<210> SEQ ID NO 373
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
aggcagaggu gaaaaaguug cau                                           23

<210> SEQ ID NO 374
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
uaugcuguag cucuuguucc caa                                           23

<210> SEQ ID NO 375
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
aauugagaga aguccaccag cag                                           23

<210> SEQ ID NO 376
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
uaagaugagg cauagcagca gga                                           23

<210> SEQ ID NO 377
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 377
aacgccgcag acacauccaa cga                                              23

<210> SEQ ID NO 378
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
uaggcauagc agcaggauga aga                                              23

<210> SEQ ID NO 379
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
uaggauuuuu gucaacaaga aaa                                              23

<210> SEQ ID NO 380
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
uaauaccaca ucauccauau aac                                              23

<210> SEQ ID NO 381
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
gaggcauagc agcaggauga aga                                              23

<210> SEQ ID NO 382
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
uagaggugaa gcgaagugca cac                                              23

<210> SEQ ID NO 383
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
uauugugagg auuuuuguca aca                                          23

<210> SEQ ID NO 384
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
uaaggcacag cuuggaggcu uga                                          23

<210> SEQ ID NO 385
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
uauagcagca ggaugaagag gaa                                          23

<210> SEQ ID NO 386
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
aagaugaggc auagcagcag gau                                          23

<210> SEQ ID NO 387
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
agaagaacca acaagaagau gag                                          23

<210> SEQ ID NO 388
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
uagaugagaa ggcacagacg ggg                                          23

<210> SEQ ID NO 389
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 389
agaaccaaca agaagaugag gca                                              23

<210> SEQ ID NO 390
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
uaagauaggg gcauuuggug guc                                              23

<210> SEQ ID NO 391
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
aguauggauc ggcagaggag cca                                              23

<210> SEQ ID NO 392
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
auugugagga uuuuugucaa caa                                              23

<210> SEQ ID NO 393
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
uugugaggau uuuugucaac aag                                              23

<210> SEQ ID NO 394
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
uaaaauugag agaaguccac cac                                              23

<210> SEQ ID NO 395
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
```
ucgaauccac acuccaaaag aca                                            23

<210> SEQ ID NO 396
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
ucgaauccac acuccaaaag aca                                            23

<210> SEQ ID NO 397
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
uagcuuggag gcuugaacaa gac                                            23

<210> SEQ ID NO 398
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
uccgcaguau ggaucggcag agg                                            23

<210> SEQ ID NO 399
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
uaccacauca uccauauaac uga                                            23

<210> SEQ ID NO 400
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
uauaaaacgc cgcagacaca ucc                                            23

<210> SEQ ID NO 401
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
uaugagaagg cacagacggg gag        23

<210> SEQ ID NO 402
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
augaacaaga gaugauuagc gag        23

<210> SEQ ID NO 403
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
gaaguccacc acgagucuag acu        23

<210> SEQ ID NO 404
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
uuccgcagua uggaucggca gag        23

<210> SEQ ID NO 405
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
uagaagaacc aacaagaaga uga        23

<210> SEQ ID NO 406
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
uccccuagaa aauugagaga agu        23

<210> SEQ ID NO 407
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
ugagagaagu ccaccacgag ucu        23

<210> SEQ ID NO 408
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
cagaggugaa gcgaagugca cac                                          23

<210> SEQ ID NO 409
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
auuuuuguca acaagaaaaa ccc                                          23

<210> SEQ ID NO 410
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
uaacaagaga ugauuaggca gag                                          23

<210> SEQ ID NO 411
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
uacucugugg uauugugagg auu                                          23

<210> SEQ ID NO 412
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
uugaggauuu uugucaacaa gaa                                          23

<210> SEQ ID NO 413
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
aaauugagag aaguccacca cga                                          23

```
<210> SEQ ID NO 414
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
aggcagaggu gaaaaaguug cau                                                  23

<210> SEQ ID NO 415
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415
uaugcuguag cucuuguucc caa                                                  23

<210> SEQ ID NO 416
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
uaagaaccaa caagaagaug agg                                                  23

<210> SEQ ID NO 417
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
uaagaugagg cauagcagca gga                                                  23

<210> SEQ ID NO 418
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
aacgccgcag acacauccaa cga                                                  23

<210> SEQ ID NO 419
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
uaggcauagc agcaggauga aga                                                  23
```

```
<210> SEQ ID NO 420
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
uaggauuuuu gucaacaaga aaa                                           23

<210> SEQ ID NO 421
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
uaaaacgccg cagacacauc cag                                           23

<210> SEQ ID NO 422
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
uaauaccaca ucauccauau aac                                           23

<210> SEQ ID NO 423
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
gaggcauagc agcaggauga aga                                           23

<210> SEQ ID NO 424
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
uagaggugaa gcgaagugca cac                                           23

<210> SEQ ID NO 425
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
uauugugagg auuuuuguca aca                                           23

<210> SEQ ID NO 426
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
uuugcgucag caaacacuug gca                                              23

<210> SEQ ID NO 427
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
uuugcgucag caaacacuug gca                                              23

<210> SEQ ID NO 428
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
uaaggcacag cuuggaggcu uga                                              23

<210> SEQ ID NO 429
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
uauagcagca ggaugaagag gaa                                              23

<210> SEQ ID NO 430
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
aagaugaggc auagcagcag gau                                              23

<210> SEQ ID NO 431
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
agaagaacca acaagaagau gag                                              23

<210> SEQ ID NO 432
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
uagaugagaa ggcacagacg ggg                                              23

<210> SEQ ID NO 433
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
agaaccaaca agaagaugag gca                                              23

<210> SEQ ID NO 434
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
uaagauaggg gcauuuggug guc                                              23

<210> SEQ ID NO 435
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
aguauggauc ggcagaggag cca                                              23

<210> SEQ ID NO 436
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
ugagagaagu ccaccacgag ucu                                              23

<210> SEQ ID NO 437
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 437
ugagagaagt ccaccacgag ucu                                              23
```

```
<210> SEQ ID NO 438
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 438
ugagagaagu ccaccacgag ucu                                            23

<210> SEQ ID NO 439
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 439
ugagagaagt ccaccacgag ucu                                            23

<210> SEQ ID NO 440
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
ugagagaagu ccaccacgag ucu                                            23

<210> SEQ ID NO 441
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
ugagagaagu ccaccacgag ucu                                            23

<210> SEQ ID NO 442
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 442
ugagagaagu ccaccacgag ucu                                            23

<210> SEQ ID NO 443
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 443
ugagagaagt ccaccacgag ucu                                              23

<210> SEQ ID NO 444
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 444
ugagagaagt ccaccacgag ucu                                              23

<210> SEQ ID NO 445
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 445
ugagagaagt ccaccacgag ucu                                              23

<210> SEQ ID NO 446
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
ugagagaagu ccaccacgag ucu                                              23

<210> SEQ ID NO 447
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
ugagagaagu ccaccacgag ucu                                              23

<210> SEQ ID NO 448
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
ugagagaagu ccaccacgag ucu                                              23

<210> SEQ ID NO 449
<211> LENGTH: 23
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 449
ugagagaagt ccaccacgag ucu                                           23

<210> SEQ ID NO 450
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 450
ugagagaagt ccaccacgag ucu                                           23

<210> SEQ ID NO 451
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 451
ugagagaagt ccaccacgag ucu                                           23

<210> SEQ ID NO 452
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
ugagagaagu ccaccacgag ucu                                           23

<210> SEQ ID NO 453
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
ugagagaagu ccaccacgag ucu                                           23

<210> SEQ ID NO 454
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 454
ugagagaagu ccaccacgag ucu                                          23

<210> SEQ ID NO 455
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 455
ugagagaagt ccaccacgag ucu                                          23

<210> SEQ ID NO 456
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 456
ugagagaagt ccaccacgag ucu                                          23

<210> SEQ ID NO 457
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 457
ugagagaagt ccaccacgag ucu                                          23

<210> SEQ ID NO 458
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
ugagagaagu ccaccacgag ucu                                          23

<210> SEQ ID NO 459
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
ugagagaagu ccaccacgag ucu                                          23
```

```
<210> SEQ ID NO 460
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 460
ugagagaagt ccaccacgag ucu                                              23

<210> SEQ ID NO 461
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
ugagagaagu ccaccacgag ucu                                              23

<210> SEQ ID NO 462
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 462
ugagagaagt ccaccacgag ucu                                              23

<210> SEQ ID NO 463
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
ugagagaagu ccaccacgag ucu                                              23

<210> SEQ ID NO 464
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
ugagagaagu ccaccacgag ucu                                              23

<210> SEQ ID NO 465
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Description of Combined DNA/RNA Molecule:
      Synthetic oligonucleotide

<400> SEQUENCE: 465
ugagagaagt ccaccacgag ucu                                              23

<210> SEQ ID NO 466
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 466
ugagagaagt ccaccacgag ucu                                              23

<210> SEQ ID NO 467
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 467
ugagagaagu ccaccacgag ucu                                              23

<210> SEQ ID NO 468
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 468
ugagagaagt ccaccacgag ucu                                              23

<210> SEQ ID NO 469
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 469
ugagagaagu ccaccacgag ucu                                              23

<210> SEQ ID NO 470
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 470
ugagagaagt ccaccacgag ucu              23

<210> SEQ ID NO 471
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 471
ugagagaagt ccaccacgag ucu              23

<210> SEQ ID NO 472
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 472
ugagagaagt ccaccacgag ucu              23

<210> SEQ ID NO 473
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473
ugagagaagu ccaccacgag ucu              23

<210> SEQ ID NO 474
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 474
ugagagaagu ccaccacgag ucu              23

<210> SEQ ID NO 475
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 475
ugagagaagt ccaccacgag ucu              23

<210> SEQ ID NO 476
<211> LENGTH: 23

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 476
ugagagaagt ccaccacgag ucu                                            23

<210> SEQ ID NO 477
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 477
ugagagaagt ccaccacgag ucu                                            23

<210> SEQ ID NO 478
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 478
ugagagaagu ccaccacgag ucu                                            23

<210> SEQ ID NO 479
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 479
aguuauaugg augauguggu a                                              21

<210> SEQ ID NO 480
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 480
ggaugugucu gcggcguuuu a                                              21

<210> SEQ ID NO 481
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
```

<223> OTHER INFORMATION: 2-hydroxymethyl-tetrahydrofurane-5-phosphate

<400> SEQUENCE: 481
nacucguggu ggacuucucu ca                                              22

<210> SEQ ID NO 482
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
acucguggug gacuucucuc a                                               21

<210> SEQ ID NO 483
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 483
acucguggug gacuuctcuc a                                               21

<210> SEQ ID NO 484
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
acucguggug gacuucucuc a                                               21

<210> SEQ ID NO 485
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 485
ucguggugga cuucucuca                                                  19

<210> SEQ ID NO 486
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 486
acucguggug gacuucucuc a                                               21

<210> SEQ ID NO 487
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 487
acucguggug gacuucucuc a                                              21

<210> SEQ ID NO 488
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 488
acucguggug gacuucucuc a                                              21

<210> SEQ ID NO 489
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 489
acucguggug gacuucucuc a                                              21

<210> SEQ ID NO 490
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 490
gugguggacu ucucuca                                                   17

<210> SEQ ID NO 491
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 491
acucguggug gacuucucuc a                                              21

<210> SEQ ID NO 492
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2-hydroxymethyl-tetrahydrofurane-5-phosphate
<220> FEATURE:
<221> NAME/KEY: modified_base
<222> LOCATION: (23)..(23)
<223> OTHER INFORMATION: 2-hydroxymethyl-tetrahydrofurane-5-phosphate

<400> SEQUENCE: 492
```
nucguggugg acuucucuca uun          23

<210> SEQ ID NO 493
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 493
acucguggug gacuucucuc a          21

<210> SEQ ID NO 494
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494
acucguggug gacuucucuc a          21

<210> SEQ ID NO 495
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
acucguggug gacuucucuc a          21

<210> SEQ ID NO 496
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 496
acucguggug gacuucucuc a          21

<210> SEQ ID NO 497
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2-hydroxymethyl-tetrahydrofurane-5-phosphate
<220> FEATURE:
<221> NAME/KEY: modified_base
<222> LOCATION: (21)..(21)
<223> OTHER INFORMATION: 2-hydroxymethyl-tetrahydrofurane-5-phosphate

<400> SEQUENCE: 497
nucguggugg acuucucuca n          21

<210> SEQ ID NO 498
<211> LENGTH: 21
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 498
acucguggug gacuucucuc a                                              21

<210> SEQ ID NO 499
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 499
acucguggug gacuucucuc a                                              21

<210> SEQ ID NO 500
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 500
acucguggug gacuucucuc a                                              21

<210> SEQ ID NO 501
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 501
uauuuccuag gguacaa                                                   17

<210> SEQ ID NO 502
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 502
acucguggug gacuucucuc a                                              21

<210> SEQ ID NO 503
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2-hydroxymethyl-tetrahydrofurane-5-phosphate
<220> FEATURE:
<221> NAME/KEY: modified_base
<222> LOCATION: (21)..(21)
<223> OTHER INFORMATION: 2-hydroxymethyl-tetrahydrofurane-5-phosphate

<400> SEQUENCE: 503

```
nucguggugg acuucucuca n                                              21
```

<210> SEQ ID NO 504
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 504

```
acucguggug gacuucucuc a                                              21
```

<210> SEQ ID NO 505
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 505

```
acucguggug gacuucucuc a                                              21
```

<210> SEQ ID NO 506
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 506

```
acucguggug gacuucucuc a                                              21
```

<210> SEQ ID NO 507
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 507

```
acucguggug gacuucucuc a                                              21
```

<210> SEQ ID NO 508
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 508

```
acucguggug gacuucucuc a                                              21
```

<210> SEQ ID NO 509
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 509
acucguggug gacuucucuc a                                        21

<210> SEQ ID NO 510
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 510
acucguggug gacuucucuc a                                        21

<210> SEQ ID NO 511
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 511
acucguggug gacuucucuc a                                        21

<210> SEQ ID NO 512
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 512
acucguggug gacuucucuc a                                        21

<210> SEQ ID NO 513
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 513
acucguggug gacuucucuc a                                        21

<210> SEQ ID NO 514
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 514
acucguggug gacuucucuc a                                        21

<210> SEQ ID NO 515
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 515
acucguggug gacuucucuc a                                        21

```
<210> SEQ ID NO 516
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 516
acucguggug gacuucucuc a                                              21

<210> SEQ ID NO 517
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 517
acucguggug gacuuctcuc a                                              21

<210> SEQ ID NO 518
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 518
acucguggug gacuucucuc a                                              21

<210> SEQ ID NO 519
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 519
acucguggug gacuuctcuc a                                              21

<210> SEQ ID NO 520
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 520
acucguggug gacuucucuc a                                              21

<210> SEQ ID NO 521
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 521
acucguggug gacuucucuc a                                                    21

<210> SEQ ID NO 522
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 522
acucguggug gacuuctcuc a                                                    21

<210> SEQ ID NO 523
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 523
acucguggug gacuucucuc a                                                    21

<210> SEQ ID NO 524
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 524
acucguggug gacuuctcuc a                                                    21

<210> SEQ ID NO 525
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525
acucguggug gacuucucuc a                                                    21

<210> SEQ ID NO 526
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 526
gugguggacu ucucucaauu u                                                    21
```

<210> SEQ ID NO 527
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 527
gugguggacu ucucucaauu u                                              21

<210> SEQ ID NO 528
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 528
gugguggacu ucucucaauu u                                              21

<210> SEQ ID NO 529
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 529
uggacuucuc ucaauuu                                                   17

<210> SEQ ID NO 530
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 530
gugguggacu ucucucaauu u                                              21

<210> SEQ ID NO 531
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2-hydroxymethyl-tetrahydrofurane-5-phosphate
<220> FEATURE:
<221> NAME/KEY: modified_base
<222> LOCATION: (23)..(23)
<223> OTHER INFORMATION: 2-hydroxymethyl-tetrahydrofurane-5-phosphate

<400> SEQUENCE: 531
ngguggacuu cucucaauuu uun                                            23

<210> SEQ ID NO 532
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 532
gugguggacu ucucucaauu u                                                  21

<210> SEQ ID NO 533
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 533
gugguggacu ucucucaauu u                                                  21

<210> SEQ ID NO 534
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 534
gugguggacu ucucucaauu u                                                  21

<210> SEQ ID NO 535
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 535
gguggacuuc ucucaauuu                                                     19

<210> SEQ ID NO 536
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 536
gugguggacu ucucucaauu u                                                  21

<210> SEQ ID NO 537
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2-hydroxymethyl-tetrahydrofurane-5-phosphate
<220> FEATURE:
<221> NAME/KEY: modified_base
<222> LOCATION: (21)..(21)
<223> OTHER INFORMATION: 2-hydroxymethyl-tetrahydrofurane-5-phosphate

<400> SEQUENCE: 537
```
ngguggacuu cucucaauuu n                                             21

<210> SEQ ID NO 538
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 538
gugguggacu ucucucaauu u                                             21

<210> SEQ ID NO 539
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 539
gugguggacu ucucucaauu u                                             21

<210> SEQ ID NO 540
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 540
uggacuucuc ucaauuu                                                  17

<210> SEQ ID NO 541
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 541
gugguggacu ucucucaauu u                                             21

<210> SEQ ID NO 542
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2-hydroxymethyl-tetrahydrofurane-5-phosphate
<220> FEATURE:
<221> NAME/KEY: modified_base
<222> LOCATION: (21)..(21)
<223> OTHER INFORMATION: 2-hydroxymethyl-tetrahydrofurane-5-phosphate

<400> SEQUENCE: 542
ngguggacuu cucucaauuu n                                             21

<210> SEQ ID NO 543
<211> LENGTH: 21
<212> TYPE: RNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 543
gugguggacu ucucucaauu u                                                    21

<210> SEQ ID NO 544
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 544
gugguggacu ucucucaauu u                                                    21

<210> SEQ ID NO 545
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 545
gugguggacu ucucucaauu u                                                    21

<210> SEQ ID NO 546
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 546
gugguggacu ucucucaauu u                                                    21

<210> SEQ ID NO 547
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 547
gugguggacu ucucucaauu u                                                    21

<210> SEQ ID NO 548
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 548
gugguggacu ucucucaauu u                                                    21

<210> SEQ ID NO 549
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 549
gugguggacu ucucucaauu u                                              21

<210> SEQ ID NO 550
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 550
gugguggacu ucucucaauu u                                              21

<210> SEQ ID NO 551
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 551
gugguggacu ucucucaauu u                                              21

<210> SEQ ID NO 552
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 552
gugguggacu ucucucaauu u                                              21

<210> SEQ ID NO 553
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 553
gugguggacu ucucucaauu u                                              21

<210> SEQ ID NO 554
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 554
gugguggact tcucucaauu u                                              21

<210> SEQ ID NO 555
<211> LENGTH: 22
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2-hydroxymethyl-tetrahydrofurane-5-phosphate

<400> SEQUENCE: 555
ngugguggac uucucucaau uu                                              22

<210> SEQ ID NO 556
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 556
gugguggacu ucucucaauu u                                               21

<210> SEQ ID NO 557
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 557
gugguggacu ucucucaauu u                                               21

<210> SEQ ID NO 558
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 558
gugguggacu tcucucaauu u                                               21

<210> SEQ ID NO 559
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 559
gugguggacu ucucucaauu u                                               21

<210> SEQ ID NO 560
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 560
```
gugguggacu ucucucaauu u                                              21

<210> SEQ ID NO 561
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 561
gugguggacu ucucucaauu u                                              21

<210> SEQ ID NO 562
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 562
gugguggacu ucucucaauu u                                              21

<210> SEQ ID NO 563
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 563
gugguggacu tcucucaauu u                                              21

<210> SEQ ID NO 564
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 564
gugguggacu ucucucaauu u                                              21

<210> SEQ ID NO 565
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 565
gugguggacu ucucucaauu u                                              21

<210> SEQ ID NO 566
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 566
gugguggacu tcucucaauu u                                                   21

<210> SEQ ID NO 567
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 567
gugguggacu ucucucaauu u                                                   21

<210> SEQ ID NO 568
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 568
gguggacuuc ucucaauuu                                                      19

<210> SEQ ID NO 569
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 569
gugguggacu ucucucaauu u                                                   21

<210> SEQ ID NO 570
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 570
gugcacuucg cuucaccucu g                                                   21

<210> SEQ ID NO 571
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 571
guugacaaaa auccucacaa u                                                   21

<210> SEQ ID NO 572
<211> LENGTH: 21
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 572
uguugacaaa aauccucaca a                                              21

<210> SEQ ID NO 573
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 573
gguggacuuc ucucaauuuu a                                              21

<210> SEQ ID NO 574
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 574
ucuuuuggag uguggauucg a                                              21

<210> SEQ ID NO 575
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 575
ucuuuuggag uguggauucg a                                              21

<210> SEQ ID NO 576
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 576
acuguucaag ccuccaagcu a                                              21

<210> SEQ ID NO 577
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 577
ucugccgauc cauacugcgg a                                              21

<210> SEQ ID NO 578
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 578
augugucugc ggcguuuuau a                                              21

<210> SEQ ID NO 579
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 579
ccccgucugu gccuucucau a                                              21

<210> SEQ ID NO 580
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 580
gccuaaucau cucuuguuca u                                              21

<210> SEQ ID NO 581
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 581
ucuagacucg ugguggacuu c                                              21

<210> SEQ ID NO 582
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 582
cugccgaucc auacugcgga a                                              21

<210> SEQ ID NO 583
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 583
uuuuucuugu ugacaaaaau a                                              21

<210> SEQ ID NO 584
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 584
aucuucuugu ugguucuucu a                                           21

<210> SEQ ID NO 585
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 585
guuuuucuug uugacaaaaa u                                           21

<210> SEQ ID NO 586
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 586
cugccuaauc aucucuuguu a                                           21

<210> SEQ ID NO 587
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 587
uccucacaau accacagagu a                                           21

<210> SEQ ID NO 588
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 588
cuuguugaca aaauccuca a                                            21

<210> SEQ ID NO 589
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 589
gcaacuuuuu caccucugcc u                                           21

<210> SEQ ID NO 590
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 590
gggaacaaga gcuacagcau a                                              21

<210> SEQ ID NO 591
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 591
cgugguggac uucucucaau u                                              21

<210> SEQ ID NO 592
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 592
cugcugcuau gccucaucuu a                                              21

<210> SEQ ID NO 593
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 593
guuggaugug ucugcggcgu u                                              21

<210> SEQ ID NO 594
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 594
uucauccugc ugcuaugccu a                                              21

<210> SEQ ID NO 595
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 595
uucuuguuga caaaaauccu a                                              21

<210> SEQ ID NO 596
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 596
```

-continued uauauggaug augugguauu a                                          21

<210> SEQ ID NO 597
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 597
uucauccugc ugcuaugccu c                                          21

<210> SEQ ID NO 598
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 598
gugcacuucg cuucaccucu a                                          21

<210> SEQ ID NO 599
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 599
uugacaaaaa uccucacaau a                                          21

<210> SEQ ID NO 600
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 600
aagccuccaa gcugugccuu a                                          21

<210> SEQ ID NO 601
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 601
ccucuucauc cugcugcuau a                                          21

<210> SEQ ID NO 602
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 602 ccgcugcua ugccucaucu u         21

<210> SEQ ID NO 603
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 603
caucuucuug uugguucuuc u         21

<210> SEQ ID NO 604
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 604
ccgucugugc cuucucaucu a         21

<210> SEQ ID NO 605
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 605
ccucaucuuc uuguugguuc u         21

<210> SEQ ID NO 606
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 606
ccaccaaaug ccccuaucuu a         21

<210> SEQ ID NO 607
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 607
gcuccucugc cgauccauac u         21

<210> SEQ ID NO 608
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 608
guugacaaaa auccucacaa u         21

<210> SEQ ID NO 609
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 609
uguugacaaa aauccucaca a                                            21

<210> SEQ ID NO 610
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 610
gguggacuuc ucucaauuuu a                                            21

<210> SEQ ID NO 611
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 611
ucuuuuggag uguggauucg a                                            21

<210> SEQ ID NO 612
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 612
acuguucaag ccuccaagcu a                                            21

<210> SEQ ID NO 613
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 613
ucugccgauc cauacugcgg a                                            21

<210> SEQ ID NO 614
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 614
aguuauaugg augauguggu a                                            21

<210> SEQ ID NO 615
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 615
augugucugc ggcguuuuau a                                             21

<210> SEQ ID NO 616
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 616
ccccgucugu gccuucucau a                                             21

<210> SEQ ID NO 617
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 617
gccuaaucau cucuuguuca u                                             21

<210> SEQ ID NO 618
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 618
ucuagacucg ugguggacuu c                                             21

<210> SEQ ID NO 619
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 619
cugccgaucc auacugcgga a                                             21

<210> SEQ ID NO 620
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 620
aucuucuugu ugguucuucu a                                             21

```
<210> SEQ ID NO 621
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 621
uucucucaau uuucuagggg a                                              21

<210> SEQ ID NO 622
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 622
acucguggug gacuucucuc a                                              21

<210> SEQ ID NO 623
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 623
gugcacuucg cuucaccucu g                                              21

<210> SEQ ID NO 624
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 624
guuuuucuug uugacaaaaa u                                              21

<210> SEQ ID NO 625
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 625
cugccuaauc aucucuuguu a                                              21

<210> SEQ ID NO 626
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 626
uccucacaau accacagagu a                                              21

<210> SEQ ID NO 627
```

-continued

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 627
cuuguugaca aaaauccuca a                                              21

<210> SEQ ID NO 628
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 628
gugguggacu ucucucaauu u                                              21

<210> SEQ ID NO 629
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 629
gcaacuuuuu caccucugcc u                                              21

<210> SEQ ID NO 630
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 630
gggaacaaga gcuacagcau a                                              21

<210> SEQ ID NO 631
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 631
ucaucuucuu guugguucuu a                                              21

<210> SEQ ID NO 632
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 632
cugcugcuau gccucaucuu a                                              21

<210> SEQ ID NO 633
<211> LENGTH: 21
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 633
guuggaugug ucugcggcgu u                                              21

<210> SEQ ID NO 634
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 634
uucauccugc ugcuaugccu a                                              21

<210> SEQ ID NO 635
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 635
uucuuguuga caaaaauccu a                                              21

<210> SEQ ID NO 636
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 636
ggaugugucu gcggcguuuu a                                              21

<210> SEQ ID NO 637
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 637
uauauggaug augugguauu a                                              21

<210> SEQ ID NO 638
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 638
uucauccugc ugcuaugccu c                                              21

<210> SEQ ID NO 639
<211> LENGTH: 21
<212> TYPE: RNA

<213> ORGANISM: Artificial Sequence
<220> FEATURE:
<223> OTHER INFORMATION: Description of Artificial Sequence: Synthetic oligonucleotide

<400> SEQUENCE: 639
gugcacuucg cuucaccucu a                                    21

<210> SEQ ID NO 640
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 640
uugacaaaaa uccucacaau a                                    21

<210> SEQ ID NO 641
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 641
ccaaguguuu gcugacgcaa a                                    21

<210> SEQ ID NO 642
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 642
ccaaguguuu gcugacgcaa a                                    21

<210> SEQ ID NO 643
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 643
aagccuccaa gcugugccuu a                                    21

<210> SEQ ID NO 644
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 644
ccucuucauc cugcugcuau a                                    21

<210> SEQ ID NO 645
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 645
ccugcugcua ugccucaucu u                                              21

<210> SEQ ID NO 646
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 646
caucuucuug uugguucuuc u                                              21

<210> SEQ ID NO 647
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 647
ccgucugugc cuucucaucu a                                              21

<210> SEQ ID NO 648
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 648
ccucaucuuc uuguugguuc u                                              21

<210> SEQ ID NO 649
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 649
ccaccaaaug ccccuaucuu a                                              21

<210> SEQ ID NO 650
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 650
gcuccucugc cgauccauac u                                              21

<210> SEQ ID NO 651
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 651
acucguggug tacuucucuc a                                           21

<210> SEQ ID NO 652
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 652
acucguggug gacuucucuc a                                           21

<210> SEQ ID NO 653
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 653
acucguggug gacuucucuc a                                           21

<210> SEQ ID NO 654
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 654
acucguggug gacuucacuc a                                           21

<210> SEQ ID NO 655
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 655
acucguggtg tacuucacuc a                                           21

<210> SEQ ID NO 656
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 656
acucguggug tacuucacuc a                                              21

<210> SEQ ID NO 657
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 657
acucguggug gacuucucuc a                                              21

<210> SEQ ID NO 658
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 658
acucguggug gacuucucuc a                                              21

<210> SEQ ID NO 659
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 659
acucguggtg gacuuctcuc a                                              21

<210> SEQ ID NO 660
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 660
acucguggug gacuucucuc a                                              21

<210> SEQ ID NO 661
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 661
acucguggug gacuucucuc a                                              21
```

<210> SEQ ID NO 662
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 662
acucguggtg tacuucacuc a                                              21

<210> SEQ ID NO 663
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 663
acucguggug gacuucucuc a                                              21

<210> SEQ ID NO 664
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 664
acucguggug gacuucucuc a                                              21

<210> SEQ ID NO 665
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 665
acucguggtg gacuucacuc a                                              21

<210> SEQ ID NO 666
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 666
acucguggug gacuucacuc a                                              21

<210> SEQ ID NO 667
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 667
acucguggug gacuucucuc a                                              21

<210> SEQ ID NO 668
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 668
acucguggtg gacuuctcuc a                                              21

<210> SEQ ID NO 669
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 669
acucguggug gacuucucuc a                                              21

<210> SEQ ID NO 670
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 670
acucguggug gacuuctcuc a                                              21

<210> SEQ ID NO 671
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 671
acucguggtg tacuucacuc a                                              21

<210> SEQ ID NO 672
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 672
acucguggtg gacuuctcuc a                                              21

<210> SEQ ID NO 673
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(17)
<223> OTHER INFORMATION: 2-hydroxymethyl-tetrahydrofurane-4-methoxy-3-
      phosphate (abasic 2'-OMe furanose)

<400> SEQUENCE: 673
acucguggug gacuucncuc a                                              21

<210> SEQ ID NO 674
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 674
acucguggug gacuuctcuc a                                              21

<210> SEQ ID NO 675
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 675
acucguggug gacuuctcuc a                                              21

<210> SEQ ID NO 676
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 676
acucguggug gacuucucuc a                                              21

<210> SEQ ID NO 677
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 677
acucguggtg gacuucacuc a     21

<210> SEQ ID NO 678
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 678
acucguggug gacuucacuc a     21

<210> SEQ ID NO 679
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 679
acucguggtg gacuucacuc a     21

<210> SEQ ID NO 680
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 680
acucguggug gacuucucuc a     21

<210> SEQ ID NO 681
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<221> NAME/KEY: modified_base
<222> LOCATION: (1)..(1)
<223> OTHER INFORMATION: 2-hydroxymethyl-tetrahydrofurane-4-methoxy-3-phosphate (abasic 2'-OMe furanose)

<400> SEQUENCE: 681
nacucguggu ggacuuctcu ca        22

<210> SEQ ID NO 682
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 682
acucguggug gacuucacuc a        21

<210> SEQ ID NO 683
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 683
acucguggtg tacuucacuc a        21

<210> SEQ ID NO 684
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 684
acucguggug gacuucccuc a        21

<210> SEQ ID NO 685
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 685
acucguggug gacuucucuc a        21

<210> SEQ ID NO 686
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 686
acucguggug gacuucucuc a        21

<210> SEQ ID NO 687
<211> LENGTH: 22

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2-hydroxymethyl-tetrahydrofurane-4-methoxy-3-
      phosphate (abasic 2'-OMe furanose)

<400> SEQUENCE: 687
nacucguggu ggacuuctcu ca                                              22

<210> SEQ ID NO 688
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 688
acucguggtg gacuuctcuc a                                               21

<210> SEQ ID NO 689
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 689
acucguggug gacuucgcuc a                                               21

<210> SEQ ID NO 690
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 690
acucguggug gacuucucuc a                                               21

<210> SEQ ID NO 691
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 691
acucguggug gacuucucuc a                                               21

<210> SEQ ID NO 692
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 692
acucguggug gacuucucuc a                                              21

<210> SEQ ID NO 693
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 693
acucguggtg gacuucacuc a                                              21

<210> SEQ ID NO 694
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 694
uaccacauca uccauauaac uga                                            23

<210> SEQ ID NO 695
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 695
uaaaacgccg cagacacauc cag                                            23

<210> SEQ ID NO 696
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 696
ugagagaagu ccaccacgag ucu                                            23

<210> SEQ ID NO 697
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 697
```
ugagagaagu ccaccacgag ucu                                              23

<210> SEQ ID NO 698
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 698
ugagagaagu ccaccacgag ucu                                              23

<210> SEQ ID NO 699
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 699
ugagagaagu ccaccacgag ucu                                              23

<210> SEQ ID NO 700
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 700
ugagagaagu ccaccacgag u                                                21

<210> SEQ ID NO 701
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 701
ugagagaagu ccaccacgag ucu                                              23

<210> SEQ ID NO 702
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 702
ugagagaagu ccaccacgag ucu                                              23

<210> SEQ ID NO 703
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 703
ugagagaagu ccaccacgag ucu                                              23

```
<210> SEQ ID NO 704
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 704
ugagagaagu ccaccacgag ucu                                               23

<210> SEQ ID NO 705
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 705
ugagagaagu ccaccacga                                                    19

<210> SEQ ID NO 706
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 706
ugagagaagu ccaccacgag ucu                                               23

<210> SEQ ID NO 707
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 707
ugagagaagu ccaccacgau u                                                 21

<210> SEQ ID NO 708
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 708
ugagagaagu ccaccacgag ucu                                               23

<210> SEQ ID NO 709
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 709
ugagagaagu ccaccacgag ucu                                               23
```

```
<210> SEQ ID NO 710
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 710
ugagagaagu ccaccacgag ucu                                              23

<210> SEQ ID NO 711
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 711
ugagagaagu ccaccacgag ucu                                              23

<210> SEQ ID NO 712
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 712
ugagagaagu ccaccacgau u                                                21

<210> SEQ ID NO 713
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 713
ugagagaagu ccaccacgag ucu                                              23

<210> SEQ ID NO 714
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 714
ugagagaagu ccaccacgag ucu                                              23

<210> SEQ ID NO 715
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 715
ugagagaagu ccaccacgag ucu                                              23
```

```
<210> SEQ ID NO 716
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 716
ugagagaagu ccaccacga                                                    19

<210> SEQ ID NO 717
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 717
ugagagaagu ccaccacgag ucu                                               23

<210> SEQ ID NO 718
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 718
ugagagaagu ccaccacgau u                                                 21

<210> SEQ ID NO 719
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 719
ugagagaagu ccaccacgag ucu                                               23

<210> SEQ ID NO 720
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 720
ugagagaagu ccaccacgag ucu                                               23

<210> SEQ ID NO 721
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 721
ugagagaagu ccaccacgag ucu                                               23

<210> SEQ ID NO 722
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 722
ugagagaagu ccaccacgag ucu                                              23

<210> SEQ ID NO 723
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 723
ugagagaagu ccaccacgag ucu                                              23

<210> SEQ ID NO 724
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 724
ugagagaagu ccaccacgag ucu                                              23

<210> SEQ ID NO 725
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 725
ugagagaagu ccaccacgag ucu                                              23

<210> SEQ ID NO 726
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 726
ugagagaagu ccaccacgag ucu                                              23

<210> SEQ ID NO 727
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 727
ugagagaagu ccaccacgag ucu                                              23

<210> SEQ ID NO 728
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 728
ugagagaagu ccaccacgag ucu                                           23

<210> SEQ ID NO 729
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 729
ugagagaagu ccaccacgag ucu                                           23

<210> SEQ ID NO 730
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 730
ugagagaagu ccaccacgag ucu                                           23

<210> SEQ ID NO 731
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 731
ugagagaagt ccaccacgag ucu                                           23

<210> SEQ ID NO 732
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 732
ugagagaagu ccaccacgag ucu                                           23

<210> SEQ ID NO 733
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 733
ugagagaagu ccaccacgag ucu                                           23
```

-continued

```
<210> SEQ ID NO 734
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 734
ugagagaagu ccaccacgag ucu                                               23

<210> SEQ ID NO 735
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 735
ugagagaagu ccaccacgag ucu                                               23

<210> SEQ ID NO 736
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 736
ugagagaagu ccaccacgag ucu                                               23

<210> SEQ ID NO 737
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 737
ugagagaagu ccaccacgag ucu                                               23

<210> SEQ ID NO 738
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 738
ugagagaagu ccaccacgag ucu                                               23

<210> SEQ ID NO 739
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

```
<400> SEQUENCE: 739
ugagagaagu ccaccacgag ucu                                          23

<210> SEQ ID NO 740
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 740
ugagagaagu ccaccacgag ucu                                          23

<210> SEQ ID NO 741
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 741
aaauugagag aaguccacca cga                                          23

<210> SEQ ID NO 742
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 742
aaauugagag aaguccacca cga                                          23

<210> SEQ ID NO 743
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 743
aaauugagag aaguccacca cga                                          23

<210> SEQ ID NO 744
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 744
aaauugagag aaguccacc                                               19

<210> SEQ ID NO 745
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 745
```
aaauugagag aaguccacca cga                                           23

<210> SEQ ID NO 746
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 746
aaauugagag aaguccaccu u                                             21

<210> SEQ ID NO 747
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 747
aaauugagag aaguccacca cga                                           23

<210> SEQ ID NO 748
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 748
aaauugagag aaguccacca cga                                           23

<210> SEQ ID NO 749
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 749
aaauugagag aaguccacca cga                                           23

<210> SEQ ID NO 750
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 750
aaauugagag aaguccacca c                                             21

<210> SEQ ID NO 751
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 751
aaauugagag aaguccacca cga                                      23

<210> SEQ ID NO 752
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 752
aaauugagag aaguccaccu u                                        21

<210> SEQ ID NO 753
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 753
aaauugagag aaguccacca cga                                      23

<210> SEQ ID NO 754
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 754
aaauugagag aaguccacca cga                                      23

<210> SEQ ID NO 755
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 755
aaauugagag aaguccacc                                           19

<210> SEQ ID NO 756
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 756
aaauugagag aaguccacca cga                                      23

<210> SEQ ID NO 757
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 757
aaauugagag aaguccaccu u                                        21

```
<210> SEQ ID NO 758
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 758
aaauugagag aaguccacca cga                                              23

<210> SEQ ID NO 759
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 759
aaauugagag aaguccacca cga                                              23

<210> SEQ ID NO 760
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 760
aaauugagag aaguccacca cga                                              23

<210> SEQ ID NO 761
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 761
aaauugagag aaguccacca cga                                              23

<210> SEQ ID NO 762
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 762
aaauugagag aaguccacca cga                                              23

<210> SEQ ID NO 763
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 763
aaauugagag aaguccacca cga                                              23
```

<210> SEQ ID NO 764
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 764
aaauugagag aaguccacca cga                                           23

<210> SEQ ID NO 765
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 765
aaauugagag aaguccacca cga                                           23

<210> SEQ ID NO 766
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 766
aaauugagag aaguccacca cga                                           23

<210> SEQ ID NO 767
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 767
aaauugagag aaguccacca cga                                           23

<210> SEQ ID NO 768
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 768
aaauugagag aaguccacca cga                                           23

<210> SEQ ID NO 769
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 769
aaauugagag aagtccacca cga                                                 23

<210> SEQ ID NO 770
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 770
aaauugagag aaguccacca cga                                                 23

<210> SEQ ID NO 771
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 771
aaauugagag aaguccacca cga                                                 23

<210> SEQ ID NO 772
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 772
aaauugagag aaguccacca cga                                                 23

<210> SEQ ID NO 773
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 773
aaauugagag aagtccacca cga                                                 23

<210> SEQ ID NO 774
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 774
aaauugagag aaguccacca cga                                                 23

<210> SEQ ID NO 775
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 775
aaauugagag aaguccacca cga                                              23

<210> SEQ ID NO 776
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 776
aaauugagag aaguccacca cga                                              23

<210> SEQ ID NO 777
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 777
aaauugagag aaguccacca cga                                              23

<210> SEQ ID NO 778
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 778
aaauugagag aagtccacca cga                                              23

<210> SEQ ID NO 779
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 779
aaauugagag aaguccacca cga                                              23

<210> SEQ ID NO 780
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 780
aaauugagag aaguccacca cga                                              23

<210> SEQ ID NO 781
<211> LENGTH: 23
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 781
aaauugagag aaguccacca cga                                              23

<210> SEQ ID NO 782
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 782
aaauugagag aaguccacca cga                                              23

<210> SEQ ID NO 783
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 783
aaauugagag aaguccacca c                                                21

<210> SEQ ID NO 784
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 784
aaauugagag aaguccacca cga                                              23

<210> SEQ ID NO 785
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 785
cagaggugaa gcgaagugca cac                                              23

<210> SEQ ID NO 786
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 786
auugugagga uuuuugucaa caa                                              23

<210> SEQ ID NO 787
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 787
uugugaggau uuuugucaac aag            23

<210> SEQ ID NO 788
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 788
uaaaauugag agaaguccac cac            23

<210> SEQ ID NO 789
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 789
ucgaauccac acuccaaaag aca            23

<210> SEQ ID NO 790
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 790
ucgaauccac acuccaaaag aca            23

<210> SEQ ID NO 791
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 791
uagcuuggag gcuugaacaa gac            23

<210> SEQ ID NO 792
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 792
uccgcaguau ggaucggcag agg            23

<210> SEQ ID NO 793
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 793
uauaaaacgc cgcagacaca ucc                                          23

<210> SEQ ID NO 794
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 794
uaugagaagg cacagacggg gag                                          23

<210> SEQ ID NO 795
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 795
augaacaaga gaugauuagc gag                                          23

<210> SEQ ID NO 796
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 796
gaaguccacc acgagucuag acu                                          23

<210> SEQ ID NO 797
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 797
uuccgcagua uggaucggca gag                                          23

<210> SEQ ID NO 798
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 798
uauuuuuguc aacaagaaaa acc                                          23

<210> SEQ ID NO 799
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 799
```

```
uagaagaacc aacaagaaga uga                                          23

<210> SEQ ID NO 800
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 800
auuuuuguca acaagaaaaa ccc                                          23

<210> SEQ ID NO 801
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 801
uaacaagaga ugauuaggca gag                                          23

<210> SEQ ID NO 802
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 802
uacucugugg uauugugagg auu                                          23

<210> SEQ ID NO 803
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 803
uugaggauuu uugucaacaa gaa                                          23

<210> SEQ ID NO 804
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 804
aggcagaggu gaaaaaguug cau                                          23

<210> SEQ ID NO 805
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 805
```
uaugcuguag cucuuguucc caa    23

<210> SEQ ID NO 806
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 806
aauugagaga aguccaccag cag    23

<210> SEQ ID NO 807
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 807
uaagaugagg cauagcagca gga    23

<210> SEQ ID NO 808
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 808
aacgccgcag acacauccaa cga    23

<210> SEQ ID NO 809
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 809
uaggcauagc agcaggauga aga    23

<210> SEQ ID NO 810
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 810
uaggauuuuu gucaacaaga aaa    23

<210> SEQ ID NO 811
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 811
uaauaccaca ucauccauau aac    23

<210> SEQ ID NO 812
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 812
gaggcauagc agcaggauga aga                                              23

<210> SEQ ID NO 813
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 813
uagaggugaa gcgaagugca cac                                              23

<210> SEQ ID NO 814
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 814
uauugugagg auuuuuguca aca                                              23

<210> SEQ ID NO 815
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 815
uaaggcacag cuuggaggcu uga                                              23

<210> SEQ ID NO 816
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 816
uauagcagca ggaugaagag gaa                                              23

<210> SEQ ID NO 817
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 817
aagaugaggc auagcagcag gau                                              23

-continued

<210> SEQ ID NO 818
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 818
agaagaacca acaagaagau gag                                           23

<210> SEQ ID NO 819
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 819
uagaugagaa ggcacagacg ggg                                           23

<210> SEQ ID NO 820
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 820
agaaccaaca agaagaugag gca                                           23

<210> SEQ ID NO 821
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 821
uaagauaggg gcauuuggug guc                                           23

<210> SEQ ID NO 822
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 822
aguauggauc ggcagaggag cca                                           23

<210> SEQ ID NO 823
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 823
auugugagga uuuuugucaa caa                                           23

```
<210> SEQ ID NO 824
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 824
uugugaggau uuuugucaac aag                                               23

<210> SEQ ID NO 825
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 825
uaaaauugag agaaguccac cac                                               23

<210> SEQ ID NO 826
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 826
ucgaauccac acuccaaaag aca                                               23

<210> SEQ ID NO 827
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 827
uagcuuggag gcuugaacaa gac                                               23

<210> SEQ ID NO 828
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 828
uccgcaguau ggaucggcag agg                                               23

<210> SEQ ID NO 829
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 829
uaccacauca uccauauaac uga                                               23

<210> SEQ ID NO 830
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 830
uauaaaacgc cgcagacaca ucc                                            23

<210> SEQ ID NO 831
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 831
uaugagaagg cacagacggg gag                                            23

<210> SEQ ID NO 832
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 832
augaacaaga gaugauuagc gag                                            23

<210> SEQ ID NO 833
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 833
gaaguccacc acgagucuag acu                                            23

<210> SEQ ID NO 834
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 834
uuccgcagua uggaucggca gag                                            23

<210> SEQ ID NO 835
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 835
uagaagaacc aacaagaaga uga                                            23

<210> SEQ ID NO 836
<211> LENGTH: 23
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 836
uccccuagaa aaugagaga agu                                              23

<210> SEQ ID NO 837
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 837
ugagagaagu ccaccacgag ucu                                             23

<210> SEQ ID NO 838
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 838
cagaggugaa gcgaagugca cac                                             23

<210> SEQ ID NO 839
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 839
auuuuuguca acaagaaaaa ccc                                             23

<210> SEQ ID NO 840
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 840
uaacaagaga ugauuaggca gag                                             23

<210> SEQ ID NO 841
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 841
uacucugugg uauugugagg auu                                             23

<210> SEQ ID NO 842
<211> LENGTH: 23
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 842
uugaggauuu uugucaacaa gaa                                              23

<210> SEQ ID NO 843
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 843
aaauugagag aaguccacca cga                                              23

<210> SEQ ID NO 844
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 844
aggcagaggu gaaaaaguug cau                                              23

<210> SEQ ID NO 845
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 845
uaugcuguag cucuuguucc caa                                              23

<210> SEQ ID NO 846
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 846
uaagaaccaa caagaagaug agg                                              23

<210> SEQ ID NO 847
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 847
uaagaugagg cauagcagca gga                                              23

<210> SEQ ID NO 848
<211> LENGTH: 23
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 848
aacgccgcag acacauccaa cga                                              23

<210> SEQ ID NO 849
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 849
uaggcauagc agcaggauga aga                                              23

<210> SEQ ID NO 850
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 850
uaggauuuuu gucaacaaga aaa                                              23

<210> SEQ ID NO 851
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 851
uaaaacgccg cagacacauc cag                                              23

<210> SEQ ID NO 852
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 852
uaauaccaca ucauccauau aac                                              23

<210> SEQ ID NO 853
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 853
gaggcauagc agcaggauga aga                                              23

<210> SEQ ID NO 854
<211> LENGTH: 23
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 854
uagaggugaa gcgaagugca cac                                         23

<210> SEQ ID NO 855
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 855
uauugugagg auuuuuguca aca                                         23

<210> SEQ ID NO 856
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 856
uuugcgucag caaacacuug gca                                         23

<210> SEQ ID NO 857
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 857
uuugcgucag caaacacuug gca                                         23

<210> SEQ ID NO 858
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 858
uaaggcacag cuuggaggcu uga                                         23

<210> SEQ ID NO 859
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 859
uauagcagca ggaugaagag gaa                                         23

<210> SEQ ID NO 860
<211> LENGTH: 23
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 860
aagaugaggc auagcagcag gau                                              23

<210> SEQ ID NO 861
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 861
agaagaacca acaagaagau gag                                              23

<210> SEQ ID NO 862
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 862
uagaugagaa ggcacagacg ggg                                              23

<210> SEQ ID NO 863
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 863
agaaccaaca agaagaugag gca                                              23

<210> SEQ ID NO 864
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 864
uaagauaggg gcauuuggug guc                                              23

<210> SEQ ID NO 865
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 865
aguauggauc ggcagaggag cca                                              23

<210> SEQ ID NO 866
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 866
ugagagaagu ccaccacgag ucu                                              23

<210> SEQ ID NO 867
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 867
ugagagaagt ccaccacgag ucu                                              23

<210> SEQ ID NO 868
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 868
ugagagaagu ccaccacgag ucu                                              23

<210> SEQ ID NO 869
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 869
ugagagaagt ccaccacgag ucu                                              23

<210> SEQ ID NO 870
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 870
ugagagaagu ccaccacgag ucu                                              23

<210> SEQ ID NO 871
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 871
```
ugagagaagu ccaccacgag ucu                                              23

<210> SEQ ID NO 872
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 872
ugagagaagu ccaccacgag ucu                                              23

<210> SEQ ID NO 873
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 873
ugagagaagt ccaccacgag ucu                                              23

<210> SEQ ID NO 874
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 874
ugagagaagt ccaccacgag ucu                                              23

<210> SEQ ID NO 875
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 875
ugagagaagt ccaccacgag ucu                                              23

<210> SEQ ID NO 876
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 876
ugagagaagu ccaccacgag ucu                                              23

<210> SEQ ID NO 877
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 877
ugagagaagu ccaccacgag ucu                                              23

<210> SEQ ID NO 878
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 878
ugagagaagu ccaccacgag ucu                                              23

<210> SEQ ID NO 879
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 879
ugagagaagt ccaccacgag ucu                                              23

<210> SEQ ID NO 880
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 880
ugagagaagt ccaccacgag ucu                                              23

<210> SEQ ID NO 881
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 881
ugagagaagt ccaccacgag ucu                                              23

```
<210> SEQ ID NO 882
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 882
ugagagaagu ccaccacgag ucu                                              23

<210> SEQ ID NO 883
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 883
ugagagaagu ccaccacgag ucu                                              23

<210> SEQ ID NO 884
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 884
ugagagaagu ccaccacgag ucu                                              23

<210> SEQ ID NO 885
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 885
ugagagaagt ccaccacgag ucu                                              23

<210> SEQ ID NO 886
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 886
ugagagaagt ccaccacgag ucu                                              23

<210> SEQ ID NO 887
<211> LENGTH: 23
<212> TYPE: DNA
<213> ORGANISM: Artificial Sequence
<220> FEATURE:
```

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 887
ugagagaagt ccaccacgag ucu                                                  23

<210> SEQ ID NO 888
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 888
ugagagaagu ccaccacgag ucu                                                  23

<210> SEQ ID NO 889
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 889
ugagagaagu ccaccacgag ucu                                                  23

<210> SEQ ID NO 890
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 890
ugagagaagt ccaccacgag ucu                                                  23

<210> SEQ ID NO 891
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 891
ugagagaagu ccaccacgag ucu                                                  23

<210> SEQ ID NO 892
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

```
<400> SEQUENCE: 892
ugagagaagt ccaccacgag ucu                                            23

<210> SEQ ID NO 893
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 893
ugagagaagu ccaccacgag ucu                                            23

<210> SEQ ID NO 894
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 894
ugagagaagu ccaccacgag ucu                                            23

<210> SEQ ID NO 895
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 895
ugagagaagt ccaccacgag ucu                                            23

<210> SEQ ID NO 896
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 896
ugagagaagt ccaccacgag ucu                                            23

<210> SEQ ID NO 897
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 897
ugagagaagu ccaccacgag ucu                                            23
```

```
<210> SEQ ID NO 898
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 898
ugagagaagt ccaccacgag ucu                                            23

<210> SEQ ID NO 899
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 899
ugagagaagu ccaccacgag ucu                                            23

<210> SEQ ID NO 900
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 900
ugagagaagt ccaccacgag ucu                                            23

<210> SEQ ID NO 901
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 901
ugagagaagt ccaccacgag ucu                                            23

<210> SEQ ID NO 902
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 902
ugagagaagt ccaccacgag ucu                                            23

<210> SEQ ID NO 903
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 903
ugagagaagu ccaccacgag ucu                                              23

<210> SEQ ID NO 904
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 904
ugagagaagu ccaccacgag ucu                                              23

<210> SEQ ID NO 905
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 905
ugagagaagt ccaccacgag ucu                                              23

<210> SEQ ID NO 906
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 906
ugagagaagt ccaccacgag ucu                                              23

<210> SEQ ID NO 907
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 907
ugagagaagt ccaccacgag ucu                                              23

<210> SEQ ID NO 908
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 908
ugagagaagu ccaccacgag ucu                                                23

<210> SEQ ID NO 909
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 909
ucguggugga cuucucuca                                                    19

<210> SEQ ID NO 910
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 910
ucguggugga cuucucuca                                                    19

<210> SEQ ID NO 911
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 911
ucguggugga cuucucuca                                                    19

<210> SEQ ID NO 912
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 912
acucguggug gacuucucuc a                                                 21

<210> SEQ ID NO 913
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 913
ucguggugga cuucucuca                                                    19

<210> SEQ ID NO 914
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 914
ucguggugga cuucucuca                                                 19

<210> SEQ ID NO 915
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 915
ucguggugga cuucucucau u                                              21

<210> SEQ ID NO 916
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 916
acucguggug gacuucucuc a                                              21

<210> SEQ ID NO 917
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 917
ucguggugga cuucucuca                                                 19

<210> SEQ ID NO 918
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 918
acucguggug gacuucucuc a                                              21

<210> SEQ ID NO 919
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 919
gugcacuucg cuucaccucu a                                              21

<210> SEQ ID NO 920
<211> LENGTH: 21
```

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 920
gugcacuucg cuucaccucu a                                              21

<210> SEQ ID NO 921
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 921
gcacuucgcu ucaccucua                                                 19

<210> SEQ ID NO 922
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 922
gugcacuucg cuucaccucu g                                              21

<210> SEQ ID NO 923
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 923
augugucugc ggcguuuuau a                                              21

<210> SEQ ID NO 924
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 924
gugcacuucg cuucaccucu g                                              21

<210> SEQ ID NO 925
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 925
gcacuucgcu ucaccucua                                                 19

<210> SEQ ID NO 926
<211> LENGTH: 19
<212> TYPE: RNA
```

<213> ORGANISM: Artificial Sequence
<220> FEATURE:
<223> OTHER INFORMATION: Description of Artificial Sequence: Synthetic
    oligonucleotide

<400> SEQUENCE: 926
gguggacuuc ucucaauuu                                                19

<210> SEQ ID NO 927
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 927
cgugguggac uucucucaau u                                             21

<210> SEQ ID NO 928
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 928
gugguggacu ucucucaauu u                                             21

<210> SEQ ID NO 929
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 929
cgugguggac uucucucaau u                                             21

<210> SEQ ID NO 930
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 930
gguggacuuc ucucaauuu                                                19

<210> SEQ ID NO 931
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 931
gugguggacu ucucucaauu u                                             21

<210> SEQ ID NO 932
<211> LENGTH: 19
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 932
uggugguctu cucuaaauu                                                    19

<210> SEQ ID NO 933
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 933
gugguggacu ucucucaauu u                                                 21

<210> SEQ ID NO 934
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 934
cguggugguc tucucuaaau u                                                 21

<210> SEQ ID NO 935
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 935
gguggacuuc ucucaauuuu a                                                 21

<210> SEQ ID NO 936
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 936
gguggacuuc ucucaauuuu a                                                 21

<210> SEQ ID NO 937
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 937
```

-continued uggacuacuc ucaaauuua                                                19

<210> SEQ ID NO 938
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 938
ugagagaagu ccaccacgau u                                             21

<210> SEQ ID NO 939
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 939
ugagagaagu ccaccacgau u                                             21

<210> SEQ ID NO 940
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 940
ugagagaagu ccaccacgau u                                             21

<210> SEQ ID NO 941
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 941
ugagagaagu ccaccacgag ucu                                           23

<210> SEQ ID NO 942
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 942
ugagagaagu ccaccacgau u                                             21

<210> SEQ ID NO 943
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 943
ugagagaagu ccaccacgau u                                        21

<210> SEQ ID NO 944
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 944
ugagagaagu ccaccacgau u                                        21

<210> SEQ ID NO 945
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 945
ugagagaagu ccaccacgag ucu                                      23

<210> SEQ ID NO 946
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 946
ugagagaagu ccaccacgau u                                        21

<210> SEQ ID NO 947
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 947
ugagagaagu ccaccacgag uuu                                      23

<210> SEQ ID NO 948
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 948
uagaggugaa gcgaagugca cuu                                      23

<210> SEQ ID NO 949
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 949
uagaggugaa gcgaagugca cac                                      23

<210> SEQ ID NO 950
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 950
uagaggugaa gcgaagugca c                                              21

<210> SEQ ID NO 951
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 951
cagaggugaa gcgaagugca cac                                            23

<210> SEQ ID NO 952
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 952
uauaaaacgc cgcagacaca ucc                                            23

<210> SEQ ID NO 953
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 953
cagaggugaa gcgaagugca cac                                            23

<210> SEQ ID NO 954
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 954
uagaggugaa gcgaagugcu u                                              21

<210> SEQ ID NO 955
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 955
aaauugagag aaguccacca c                                              21

```
<210> SEQ ID NO 956
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 956
aauugagaga aguccaccag cag                                              23

<210> SEQ ID NO 957
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 957
aaauugagag aaguccacca cga                                              23

<210> SEQ ID NO 958
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 958
aauugagaga aguccaccag cag                                              23

<210> SEQ ID NO 959
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 959
aaauugagag aaguccacca c                                                21

<210> SEQ ID NO 960
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 960
aaauugagag aaguccacca cga                                              23

<210> SEQ ID NO 961
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 961
aauugagaga aguccaccau u                                                21
```

```
<210> SEQ ID NO 962
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 962
aaauugagag aaguccacca cga                                            23

<210> SEQ ID NO 963
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 963
aauugagaga aguccaccag cuu                                            23

<210> SEQ ID NO 964
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 964
uaaaauugag agaaguccac cac                                            23

<210> SEQ ID NO 965
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 965
uaaaauugag agaaguccac cac                                            23

<210> SEQ ID NO 966
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 966
uaaaauugag agaaguccau u                                              21

<210> SEQ ID NO 967
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 967
ucguggugga cuucucuca                                                 19

<210> SEQ ID NO 968
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 968
ucguggugga cuucucuca                                                        19

<210> SEQ ID NO 969
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2-hydroxymethyl-tetrahydrofurane-5-phosphate
<220> FEATURE:
<221> NAME/KEY: modified_base
<222> LOCATION: (21)..(21)
<223> OTHER INFORMATION: 2-hydroxymethyl-tetrahydrofurane-5-phosphate

<400> SEQUENCE: 969
nucguggugg acuucucuca n                                                     21

<210> SEQ ID NO 970
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2-hydroxymethyl-tetrahydrofurane-5-phosphate

<400> SEQUENCE: 970
nacucguggu ggacuucucu ca                                                    22

<210> SEQ ID NO 971
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 971
ucguggugga cuucucuca                                                        19

<210> SEQ ID NO 972
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 972
ucguggugga cuucucuca                                                        19

<210> SEQ ID NO 973
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2-hydroxymethyl-tetrahydrofurane-5-phosphate
<220> FEATURE:
<221> NAME/KEY: modified_base
<222> LOCATION: (23)..(23)
<223> OTHER INFORMATION: 2-hydroxymethyl-tetrahydrofurane-5-phosphate

<400> SEQUENCE: 973
nucguggugg acuucucuca uun                                           23

<210> SEQ ID NO 974
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 974
acucguggug gacuucucuc a                                             21

<210> SEQ ID NO 975
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 975
ucguggugga cuucucuca                                                19

<210> SEQ ID NO 976
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 976
acucguggug gacuucucuc a                                             21

<210> SEQ ID NO 977
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 977
gugcacuucg cuucaccucu a                                             21

<210> SEQ ID NO 978
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 978
```
gugcacuucg cuucaccucu a                                              21

<210> SEQ ID NO 979
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 979
gcacuucgcu ucaccucua                                                 19

<210> SEQ ID NO 980
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 980
gugcacuucg cuucaccucu g                                              21

<210> SEQ ID NO 981
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 981
augugucugc ggcguuuuau a                                              21

<210> SEQ ID NO 982
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 982
gugcacuucg cuucaccucu g                                              21

<210> SEQ ID NO 983
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 983
gcacuucgcu ucaccucua                                                 19

<210> SEQ ID NO 984
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 984
gguggacuuc ucucaauuu                                                  19

<210> SEQ ID NO 985
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 985
cgugguggac uucucucaau u                                               21

<210> SEQ ID NO 986
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 986
gugguggacu ucucucaauu u                                               21

<210> SEQ ID NO 987
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 987
cgugguggac uucucucaau u                                               21

<210> SEQ ID NO 988
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 988
gguggacuuc ucucaauuu                                                  19

<210> SEQ ID NO 989
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 989
gugguggacu ucucucaauu u                                               21

<210> SEQ ID NO 990
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Description of Combined DNA/RNA Molecule:
      Synthetic oligonucleotide

<400> SEQUENCE: 990
uggugguctu cucuaaauu                                                        19

<210> SEQ ID NO 991
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 991
gugguggacu ucucucaauu u                                                     21

<210> SEQ ID NO 992
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 992
cguggugguc tucucuaaau u                                                     21

<210> SEQ ID NO 993
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 993
gguggacuuc ucucaauuuu a                                                     21

<210> SEQ ID NO 994
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 994
gguggacuuc ucucaauuuu a                                                     21

<210> SEQ ID NO 995
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 995
uggacuactc ucaaauuua                                                        19

```
<210> SEQ ID NO 996
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 996
ugagagaagu ccaccacgau u                                              21

<210> SEQ ID NO 997
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 997
ugagagaagu ccaccacgau u                                              21

<210> SEQ ID NO 998
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 998
ugagagaagu ccaccacgau u                                              21

<210> SEQ ID NO 999
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 999
ugagagaagu ccaccacgag ucu                                            23

<210> SEQ ID NO 1000
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1000
ugagagaagu ccaccacgau u                                              21

<210> SEQ ID NO 1001
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1001
ugagagaagu ccaccacgau u                                              21

<210> SEQ ID NO 1002
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1002
ugagagaagu ccaccacgau u                                           21

<210> SEQ ID NO 1003
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1003
ugagagaagu ccaccacgag ucu                                         23

<210> SEQ ID NO 1004
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1004
ugagagaagu ccaccacgau u                                           21

<210> SEQ ID NO 1005
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1005
ugagagaagu ccaccacgag uuu                                         23

<210> SEQ ID NO 1006
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1006
uagaggugaa gcgaagugca cuu                                         23

<210> SEQ ID NO 1007
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1007
uagaggugaa gcgaagugca cac                                         23

<210> SEQ ID NO 1008
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1008
uagaggugaa gcgaagugca c                                              21

<210> SEQ ID NO 1009
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1009
cagaggugaa gcgaagugca cac                                            23

<210> SEQ ID NO 1010
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1010
uauaaaacgc cgcagacaca ucc                                            23

<210> SEQ ID NO 1011
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1011
cagaggugaa gcgaagugca cac                                            23

<210> SEQ ID NO 1012
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1012
uagaggugaa gcgaagugcu u                                              21

<210> SEQ ID NO 1013
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1013
aaauugagag aaguccacca c                                              21
```

```
<210> SEQ ID NO 1014
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1014
aauugagaga aguccaccag cag                                              23

<210> SEQ ID NO 1015
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1015
aaauugagag aaguccacca cga                                              23

<210> SEQ ID NO 1016
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1016
aauugagaga aguccaccag cag                                              23

<210> SEQ ID NO 1017
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1017
aaauugagag aaguccacca c                                                21

<210> SEQ ID NO 1018
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1018
aaauugagag aaguccacca cga                                              23

<210> SEQ ID NO 1019
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1019
aauugagaga aguccaccau u                                                21
```

<210> SEQ ID NO 1020
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1020
aaauugagag aaguccacca cga                                                23

<210> SEQ ID NO 1021
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1021
aauugagaga aguccaccag cuu                                                23

<210> SEQ ID NO 1022
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1022
uaaaauugag agaaguccac cac                                                23

<210> SEQ ID NO 1023
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1023
uaaaauugag agaaguccac cac                                                23

<210> SEQ ID NO 1024
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1024
uaaaauugag agaaguccau u                                                  21

<210> SEQ ID NO 1025
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1025
ucguggugga cuucucuca                                                19

<210> SEQ ID NO 1026
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1026
ucguggugga cuucucuca                                                19

<210> SEQ ID NO 1027
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1027
ucguggugga cuucucuca                                                19

<210> SEQ ID NO 1028
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1028
gugcacuucg cuucaccucu a                                             21

<210> SEQ ID NO 1029
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1029
gugcacuucg cuucaccucu a                                             21

<210> SEQ ID NO 1030
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1030
gugcacuucg cuucaccucu a                                             21

<210> SEQ ID NO 1031
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1031
cgugguggac uucucucaau u                                              21

<210> SEQ ID NO 1032
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1032
cguggugguc tucucuaaau u                                              21

<210> SEQ ID NO 1033
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1033 ggguggacuuc ucucaauuuu a                                             21

<210> SEQ ID NO 1034
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1034 ggugggacuuc ucucaauuuu a                                             21

<210> SEQ ID NO 1035
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1035 ggugggacuuc ucucaauuuu a                                             21

<210> SEQ ID NO 1036
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1036
ugagagaagu ccaccacgau u                                              21

<210> SEQ ID NO 1037
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1037
ugagagaagu ccaccacgau u                                            21

<210> SEQ ID NO 1038
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1038
ugagagaagu ccaccacgau u                                            21

<210> SEQ ID NO 1039
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1039
uagaggugaa gcgaagugca cuu                                          23

<210> SEQ ID NO 1040
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1040
uagaggugaa gcgaagugca cuu                                          23

<210> SEQ ID NO 1041
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1041
uagaggugaa gcgaagugca cuu                                          23

<210> SEQ ID NO 1042
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1042
aauugagaga aguccaccag cag                                          23

<210> SEQ ID NO 1043
<211> LENGTH: 23
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 1043
aauugagaga aguccaccag cuu                                          23

<210> SEQ ID NO 1044
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1044
uaaaauugag agaaguccac cac                                          23

<210> SEQ ID NO 1045
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1045
uaaaauugag agaaguccac cac                                          23

<210> SEQ ID NO 1046
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1046
uaaaauugag agaaguccac cac                                          23

<210> SEQ ID NO 1047
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1047
ucguggugga cuucucuca                                               19

<210> SEQ ID NO 1048
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1048
ucguggugga cuucucuca                                               19

<210> SEQ ID NO 1049
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1049
ucguggugga cuucucuca                                                    19

<210> SEQ ID NO 1050
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1050
gugcacuucg cuucaccucu a                                                 21

<210> SEQ ID NO 1051
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1051
gugcacuucg cuucaccucu a                                                 21

<210> SEQ ID NO 1052
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1052
gugcacuucg cuucaccucu a                                                 21

<210> SEQ ID NO 1053
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1053
cgugguggac uucucucaau u                                                 21

<210> SEQ ID NO 1054
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1054
cguggugguc tucucuaaau u                                                 21

<210> SEQ ID NO 1055
<211> LENGTH: 21
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 1055
gguggacuuc ucucaauuuu a                                              21

<210> SEQ ID NO 1056
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1056
gguggacuuc ucucaauuuu a                                              21

<210> SEQ ID NO 1057
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1057
gguggacuuc ucucaauuuu a                                              21

<210> SEQ ID NO 1058
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1058
ugagagaagu ccaccacgau u                                              21

<210> SEQ ID NO 1059
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1059
ugagagaagu ccaccacgau u                                              21

<210> SEQ ID NO 1060
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1060
ugagagaagu ccaccacgau u                                              21

<210> SEQ ID NO 1061
<211> LENGTH: 23
<212> TYPE: RNA
<213> ORGANISM: Artificial Sequence
<220> FEATURE:
<223> OTHER INFORMATION: Description of Artificial Sequence: Synthetic
```

```
      oligonucleotide

<400> SEQUENCE: 1061
uagaggugaa gcgaagugca cuu                                          23

<210> SEQ ID NO 1062
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1062
uagaggugaa gcgaagugca cuu                                          23

<210> SEQ ID NO 1063
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1063
uagaggugaa gcgaagugca cuu                                          23

<210> SEQ ID NO 1064
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1064
aauugagaga aguccaccag cag                                          23

<210> SEQ ID NO 1065
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1065
aauugagaga aguccaccag cuu                                          23

<210> SEQ ID NO 1066
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1066
uaaaauugag agaaguccac cac                                          23

<210> SEQ ID NO 1067
<211> LENGTH: 23
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 1067
uaaaauugag agaaguccac cac                                           23

<210> SEQ ID NO 1068
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1068
uaaaauugag agaaguccac cac                                           23

<210> SEQ ID NO 1069
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1069
ugugcacuuc gcuucaccuc u                                             21

<210> SEQ ID NO 1070
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1070
ugcacuucgc uucaccucug a                                             21

<210> SEQ ID NO 1071
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1071
gugugcacuu cgcuucaccu a                                             21

<210> SEQ ID NO 1072
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1072
cgugugcacu ucgcuucacc u                                             21

<210> SEQ ID NO 1073
<211> LENGTH: 21
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 1073
gugcacuucg cuucaccucu a                                              21

<210> SEQ ID NO 1074
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1074
ccgugugcac uucgcuucac a                                              21

<210> SEQ ID NO 1075
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1075
cacuucgcuu caccucugca a                                              21

<210> SEQ ID NO 1076
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1076
acuucgcuuc accucugcac a                                              21

<210> SEQ ID NO 1077
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1077
ggcuguaggc auaaauuggu a                                              21

<210> SEQ ID NO 1078
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1078
uucgcuucac cucugcacgu a                                              21

<210> SEQ ID NO 1079
<211> LENGTH: 21
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 1079
ucgcuucacc ucugcacguc a                                              21

<210> SEQ ID NO 1080
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1080
cuucgcuuca ccucugcacg u                                              21

<210> SEQ ID NO 1081
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1081
ccccgucugu gccuucucau a                                              21

<210> SEQ ID NO 1082
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1082
ccgucugugc cuucucaucu a                                              21

<210> SEQ ID NO 1083
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1083
ccagcaccau gcaacuuuuu a                                              21

<210> SEQ ID NO 1084
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1084
caccagcacc augcaacuuu u                                              21

<210> SEQ ID NO 1085
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1085
caccaugcaa cuuuuucacc u                                              21

<210> SEQ ID NO 1086
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1086
caaugucaac gaccgaccuu a                                              21

<210> SEQ ID NO 1087
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1087
cgcuucaccu cugcacgucg a                                              21

<210> SEQ ID NO 1088
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1088
accuugaggc auacuucaaa g                                              21

<210> SEQ ID NO 1089
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1089
ccgaccuuga ggcauacuuc a                                              21

<210> SEQ ID NO 1090
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1090
gaccuugagg cauacuucaa a                                              21

<210> SEQ ID NO 1091
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1091
accgaccuug aggcauacuu a                                              21

<210> SEQ ID NO 1092
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1092
ucgcauggag accaccguga a                                              21

<210> SEQ ID NO 1093
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1093
uuacauaaga ggacucuugg a                                              21

<210> SEQ ID NO 1094
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1094
ucuuacauaa gaggacucuu a                                              21

<210> SEQ ID NO 1095
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1095
acuucaaaga cuguuuguuu a                                              21

<210> SEQ ID NO 1096
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1096
uacuucaaag acuguuuguu u                                              21

<210> SEQ ID NO 1097
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1097
```
auacuucaaa gacuguuugu u                                          21

<210> SEQ ID NO 1098
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1098
uuguuuaaag acugggagga a                                          21

<210> SEQ ID NO 1099
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1099
gcauacuuca aagacuguuu a                                          21

<210> SEQ ID NO 1100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1100
caaagacugu uuguuuaaag a                                          21

<210> SEQ ID NO 1101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1101
agacuguuug uuuaaagacu a                                          21

<210> SEQ ID NO 1102
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1102
guuuguuuaa agacugggag a                                          21

<210> SEQ ID NO 1103
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1103

```
gggggaggag auuagauuaa a                                              21
```

<210> SEQ ID NO 1104
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1104

```
ggggaggaga uuagauuaaa g                                              21
```

<210> SEQ ID NO 1105
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1105

```
guuggggag gagauuagau u                                               21
```

<210> SEQ ID NO 1106
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1106

```
uuggggagg agauuagauu a                                               21
```

<210> SEQ ID NO 1107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1107

```
gggaggagau uagauuaaag a                                              21
```

<210> SEQ ID NO 1108
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1108

```
uuagauuaaa ggucuuugua a                                              21
```

<210> SEQ ID NO 1109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1109

```
uagauuaaag gucuuuguac u                                              21
```

<210> SEQ ID NO 1110
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1110
auuagauuaa aggucuuugu a                                             21

<210> SEQ ID NO 1111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1111
gaggagauua gauuaaaggu a                                             21

<210> SEQ ID NO 1112
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1112
ggacucuugg acucucugca a                                             21

<210> SEQ ID NO 1113
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1113
acucuuggac ucucugcaau a                                             21

<210> SEQ ID NO 1114
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1114
agauuaaagg ucuuuguacu a                                             21

<210> SEQ ID NO 1115
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1115
agaggugaag cgaagugcac acg                                           23

<210> SEQ ID NO 1116
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1116
ucagagguga agcgaagugc aca                                           23

<210> SEQ ID NO 1117
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1117
uaggugaagc gaagugcaca cgg                                           23

<210> SEQ ID NO 1118
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1118
aggugaagcg aagugcacac ggu                                           23

<210> SEQ ID NO 1119
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1119
uagaggugaa gcgaagugca cac                                           23

<210> SEQ ID NO 1120
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1120
ugugaagcga agugcacacg guc                                           23

<210> SEQ ID NO 1121
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1121
uugcagaggu gaagcgaagu gca                                           23

```
<210> SEQ ID NO 1122
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1122
ugugcagagg ugaagcgaag ugc                                             23

<210> SEQ ID NO 1123
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1123
uaccaauuua ugccuacagc cuc                                             23

<210> SEQ ID NO 1124
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1124
uacgugcaga ggugaagcga agu                                             23

<210> SEQ ID NO 1125
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1125
ugacgugcag aggugaagcg aag                                             23

<210> SEQ ID NO 1126
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1126
acgugcagag gugaagcgaa gug                                             23

<210> SEQ ID NO 1127
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1127
uaugagaagg cacagacggg gag                                             23

<210> SEQ ID NO 1128
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1128
uagaugagaa ggcacagacg ggg                                          23

<210> SEQ ID NO 1129
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1129
uaaaaaguug cauggugcug gug                                          23

<210> SEQ ID NO 1130
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1130
aaaaguugca uggugcuggu gcg                                          23

<210> SEQ ID NO 1131
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1131
aggugaaaaa guugcauggu gcu                                          23

<210> SEQ ID NO 1132
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1132
uaaggucggu cguugacauu gca                                          23

<210> SEQ ID NO 1133
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1133
ucgacgugca gaggugaagc gaa                                          23

<210> SEQ ID NO 1134
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1134
cuuugaagua ugccucaagg ucg                                                 23

<210> SEQ ID NO 1135
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1135
ugaaguaugc cucaaggucg guc                                                 23

<210> SEQ ID NO 1136
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1136
uuugaaguau gccucaaggu cgg                                                 23

<210> SEQ ID NO 1137
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1137
uaaguaugcc ucaaggucgg ucg                                                 23

<210> SEQ ID NO 1138
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1138
uucacggugg ucuccaugcg acg                                                 23

<210> SEQ ID NO 1139
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1139
uccaagaguc cucuuaugua aga                                                 23

<210> SEQ ID NO 1140
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1140
uaagaguccu cuuauguaag acc                                               23

<210> SEQ ID NO 1141
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1141
uaaacaaaca gucuuugaag uau                                               23

<210> SEQ ID NO 1142
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1142
aaacaaacag ucuuugaagu aug                                               23

<210> SEQ ID NO 1143
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1143
aacaaacagu cuuugaagua ugc                                               23

<210> SEQ ID NO 1144
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1144
uuccucccag ucuuuaaaca aac                                               23

<210> SEQ ID NO 1145
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1145
uaaacagucu uugaaguaug ccu                                               23

<210> SEQ ID NO 1146
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1146
ucuuuaaaca aacagucuuu gaa                                              23

<210> SEQ ID NO 1147
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1147
uagucuuuaa acaaacaguc uuu                                              23

<210> SEQ ID NO 1148
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1148
ucucccaguc uuuaaacaaa cag                                              23

<210> SEQ ID NO 1149
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1149
uuuaaucuaa ucuccucccc caa                                              23

<210> SEQ ID NO 1150
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1150
cuuuaaucua aucuccuccc cca                                              23

<210> SEQ ID NO 1151
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1151
aaucuaaucu ccuccccaa cuc                                               23

<210> SEQ ID NO 1152
<211> LENGTH: 23
<212> TYPE: RNA
<213> ORGANISM: Artificial Sequence
<220> FEATURE:
```

<223> OTHER INFORMATION: Description of Artificial Sequence: Synthetic
       oligonucleotide

<400> SEQUENCE: 1152
uaaucuaauc uccuccccca acu                                            23

<210> SEQ ID NO 1153
<211> LENGTH: 23
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 1153
ucuuuaaucu aaucuccucc ccc                                            23

<210> SEQ ID NO 1154
<211> LENGTH: 23
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 1154
uuacaaagac cuuuaaucua auc                                            23

<210> SEQ ID NO 1155
<211> LENGTH: 23
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 1155
aguacaaaga ccuuuaaucu aau                                            23

<210> SEQ ID NO 1156
<211> LENGTH: 23
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 1156
uacaaagacc uuuaaucuaa ucu                                            23

<210> SEQ ID NO 1157
<211> LENGTH: 23
<212> TYPE: RNA
<213> ORGANISM: Artificial Sequence
<220> FEATURE:
<223> OTHER INFORMATION: Description of Artificial Sequence: Synthetic
       oligonucleotide

<400> SEQUENCE: 1157
uaccuuuaau cuaaucuccu ccc                                            23

<210> SEQ ID NO 1158
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1158
uugcagagag uccaagaguc cuc                                               23

<210> SEQ ID NO 1159
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1159
uauugcagag aguccaagag ucc                                               23

<210> SEQ ID NO 1160
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1160
uaguacaaag accuuuaauc uaa                                               23

<210> SEQ ID NO 1161
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1161
ugugcacuuc gcuucaccuc u                                                 21

<210> SEQ ID NO 1162
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1162
ugcacuucgc uucaccucug a                                                 21

<210> SEQ ID NO 1163
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1163
gugugcacuu cgcuucaccu a                                                 21

<210> SEQ ID NO 1164
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1164
cgugugcacu ucgcuucacc u                                              21

<210> SEQ ID NO 1165
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1165
gugcacuucg cuucaccucu a                                              21

<210> SEQ ID NO 1166
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1166
ccgugugcac uucgcuucac a                                              21

<210> SEQ ID NO 1167
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1167
cacuucgcuu caccucugca a                                              21

<210> SEQ ID NO 1168
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1168
acuucgcuuc accucugcac a                                              21

<210> SEQ ID NO 1169
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1169
ggcuguaggc auaaauuggu a                                              21

<210> SEQ ID NO 1170
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1170
uucgcuucac cucugcacgu a                                              21

<210> SEQ ID NO 1171
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1171
ucgcuucacc ucugcacguc a                                              21

<210> SEQ ID NO 1172
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1172
cuucgcuuca ccucugcacg u                                              21

<210> SEQ ID NO 1173
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1173
ccccgucugu gccuucucau a                                              21

<210> SEQ ID NO 1174
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1174
ccgucugugc cuucucaucu a                                              21

<210> SEQ ID NO 1175
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1175
ccagcaccau gcaacuuuuu a                                              21

<210> SEQ ID NO 1176
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1176
```
caccagcacc augcaacuuu u                                    21

<210> SEQ ID NO 1177
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1177
caccaugcaa cuuuuucacc u                                    21

<210> SEQ ID NO 1178
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1178 caaugcaac gaccgaccuu a                                     21

<210> SEQ ID NO 1179
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1179
cgcuucaccu cugcacgucg a                                    21

<210> SEQ ID NO 1180
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1180
accuugaggc auacuucaaa g                                    21

<210> SEQ ID NO 1181
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1181
ccgaccuuga ggcauacuuc a                                    21

<210> SEQ ID NO 1182
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1182
gaccuugagg cauacuucaa a					21

<210> SEQ ID NO 1183
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1183
accgaccuug aggcauacuu a					21

<210> SEQ ID NO 1184
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1184
ucgcauggag accaccguga a					21

<210> SEQ ID NO 1185
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1185
uuacauaaga ggacucuugg a					21

<210> SEQ ID NO 1186
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1186
ucuuacauaa gaggacucuu a					21

<210> SEQ ID NO 1187
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1187
acuucaaaga cuguuuguuu a					21

<210> SEQ ID NO 1188
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1188
uacuucaaag acuguuuguu u					21

<210> SEQ ID NO 1189
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1189
auacuucaaa gacuguuugu u                                              21

<210> SEQ ID NO 1190
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1190
uuguuuaaag acugggagga a                                              21

<210> SEQ ID NO 1191
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1191
gcauacuuca aagacuguuu a                                              21

<210> SEQ ID NO 1192
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1192
caaagacugu uuguuuaaag a                                              21

<210> SEQ ID NO 1193
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1193
agacuguuug uuuaaagacu a                                              21

<210> SEQ ID NO 1194
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1194
guuuguuuaa agacugggag a                                              21

```
<210> SEQ ID NO 1195
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1195
gggggaggag auuagauuaa a                                           21

<210> SEQ ID NO 1196
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1196
ggggaggaga uuagauuaaa g                                           21

<210> SEQ ID NO 1197
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1197 guuggggag gagauuagau u                                            21

<210> SEQ ID NO 1198
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1198 uuggggagg agauuagauu a                                            21

<210> SEQ ID NO 1199
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1199
gggaggagau uagauuaaag a                                           21

<210> SEQ ID NO 1200
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1200
uuagauuaaa ggucuuugua a                                           21
```

```
<210> SEQ ID NO 1201
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1201
uagauuaaag gucuuuguac u                                             21

<210> SEQ ID NO 1202
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1202
auuagauuaa aggucuuugu a                                             21

<210> SEQ ID NO 1203
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1203
gaggagauua gauuaaaggu a                                             21

<210> SEQ ID NO 1204
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1204
ggacucuugg acucucugca a                                             21

<210> SEQ ID NO 1205
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1205
acucuuggac ucucugcaau a                                             21

<210> SEQ ID NO 1206
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1206
agauuaaagg ucuuuguacu a                                             21

<210> SEQ ID NO 1207
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1207
agaggugaag cgaagugcac acg                                               23

<210> SEQ ID NO 1208
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1208
ucagagguga agcgaagugc aca                                               23

<210> SEQ ID NO 1209
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1209
uaggugaagc gaagugcaca cgg                                               23

<210> SEQ ID NO 1210
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1210
aggugaagcg aagugcacac ggu                                               23

<210> SEQ ID NO 1211
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1211
uagaggugaa gcgaagugca cac                                               23

<210> SEQ ID NO 1212
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1212
ugugaagcga agugcacacg guc                                               23

<210> SEQ ID NO 1213
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1213
uugcagaggu gaagcgaagu gca                                           23

<210> SEQ ID NO 1214
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1214
ugugcagagg ugaagcgaag ugc                                           23

<210> SEQ ID NO 1215
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1215
uaccaauuua ugccuacagc cuc                                           23

<210> SEQ ID NO 1216
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1216
uacgugcaga ggugaagcga agu                                           23

<210> SEQ ID NO 1217
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1217
ugacgugcag aggugaagcg aag                                           23

<210> SEQ ID NO 1218
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1218
acgugcagag gugaagcgaa gug                                           23

<210> SEQ ID NO 1219
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1219
uaugagaagg cacagacggg gag                                            23

<210> SEQ ID NO 1220
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1220
uagaugagaa ggcacagacg ggg                                            23

<210> SEQ ID NO 1221
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1221
uaaaaaguug cauggugcug gug                                            23

<210> SEQ ID NO 1222
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1222
aaaaguugca uggugcuggu gcg                                            23

<210> SEQ ID NO 1223
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1223
aggugaaaaa guugcauggu gcu                                            23

<210> SEQ ID NO 1224
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1224
uaaggucggu cguugacauu gca                                            23

<210> SEQ ID NO 1225
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1225
ucgacgugca gaggugaagc gaa                                              23

<210> SEQ ID NO 1226
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1226
cuuugaagua ugccucaagg ucg                                              23

<210> SEQ ID NO 1227
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1227
ugaaguaugc cucaaggucg guc                                              23

<210> SEQ ID NO 1228
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1228
uuugaaguau gccucaaggu cgg                                              23

<210> SEQ ID NO 1229
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1229
uaaguaugcc ucaaggucgg ucg                                              23

<210> SEQ ID NO 1230
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1230
uucacggugg ucuccaugcg acg                                              23

<210> SEQ ID NO 1231
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1231
uccaagaguc cucuuaugua aga                                          23

<210> SEQ ID NO 1232
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1232
uaagaguccu cuuauguaag acc                                          23

<210> SEQ ID NO 1233
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1233
uaaacaaaca gucuuugaag uau                                          23

<210> SEQ ID NO 1234
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1234
aaacaaacag ucuuugaagu aug                                          23

<210> SEQ ID NO 1235
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1235
aacaaacagu cuuugaagua ugc                                          23

<210> SEQ ID NO 1236
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1236
uuccucccag ucuuuaaaca aac                                          23

<210> SEQ ID NO 1237
<211> LENGTH: 23
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 1237
uaaacagucu uugaaguaug ccu                                              23

<210> SEQ ID NO 1238
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1238
ucuuuaaaca aacagucuuu gaa                                              23

<210> SEQ ID NO 1239
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1239
uagucuuuaa acaaacaguc uuu                                              23

<210> SEQ ID NO 1240
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1240
ucucccaguc uuuaaacaaa cag                                              23

<210> SEQ ID NO 1241
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1241
uuuaaucuaa ucuccucccc caa                                              23

<210> SEQ ID NO 1242
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1242
cuuuaaucua aucuccuccc cca                                              23

<210> SEQ ID NO 1243
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1243
aaucuaaucu ccuccccaa cuc                                              23

<210> SEQ ID NO 1244
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1244
uaaucuaauc uccucccca acu                                              23

<210> SEQ ID NO 1245
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1245
ucuuuaaucu aaucuccucc ccc                                             23

<210> SEQ ID NO 1246
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1246
uuacaaagac cuuuaaucua auc                                             23

<210> SEQ ID NO 1247
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1247
aguacaaaga ccuuuaaucu aau                                             23

<210> SEQ ID NO 1248
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1248
uacaaagacc uuuaaucuaa ucu                                             23

<210> SEQ ID NO 1249
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1249
uaccuuuaau cuaaucuccu ccc                                              23

<210> SEQ ID NO 1250
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1250
uugcagagag uccaagaguc cuc                                              23

<210> SEQ ID NO 1251
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1251
uauugcagag aguccaagag ucc                                              23

<210> SEQ ID NO 1252
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1252
uaguacaaag accuuuaauc uaa                                              23

<210> SEQ ID NO 1253
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1253
gucugugccu ucucaucua                                                   19

<210> SEQ ID NO 1254
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1254
gucugugccu ucucaucua                                                   19

<210> SEQ ID NO 1255
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1255
```

```
gugugcacuu cgcuucaca                                                    19

<210> SEQ ID NO 1256
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1256
gugugcacuu cgcuucaca                                                    19

<210> SEQ ID NO 1257
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1257
ugugcacuuc gcuucaccuc u                                                 21

<210> SEQ ID NO 1258
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1258
ugugcacuuc gcuucaccuc u                                                 21

<210> SEQ ID NO 1259
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1259
caccagcacc augcaacuuu u                                                 21

<210> SEQ ID NO 1260
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1260
caccagcacc augcaacuuu u                                                 21

<210> SEQ ID NO 1261
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1261
```

```
caccaugcaa cuuuuucacc u                                              21
```

<210> SEQ ID NO 1262
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1262

```
caccaugcaa cuuuuucacc u                                              21
```

<210> SEQ ID NO 1263
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1263

```
uagaugagaa ggcacagacu u                                              21
```

<210> SEQ ID NO 1264
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1264

```
uagaugagaa ggcacagacu u                                              21
```

<210> SEQ ID NO 1265
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1265

```
ugugaagcga agugcacacu u                                              21
```

<210> SEQ ID NO 1266
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1266

```
ugugaagcga agugcacacu u                                              21
```

<210> SEQ ID NO 1267
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1267

```
agaggugaag cgaagugcac auu                                            23
```

<210> SEQ ID NO 1268
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1268
agaggugaag cgaagugcac auu                                             23

<210> SEQ ID NO 1269
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1269
aaaaguugca uggugcuggu guu                                             23

<210> SEQ ID NO 1270
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1270
aaaaguugca uggugcuggu guu                                             23

<210> SEQ ID NO 1271
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1271
aggugaaaaa guugcauggu guu                                             23

<210> SEQ ID NO 1272
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1272
aggugaaaaa guugcauggu guu                                             23

<210> SEQ ID NO 1273
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1273
gucugugccu ucucaucua                                                  19

```
<210> SEQ ID NO 1274
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1274
gucugugccu ucucaucua                                                    19

<210> SEQ ID NO 1275
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1275
gugugcacuu cgcuucaca                                                    19

<210> SEQ ID NO 1276
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1276
gugugcacuu cgcuucaca                                                    19

<210> SEQ ID NO 1277
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1277
ugugcacuuc gcuucaccuc u                                                 21

<210> SEQ ID NO 1278
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1278
ugugcacuuc gcuucaccuc u                                                 21

<210> SEQ ID NO 1279
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1279
caccagcacc augcaacuuu u                                                 21
```

-continued

```
<210> SEQ ID NO 1280
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1280
caccagcacc augcaacuuu u                                          21

<210> SEQ ID NO 1281
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1281
caccaugcaa cuuuuucacc u                                          21

<210> SEQ ID NO 1282
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1282
caccaugcaa cuuuuucacc u                                          21

<210> SEQ ID NO 1283
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1283
uagaugagaa ggcacagacu u                                          21

<210> SEQ ID NO 1284
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1284
uagaugagaa ggcacagacu u                                          21

<210> SEQ ID NO 1285
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1285
ugugaagcga agugcacacu u                                          21

<210> SEQ ID NO 1286
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1286
ugugaagcga agugcacacu u                                                 21

<210> SEQ ID NO 1287
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1287
agaggugaag cgaagugcac auu                                               23

<210> SEQ ID NO 1288
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1288
agaggugaag cgaagugcac auu                                               23

<210> SEQ ID NO 1289
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1289
aaaaguugca uggugcuggu guu                                               23

<210> SEQ ID NO 1290
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1290
aaaaguugca uggugcuggu guu                                               23

<210> SEQ ID NO 1291
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1291
aggugaaaaa guugcauggu guu                                               23

<210> SEQ ID NO 1292
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1292
aggugaaaaa guugcauggu guu                                          23

<210> SEQ ID NO 1293
<211> LENGTH: 19
<212> TYPE: RNA
<213> ORGANISM: Hepatitis B virus

<400> SEQUENCE: 1293
ucguggugga cuucucuca                                               19

<210> SEQ ID NO 1294
<211> LENGTH: 19
<212> TYPE: RNA
<213> ORGANISM: Hepatitis B virus

<400> SEQUENCE: 1294
gugguggacu ucucucaau                                               19

<210> SEQ ID NO 1295
<211> LENGTH: 19
<212> TYPE: RNA
<213> ORGANISM: Hepatitis B virus

<400> SEQUENCE: 1295
gccgauccau acugcggaa                                               19

<210> SEQ ID NO 1296
<211> LENGTH: 19
<212> TYPE: RNA
<213> ORGANISM: Hepatitis B virus

<400> SEQUENCE: 1296
ccgauccaua cugcggaac                                               19

<210> SEQ ID NO 1297
<211> LENGTH: 19
<212> TYPE: RNA
<213> ORGANISM: Hepatitis B virus

<400> SEQUENCE: 1297
cauccugcug cuaugccuc                                               19

<210> SEQ ID NO 1298
<211> LENGTH: 19
<212> TYPE: RNA
<213> ORGANISM: Hepatitis B virus

<400> SEQUENCE: 1298
ugcugcuaug ccucaucuu                                               19

<210> SEQ ID NO 1299
<211> LENGTH: 19
<212> TYPE: RNA
<213> ORGANISM: Hepatitis B virus

<400> SEQUENCE: 1299
gguggacuuc ucucaauuu                                               19
```

```
<210> SEQ ID NO 1300
<211> LENGTH: 19
<212> TYPE: RNA
<213> ORGANISM: Hepatitis B virus

<400> SEQUENCE: 1300
ugguggacuu cucucaauu                                                  19

<210> SEQ ID NO 1301
<211> LENGTH: 19
<212> TYPE: RNA
<213> ORGANISM: Hepatitis B virus

<400> SEQUENCE: 1301
uagacucgug guggacuuc                                                  19

<210> SEQ ID NO 1302
<211> LENGTH: 19
<212> TYPE: RNA
<213> ORGANISM: Hepatitis B virus

<400> SEQUENCE: 1302
uccucugccg auccauacu                                                  19

<210> SEQ ID NO 1303
<211> LENGTH: 19
<212> TYPE: RNA
<213> ORGANISM: Hepatitis B virus

<400> SEQUENCE: 1303
ugccgaucca uacugcgga                                                  19

<210> SEQ ID NO 1304
<211> LENGTH: 19
<212> TYPE: RNA
<213> ORGANISM: Hepatitis B virus

<400> SEQUENCE: 1304
uggauguguc ugcggcguu                                                  19

<210> SEQ ID NO 1305
<211> LENGTH: 19
<212> TYPE: RNA
<213> ORGANISM: Hepatitis B virus

<400> SEQUENCE: 1305
cgauccauac ugcggaacu                                                  19

<210> SEQ ID NO 1306
<211> LENGTH: 19
<212> TYPE: RNA
<213> ORGANISM: Hepatitis B virus

<400> SEQUENCE: 1306
cgcaccucuc uuuacgcgg                                                  19

<210> SEQ ID NO 1307
<211> LENGTH: 19
<212> TYPE: RNA
<213> ORGANISM: Hepatitis B virus

<400> SEQUENCE: 1307
```

| | |
|---|---|
| cugccgaucc auacugcgg | 19 |

<210> SEQ ID NO 1308
<211> LENGTH: 19
<212> TYPE: RNA
<213> ORGANISM: Hepatitis B virus

<400> SEQUENCE: 1308

| | |
|---|---|
| cgugguggac uucucucaa | 19 |

<210> SEQ ID NO 1309
<211> LENGTH: 19
<212> TYPE: RNA
<213> ORGANISM: Hepatitis B virus

<400> SEQUENCE: 1309

| | |
|---|---|
| cugcugcuau gccucaucu | 19 |

<210> SEQ ID NO 1310
<211> LENGTH: 19
<212> TYPE: RNA
<213> ORGANISM: Hepatitis B virus

<400> SEQUENCE: 1310

| | |
|---|---|
| ccugcugcua ugccucauc | 19 |

<210> SEQ ID NO 1311
<211> LENGTH: 19
<212> TYPE: RNA
<213> ORGANISM: Hepatitis B virus

<400> SEQUENCE: 1311

| | |
|---|---|
| cuagacucgu gguggacuu | 19 |

<210> SEQ ID NO 1312
<211> LENGTH: 19
<212> TYPE: RNA
<213> ORGANISM: Hepatitis B virus

<400> SEQUENCE: 1312

| | |
|---|---|
| uccugcugcu augccucau | 19 |

<210> SEQ ID NO 1313
<211> LENGTH: 19
<212> TYPE: RNA
<213> ORGANISM: Hepatitis B virus

<400> SEQUENCE: 1313

| | |
|---|---|
| gacucguggu ggacuucuc | 19 |

<210> SEQ ID NO 1314
<211> LENGTH: 19
<212> TYPE: RNA
<213> ORGANISM: Hepatitis B virus

<400> SEQUENCE: 1314

| | |
|---|---|
| auccauacug cggaacucc | 19 |

<210> SEQ ID NO 1315
<211> LENGTH: 19
<212> TYPE: RNA
<213> ORGANISM: Hepatitis B virus

<400> SEQUENCE: 1315
cucugccgau ccauacugc                                          19

<210> SEQ ID NO 1316
<211> LENGTH: 19
<212> TYPE: RNA
<213> ORGANISM: Hepatitis B virus

<400> SEQUENCE: 1316
gauccauacu gcggaacuc                                          19

<210> SEQ ID NO 1317
<211> LENGTH: 19
<212> TYPE: RNA
<213> ORGANISM: Hepatitis B virus

<400> SEQUENCE: 1317
gaagaacucc cucgccucg                                          19

<210> SEQ ID NO 1318
<211> LENGTH: 19
<212> TYPE: RNA
<213> ORGANISM: Hepatitis B virus

<400> SEQUENCE: 1318
aagccuccaa gcugugccu                                          19

<210> SEQ ID NO 1319
<211> LENGTH: 19
<212> TYPE: RNA
<213> ORGANISM: Hepatitis B virus

<400> SEQUENCE: 1319
agaagaacuc ccucgccuc                                          19

<210> SEQ ID NO 1320
<211> LENGTH: 19
<212> TYPE: RNA
<213> ORGANISM: Hepatitis B virus

<400> SEQUENCE: 1320
ggagugugga uucgcacuc                                          19

<210> SEQ ID NO 1321
<211> LENGTH: 19
<212> TYPE: RNA
<213> ORGANISM: Hepatitis B virus

<400> SEQUENCE: 1321
ccucugccga uccauacug                                          19

<210> SEQ ID NO 1322
<211> LENGTH: 19
<212> TYPE: RNA
<213> ORGANISM: Hepatitis B virus

<400> SEQUENCE: 1322
caagccucca agcugugcc                                          19

<210> SEQ ID NO 1323
<211> LENGTH: 19
<212> TYPE: RNA
<213> ORGANISM: Hepatitis B virus

```
<400> SEQUENCE: 1323
uccauacugc ggaacuccu                                                19

<210> SEQ ID NO 1324
<211> LENGTH: 19
<212> TYPE: RNA
<213> ORGANISM: Hepatitis B virus

<400> SEQUENCE: 1324
cagagucuag acucguggu                                                19

<210> SEQ ID NO 1325
<211> LENGTH: 19
<212> TYPE: RNA
<213> ORGANISM: Hepatitis B virus

<400> SEQUENCE: 1325
aagaagaacu cccucgccu                                                19

<210> SEQ ID NO 1326
<211> LENGTH: 19
<212> TYPE: RNA
<213> ORGANISM: Hepatitis B virus

<400> SEQUENCE: 1326
gaguguggau ucgcacucc                                                19

<210> SEQ ID NO 1327
<211> LENGTH: 19
<212> TYPE: RNA
<213> ORGANISM: Hepatitis B virus

<400> SEQUENCE: 1327
ucuagacucg ugguggacu                                                19

<210> SEQ ID NO 1328
<211> LENGTH: 19
<212> TYPE: RNA
<213> ORGANISM: Hepatitis B virus

<400> SEQUENCE: 1328
gcugcuaugc cucaucuuc                                                19

<210> SEQ ID NO 1329
<211> LENGTH: 19
<212> TYPE: RNA
<213> ORGANISM: Hepatitis B virus

<400> SEQUENCE: 1329
agucuagacu cguggugga                                                19

<210> SEQ ID NO 1330
<211> LENGTH: 19
<212> TYPE: RNA
<213> ORGANISM: Hepatitis B virus

<400> SEQUENCE: 1330
cuccucugcc gauccauac                                                19

<210> SEQ ID NO 1331
<211> LENGTH: 19
<212> TYPE: RNA
<213> ORGANISM: Hepatitis B virus
```

<400> SEQUENCE: 1331
uggcucaguu uacuagugc                                           19

<210> SEQ ID NO 1332
<211> LENGTH: 19
<212> TYPE: RNA
<213> ORGANISM: Hepatitis B virus

<400> SEQUENCE: 1332
gucuagacuc gugguggac                                           19

<210> SEQ ID NO 1333
<211> LENGTH: 19
<212> TYPE: RNA
<213> ORGANISM: Hepatitis B virus

<400> SEQUENCE: 1333
uucaagccuc caagcugug                                           19

<210> SEQ ID NO 1334
<211> LENGTH: 19
<212> TYPE: RNA
<213> ORGANISM: Hepatitis B virus

<400> SEQUENCE: 1334
cuaugggagu gggccucag                                           19

<210> SEQ ID NO 1335
<211> LENGTH: 19
<212> TYPE: RNA
<213> ORGANISM: Hepatitis B virus

<400> SEQUENCE: 1335
cucguggugg acuucucuc                                           19

<210> SEQ ID NO 1336
<211> LENGTH: 19
<212> TYPE: RNA
<213> ORGANISM: Hepatitis B virus

<400> SEQUENCE: 1336
ccuaugggag ugggccuca                                           19

<210> SEQ ID NO 1337
<211> LENGTH: 19
<212> TYPE: RNA
<213> ORGANISM: Hepatitis B virus

<400> SEQUENCE: 1337
aagaacuccc ucgccucgc                                           19

<210> SEQ ID NO 1338
<211> LENGTH: 19
<212> TYPE: RNA
<213> ORGANISM: Hepatitis B virus

<400> SEQUENCE: 1338
ucugccgauc cauacugcg                                           19

<210> SEQ ID NO 1339
<211> LENGTH: 19
<212> TYPE: RNA

```
<213> ORGANISM: Hepatitis B virus

<400> SEQUENCE: 1339
agagucuaga cucguggug                                              19

<210> SEQ ID NO 1340
<211> LENGTH: 19
<212> TYPE: RNA
<213> ORGANISM: Hepatitis B virus

<400> SEQUENCE: 1340
gaagaagaac ucccucgcc                                              19

<210> SEQ ID NO 1341
<211> LENGTH: 19
<212> TYPE: RNA
<213> ORGANISM: Hepatitis B virus

<400> SEQUENCE: 1341
ucaagccucc aagcugugc                                              19

<210> SEQ ID NO 1342
<211> LENGTH: 19
<212> TYPE: RNA
<213> ORGANISM: Hepatitis B virus

<400> SEQUENCE: 1342
agccuccaag cugugccuu                                              19

<210> SEQ ID NO 1343
<211> LENGTH: 19
<212> TYPE: RNA
<213> ORGANISM: Hepatitis B virus

<400> SEQUENCE: 1343
agacucgugg uggacuucu                                              19

<210> SEQ ID NO 1344
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1344
ucguggugga cuucucuca                                              19

<210> SEQ ID NO 1345
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1345
gugguggacu ucucucaau                                              19

<210> SEQ ID NO 1346
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 1346
gccgauccau acugcggaa                                          19

<210> SEQ ID NO 1347
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1347
ccgauccaua cugcggaac                                          19

<210> SEQ ID NO 1348
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1348
cauccugcug cuaugccuc                                          19

<210> SEQ ID NO 1349
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1349
ugcugcuaug ccucaucuu                                          19

<210> SEQ ID NO 1350
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1350
gguggacuuc ucucaauuu                                          19

<210> SEQ ID NO 1351
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1351
ugguggacuu cucucaauu                                          19

<210> SEQ ID NO 1352
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 1352
uagacucgug guggacuuc                                                19

<210> SEQ ID NO 1353
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1353
uccucugccg auccauacu                                                19

<210> SEQ ID NO 1354
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1354
ugccgaucca uacugcgga                                                19

<210> SEQ ID NO 1355
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1355
uggauguguc ugcggcguu                                                19

<210> SEQ ID NO 1356
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1356
cgauccauac ugcggaacu                                                19

<210> SEQ ID NO 1357
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1357
cgcaccucuc uuuacgcgg                                                19

<210> SEQ ID NO 1358
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1358
cugccgaucc auacugcgg                                                19

<210> SEQ ID NO 1359
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1359
cgugguggac uucucucaa                                                19

<210> SEQ ID NO 1360
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1360
cugcugcuau gccucaucu                                                19

<210> SEQ ID NO 1361
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1361
ccugcugcua ugccucauc                                                19

<210> SEQ ID NO 1362
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1362
cuagacucgu ggugacuu                                                 19

<210> SEQ ID NO 1363
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1363
uccugcugcu augccucau                                                19

<210> SEQ ID NO 1364
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1364
```
gacucguggu ggacuucuc 19

<210> SEQ ID NO 1365
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1365
auccauacug cggaacucc 19

<210> SEQ ID NO 1366
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1366
cucugccgau ccauacugc 19

<210> SEQ ID NO 1367
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1367
gauccauacu gcggaacuc 19

<210> SEQ ID NO 1368
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1368
gaagaacucc cucgccucg 19

<210> SEQ ID NO 1369
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1369
aagccuccaa gcugugccu 19

<210> SEQ ID NO 1370
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1370
agaagaacuc ccucgccuc                                                19

<210> SEQ ID NO 1371
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1371
ggagugugga uucgcacuc                                                19

<210> SEQ ID NO 1372
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1372
ccucugccga uccauacug                                                19

<210> SEQ ID NO 1373
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1373
caagccucca agcugugcc                                                19

<210> SEQ ID NO 1374
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1374
uccauacugc ggaacuccu                                                19

<210> SEQ ID NO 1375
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1375
cagagucuag acucguggu                                                19

<210> SEQ ID NO 1376
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1376
aagaagaacu cccucgccu                                                19

```
<210> SEQ ID NO 1377
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1377
gaguguggau ucgcacucc                                                19

<210> SEQ ID NO 1378
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1378
ucuagacucg ugguggacu                                                19

<210> SEQ ID NO 1379
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1379
gcugcuaugc cucaucuuc                                                19

<210> SEQ ID NO 1380
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1380
agucuagacu cguggugga                                                19

<210> SEQ ID NO 1381
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1381
cuccucugcc gauccauac                                                19

<210> SEQ ID NO 1382
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1382
uggcucaguu uacuagugc                                                19
```

<210> SEQ ID NO 1383
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1383
gucuagacuc gugguggac                    19

<210> SEQ ID NO 1384
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1384
uucaagccuc caagcugug                    19

<210> SEQ ID NO 1385
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1385
cuaugggagu gggccucag                    19

<210> SEQ ID NO 1386
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1386
cucguggugg acuucucuc                    19

<210> SEQ ID NO 1387
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1387
ccuaugggag ugggccuca                    19

<210> SEQ ID NO 1388
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1388
aagaacuccc ucgccucgc                    19

```
<210> SEQ ID NO 1389
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1389
ucugccgauc cauacugcg                                                        19

<210> SEQ ID NO 1390
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1390
agagucuaga cucguggug                                                        19

<210> SEQ ID NO 1391
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1391
gaagaagaac ucccucgcc                                                        19

<210> SEQ ID NO 1392
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1392
ucaagccucc aagcugugc                                                        19

<210> SEQ ID NO 1393
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1393
agccuccaag cugugccuu                                                        19

<210> SEQ ID NO 1394
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1394
agacucgugg uggacuucu                                                        19

<210> SEQ ID NO 1395
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1395
ugagagaagu ccaccacga                                                   19

<210> SEQ ID NO 1396
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1396
auugagagaa guccaccac                                                   19

<210> SEQ ID NO 1397
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1397
uuccgcagua uggaucggc                                                   19

<210> SEQ ID NO 1398
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1398
guuccgcagu auggaucgg                                                   19

<210> SEQ ID NO 1399
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1399
gaggcauagc agcaggaug                                                   19

<210> SEQ ID NO 1400
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1400
aagaugaggc auagcagca                                                   19

<210> SEQ ID NO 1401
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1401
aaauugagag aaguccacc                                                   19

<210> SEQ ID NO 1402
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1402
aauugagaga aguccacca                                                   19

<210> SEQ ID NO 1403
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1403
gaaguccacc acgagucua                                                   19

<210> SEQ ID NO 1404
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1404
aguauggauc ggcagagga                                                   19

<210> SEQ ID NO 1405
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1405
uccgcaguau ggaucggca                                                   19

<210> SEQ ID NO 1406
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1406
aacgccgcag acacaucca                                                   19

<210> SEQ ID NO 1407
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1407
aguuccgcag uauggaucg                                                19

<210> SEQ ID NO 1408
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1408
ccgcguaaag agaggugcg                                                19

<210> SEQ ID NO 1409
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1409
ccgcaguaug gaucggcag                                                19

<210> SEQ ID NO 1410
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1410
uugagagaag uccaccacg                                                19

<210> SEQ ID NO 1411
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1411
agaugaggca uagcagcag                                                19

<210> SEQ ID NO 1412
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1412
gaugaggcau agcagcagg                                                19

<210> SEQ ID NO 1413
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1413
aaguccacca cgagucuag                                                19

<210> SEQ ID NO 1414
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1414
augaggcaua gcagcagga                                                19

<210> SEQ ID NO 1415
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1415
gagaagucca ccacgaguc                                                19

<210> SEQ ID NO 1416
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1416
ggaguuccgc aguauggau                                                19

<210> SEQ ID NO 1417
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1417
gcaguaugga ucggcagag                                                19

<210> SEQ ID NO 1418
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1418
gaguuccgca guauggauc                                                19

<210> SEQ ID NO 1419
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1419
cgaggcgagg gaguucuuc                                                19

<210> SEQ ID NO 1420
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1420
aggcacagcu uggaggcuu                                                19

<210> SEQ ID NO 1421
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1421
gaggcgaggg aguucuucu                                                19

<210> SEQ ID NO 1422
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1422
gagugcgaau ccacacucc                                                19

<210> SEQ ID NO 1423
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1423
caguauggau cggcagagg                                                19

<210> SEQ ID NO 1424
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1424
ggcacagcuu ggaggcuug                                                19

<210> SEQ ID NO 1425
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1425
aggaguuccg caguaugga                                                19

<210> SEQ ID NO 1426
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1426
accacgaguc uagacucug                                                19

<210> SEQ ID NO 1427
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1427
aggcgaggga guucuucuu                                                19

<210> SEQ ID NO 1428
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1428
ggagugcgaa uccacacuc                                                19

<210> SEQ ID NO 1429
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1429
aguccaccac gagucuaga                                                19

<210> SEQ ID NO 1430
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1430
gaagaugagg cauagcagc                                                19

<210> SEQ ID NO 1431
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1431
uccaccacga gucuagacu                                                19

<210> SEQ ID NO 1432
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1432
guauggaucg gcagaggag                                                19

<210> SEQ ID NO 1433
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1433
gcacuaguaa acugagcca                                                19

<210> SEQ ID NO 1434
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1434
guccaccacg agucuagac                                                19

<210> SEQ ID NO 1435
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1435
cacagcuugg aggcuugaa                                                19

<210> SEQ ID NO 1436
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1436
cugaggccca cucccauag                                                19

<210> SEQ ID NO 1437
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1437
gagagaaguc caccacgag                                                19

<210> SEQ ID NO 1438
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1438
ugaggcccac ucccauagg                                                19

<210> SEQ ID NO 1439
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1439
gcgaggcgag ggaguucuu                                                19

<210> SEQ ID NO 1440
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1440
cgcaguaugg aucggcaga                                                19

<210> SEQ ID NO 1441
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1441
caccacgagu cuagacucu                                                19

<210> SEQ ID NO 1442
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1442
ggcgagggag uucuucuuc                                                  19

<210> SEQ ID NO 1443
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1443
gcacagcuug gaggcuuga                                                  19

<210> SEQ ID NO 1444
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1444
aaggcacagc uuggaggcu                                                  19

<210> SEQ ID NO 1445
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1445
agaaguccac cacgagucu                                                  19
```